(12) United States Patent
Purschke et al.

(10) Patent No.: US 8,691,784 B2
(45) Date of Patent: Apr. 8, 2014

(54) MCP-1 BINDING NUCLEIC ACIDS

(75) Inventors: Werner Purschke, Berlin (DE); Florian Jarosch, Berlin (DE); Dirk Eulberg, Berlin (DE); Sven Klussmann, Berlin (DE); Klaus Buchner, Berlin (DE); Christian Maasch, Berlin (DE)

(73) Assignee: NOXXON Pharma AG, Berlin (DE)

( * ) Notice: Subject to any disclaimer, the term of this patent is extended or adjusted under 35 U.S.C. 154(b) by 0 days.

(21) Appl. No.: 13/487,341

(22) Filed: Jun. 4, 2012

(65) Prior Publication Data

US 2013/0035376 A1    Feb. 7, 2013

Related U.S. Application Data

(63) Continuation of application No. 12/279,183, filed as application No. PCT/EP2007/001294 on Feb. 14, 2007, now Pat. No. 8,193,159.

(30) Foreign Application Priority Data

Feb. 14, 2006  (EP) ..................................... 06002935
Nov. 22, 2006  (EP) ..................................... 06024202

(51) Int. Cl.
| | |
|---|---|
| *C07H 21/02* | (2006.01) |
| *C07H 21/04* | (2006.01) |
| *A61K 31/70* | (2006.01) |
| *C12Q 1/68* | (2006.01) |
| *C12N 5/00* | (2006.01) |

(52) U.S. Cl.
USPC ...... 514/44 R; 514/44 A; 536/23.1; 536/24.1; 536/24.5; 435/375; 435/377

(58) Field of Classification Search
None
See application file for complete search history.

(56) References Cited

U.S. PATENT DOCUMENTS

| | | |
|---|---|---|
| 6,524,581 B1 | 2/2003 | Adamis |
| 6,670,321 B1 | 12/2003 | Adamis |
| 7,629,456 B2 | 12/2009 | Lange et al. |
| 7,750,140 B2 | 7/2010 | Helmling et al. |
| 2006/0003326 A1 | 1/2006 | Lange et al. |
| 2006/0030535 A1 | 2/2006 | Healy et al. |
| 2006/0257867 A1 | 11/2006 | Helmling et al. |
| 2009/0156542 A1 | 6/2009 | Purschke |
| 2010/0284961 A1 | 11/2010 | Purschke |

FOREIGN PATENT DOCUMENTS

| | | |
|---|---|---|
| EP | 1386972 | 2/2004 |
| WO | 200501408431 | 11/2005 |
| WO | 2007093409 | 8/2007 |

OTHER PUBLICATIONS

Helmling et al., PNAS 101(36)13174-13179, 2004.
Drolet et al., Pharm Res 17(12)1503-1510, 2000.
Eulberg & Klussmann, ChemBioChem 4, 979-983, 2003.
Kulkarni et al., J Pharm Exp Ther DOI:10.1124/jpet.108.142722, 2008.
Kulkarni et al., J Am Soc Nephrol 18(8)2350-2358, 2007.
Rhodes et al., FEBS Lett 506:85-90, 2001.
Eulberg et al., NAR 33(4)e45, 2005.
Anders et al., Naunyn-Sch Arch Pharm 375(Supp 1)53, 2007, Abstract 241.

*Primary Examiner* — Sean McGarry
(74) *Attorney, Agent, or Firm* — MDIP LLC

(57) ABSTRACT

The present invention is related to a nucleic acid, preferably binding to MCP-1, selected from the group consisting of Type 1A nucleic acids, type 1B nucleic acids, Type 2 nucleic acids, Type 3 nucleic acids, Type 4 nucleic acids and nucleic acids comprising SEQ ID NOs:87-115.

21 Claims, 55 Drawing Sheets

| | B1A | B2 | B3 | B4 | B5 | B6 | B1B | Length (nt) | Pull-down | IC$_{50}$ Ca$^{++}$-Assay [nM] |
|---|---|---|---|---|---|---|---|---|---|---|
| | AGCGUG | CCCGGA | *GUG* | GCA | GGGGGACGCGACC | UGCAAUAAUG | CACGCU | 47 | >> E10trc | 8 |
| | AGCGUG | CCCGGA | *GUG* | GCA | GGGGGACGCGACC | UGCAAUUG | CACGCU | 45 | >> E10trc | 10 |
| | AGCGUG | CCCGGA | *GUG* | GCA | GGGGGACGCGACC | UGUAAAAUG | CACGCU | 47 | >> E10trc | |
| | AGCGUG | CCCGGU | *GUG* | GCA | GGGGGACGCGACC | UGCAAAAUG | CGCGCU | 47 | >> E10trc | |
| | AGCGUG | CCCGGA | *GUA* | GCA | GGGGGACGCGACC | UGCAAUAAUG | CACGCU | 47 | >> E10trc | |
| | AGCGUG | CCCGGA | *GUG* | GCA | GGGGGCGCGACC | UACAAUUG | CACGCU | 45 | >> E10trc | |
| | AGCGUG | CCCGGU | *GUG* | GUA | GGGGGCGCGAUC | UGCAUUUG | CACGCU | 45 | >> E10trc | |
| | AGCGUG | CCCGGU | *GUG* | ACA | GGGGGCGCGACC | UGUAUUG | CACGCU | 45 | > E10trc | 14 |
| | AGCGUG | CCCGGU | *GUG* | GCA | GGGGGCGCGACC | UGCAAUAAUG | CACGCU | 47 | > E10trc | |
| | AGCGUG | CCCGGU | *GUG* | GCA | GGGGGCGCGACC | UGCAAUUG | CACGCU | 45 | > E10trc | |
| | AGCGUG | CCCGGU | *GUG* | GCA | GGGGGCGCGACC | UGCAUUG | CACGCU | 45 | > E10trc | |
| | AGCAUG | CCCGGU | *GUA* | GUA | GGGGGCGCGACC | UACAUUG | CACGCU | 45 | 5 nM | 4-5 | weaker binding than 176-E10trc as determined in competition assay
much weaker binding than 176-E10trc as determined in competition assay

Fig. 1

| B1A | B2 | B3 | B4 | B5 | B6 | B1B | Length (nt) | Pull-down | IC$_{50}$ Ca$^{++}$-Assay [nM] |
|---|---|---|---|---|---|---|---|---|---|
| AGUGUG | CCAGCU | GUG | AUG | GGGGGGCGCGACC | CAUUUUA | CACACU | 44 | > C9trc | |
| AGUGUG | CCAGC | GUG | AUG | GGGGGGCGCGACC | CAUUUUA | CACACU | 43 | > C9trc | 6 |
| AGUGUG | CGAGC | GUG | AUG | GGGGGGCGCGACC | CAUUUUA | CAUACU | 43 | > C9trc | |
| AGUGUG | CCAGC | GUG | AUG | GGGGGGCGCGACC | CAUUUUA | CAUACU | 43 | > C9trc | |
| AGUAUG | CCAGC | GUG | AUG | GGGGGGCGCGACC | CAUUUA | CAUACU | 42 | > C9trc | 30 |
| AGUGUG | CCAG U | GUG | AUG | GGGGGGCGCGACC | CAUUUUA | CACACU | 43 | > C9trc | 6 |
| AGCGUG | CCAG U | GUG | AUG | GGGGGGCGCGACC | CAUUUUA | CACGCU | 43 | = C9trc 5 nM | 4-5 | milar binding as 176-C9trc as determined in competition assay
aker binding than 176-C9trc as determined in competition assay

Fig. 2

| B1A | | B2 | | B1B | Length (nt) | Pull-down | IC₅₀ Ca⁺⁺- Assay | IC₅₀ Chemotaxis |
|---|---|---|---|---|---|---|---|---|
| ACGCA | | CGUCCCUCACCGGUGCAAGUGAAGCCGGGCUC | | UGCGU | 43 | > D1-002 | | |
| ACGCA | | CCUCCCUCACCGGUGCAAGUGAAGCCGUGGCUC | | UGCGC | 43 | > D1-002 | | |
| ACGCA | | CGUCCCUCACCGGUGCAAGUGAAGCCGUGGCUC | | UGCGU | 43 | 0.7 nM | 5 nM | < 1 nM | as of 180-D1-002

| B1A | | B2 | | B1B | Length (nt) | Pull-down | IC₅₀ Ca⁺⁺- Assay | IC₅₀ Chemotaxis |
|---|---|---|---|---|---|---|---|---|
| GCA | | CGUCCCUCACCGGUGCAAGUGAAGCCGUGGCUC | | UGCGU | 41 | = D1-002 | 5 nM | 1.2 nM |
| ACGCA | | GUCCCUCACCGGUGCAAGUGAAGCCGUGGCUC | | UGC | 41 | = D1-002 | 6 nM | 2.6 nM |
| GCA | | GUCCCUCACCGGUGCAAGUGAAGCCGUGGCUC | | UGC | 39 | > D1-002 | <10 nM | 2 nM |
| CGCA | | CGUCCCUCACCGGUGCAAGUGAAGCCGUGGCUC | | UGCGU | 42 | > D1-002 | | |
| CGCA | | CGUCCCUCACCGGUGCAAGUGAAGCCGUGGCUC | | UGCG | 41 | = D1-002 | | |
| GCA | | CGUCCCUCACCGGUGCAAGUGAAGCCGUGGCUC | | UGCG | 40 | = D1-002 | 3-4 nM | 0.5 nM | imilar binding as 180-D1-002 as determined in competition assay
eaker binding than 180-D1-002 as determined in competition assay

Fig. 3

| B1A | B2A | B3 | B2B | B4 | B5A | B6 | B5B | B1B | length (nt) | Pull-down | IC$_{50}$ Chemotaxis [nM] |
|---|---|---|---|---|---|---|---|---|---|---|---|
| UGCUGC | GUAGU | GGAAG | ACUAC | CUAAUGA | CAGC | CGAAU | GCUG | GCAGCAC | 49 | > 178-D5 | |
| UGCUGC | GUAGU | GGAAG | ACUAC | CUAAUGA | CAGC | CUAAU | GCUG | GCAGCAC | 49 | > 178-D5 | |
| UGCUGC | GUAGU | GGAAG | ACUAC | CUAAUGA | CAGC | CGAAU | GCUG | GCAGCAC | 49 | > 178-D5 | |
| UGCUGC | GUAGU | GAAAA | ACUAC | UGCCAGUG | GGU | CAGA | GCUA | GCAGCAC | 48 | > 178-D5 | |
| UGCUGC | GGAGU | UAAAA | ACUCC | CUAAGACA | GGC | CAGA | GCCG | GCAGCAC | 48 | > 178-D5 | |
| UGCUGC | GGAGU | UGAAA | ACUCC | CUAAGACA | GGC | CAGA | GCCG | GCAGCAC | 48 | > 178-D5 | |
| UGCUGC | GUAGU | GGAAG | ACUCC | CUAAUGA | CAGC | CUAAU | GCUG | GCAGCAC | 48 | > 178-D5 | |
| UGCUGC | GGAGU | UAAAA | ACUCC | CUAAGACA | GGC | UAGA | GCCG | GCAGCAC | 48 | 4 | |
| UGCUGC | GGCGU | GAAAA | ACGCC | CUGCGA | CUGC | CCUUUAU | GCAG | GCAGCAC | 48 | = 178-D5 | |
| UGCUGC | GUAGU | GAAAA | ACUAC | CAACGACU | GGC | UAGA | GCCG | GCAGCAC | 48 | = 178-D5 | |
| UGCUGC | GUAGU | GAAAG | ACUAC | CUGUGA | CAGC | CGAAU | GCUG | GCAGCAC | 48 | = 178-D5 | |
| UGCUGC | GUAGU | UAAAA | ACUAC | CAACGACU | GGC | UAGA | GCCG | GCAGCAC | 48 | = 178-D5 | |
| UACUGC | GUAGU | UAAAA | ACUAC | CAACGACU | GGC | UAGA | GCCG | GCAGCAC | 48 | 0.5 nM | 0.5 |
| UGCUGC | GUAGU | UAAAA | ACUAC | CAGCGACU | GGC | UAGA | GCCG | GCAGCAC | 48 | 0.5 nM | 0.5 |
| UGCUGC | GUAGU | GAGAA | ACUAC | CAACGACU | GCC | UAGA | GCCG | GCAGCAC | 48 | 0.1 nM | 0.5 | imilar binding as 178-D5 as determined in competition assay
eaker binding than 178-D5 as determined in competition assay

Fig. 4

DERIVATIVES OF 178-D5 AND 181-A2

| | B1A | B2A | B3 | B2B | B4 | B5A | B6 | B5B | B1B | LENGTH (nt) | PULL-DOWN | BIACORE |
|---|---|---|---|---|---|---|---|---|---|---|---|---|
| 178-D5-020 | GGCUGC | GUAGU | UAAAA | ACUAC | CAGCGACU | GGC | UAGA | GCCG | GCAGCC | 46 | 1.5 nM | |
| 178-D5-027 | GGCGC | GUAGU | UAAAA | ACUAC | CAGCGACU | GGC | UAGA | GCCG | GCGCC | 44 | 27 nM | |
| 178-D5-030 | GUGCGC | GUAGU | UAAAA | ACUAC | CAGCGACU | GGC | UAGA | GCCG | GCGCAC | 46 | =178-D5 | |
| 181-A2 | GUGCUGC | GUAGU | GAGAA | ACUAC | CAACGACU | GGC | UAGA | GCCG | GCAGCAC | 48 | | 0.37 nM |
| 181-A2-002 | GUGCGC | GUAGU | GAGAA | ACUAC | CAACGACU | GGC | UAGA | GCCG | GCGCAC | 46 | | =181-A2 |
| 181-A2-004 | GUGCC | GUAGU | GAGAA | ACUAC | CAACGACU | GGC | UAGA | GCCG | GGCAC | 44 | | =181-A2 |
| 181-A2-005 | GUGCC | GUAGU | GAGAA | ACUAC | CAACGACU | GGC | UAGA | GCCG | GCCAC | 44 | | =181-A2 |
| 181-A2-006 | GUCGC | GUAGU | GAGAA | ACUAC | CAACGACU | GGC | UAGA | GCCG | GCGAC | 44 | | =181-A2 |
| 181-A2-007 | UCGC | GUAGU | GAGAA | ACUAC | CAACGACU | GGC | UAGA | GCCG | GCAGC | 44 | | =181-A2 |
| 181-A2-008 | UCGC | GUAGU | GAGAA | ACUAC | CAACGACU | GGC | UAGA | GCCG | GCCGC | 44 | | >181-A2 |
| 181-A2-011 | GCUGC | GUAGU | GAGAA | ACUAC | CAACGACU | GGC | UAGA | GCCG | GCAGC | 44 | | >181-A2 |
| 181-A2-012 | GCGCC | GUAGU | GAGAA | ACUAC | CAACGACU | GGC | UAGA | GCCG | GCACC | 44 | | =181-A2 |
| 181-A2-015 | UGGC | GUAGU | GAGAA | ACUAC | CAACGACU | GGC | UAGA | GCCG | GCCA | 42 | | >181-A2 |
| 181-A2-016 | GCGC | GUAGU | GAGAA | ACUAC | CAACGACU | GGC | UAGA | GCCG | GCGC | 42 | | >181-A2 |
| 181-A2-017 | GCCC | GUAGU | GAGAA | ACUAC | CAACGACU | GGC | UAGA | GCCG | GCAC | 42 | | =181-A2 |
| 181-A2-018 | GGCC | GUAGU | GAGAA | ACUAC | CAACGACU | GGC | UAGA | GCCG | GCCC | 42 | | =181-A2 |
| 181-A2-019 | CGCC | GUAGU | GAGAA | ACUAC | CAACGACU | GGC | UAGA | GCCG | GCUC | 42 | | =181-A2 |
| 181-A2-020 | CCCC | GUAGU | GAGAA | ACUAC | CAACGACU | GGC | UAGA | GCCG | GCCG | 42 | | =181-A2 |
| 181-A2-021 | CAGC | GUACU | GAGAA | ACUAC | CAACGACU | GGC | UAGA | GCCG | GCUG | 42 | | >181-A2 |
| 181-A2-022 | CAGC | GUAGU | GAGAA | ACUAC | CAACGACU | GGC | UAGA | GCCG | GCUG | 42 | | =181-A2 |
| 181-A2-023 | CUGC | GUAGU | GAGAA | ACUAC | CAACGACU | GGC | UAGA | GCCG | GCAG | 42 | | =181-A2 |
| Boxes | B1A | B2A | B3 | B2B | B4 | B5A | B6 | B5B | B1B | | | |

= 178-D5, SIMILAR BINDING AS 178-D5 AS DETERMINED IN COMPETITION ASSAY
= 181-A2, SIMILAR BINDING AS 181-A2 IN BIACORE MEASUREMENT
> 181-A2, WEAKER BINDING THAN 181-A2 IN BIACORE MEASUREMENT

FIG. 5

| OTHER SEQUENCES | | LENGTH (nt) | PULL-DOWN | BIACORE | IC50 Ca++-ASSAY | IC50 CHEMOTAXIS |
|---|---|---|---|---|---|---|
| 177-B3 | GGACGAGAGUGACAAAUGAUAUAACCUCUGACUAACGCUGCGGGCGACAGG | 52 | 12 nM | > 178-D5 | | |
| 177-C1 | GGACCUAUCGCUUAAGACAACGCCAGUCUACGGACAUUCUCCGGAGACAGG | 52 | > 178-D5 | | | |
| 177-C2 | GGACAAUUGUUACCCCGAGAGACAAAUGAGACAACCUCCCUGAAUCCGACAGG | 52 | 9 | > 178-D5 | | |
| 177-E3 | GGACGAAAGUGAGAAUGAUACAACUCCCUGUGCUGCGAAGGGUAGACCGACAGG | 51 | > 178-D5 | | | |
| 177-D1 | GGACGUAAAAGACCUACAAUGCGGCCAGUCAGGAGGGUAGACCGACAGG | 50 | > 178-D5 | | | |
| 177-E1 | GGACGUAAGAAACUACAAUAGCGGCCAGUUGCACCGCGUUAUCAACGACAGG | 50 | > 178-D5 | | | |
| 177-A1 | GGACUAGAGUCAGCCACGUCGUGUAUAUCCGACCGCGGUUUAUUUACUGACAGG | 50 | > 178-D5 | | | |
| 177-G3 | GGACUGUCCGGACUGUGAAUACUCCCGAGACCGCCAGAAGCGGGGACAGG | 50 | 5 nM | > 178-D5 | 20 nM | |
| 177-C3 | GGACUUCUAUCCAGGUGGUGUGAAUAUAACCUUCUGAGUAUGUAAAGAGUGACAGG | 50 | 5 nM | > 178-D5 | + | |
| 177-A2 | GGACGAGCGAACAAUGAUAUAACCUCCUGACGAAAGAGAAUCGACAGG | 50 | 13 nM | > 178-D5 | + | |
| 170-E4trc | CCUGUGCUACACGCCAGUAAGAAGUGAACGUUCAGUAGUGUGCACAGG | 48 | | | | |
| 166-D2trc | CGUGAGCCAGGACCUAAGCUAGCAGGGCCGUUAUUGGACACGACACG | 48 | | | | |
| 174-A2trc | CGUGAACAUCCAAGCUAAGCAACUGAGCGGCCGGUUGUCUUGGCCCGCACG | 48 | | | | |
| 174-E2trc | CGUGAGAGAGAAUGACCAACCACGUCAAAAAUCAACCUAAUGGGCCGCACG | 48 | | | | |
| 183-G3trc | CGUGCAGAGAGAGACCAACCACGUCAAAAAUCAACCUAAUGGCCGCACG | 48 | 2-5 nM | | 2-3 nM | + |
| 183-B2trc | CGUGAACAUUCAAGCUAAGCAACUGAGCCUGUUGUUGGGCCUGCUUGGCCACG | 48 | 5-10 nM | | 2-6 nM | + |
| 166-B2trc | CGUGCCGAGGCGGCCAGCAGGGCGUUAACUUUAGAGGCCUUGCCACCACG | 48 | 25 nM | | 2-15 nM | + |
| 166-G3trc | CGUGAUAACAGCCGCUCGGUCAAGAAACAAGCCACCAGUAAAAGAUAGACCG | 47 | | | + | |
| 166-D1trc | CGUGGGGCCACCGAGGGCGUAAAAAGAGAUAGACCG | 47 | 2-5 nM | | + | |
| 183-H2trc | CGUGAUCUCCUUUGGGGUGAUUAGCUUAGAGACUUCCACACG | 45 | | 180 nM | 10 nM | + |
| 167-A7trc | GCACCUUCGCCUAAAUACACGUGCCGGCUAACGUCUAAUACUCGUCCG | 45 | | 5 nM | 150 nM | + |
| 167-C7trc | GCACGACUUGGCCGACCAGUGAUACUAGAGACCAAGUCGUCGG | 45 | | | + | + |
| 167-B5trc | GCGCGCCGCUCACAGUUAAGGAGAAAUGAAGUUCAGAAUGCGUCGUCGG | 44 | | | + | + |
| 184-D7trc | AGUGUGUGGCCAGUAAGGCUAAGGACUAUGGAGAUUCCGAGACCACGCU | 39 | 800 nM | | | |
| 184-D6trc | AGUGUGUGGCCAGACUAUUGGACUACCGAGAUGACUCGCGCU | 39 | 650 nM | | | |
| 184-E5trc | AGCGUGAGGGCAGCCGACCAGCGGCAUUACUUAGAGAGUCACGCU | 39 | 100 nM | | | |
| 184-G6trc | AGCGUGAAGGGACCAGCGGUCGGUUACACCGUUACAGAGUUCACGCU | 39 | 160 nM | | | |
| 184-B7trc | AGCGUGUGAUGUAUGGACCCCGUGUUUCGUAGAGAGACACGCU | 39 | 27 nM | | | |
| 184-B6trc | AGCGUGCGACCCGACCAGUAUCACGGUUUCGUAGAGAGUCACGCU | 37 | 60 nM | | | |

+, SUBSTANCE ACTIVE IN ASSAY; NO IC50 DETERMINED
> 178-D5, WEAKER BINDING THAN 178-D5 AS DETERMINED IN COMPETITION ASSAY

FIG. 7

MURINE-SPECIFIC SPIEGELMERS

188-A3-001 AND DERIVATIVES

| | | LENGTH (nt) | PULL-DOWN | IC$_{50}$ Ca$^{++}$- ASSAY [nM] | IC$_{50}$ CHEMOTAXIS [nM] |
|---|---|---|---|---|---|
| 188-A3-001 | GAGAUGGGCGACAUUGGUUGGGCAUGAGGCCCUUUGAUGAAUCCGGCCAUUC | 58 | <1 nM | | |
| 188-A3-004 | GAUGGCACAUUGGUUGGGCAUGAGGCCCUUUGAUGAAUCCGGCCAUUC | 56 | <1 nM | | |
| 188-A3-005 | GGCGACAUUGGUUGGGCAUGAGGCCCUUUGAUGAAUCCGGCCAUUC | 53 | <1 nM | | |
| 188-A3-006 | GCGACAUUGGUUGGGCAUGAGGCCCUUUGAUGAAUCCGGCCAUU | 52 | <1 nM | 12 | 4 |
| 188-A3-007 = mNOX-E36 | GGCGACAUUGGUUGGGCAUGAGGCCCUUUGAUGAAUCCGGCCA | 50 | ~0.2 nM | 12 | 7 |

189-G7-001 AND DERIVATIVES

| | | LENGTH (nt) | PULL-DOWN | IC$_{50}$ Ca$^{++}$- ASSAY [nM] | IC$_{50}$ CHEMOTAXIS [nM] |
|---|---|---|---|---|---|
| 189-G7-001 | GCUGGUUACCGAGGGGCGUCGUUGGAGUUUGGUUGUCACCAGC | 48 | <1 nM | 20-30 | |
| 189-G7-002 | CUGGUUACCGAGGGGCGUCGUUGGAGUUUGGUUGUCACCAG | 46 | <1 nM | 40-50 | 6.5 |
| 189-G7-003 | UGGUUACCGAGGGGCGUCGUUGGAGUUUGGUUGUCACCA | 44 | <1 nM | | |
| 189-G7-007 | GCCGGUUACCGAGGGGCGUCGUUGGAGUUUGGUUGUCACCGGC | 48 | | 20 | |
| 189-G7-008 | GCCGCUACCGAGGGGCGUCGUUGGAGUUUGGUUGUGUCGCCGGC | 48 | ~1 nM | 12 | 5 |
| 189-G7-010 | GCGCGUACCGAGGGGCGUCGUUGGAGUUUGGUUGUGUCCGCGC | 46 | | 40 | |
| 189-G7-012 | GGGCCUACCGAGGGGCGUCGUUGGAGUUUGGUUGUCGGCCC | 46 | | >50 | |

FIG. 8

Fig. 20  Kinetics of Spiegelmer 181-A2-018 binding human MCP-1

```
1   QPDAINAPVTCCYNFTNRKISVQRLASYRRITSSKCPKEAVIFKTIVAKEICADPKQKWVQDSMDHLDKQTQTPKT
2   QPDAINAPVTCCYNFTNRKISVQRLASYRRITSSKCPKEAVIFKTIVAKEICADPKQKWVQDSMDHLDKQIQTPKP
3   QPDAINSPVTCCYTLTSKKISMQRLMSYRRVTSSKCPKEAVIFKTIAGKEICAEPKQKWVQDSISHLDKKNQTPKP
4   QPDAINSPVTCCYTFTGKKISSQRLGSYKRVTSSKCPKEAVIFKTILAKEICADPEQKWVQDAVKQLDKKAQTPKP
5   QPDAIISPVTCCYTLTNKKISIQRLASYKRVTSSKCPKEAVIFKTVLNKEICADPKQKWVQDSMAHLDKKSQTQTA
6   QPDAVNSPVTCCYTFTNKTISVKRLMSYRRINSTKCPKEAVIFMTKLAKGICADPKQKWVQDAIANLDKKMQTPKT
7   QPDAINSQVACCYTFNSKKISMQRLMNYRRVTSSKCPKEAVIFKTILGKELCADPKQKWVQDSINYLNKKNQTPKP
8   QPVGINTSTTCCYRFINKKIPKQRLESYRRTTSSHCPREAVIFKTKLDKEICADPTQKWVQDFMKHLDKKTQTPKL
9   GP--ASVPTTCCFNLANRKIPLQRLESYRRITSGKCPQKAVIFKTKLAKDICADPKKKWVQDSMKYLDQKSPTPKP
10  QPDSVSIPITCCFNVINRKIPIQRLESYTRITNIQCPKEAVIFKTKRGKEVCADPKERWVRDSMKHLDQIFQNLKP
11  QPDAVNAPLTCCYSFTSKMIPMSRLESYKRITSSRCPKEAVVFVTKLKREVCADPKKEWVQTYIKNLDRNQMRSEP
12  QPDAVNAPLTCCYSFTGKMIPMSRLENYKRITSSRCPKEAVVFVTKLKREICADPNKEWVQKYIRKLDQNQVRSET
```

| | PROTEIN | % IDENTITY WITH HUMAN MCP-1 |
|---|---|---|
| 1 | *HOMO SAPIENS* MCP-1 | 100% |
| 2 | *MACACA MULATTA* (RHESUS MONKEY) MCP-1 | 97% |
| 3 | *SUS SCROFA* (PIG) MCP-1 | 79% |
| 4 | *EQUUS CABALLUS* (HORSE) | 78% |
| 5 | *CANIS FAMILIARIS* (DOG) MCP-1 | 76% |
| 6 | *ORYCTOLAGUS CUNICULUS* (RABBIT) MCP-1 | 75% |
| 7 | *BOS TAURUS* (BOVINE) | 72% |
| 8 | *HOMO SAPIENS* MCP-3 | 71% |
| 9 | *HOMO SAPIENS* EOTAXIN | 64% |
| 10 | *HOMO SAPIENS* MCP-2 | 62% |
| 11 | *MUS MUSCULUS* (MOUSE) MCP-1 | 55% |
| 12 | *RATTUS NORVEGICUS* (RAT) MCP-1 | 55% |

FIG. 23

SPECIFICITY OF NOX-E36 AND 181-A2-018

| | NOX-E-036 $K_D$ [nM] | 181-A2-018 $K_D$ [nM] |
|---|---|---|
| hMCP-1 | 0.89 | 0.37-0.6 |
| hMCP-2 | 5-10 | 10 |
| hMCP-3 | - | 10 |
| EOTAXIN | 5-10 | 10-20 |
| MONKEY MCP-1 | 0.90 | 0.6 |
| PORCINE MCP-1 | 0.82 | > 1000 |
| CANINE MCP-1 | 1.2 | > 1000 |
| RABBIT MCP-1 | - | > 1000 |
| RAT MCP-1 | - | - |
| MOUSE MCP-1 | - | - |

-, NOT BINDING

FIG. 24A

| Chemokine/synonym | binding |
|---|---|
| CCL1/I-309 | - |
| CCL2/MCP-1 | + |
| CCL3/MIP-1α | + |
| CCL4/MIP-1β | - |
| CCL5/RANTES | -* |
| CCL7/MCP-3 | - |
| CCL8/MCP-2 | + |
| CCL11/eotaxin | + |
| CCL13/MCP-4 | (+) |
| CCL14/HCC-1 | - |
| CXCL1/GROα | - |
| CXCL2/GROβ | - |
| CXCL3/GROγ | - |
| CXCL4/PF4 | -** |
| CXCL5/ENA-78 | - |
| CXCL6/GCP-2 | -** |
| CXCL7/NAP-2 | + |
| CXCL8/IL-8 | - |
| CXCL9/MIG | -* |
| CXCL10/IP-10 | - |
| CXCL11/I-TAC | -** |
| CXCL12α/SDF-1α | - |
| CXCL12β/SDF-1β | - |
| CX$_3$CL1/Fractalkine | - |
| XCL1/Lymphotactin | - |

Binding was classified as follows:

+, specific binding < 10 nM;

(+), NOX-E36 specific binding > 1 µM;

-, no interaction measurable;

-*, unspecific polyanion (PoC or dextran matrix) binding > 250 nM;

-**, unspecific polyanion (PoC or dextran matrix) binding > 10 µM.

Fig. 24 B

| Association rate constant $k_a$ [M$^{-1}$s$^{-1}$] | Dissociation rate constant $k_d$ [s$^{-1}$] | Dissociation constant $K_D$ [nM] |
|---|---|---|
| 1.8 ± 0.4 x 10$^5$ | 1.9 ± 0.1 x 10$^{-4}$ | 1.1 ± 0.2 |
| 1.6 ± 0.3 x 10$^5$ | 6.4 ± 1.1 x 10$^{-4}$ | 4.1 ± 1.3 |
| – | – | – |
| 2.0 ± 0.7 x 10$^5$ | 6.7 ± 2.0 x 10$^{-4}$ | 4.2 ± 2.5 |
| 1.6 ± 0.4 x 10$^5$ | 1.1 ± 0.6 x 10$^{-3}$ | 7.7 ± 5.2 |
| – | – | > 1,000 |
| 1.8 ± 0.5 x 10$^5$ | 4.1 ± 0.4 x 10$^{-4}$ | 2.5 ± 0.9 |

Fig. 24 C

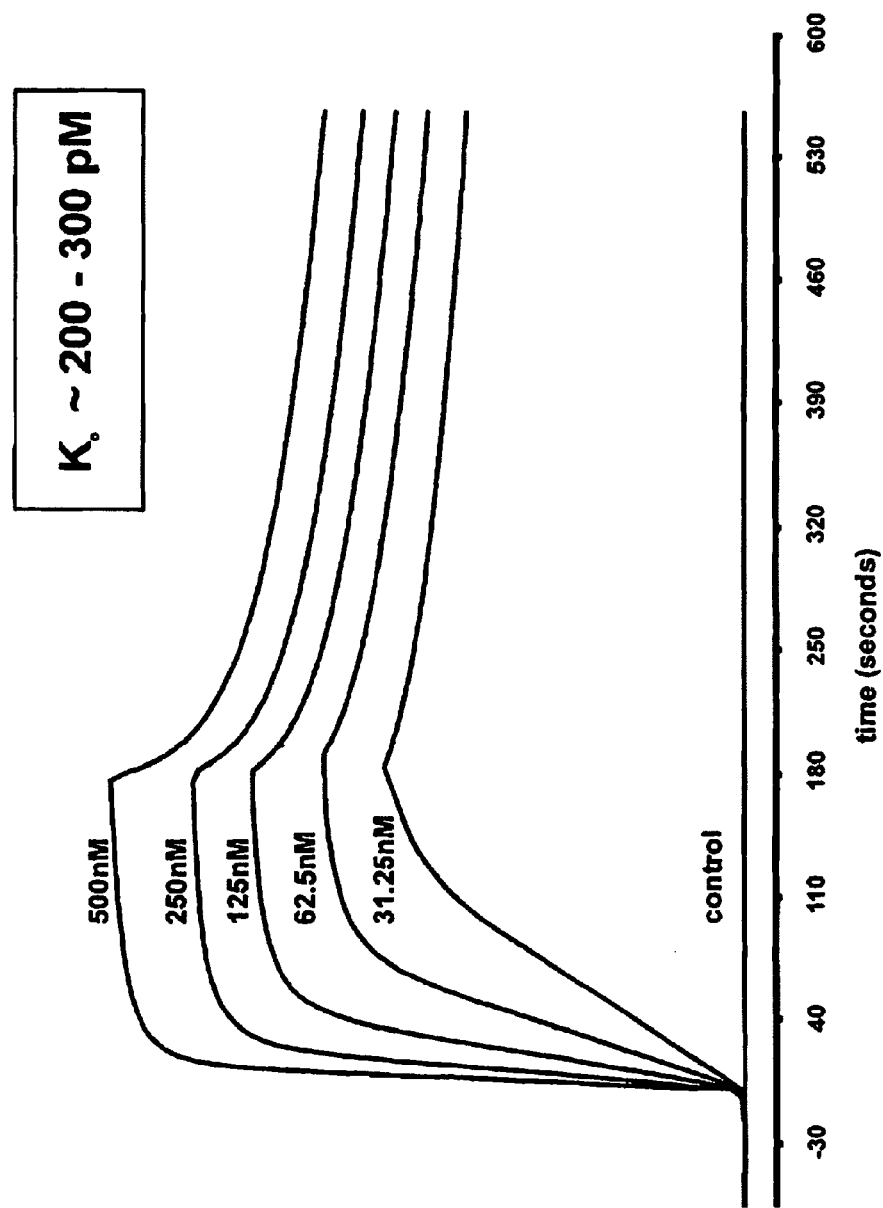
Fig. 32  Kinetics of D-mNOX-E36 binding to murine D-MCP-1

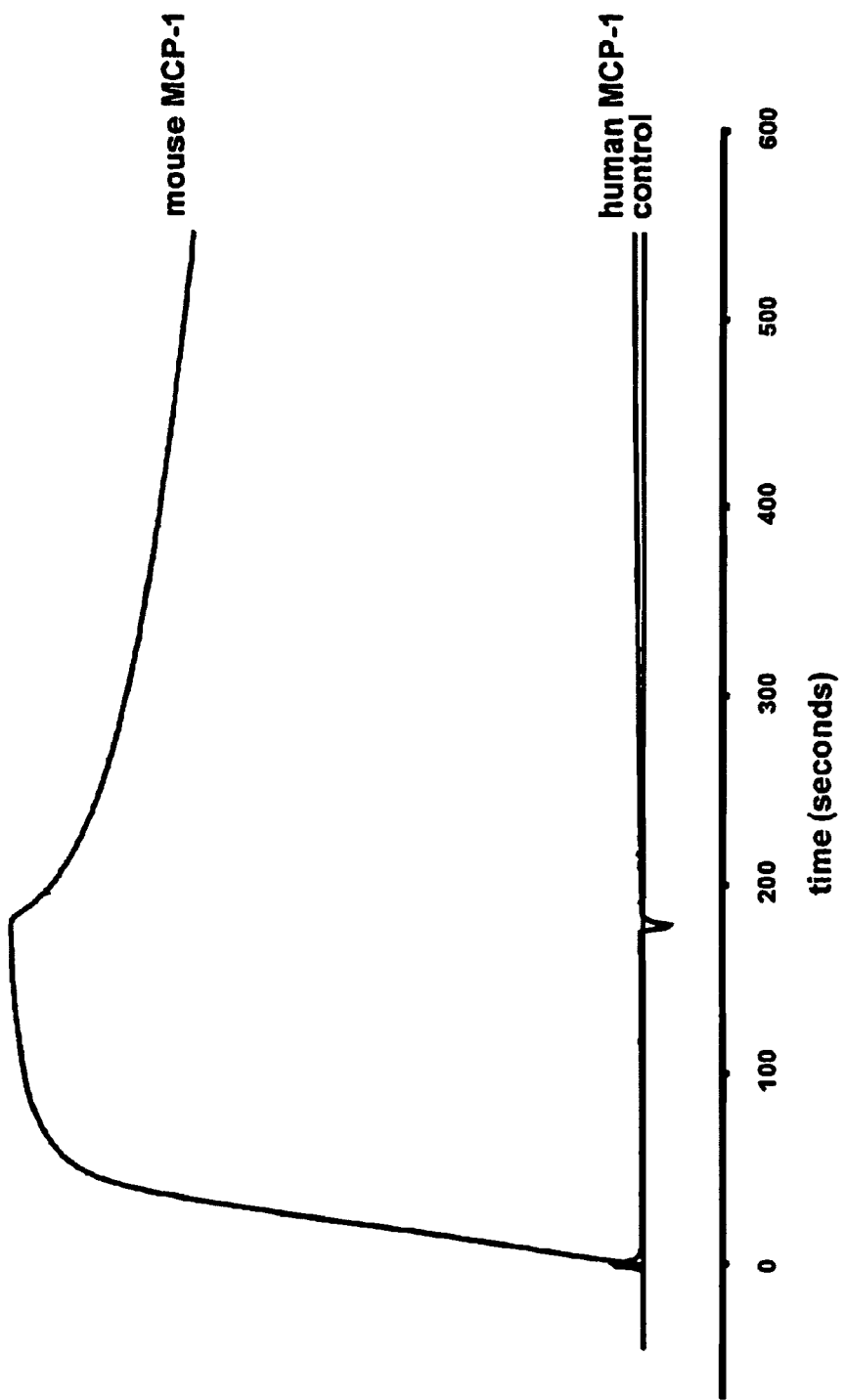
Fig. 33 D-mNOX-E36 binding to murine and human D-MCP-1

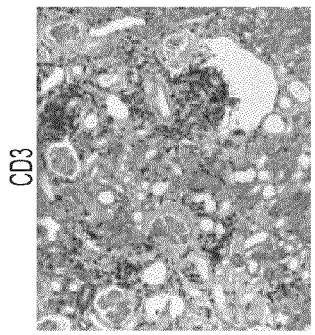
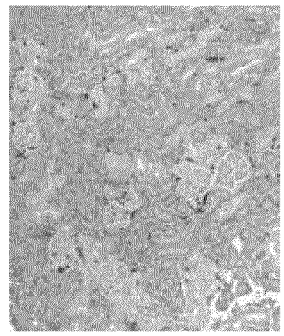
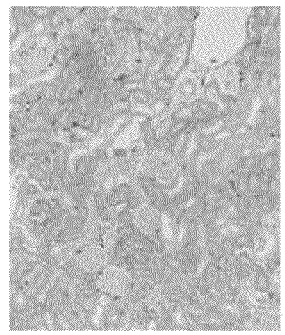
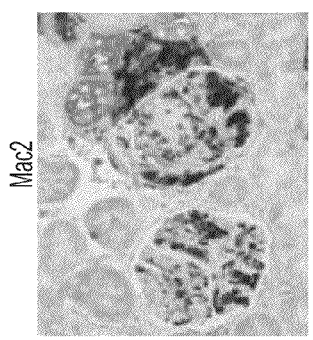
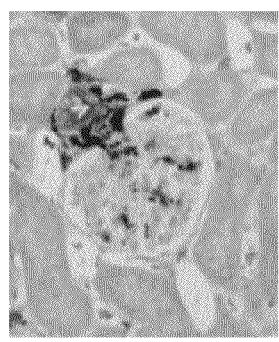
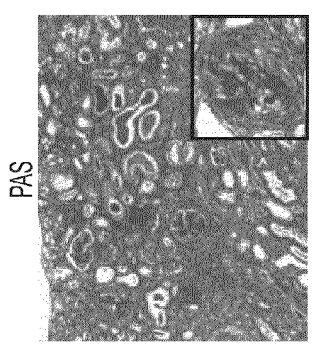
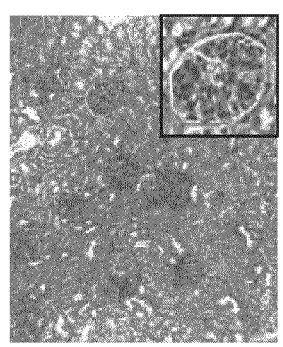
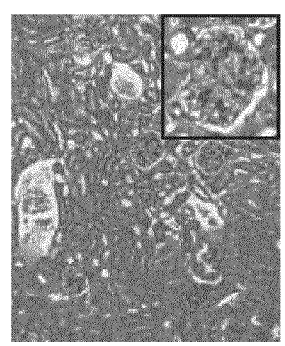

| | VEHICLE | PoC | mNOX-E36 | PoC-PEG | mNOX-E36-3'PEG |
|---|---|---|---|---|---|
| RENAL DISEASE | | | | | |
| GFR [μl/MIN] | 179 ± 41 | 200 ± 49 | 245 ± 69 | 157 ± 74 | 293 ± 72 |
| U ALBUMIN/CREATININ RATIO | 15.6 ± 10.1 | 4.3 ± 1.4 | 6.8 ± 1.8 | 3.8 ± 0.5 | 2.4 ± 0.7 |
| IgG$_1$ [GLOM. SCORE] | 1.5 ± 0.4 | 1.6 ± 0.2 | 1.6 ± 0.5 | 1.7 ± 0.2 | 1.7 ± 0.5 |
| IgG$_{2a}$ [GLOM. SCORE] | 0.9 ± 0.3 | 1.0 ± 0.3 | 1.0 ± 0.3 | 1.1 ± 0.3 | 1.0 ± 0.3 |
| ACTIVITY INDEX [SCORE] | 17.4 ± 4.9 | 17.8 ± 4.2 | 10.3 ± 5.0* | 17.4 ± 2.7 | 9.4 ± 4.2* |
| CHRONICITY INDEX [SCORE] | 6.0 ± 2.0 | 7.2 ± 2.6 | 2.6 ± 2.5 | 5.4 ± 1.0 | 1.6 ± 1.8* |
| Mac-2+ [CELLS/GLOM] | 13.4 ± 2.0 | 12.6 ± 0.9 | 8.5 ± 2.3* | 13.6 ± 2.3 | 8.2 ± 3.5* |
| Mac-2+ [CELLS/HPF] | 20.3 ± 8.1 | 20.6 ± 6.7 | 10.8 ± 5.1 | 19.3 ± 3.7 | 7.7 ± 4.0* |
| CD3+ [CELLS/HPF] | 44.6 ± 14.7 | 39.4 ± 7.5 | 23.8 ± 10.2 | 36.2 ± 3.1 | 19.0 ± 8.0* |
| LUNG INJURY [SCORE] | 1.6 ± 0.8 | 1.6 ± 0.4 | 0.6 ± 0.5* | 1.4 ± 0.4 | 0.4 ± 0.5* |
| SKIN LESIONS [% OF MICE] | 60 | 60 | 28 | 80 | 28 |

U ALBUMIN/CREATININ RATIO = URINARY ALBUMIN/CREATININE RATIO IN μg/mg, VALUES ARE MEANS ± SEM; * p < 0.05 SPIEGELMER VS. RESPECTIVE PoC CONTROL

FIG. 35

|  | VEHICLE | PoC | mNOX-E36 | PoC-PEG | mNOX-E36-3'PEG |
| --- | --- | --- | --- | --- | --- |
| LYMPHOPROLIFERATION | | | | | |
| SPLEEN WEIGHT [% BW] | 1.8 ± 0.4 | 2.0 ± 0.2 | 1.6 ± 0.4 | 1.7 ± 0.1 | 1.6 ± 0.3 |
| LN WEIGHT [% BW] | 2.3 ± 0.7 | 1.8 ± 0.1 | 1.7 ± 0.3 | 1.7 ± 0.2 | 1.7 ± 0.7 |
| SERUM ANTI dsDNA | | | | | |
| IgG1 [µg/ml] | 11.7 ± 3.6 | 7.5 ± 2.8 | 11.7 ± 3.4 | 8.2 ± 1.2 | 6.6 ± 1.2 |
| IgG2a [µg/ml] | 2.0 ± 0.3 | 1.9 ± 0.3 | 2.1 ± 0.1 | 2.0 ± 0.2 | 1.9 ± 0.2 |
| IgG2b [µg/ml] | 17.6 ± 5.6 | 18.9 ± 5.2 | 22.6 ± 3.3 | 28.3 ± 2.5 | 20.6 ± 3.8 |

LN = BULK OF MESENTERIAL LYMPH NODES, VALUES ARE MEANS ± SEM

FIG. 41

| | | 2K | 1K | |
|---|---|---|---|---|
| | WILDTYPE NIL | db/db NIL | db/db NIL | db/db PoC-PEG | db/db mNOX-E36-3'PEG |

CELLULAR RESPONSE [CELLS/GLOMERULUS OR HPF]

| | | WILDTYPE NIL | db/db NIL | db/db NIL | db/db PoC-PEG | db/db mNOX-E36-3'PEG |
|---|---|---|---|---|---|---|
| GLOMERULAR | Mac-2+ CELLS | 0.3 ± 0.1 | 1.8 ± 0.2 | 5.0 ± 0.7* | 5.9 ± 0.4 | 3.5 ± 0.3# |
| | Ki-67+ CELLS | 0.7 ± 0.1 | 0.9 ± 0.2 | 2.4 ± 0.2* | 3.1 ± 0.3 | 1.1 ± 0.2# |
| INTERSTITIAL | Mac-2+ CELLS | 3.2 ± 0.3 | 8.6 ± 1.0 | 19.2 ± 2.8* | 23.8 ± 3.3 | 12.3 ± 1.2# |

VALUES ARE MEANS ± SEM; *, , $p < 0.05$ 1K db/db VS 2K db/db; #, $p < 0.05$ mNOX-E36-3'PEG VS. PoC-PEG

FIG. 45

MCP-1 BINDING NUCLEIC ACIDS

The present invention is related to nucleic acids binding to MCP-1, and the use thereof for the manufacture of a medicament and a diagnostic agent, respectively.

Human MCP-1 (monocyte chemoattractant protein-1; alternative names, MCAF [monocyte chemoattracting and activating factor]; CCL2; SMC-CF [smooth muscle cell-colony simulating factor]; HC-11; LDCF; GDCF; TSG-8; SCYA2; A2; SwissProt accession code, P13500) was characterized by three groups independently (Matsushima 1988; Rollins 1989; Yoshimura 1989). It consists of 76 amino acids and features a heparin binding site like all chemokines. The two intramolecular disulfide bonds confer a stable, rigid structure to the molecule. Furthermore, MCP-1 carries a pyroglutamate at its amino terminus. At Thr 71, a potential O-linked glycosylation site is located. Additional MCP family members exist both in humans (MCP-2, -3, -4) and mice (MCP-2, -3, -5). The human proteins are approximately 70% homologous to human MCP-1.

The structure of MCP-1 has been solved by NMR (Handel 1996) and X-ray (Lubkowski 1997). The MCP-1 monomer has the typical chemokine fold in which the amino-terminal cysteines are followed by a long loop that leads into three antiparallel β-pleated sheets in a Greek key motif. The protein terminates in an a helix that overlies the three β sheets (PDB data accession code 1DOK).

Although the three-dimensional structure of MCP-1 forms from different mammalian species has generally been maintained, the amino acid sequence has not particularly well been conserved during evolution. Sequence alignment results demonstrate 55% overall sequence similarity between human and murine MCP-1 (also called JE) within the first 76 amino acids. Apart from the amino acid sequence, murine MCP-1 differs from human MCP-1 in molecular size (125 amino acids) and the extent of glycosylation. Murine MCP-1 contains a 49-amino acid carboxyterminal domain that is not present in human MCP-1 and is not required for in vitro bioactivity. Human MCP-1 shares the following percentage of identical amino acids with MCP-1 from:

| | |
|---|---|
| *Macaca mulatta* (Rhesus monkey) MCP-1 | 97% |
| *Sus scrofa* (Pig) MCP-1 | 79% |
| *Equus caballus* (Horse) | 78% |
| *Canis familiaris* (Dog) MCP-1 | 76% |
| *Oryctolagus cuniculus* (Rabbit) MCP-1 | 75% |
| *Bos Taurus* (Bovine) | 72% |
| *Homo sapiens* MCP-3 | 71% |
| *Homo sapiens* Eotaxin | 64% |
| *Homo sapiens* MCP-2 | 62% |
| *Mus musculus* (Mouse) MCP-1 | 55% |
| *Rattus norvegicus* (Rat) MCP-1 | 55% |

Given this high degree of divergence it may be necessary to generate antagonists of rodent MCP-1 for successful performance of pharmacological studies in rodent models.

MCP-1 is a potent attractor of monocytes/macrophages, basophils, activated T cells, and NK cells. A wide variety of cell types, such as endothelial cells, epithelial cells, fibroblasts, keratinocytes, synovial cells, mesangial cells, osteoblasts, smooth muscle cells, as well as a multitude of tumor cells express MCP-1 (Baggiolini 1994). Its expression is stimulated by several types of proinflammatory agents such as IL-1β, TNF-α, IFN-γ, LPS (lipopolysaccharide), and GM-CSF.

Rather unusual in the promiscuous chemokine network, MCP-1 is highly specific in its receptor usage, binding only to the chemokine receptor CCR2 with high affinity. Like all chemokine receptors, CCR2 is a GPCR (Dawson 2003). CCR2 seems to be expressed in two slightly different forms due to alternative splicing of the mRNA encoding the carboxyterminal region, CCR2a and CCR2b (Charo 1994). These receptors are expressed in monocytes, myeloid precursor cells and activated T cells (Myers 1995; Qin 1996). The dissociation constant of MCP-1 to the receptor transfected into HEK-293 cells is 260 pM which is in agreement with values measured on monoytes (Myers 1995; Van Riper 1993). Activation of CCR2b on transfected HEK-293 cells with MCP-1 inhibits adenylyl cyclase at a concentration of 90 pM, and mobilizes intracellular calcium at slightly higher concentrations, seemingly independent of phosphatidyl inositol hydrolysis. The effects on adenylyl cyclase and intracellular calcium release are strongly inhibited by pertussis toxin, implying the involvement of $G_i$ type heterotrimeric G-proteins in signal transduction (Myers 1995).

MCP-1 is involved in monocyte recruitment into inflamed tissues. There, resident macrophages release chemokines such as MCP-1 and others, and cytokines like TNF, IL-1β and others, which activate endothelial cells to express a battery of adhesion molecules. The resulting "sticky" endothelium causes monocytes in the blood vessel to roll along its surface. Here, the monocytes encounter MCP-1 presented on the endothelial surface, which binds to CCR2 on monocytes and activates them. This finally leads to firm arrest, spreading of monocytes along the endothelium, and transmigration into the surrounding tissue, where the monocytes differentiate into macrophages and migrate towards the site of maximal MCP-1 concentration.

MCP-1 is a member of the chemokine family which is a family of small (ca. 8-14 kDa) heparin-binding, mostly basic and structurally related molecules. They are formed predominantly in inflamed tissues and regulate the recruitment, activation, and proliferation of white blood cells (leukocytes) (Baggiolini 1994; Springer 1995; Schall 1994). Chemokines selectively induce chemotaxis of neutrophils, eosinophils, basophils, monocytes, macrophages, mast cells, T and B cells. In addition to their chemotactic effect, they can selectively exert other effects in responsive cells like changes in cell shape, transient increase in the concentration of free intracellular calcium ions, degranulation, upregulation of integrins, formation of bioactive lipids such as leukotrienes, prostaglandins, thromboxans, or respiratory burst (release of reactive oxygen species for destruction of pathogenic organisms or tumor cells). Thus, by provoking the release of further proinflammatory mediators, chemotaxis and extravasation of leukocytes towards sites of infection or inflammation, chemokines trigger escalation of the inflammatory response.

Based on the arrangement of the first two of four conserved cystein residues, the chemokines are divided into four classes: CC or β-chemokines in which the cysteins are in tandem, CXC or α-chemokines, where they are separated by one additional amino acid residue, XC or γ chemokines with lymphotactin as only representant to date, that possess only one disulfide bridge, and CX3C-chemokines which feature three amino acid residues between the cysteins, with membrane-bound fractalkin as only class member known to date (Bazan 1997).

The CXC chemokines act primarily on neutrophils, in particular those CXC chemokines that carry the amino acid sequence ELR on their amino terminus. Examples of CXC chemokines that are active on neutrophils are IL-8, GROα, -β, and -γ, NAP-2, ENA-78 and GCP-2. The CC chemokines act on a larger variety of leukocytes, such as monocytes, macrophages, eosinophils, basophils, as well as T and B lymphocytes (Oppenheim 1991; Baggiolini 1994; Miller 1992; Jose 1994; Ponath 1996a). Examples of these are I-309; MCP-1, -2, -3, -4, MIP-1α and -β, RANTES, and eotaxin.

Chemokines act through receptors that belong to a superfamily of seven transmembrane-spanning G protein-coupled receptors (GPCRs; Murphy 2000). Generally speaking, chemokine and chemokine receptor interactions tend to be promiscuous in that one chemokine can bind many chemokine receptors and conversely a single chemokine receptor can interact with several chemokines. Some known receptors for the CC chemokines include CCR1, which binds MIP-1α and RANTES (Neote 1993; Gao 1993); CCR2, which binds chemokines including MCP-1, -2, -3, and -4 (Charo 1994; Myers 1995; Gong 1997; Garcia-Zepeda 1996); CCR3, which binds chemokines including eotaxin, RANTES, and MCP-3 (Ponath 1996b); CCR4, which has been found to signal in response to MCP-1, MIP-1α, and RANTES (Power 1995); and CCR5, which has been shown to signal in response to MIP-1α and -β, and RANTES (Boring 1996; Raport 1996; Samson 1996).

As mentioned above, all four members of the MCP family (1-4) bind to CCR2, whereas MCP-2, MCP-3, and MCP-4 can also interact with CCR1 and CCR3 (Gong 1997; Heath 1997; Uguccioni 1997) and, in the case of MCP-2, CCR5 (Ruffing 1998). Another CC chemokine showing high homology with the MCP family is eotaxin, which was originally isolated from the bronchoalveolar lavage fluid taken from allergen-challenged, sensitized guinea pigs (Jose 1994). It has been shown that eotaxin is also able to activate CCR2 (Martinelli 2001).

The problem underlying the present invention is to provide a means which specifically interacts with MCP-1. More specifically, the problem underlying the present invention is to provide for a nucleic acid based means which specifically interacts with MCP-1.

A further problem underlying the present invention is to provide a means for the manufacture of a medicament for the treatment of a human or non-human diseases, whereby the disease is characterized by MCP-1 being either directly or indirectly involved in the pathogenetic mechanism of such disease.

A still further problem underlying the present invention is to provide a means for the manufacture of a diagnostic agent for the treatment of a disease, whereby the disease is characterized by MCP-1 being either directly or indirectly involved in the pathogenetic mechanism of such disease.

These and other problems underlying the present invention are solved by the subject matter of the attached independent claims. Preferred embodiments may be taken from the dependent claims.

The problem underlying the present invention is also solved in a first aspect by a nucleic acid, preferably binding to MCP-1, selected from the group comprising type 1A nucleic acids, type 1B nucleic acids, type 2 nucleic acids, type 3 nucleic acids, type 4 nucleic acids and nucleic acids having a nucleic acid sequence according to any of SEQ. ID. No. 87 to 115.

In a first subaspect of the first aspect the type 1A nucleic acid comprises in 5'->3' direction a first stretch Box B1A, a second stretch Box B2, a third stretch Box B3, a fourth stretch Box B4, a fifth stretch Box B5, a sixth stretch Box B6 and a seventh stretch Box B1B, whereby
the first stretch Box B1A and the seventh stretch Box B1B optionally hybridize with each other, whereby upon hybridization a double-stranded structure is formed,
the first stretch Box B1A comprises a nucleotide sequence of AGCRUG, the second stretch Box B2 comprises a nucleotide sequence of CCCGGW,
the third stretch Box B3 comprises a nucleotide sequence of GUR,
the fourth stretch Box B4 comprises a nucleotide sequence of RYA,
the fifth stretch Box B5 comprises a nucleotide sequence of GGGGGRCGCGAYC (SEQ ID NO:292)
the sixth stretch Box B6 comprises a nucleotide sequence of UGCAAUAAUG (SEQ ID NO:293) or URYAWUUG, and
the seventh stretch Box B1B comprises a nucleotide sequence of CRYGCU.

In a preferred embodiment of the first subaspect
the first stretch Box B1A comprises a nucleotide sequence of AGCGUG.

In an embodiment of the first subaspect
the second stretch Box B2 comprises a nucleotide sequence of CCCGGU.

In an embodiment of the first subaspect
the third stretch Box B3 comprises a nucleotide sequence of GUG.

In an embodiment of the first subaspect
the fourth stretch Box B4 comprises a nucleotide sequence of GUA.

In an embodiment of the first subaspect
the fifth stretch Box B5 comprises a nucleotide sequence of GGGGGGCGCGACC (SEQ ID NO:294).

In an embodiment of the first subaspect
the sixth stretch Box B6 comprises a nucleotide sequence of UACAUUUG.

In an embodiment of the first subaspect
the seventh stretch Box B1B comprises a nucleotide sequence of CACGCU.

In an embodiment of the first subaspect the nucleic acid comprises a nucleic acid sequence according to SEQ. ID. No. 21.

In a second subaspect of the first aspect the type 1B nucleic acid comprises in 5'->3' direction a first stretch Box B1A, a second stretch Box B2, a third stretch Box B3, a fourth stretch Box B4, a fifth stretch Box B5, a sixth stretch Box B6 and a seventh stretch Box B1B, whereby
the first stretch Box B1A and the seventh stretch Box B1B optionally hybridize with each other, whereby upon hybridization a double-stranded structure is formed,
the first stretch Box B1A comprises a nucleotide sequence of AGYRUG,
the second stretch Box B2 comprises a nucleotide sequence of CCAGCU or CCAGY,
the third stretch Box B3 comprises a nucleotide sequence of GUG,
the fourth stretch Box B4 comprises a nucleotide sequence of AUG,
the fifth stretch Box B5 comprises a nucleotide sequence of GGGGGGCGCGACC SEQ ID NO:294)
the sixth stretch Box B6 comprises a nucleotide sequence of CAUUUUA or CAUUUA, and
the seventh stretch Box B1B comprises a nucleotide sequence of CAYRCU.

In an embodiment of the second subaspect
the first stretch Box B1A comprises a nucleotide sequence of AGCGUG.

In an embodiment of the second subaspect
the second stretch Box B2 comprises a nucleotide sequence of CCAGU.

In an embodiment of the second subaspect
the sixth stretch Box B6 comprises a nucleotide sequence of CAUUUUA.

In an embodiment of the second subaspect
the seventh stretch Box B1B comprises a nucleotide sequence of CACGCU.
In an embodiment of the second subaspect the nucleic acid comprises a nucleic acid sequence according to SEQ. ID. No. 28 and SEQ. ID. No. 27.

In a third subaspect of the first aspect the type 2 nucleic acid comprises in 5'->3' direction a first stretch Box B1A, a second stretch Box B2, and a third stretch Box B1B, whereby
the first stretch Box B1A and the third stretch Box B1B optionally hybridize with each other, whereby upon hybridization a double-stranded structure is formed,
the first stretch Box B1A comprises a nucleotide sequence selected from the group comprising ACGCA, CGCA and GCA,
the second stretch Box B2 comprises a nucleotide sequence of CSUCCCUCACCGGUG-CAAGUGAAGCCGYGGCUC (SEQ ID NO.: 287), and
the third stretch Box B1B comprises a nucleotide sequence selected from the group comprising UGCGU, UGCG and UGC.

In an embodiment of the third subaspect
the second stretch Box B2 comprises a nucleotide sequence of CGUCCCUCACCGGUG-CAAGUGAAGCCGUGGCUC (SEQ ID NO: 288).

In an embodiment of the third subaspect
a) the first stretch Box B1A comprises a nucleotide sequence of ACGCA,
and
the third stretch Box B1B comprises a nucleotide sequence of UGCGU; or
b) the first stretch Box B1A comprises a nucleotide sequence of CGCA,
and
the third stretch Box B1B comprises a nucleotide sequence of UGCG; or
c) the first stretch Box B1A comprises a nucleotide sequence of GCA,
and
the third stretch Box B1B comprises a nucleotide sequence of UGC or UGCG.

In an embodiment of the third subaspect
the first stretch Box B1A comprises a nucleotide sequence of GCA.

In a preferred embodiment of the third subaspect
the third stretch Box B1B comprises a nucleotide sequence of UGCG.

In an embodiment of the third subaspect the nucleic acid comprises a nucleic acid sequence according to SEQ. ID. No. 37, SEQ. ID. No. 116, SEQ. ID. No. 117 and SEQ. ID. No. 278.

In a fourth subaspect of the first aspect the type 3 nucleic acid comprises in 5'->3' direction a first stretch Box B1A, a second stretch Box B2A, a third stretch Box B3, a fourth stretch Box B2B, a fifth stretch Box B4, a sixth stretch Box B5A, a seventh stretch Box B6, an eighth stretch Box B5B and a ninth stretch Box B1B, whereby
the first stretch Box B1A and the ninth stretch Box B1B optionally hybridize with each other, whereby upon hybridization a double-stranded structure is formed,
the second stretch Box B2A and the fourth Box B2B optionally hybridize with each other, whereby upon hybridization a double-stranded structure is formed,
the sixth stretch Box B5A and the eighth Box B5B optionally hybridize with each other, whereby upon hybridization a double-stranded structure is formed,
the first stretch Box B1A comprises a nucleotide sequence which is selected from the group comprising GUR-CUGC, GKSYGC, KBBSC and BNGC,
the second stretch Box B2A comprises a nucleotide sequence of GKMGU,
the third stretch Box B3 comprises a nucleotide sequence of KRRAR,
the fourth stretch Box B2B comprises a nucleotide sequence of ACKMC,
the fifth stretch Box B4 comprises a nucleotide sequence selected from the group comprising CURYGA, CUWAUGA, CWRMGACW and UGCCAGUG,
the sixth stretch Box B5A comprises a nucleotide sequence selected from the group comprising GGY and CWGC,
the seventh stretch Box B6 comprises a nucleotide sequence selected from the group comprising YAGA, CKAAU and CCUUUAU,
the eighth stretch Box B5B comprises a nucleotide sequence selected from the group comprising GCYR and GCWG, and
the ninth stretch Box B1B comprises a nucleotide sequence selected from the group c comprising GCAGCAC, GCRSMC, GSVVM and GCNV.

In an embodiment of the fourth subaspect
the third stretch Box B3 comprises a nucleotide sequence of GAGAA or UAAAA In an embodiment of the fourth subaspect
the fifth stretch Box B4 comprises a nucleotide sequence of CAGCGACU or CAACGACU.

In an embodiment of the fourth subaspect
the fifth stretch Box B4 comprises a nucleotide sequence of CAGCGACU and Box B3 comprises a nucleotide sequence of UAAAA.

In an embodiment of the fourth subaspect
the fifth stretch Box B4 comprises a nucleotide sequence of CAACGACU and Box B3 comprises a nucleotide sequence of GAGAA.

In an embodiment of the fourth subaspect
the seventh stretch Box B6 comprises a nucleotide sequence of UAGA.

In an embodiment of the fourth subaspect
a) the first stretch Box B1A comprises a nucleotide sequence of GURCUGC,
and
the ninth stretch Box B1B comprises a nucleotide sequence of GCAGCAC; or
b) the first stretch Box B1A comprises a nucleotide sequence of GKSYGC,
and
the ninth stretch Box B1B comprises a nucleotide sequence of GCRSMC; or
c) the first stretch Box B1A comprises a nucleotide sequence of KBBSC,
and
the ninth stretch Box B1B comprises a nucleotide sequence of GSVVM; or
d) the first stretch Box B1A comprises a nucleotide sequence of BNGC,
and
the ninth stretch Box B1B comprises a nucleotide sequence of GCNV.

In a preferred embodiment of the fourth subaspect
a) the first stretch Box B1A comprises a nucleotide sequence of GUGCUGC,
and
the ninth stretch Box B1B comprises a nucleotide sequence of GCAGCAC; or b) the first stretch Box B1A comprises a nucleotide sequence of GUGCGC,
and
the ninth stretch Box B1B comprises a nucleotide sequence of GCGCAC; or
c) the first stretch Box B1A comprises a nucleotide sequence of KKSSC,
and
the ninth stretch Box B1B comprises a nucleotide sequence of GSSMM; or
d) the first stretch Box B1A comprises a nucleotide sequence of SNGC,
and
the ninth stretch Box B1B comprises a nucleotide sequence of GCNS.

In a further preferred embodiment of the fourth subaspect the first stretch Box B1A comprises a nucleotide sequence of GGGC,
and
the ninth stretch Box B1B comprises a nucleotide sequence of GCCC.

In an embodiment of the fourth subaspect the second stretch Box B2A comprises a nucleotide sequence of GKMGU and the fourth stretch Box B2B comprises a nucleotide sequence of ACKMC.

In a preferred embodiment of the fourth subaspect the second stretch Box B2A comprises a nucleotide sequence of GUAGU and the fourth stretch Box B2B comprises a nucleotide sequence of ACUAC.

In an embodiment of the fourth subaspect
a) the sixth stretch Box B5A comprises a nucleotide sequence of GGY,
and
the eighth stretch Box B5B comprises a nucleotide sequence of GCYR; or
b) the sixth stretch Box B5A comprises a nucleotide sequence of CWGC,
and
the eighth stretch Box B5B comprises a nucleotide sequence of GCWG.

In a preferred embodiment of the fourth subaspect the sixth stretch Box B5A comprises a nucleotide sequence of GGC,
and
the eighth stretch Box B5B comprises a nucleotide sequence of GCCG.

In a more preferred embodiment of the fourth subaspect the sixth stretch Box B5A hybridizes with the nucleotides GCY of the eighth stretch Box B5B.

In an embodiment of the fourth subaspect the nucleic acid comprises a nucleic acid sequence according to SEQ. ID. No. 56.

In an embodiment of the fourth subaspect the nucleic acid comprises a nucleic acid sequence selected from the group comprising the nucleic acid sequences according to SEQ. ID. No. 57 to 61, SEQ. ID. No. 67 to 71 and SEQ. ID. No. 73.

In a fifth subaspect of the first aspect the type 4 nucleic acid comprises in 5'->3' direction a first stretch Box B1A, a second stretch Box B2, a third stretch Box B1B whereby
the first stretch Box B1A and the third stretch Box B1B optionally hybridize with each other, whereby upon hybridization a double-stranded structure is formed,
the first stretch Box B1A comprises a nucleotide sequence selected from the group comprising AGCGUGDU, GCGCGAG, CSKSUU, GUGUU, and UGUU;

the second stretch Box B2 comprises a nucleotide sequence selected from the group comprising AGNDRDGBKGGURGYARGUAAAG (SEQ ID NO: 289),
AGGUGGGUGGUAGUAAGUAAAG (SEQ ID NO:290) and CAGGUGGGUGGUAGAAUGUAAAGA (SEQ ID NO:291), and
the third stretch Box B1B comprises a nucleotide sequence selected from the group comprising GNCASGCU, CUCGCGUC, GRSMSG, GRCAC, and GGCA.

In an embodiment of the fifth subaspect
a) the first stretch Box B1A comprises a nucleotide sequence of GUGUU,
and
the third stretch Box B1B comprises a nucleotide sequence of GRCAC;
b) the first stretch Box B1A comprises a nucleotide sequence of GCGCGAG,
and
the third stretch Box B1B comprises a nucleotide sequence of CUCGCGUC; or
c) the first stretch Box B1A comprises a nucleotide sequence of CSKSUU,
and
the third stretch Box B1B comprises a nucleotide sequence of GRSMSG, or
d) the first stretch Box B1A comprises a nucleotide sequence of UGUU,
and
the third stretch Box B1B comprises a nucleotide sequence of GGCA, or
e) the first stretch Box B1A comprises a nucleotide sequence of AGCGUGDU,
and
the third stretch Box B1B comprises a nucleotide sequence of GNCASGCU.

In a preferred embodiment of the fifth subaspect the first stretch Box B1A comprises a nucleotide sequence of CSKSUU and the third stretch Box B1B comprises a nucleotide sequence of GRSMSG.

In a more preferred embodiment of the fifth subaspect the first stretch Box B1A comprises a nucleotide sequence of CCGCUU and the third stretch Box B1B comprises a nucleotide sequence of GGGCGG.

In an embodiment of the fifth subaspect
the second stretch Box B2 comprises a nucleotide sequence of AGGUGGGGUGGUAGUAAGUAAAG (SEQ ID NO:290).

In an embodiment of the fifth subaspect the nucleic acid comprises a nucleic acid sequence according to SEQ. ID. No. 80.

In an embodiment of the first to the fifth subaspect the nucleic acid is capable of binding MCP-1, preferably human MCP-1.

In an embodiment of the first to the fifth subaspect the nucleic acid is capable of binding a chemokine, whereby the chemokine is selected from the group comprising eotaxin, MCP-1, MCP-2 and MCP-3.

In an embodiment of the first to the fifth subaspect the nucleic acid is capable of binding a chemokine, whereby the chemokine is selected from the group comprising human eotaxin, human MCP-1, human MCP-2 and human MCP-3.

In an embodiment of the first to the fifth subaspect the nucleic acid is capable of binding MCP-1, whereby MCP-1 is preferably selected from the group comprising monkey MCP-1, horse MCP-1, rabbit MCP-1, bovine MCP-1, canine MCP-1, porcine MCP-1 and human MCP-1.

In an embodiment of the first to the fifth subaspect the nucleic acid is capable of binding human MCP-1.

In a preferred embodiment of the first to the fifth subaspect the MCP-1 has an amino acid sequence according to SEQ ID No. 1.

The problem underlying the present invention is solved in a second aspect by a nucleic acid, preferably binding to murine MCP-1, whereby the nucleic acid comprises a nucleic acid sequence according to SEQ. ID. No. 122, SEQ. ID. No. 253 and SEQ. ID. No. 254.

The problem underlying the present invention is solved in a third aspect by a nucleic acid, preferably binding to murine MCP-1, whereby the nucleic acid comprises a nucleic acid sequence according to SEQ. ID. No. 127.

In an embodiment of the second and third aspect the murine MCP-1 comprises an amino acid sequence according to SEQ ID No. 2.

In an embodiment of the first to the third aspect the nucleic acid comprises a modification, whereby the modification is preferably a high molecular weight moiety and/or whereby the modification preferably allows to modify the characteristics of the nucleic acid according to any of the first, second and third aspect in terms of residence time in the animal or human body, preferably the human body.

In a preferred embodiment of the first to the third aspect the modification is selected from the group comprising a HES moiety and a PEG moiety.

In a more preferred embodiment of the first to the third aspect the modification is a PEG moiety consisting of a straight or branched PEG, whereby the molecular weight of the PEG moiety is preferably from about 20 to 120 kD, more preferably from about 30 to 80 kD and most preferably about 40 kD.

In an alternative more preferred embodiment of the first to the third aspect the modification is a HES moiety, whereby preferably the molecular weight of the HES moiety is from about 10 to 130 kD, more preferably from about 30 to 130 kD and most preferably about 100 kD.

In an embodiment of the first to the third aspect the modification is coupled to the nucleic acid via a linker.

In an embodiment of the first to the third aspect the modification is coupled to the nucleic acid at its 5'-terminal nucleotide and/or its 3'-terminal nucleotide and/or to a nucleotide of the nucleic acid between the 5'-terminal nucleotide and the 3'-terminal nucleotide.

In an embodiment of the first to the third aspect the nucleotides of or the nucleotides forming the nucleic acid are L-nucleotides.

In an embodiment of the first to the third aspect the nucleic acid is an L-nucleic acid.

In an embodiment of the first to the third aspect the moiety of the nucleic acid capable of binding MCP-1 consists of L-nucleotides.

The problem underlying the present invention is solved in a fourth aspect by a pharmaceutical composition comprising a nucleic acid according to the first, second and third aspect and optionally a further constituent, whereby the further constituent is selected from the group comprising pharmaceutically acceptable excipients, pharmaceutically acceptable carriers and pharmaceutically active agents.

In an embodiment of the fourth aspect the pharmaceutical composition comprises a nucleic acid according to any of the first to third aspect and a pharmaceutically acceptable carrier.

The problem underlying the present invention is solved in a fifth aspect by the use of a nucleic acid according to the first, second and third aspect for the manufacture of a medicament.

In an embodiment of the fifth aspect the medicament is for use in human medicine or for use in veterinary medicine.

The problem underlying the present invention is solved in a sixth aspect by the use of a nucleic acid according to the first, second and third aspect for the manufacture of a diagnostic means.

In an embodiment of the fifth aspect and in an embodiment of the sixth aspect the medicament and diagnostic means, respectively, is for the treatment and/or prevention and diagnosis, respectively, of a disease or disorder selected from the group comprising inflammatory diseases, autoimmune diseases, autoimmune encephalomyelitis, stroke, acute and chronic multiple sclerosis, chronic inflammation, rheumatoid arthritis, renal diseases, restenosis, restenosis after angioplasty, acute and chronic allergic reactions, primary and secondary immunologic or allergic reactions, asthma, conjunctivitis, bronchitis, cancer, atherosclerosis, artheriosclerotic cardiovasular heart failure or stroke, psoriasis, psoriatic arthritis, inflammation of the nervous system, atopic dermatitis, colitis, endometriosis, uveitis, retinal disorders including macular degeneration, retinal detachment, diabetic retinopathy, retinopathy of prematurity, retinitis pigmentosa, proliferative vitreoretinopathy, and central serous chorioretinopathy; idiopathic pulmonary fibrosis, sarcoidosis, polymyositis, dermatomyositis, avoidance of immunosuppression, reducing the risk of infection, sepsis, renal inflammation, glomerulonephritis, rapid progressive glomerulonephritis, proliferative glomerulonephritis, diabetic nephropathy, obstructive nephropathy, acute tubular necrosis, and diffuse glomerulosclerosis, systemic lupus erythematosus, chronic bronchitis, Behçet's disease, amyotrophic lateral sclerosis (ALS), premature atherosclerosis after Kawasaki's disease, myocardial infarction, obesity, chronic liver disease, peyronie's disease, acute spinal chord injury, lung or kidney transplantation, myocarditis, Alzheimer's disease and neuropathy, breast carcinoma, gastric carcinoma, bladder cancer, ovarian cancer, hamartoma, colorectal carcinoma, colonic adenoma, pancreatitis, chronic obstructive pulmonary disease (COPD) and inflammatory bowel diseases such as Crohn's disease or ulcerative colitis.

Without wishing to be bound be any theory, the suitability of the nucleic acids of the present invention for diagnostic purposes is mostly based on an increased or decreased chemokine level, whereby such chemokine is selected from the group comprising eotaxin, MCP-1, MCP-2 and MCP-3, more specifically MCP-1. It will be acknowledged by the person skilled in the art that most of the aforementioned diseases show such increased or decreased chemokine level.

The problem underlying the present invention is solved in a seventh aspect by a complex comprising a chemokine and a nucleic acid according to the first, second and third aspect, whereby the chemokine is selected from the group comprising eotaxin, MCP-1, MCP-2 and MCP-3, whereby preferably the complex is a crystalline complex.

In an embodiment of the seventh aspect the chemokine is selected from the group comprising human eotaxin, human MCP-1, human MCP-2 and human MCP-3.

In an embodiment of the seventh aspect the chemokine is MCP-1, whereby MCP-1 is preferably selected from the group comprising human MCP-1, monkey MCP-1, horse MCP-1, rabbit MCP-1, bovine MCP-1, canine MCP-1 and porcine MCP-1, more preferably MCP-1 is human MCP-1.

The problem underlying the present invention is solved in an eighth aspect by the use of a nucleic acid according to the first, second and third aspect for the detection of a chemokine, whereby the chemokine is selected from the group comprising eotaxin, MCP-1, MCP-2 and MCP-3.

In an embodiment of the eighth aspect the chemokine is selected from the group comprising human eotaxin, human MCP-1, human MCP-2 and human MCP-3.

In an embodiment of the eighth aspect the chemokine is MCP-1, whereby MCP-1 is preferably selected from the group comprising human MCP-1, monkey MCP-1, horse MCP-1, rabbit MCP-1, bovine MCP-1, canine MCP-1 and porcine MCP-1, more preferably MCP-1 is human MCP-1.

The problem underlying the present invention is solved in a ninth aspect by a method for the screening of a chemokine antagonist or a chemokine agonist comprising the following steps:
  providing a candidate chemokine antagonist and/or a candidate chemokine agonist,
  providing a nucleic acid according to the first, second or third aspect,
  providing a test system which provides a signal in the presence of a chemokine antagonist and/or a chemokine agonist, and
  determining whether the candidate chemokine antagonist is a chemokine antagonist and/or whether the candidate chemokine agonist is a chemokine agonist,
  whereby the chemokine is selected from the group comprising eotaxin, MCP-1, MCP-2 and MCP-3.

In an embodiment of the ninth aspect the chemokine is selected from the group comprising human eotaxin, human MCP-1, human MCP-2 and human MCP-3.

In an embodiment of the ninth aspect the chemokine is MCP-1, whereby MCP-1 is preferably selected from the group comprising human MCP-1, monkey MCP-1, horse MCP-1, rabbit MCP-1, bovine MCP-1, canine MCP-1 and porcine MCP-1, more preferably MCP-1 is human MCP-1.

The problem underlying the present invention is solved in a tenth aspect by a method for the screening of a chemokine agonist and/or a chemokine antagonist comprising the following steps:
  providing a chemokine immobilised to a phase, preferably a solid phase,
  providing a nucleic acid according to the first, second or third aspect, preferably a nucleic acid according to the first aspect which is labelled,
  adding a candidate chemokine agonist and/or a candidate chemokine antagonist, and
  determining whether the candidate chemokine agonist is a chemokine agonist and/or whether the candidate chemokine antagonist is a chemokine antagonist,
  whereby the chemokine is selected from the group comprising eotaxin, MCP-1, MCP-2 and MCP-3.

In an embodiment of the tenth aspect the determining is carried out such that it is assessed whether the nucleic acid is replaced by the candidate chemokine_agonist or by a candidate chemokine antagonist.

In an embodiment of the tenth aspect the chemokine is selected from the group comprising human eotaxin, human MCP-1, human MCP-2 and human MCP-3.

In an embodiment of the tenth aspect the chemokine is MCP-1, whereby MCP-1 is preferably selected from the group comprising human MCP-1, monkey MCP-1, horse MCP-1, rabbit MCP-1, bovine MCP-1, canine MCP-1 and porcine MCP-1, more preferably MCP-1 is human MCP-1.

The problem underlying the present invention is solved in an eleventh aspect by a kit for the detection of a chemokine, comprising a nucleic acid according to the first, second and third aspect, whereby the chemokine is selected from the group comprising eotaxin, MCP-1, MCP-2 and MCP-3.

In an embodiment of the eleventh aspect the chemokine is selected from the group comprising human eotaxin, human MCP-1, human MCP-2 and human MCP-3.

In an embodiment of the eleventh aspect the chemokine is MCP-1, whereby MCP-1 is preferably selected from the group comprising human MCP-1, monkey MCP-1, horse MCP-1, rabbit MCP-1, bovine MCP-1, canine MCP-1 and porcine MCP-1, more preferably MCP-1 is human MCP-1.

The problem underlying the present invention is solved in a twelfth aspect by a chemokine antagonist obtainable by the method according to the tenth aspect or the ninth aspect, whereby the chemokine is selected from the group comprising eotaxin, MCP-1, MCP-2 and MCP-3.

In an embodiment of the twelfth aspect the chemokine is selected from the group comprising human eotaxin, human MCP-1, human MCP-2 and human MCP-3.

In an embodiment of the twelfth aspect the chemokine is MCP-1, whereby MCP-1 is preferably selected from the group comprising human MCP-1, monkey MCP-1, horse MCP-1, rabbit MCP-1, bovine MCP-1, canine MCP-1 and porcine MCP-1, more preferably MCP-1 is human MCP-1.

The problem underlying the present invention is solved in a thirteenth aspect by a chemokine agonist obtainable by the method according to the tenth aspect or the ninth aspect, whereby the chemokine is selected from the group comprising eotaxin, MCP-1, MCP-2 and MCP-3.

In an embodiment of the thirteenth aspect the chemokine is selected from the group comprising human eotaxin, human MCP-1, human MCP-2 and human MCP-3.

In an embodiment of the thirteenth aspect the chemokine is MCP-1, whereby MCP-1 is preferably selected from the group comprising human MCP-1, monkey MCP-1, horse MCP-1, rabbit MCP-1, bovine MCP-1, canine MCP-1 and porcine MCP-1, more preferably MCP-1 is human MCP-1.

It will be acknowledged by the person skilled in the art that a chemokine agonist and/or a chemokine antagonist is preferably an agonist and antagonist, respectively, addressing the respective chemokine as specified herein. Accordingly, the chemokine agonist and chemokine antagonist is, for example, an MCP-1 agonist and MCP-1 antagonist, respectively.

The problem underlying the present invention is solved in a fourteenth aspect by a method for the detection of the nucleic acid according to any of the first, second and third aspect in a sample, whereby the method comprises the steps of:
  a) providing a sample containing the nucleic acid according to the present invention;
  b) providing a capture probe, whereby the capture probe is at least partially complementary to a first part of the nucleic acid according to any of the first, second and third aspect, and a detection probe, whereby the detection probe is at least partially complementary to a second part of the nucleic acid according to any of the first, second and third aspect, or, alternatively, the capture probe is at least partially complementary to a second part of the nucleic acid according to any of the first, second and third aspect and the detection probe is at least partially complementary to the first part of the nucleic acid according to any of the first, second and third aspect;
  c) allowing the capture probe and the detection probe to react either simultaneously or in any order sequentially with the nucleic acid according to any of the first, second and third aspect or part thereof;
  d) optionally detecting whether or not the capture probe is hybridized to the nucleic acid according to the nucleic acid according to any of the first, second and third aspect provided in step a); and e) detecting the complex formed in step c) consisting of the nucleic acid according to any of the first, second and third aspect, and the capture probe and the detection probe.

In an embodiment of the fourteenth aspect the detection probe comprises a detection means, and/or whereby the capture probe can be immobilized to a support, preferably a solid support.

In an embodiment of the fourteenth aspect any detection probe which is not part of the complex is removed from the reaction so that in step e) only a detection probe which is part of the complex, is detected.

In an embodiment of the fourteenth aspect step e) comprises the step of comparing the signal generated by the detection means when the capture probe and the detection probe are hybridized in the presence of the nucleic acid according to any of the first, second or third aspect or part thereof, and in the absence of said nucleic acid or part thereof.

In an embodiment of the fourteenth aspect the nucleic acid to be detected is the nucleic acid having a nucleic acid sequence according to SEQ. ID. NOs. 37, 116, 117 or 278, and the capture probe or detection probe comprises a nucleic acid sequence according to SEQ. ID. NO. 255 or SEQ. ID. NO. 256.

In an embodiment of the fourteenth aspect the nucleic acid to be detected is the nucleic acid having a nucleic acid sequence according to SEQ. ID. NOs. 122, 253 or 254 and the capture probe or detection probe comprises a nucleic acid sequence according to SEQ. ID. NO. 281 and SEQ. ID. NO. 282.

The problem underlying the present invention is also solved by the subject matter of the independent claims attached hereto. Preferred embodiment may be taken from the attached dependent claims.

The features of the nucleic acid according to the present invention as described herein can be realised in any aspect of the present invention where the nucleic acid is used, either alone or in any combination.

Human as well as murine MCP-1 are basic proteins having the amino acid sequence according to SEQ. ID. Nos. 1 and 2, respectively.

The finding that short high affinity binding nucleic acids to MCP-1 could be identified, is insofar surprising as Eaton et al. (1997) observed that the generation of aptamers, i.e. D-nucleic acids binding to a target molecule, directed to a bask protein is in general very difficult because this kind of target produces a high but non-specific signal-to-noise ratio. This high signal-to-noise ratio results from the high non-specific affinity shown by nucleic acids for basic targets such as MCP-1.

As outlined in more detail in the claims and example 1, the present inventors could more surprisingly identify a number of different MCP-1 binding nucleic acid molecules, whereby most of the nucleic acids could be characterised in terms of stretches of nucleotide which are also referred to herein as Boxes. The various MCP-1 binding nucleic acid molecules can be categorised based on said Boxes and some structural features and elements, respectively. The various categories thus defined are also referred to herein as types and more specifically as type 1A, type 1B, type 2, type 3 and type 4.

The nucleic acids according to the present invention shall also comprise nucleic acids which are essentially homologous to the particular sequences disclosed herein. The term substantially homologous shall be understood such that the homology is at least 75%, preferably 85%, more preferably 90% and most preferably more than 95%, 96%, 97%, 98% or 99%.

The actual percentage of homologous nucleotides present in the nucleic acid according to the present invention will depend on the total number of nucleotides present in the nucleic acid. The percent modification can be based upon the total number of nucleotides present in the nucleic acid.

The homology can be determined as known to the person skilled in the art. More specifically, a sequence comparison algorithm then calculates the percent sequence identity for the test sequence(s) relative to the reference sequence, based on the designated program parameters. The test sequence is preferably the sequence or nucleic acid molecule which is said to be or to be tested whether it is homologous, and if so, to what extent, to another nucleic acid molecule, whereby such another nucleic acid molecule is also referred to as the reference sequence. In an embodiment, the reference sequence is a nucleic acid molecule as described herein, more preferably a nucleic acid molecule having a sequence according to any of SEQ. ID. NOs. 10 to 129, 132 to 256 and 278-282. Optimal alignment of sequences for comparison can be conducted, e.g., by the local homology algorithm of Smith & Waterman (Smith & Waterman, 1981) by the homology alignment algorithm of Needleman & Wunsch (Needleman & Wunsch, 1970) by the search for similarity method of Pearson & Lipman (Pearson & Lipman, 1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

One example of an algorithm that is suitable for determining percent sequence identity is the algorithm used in the basic local alignment search tool (hereinafter "BLAST"), see, e.g. Altschul et al (Altschul et al. 1990 and Altschul et al, 1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al (McGinnis et al, 2004).

The term inventive nucleic acid or nucleic acid according to the present invention shall also comprise those nucleic acids comprising the nucleic acids sequences disclosed herein or part thereof, preferably to the extent that the nucleic acids or said parts are involved in the binding to MCP-1. The term inventive nucleic acid as preferably used herein, shall also comprise in an embodiment a nucleic acid which is suitable to bind to any molecule selected from the group comprising MCP-2, MCP-3, MCP-4, and eotaxin. It will be acknowledged by the ones skilled in the art that the individual nucleic acids according to the present invention will bind to one or several of such molecules. Such nucleic acid is, in an embodiment, one of the nucleic acid molecules described herein, or a derivative and/or a metabolite thereof, whereby such derivative and/or metabolite are preferably a truncated nucleic acid compared to the nucleic acid molecules described herein. Truncation may be related to either or both of the ends of the nucleic acids as disclosed herein. Also, truncation may be related to the inner sequence of nucleotides of the nucleic acid, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long. The binding of a nucleic acid according to the present invention, preferably to a molecule selected from the group comprising MCP-1, MCP-2, MCP-3, MCP-4 and eotaxin, can be determined by the ones skilled in the art using routine experiments or by using or adopting a method as described herein, preferably as described herein in the example part. It is within an embodiment of the present invention, unless explicitly indicated to the contrary, that whenever it is referred herein to the binding of the nucleic acids according to the present invention to or with MCP-1, this applies also to the binding of the nucleic acids according to the present invention to or with any molecule selected from the group comprising MCP-2, MCP-3, MCP-4 and eotaxin.

The nucleic acids according to the present invention may be either D-nucleic acids or L-nucleic acids. Preferably, the inventive nucleic acids are L-nucleic acids. In addition it is possible that one or several parts of the nucleic acid are present as D-nucleic acids or at least one or several parts of the nucleic acids are L-nucleic acids. The term "part" of the nucleic acids shall mean as little as one nucleotide. Such nucleic acids are generally referred to herein as D- and L-nucleic acids, respectively. Therefore, in a particularly preferred embodiment, the nucleic acids according to the present invention consist of L-nucleotides and comprise at least one D-nucleotide. Such D-nucleotide is preferably attached to a part different from the stretches defining the nucleic acids according to the present invention, preferably those parts thereof, where an interaction with other parts of the nucleic acid is involved. Preferably, such D-nucleotide is attached at a terminus of any of the stretches and of any nucleic acid according to the present invention, respectively. In a further preferred embodiment, such D-nucleotides may act as a spacer or a linker, preferably attaching modifications such as PEG and HES to the nucleic acids according to the present invention.

It is also within an embodiment of the present invention that each and any of the nucleic acid molecules described herein in their entirety in terms of their nucleic acid sequence(s) are limited to the particular nucleotide sequence(s). In other words, the terms "comprising" or "comprise(s)" shall be interpreted in such embodiment in the meaning of containing or consisting of.

It is also within the present invention that the nucleic acids according to the present invention are part of a longer nucleic acid whereby this longer nucleic acid comprises several parts whereby at least one such part is a nucleic acid according to the present invention, or a part thereof. The other part(s) of these longer nucleic acids can be either one or several D-nucleic acid(s) or one or several L-nucleic acid(s). Any combination may be used in connection with the present invention. These other part(s) of the longer nucleic acid either alone or taken together, either in their entirety or in a particular combination, can exhibit a function which is different from binding, preferably from binding to MCP-1. One possible function is to allow interaction with other molecules, whereby such other molecules preferably are different from MCP-1, such as, e.g., for immobilization, cross-linking, detection or amplification. In a further embodiment of the present invention the nucleic acids according to the invention comprise, as individual or combined moieties, several of the nucleic acids of the present invention. Such nucleic acid comprising several of the nucleic acids of the present invention is also encompassed by the term longer nucleic acid.

L-nucleic acids as used herein are nucleic acids consisting of L-nucleotides, preferably consisting completely of L-nucleotides.

D-nucleic acids as used herein are nucleic acids consisting of D-nucleotides, preferably consisting completely of D-nucleotides.

The terms nucleic acid and nucleic acid molecule are used herein in an interchangeable manner if not explicitly indicated to the contrary.

Also, if not indicated to the contrary, any nucleotide sequence is set forth herein in 5'→3' direction.

Irrespective of whether the inventive nucleic acid consists of D-nucleotides, L-nucleotides or a combination of both with the combination being e.g. a random combination or a defined sequence of stretches consisting of at least one L-nucleotide and at least one D-nucleic acid, the nucleic acid may consist of deoxyribonucleotide(s), ribonucleotide(s) or combinations thereof.

Designing the inventive nucleic acids as L-nucleic acid is advantageous for several reasons. L-nucleic acids are enantiomers of naturally occurring nucleic acids. D-nucleic acids, however, are not very stable in aqueous solutions and particularly in biological systems or biological samples due to the widespread presence of nucleases. Naturally occurring nucleases, particularly nucleases from animal cells are not capable of degrading L-nucleic acids. Because of this the biological half-life of the L-nucleic acid is significantly increased in such a system, including the animal and human body. Due to the lacking degradability of L-nucleic acid no nuclease degradation products are generated and thus no side effects arising therefrom observed. This aspect delimits the L-nucleic acid of factually all other compounds which are used in the therapy of diseases and/or disorders involving the presence of MCP-1. L-nucleic acids which specifically bind to a target molecule through a mechanism different from Watson Crick base pairing, or aptamers which consists partially or completely of L-nucleotides, particularly with those parts of the aptamer being involved in the binding of the aptamer to the target molecule, are also called spiegelmers.

It is also within the present invention that the inventive nucleic acids, also referred to herein as nucleic acids according to the invention, regardless whether they are present as D-nucleic acids, L-nucleic acids or D,L-nucleic acids or whether they are DNA or RNA, may be present as single-stranded or double-stranded nucleic acids. Typically, the inventive nucleic acids are single-stranded nucleic acids which exhibit defined secondary structures due to the primary sequence and may thus also form tertiary structures. The inventive nucleic acids, however, may also be double-stranded in the meaning that two strands which are complementary or partially complementary to each other are hybridised to each other. This confers stability to the nucleic acid which, in particular, will be advantageous if the nucleic acid is present in the naturally occurring D-form rather than the L-form.

The inventive nucleic acids may be modified. Such modifications may be related to the single nucleotide of the nucleic acid and are well known in the art. Examples for such modification are described in, among others, Venkatesan (2003); Kusser (2000); Aurup (1994); Cummins (1995); Eaton (1995); Green (1995); Kawasaki (1993); Lesnik (1993); and Miller (1993). Such modification can be a H atom, a F atom or O—CH3 group or NH2-group at the 2' position of the individual nucleotide of which the nucleic acid consists. Also, the nucleic acid according to the present invention can comprises at least one LNA nucleotide. In an embodiment the nucleic acid according to the present invention consists of LNA nucleotides.

In an embodiment, the nucleic acids according to the present invention may be a multipartite nucleic acid. A multipartite nucleic acid as used herein, is a nucleic acid which consists of at least two nucleic acid strands. These at least two nucleic acid strands form a functional unit whereby the functional unit is a ligand to a target molecule. The at least two nucleic acid strands may be derived from any of the inventive nucleic acids by either cleaving the nucleic acid to generate two strands or by synthesising one nucleic acid corresponding to a first part of the inventive, i.e. overall nucleic acid and another nucleic acid corresponding to the second part of the overall nucleic acid. It is to be acknowledged that both the cleavage and the synthesis may be applied to generate a multipartite nucleic acid where there are more than two strands as exemplified above. In other words, the at least two nucleic acid strands are typically different from two strands being complementary and hybridising to each other although a certain extent of complementarity between the various nucleic acid parts may exist.

Finally it is also within the present invention that a fully closed, i.e. circular structure for the nucleic acids according to the present invention is realized, i.e. that the nucleic acids according to the present invention are closed, preferably through a covalent linkage, whereby more preferably such covalent linkage is made between the 5' end and the 3' end of the nucleic acid sequences as disclosed herein.

The present inventors have discovered that the nucleic acids according to the present invention exhibit a very favourable $K_D$ value range.

A possibility to determine the binding constant is the use of the so called biacore device, which is also known to the one skilled in the art. Affinity as used herein was also measured by the use of the "pull-down assay" as described in the examples. An appropriate measure in order to express the intensity of the binding between the nucleic acid according to the target which is in the present case MCP-1, is the so-called $K_D$ value which as such as well the method for its determination are known to the one skilled in the art.

The nucleic acids according to the present invention are characterized by a certain $K_D$ value. Preferably, the $K_D$ value shown by the nucleic acids according to the present invention is below 1 µM. A $K_D$ value of about 1 µM is said to be characteristic for a non-specific binding of a nucleic acid to a target. As will be acknowledged by the ones in the art, the $K_D$ value of a group of compounds such as the nucleic acids according to the present invention are within a certain range. The above-mentioned $K_D$ of about 1 µM is a preferred upper limit for the $K_D$ value. The preferred lower limit for the $K_D$ of target binding nucleic acids can be about 10 picomolar or higher. It is within the present invention that the $K_D$ values of individual nucleic acids binding to MCP-1 is preferably within this range. Preferred ranges can be defined by choosing any first number within this range and any second number within this range. Preferred upper values are 250 nM and 100 nM, preferred lower values are 50 nM, 10 nM, 1 nM, 100 pM and 10 pM.

The nucleic acid molecules according to the present invention may have any length provided that they are still able to bind to the target molecule. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 50 nucleotides and about 30 to 50 nucleotides.

It is within the present invention that the nucleic acids disclosed herein comprise a moiety which preferably is a high molecular weight moiety and/or which preferably allows to modify the characteristics of the nucleic acid in terms of, among others, residence time in the animal body, preferably the human body. A particularly preferred embodiment of such modification is PEGylation and HESylation of the nucleic acids according to the present invention. As used herein PEG stands for poly(ethylene glycole) and HES for hydroxyethly starch. PEGylation as preferably used herein is the modification of a nucleic acid according to the present invention whereby such modification consists of a PEG moiety which is attached to a nucleic acid according to the present invention. HESylation as preferably used herein is the modification of a nucleic acid according to the present invention whereby such modification consists of a HES moiety which is attached to a nucleic acid according to the present invention. These modifications as well as the process of modifying a nucleic acid using such modifications, is described in European patent application EP 1 306 382, the disclosure of which is herewith incorporated in its entirety by reference.

Preferably, the molecular weight of a modification consisting of or comprising a high molecular weight moiety is about from 2,000 to 200,000 Da, preferably 20,000 to 120,000 Da, particularly in case of PEG being such high molecular weight moiety, and is preferably about from 3,000 to 180,000 Da, more preferably from 5,000 to 130,000 Da, particularly in case of HES being such high molecular weight moiety. The process of HES modification is, e.g., described in German patent application DE 1 2004 006 249.8 the disclosure of which is herewith incorporated in its entirety by reference.

It is within the present invention that either of PEG and HES may be used as either a linear or branched from as further described in the patent applications WO2005074993 and PCT/EP02/11950. Such modification can, in principle, be made to the nucleic acid molecules of the present invention at any position thereof. Preferably such modification is made either to the 5'-terminal nucleotide, the 3'-terminal nucleotide and/or any nucleotide between the 5' nucleotide and the 3' nucleotide of the nucleic acid molecule.

The modification and preferably the PEG and/or HES moiety can be attached to the nucleic acid molecule of the present invention either directly or through a linker. It is also within the present invention that the nucleic acid molecule according to the present invention comprises one or more modifications, preferably one or more PEG and/or HES moiety. In an embodiment the individual linker molecule attaches more than one PEG moiety or HES moiety to a nucleic acid molecule according to the present invention. The linker used in connection with the present invention can itself be either linear or branched. This kind of linkers are known to the ones skilled in the art and are further described in the patent applications WO2005074993 and PCT/EP02/11950.

Without wishing to be bound by any theory, it seems that by modifying the nucleic acids according to the present invention with high molecular weight moiety such as a polymer and more particularly the polymers disclosed herein, which are preferably physiologically acceptable, the excretion kinetic is changed. More particularly, it seems that due to the increased molecular weight of such modified inventive nucleic acids and due to the nucleic acids not being subject to metabolism particularly when in the L form, excretion from an animal body, preferably from a mammalian body and more preferably from a human body is decreased. As excretion typically occurs via the kidneys, the present inventors assume that the glomerular filtration rate of the thus modified nucleic acid is significantly reduced compared to the nucleic acids not having this kind of high molecular weight modification which results in an increase in the residence time in the body. In connection therewith it is particularly noteworthy that, despite such high molecular weight modification the specificity of the nucleic acid according to the present invention is not affected in a detrimental manner. Insofar, the nucleic acids according to the present invention have surprising characteristics—which normally cannot be expected from pharmaceutically active compounds—such that a pharmaceutical formulation providing for a sustained release is not necessarily required to provide for a sustained release. Rather the nucleic acids according to the present invention in their modified form comprising a high molecular weight moiety, can as such already be used as a sustained release-formulation. Insofar, the modification(s) of the nucleic acid molecules as disclosed herein and the thus modified nucleic acid molecules and any composition comprising the same may provide for a distinct, preferably controlled pharmacokinetics and biodistribution thereof. This also includes residence time in circulation and distribution to tissues. Such modifications are further described in the patent application PCT/EP02/11950.

However, it is also within the present invention that the nucleic acids disclosed herein do not comprise any modification and particularly no high molecular weight modification such as PEGylation or HESylation. Such embodiment is particularly preferred when the nucleic acid shows preferential distribution to any target organ or tissue in the body. Nucleic acid agents with such a distributive profile would allow establishment of effective local concentrations in the target tissue while keeping systemic concentration low. This would allow the use of low doses which is not only beneficial from an economic point of view, but also reduces unnecessary exposure of other tissues to the nucleic acid agent, thus reducing the potential risk of side effects.

The inventive nucleic acids, which are also referred to herein as the nucleic acids according to the present invention, and/or the antagonists according to the present invention may be used for the generation or manufacture of a medicament. Such medicament or a pharmaceutical composition according to the present invention contains at least one of the inventive nucleic acids, optionally together with further pharmaceutically active compounds, whereby the inventive nucleic acid preferably acts as pharmaceutically active compound itself. Such medicaments comprise in preferred embodiments at least a pharmaceutically acceptable carrier. Such carrier may be, e.g., water, buffer, PBS, glucose solution, preferably a 5% glucose salt balanced solution, starch, sugar, gelatine or any other acceptable carrier substance. Such carriers are generally known to the one skilled in the art. It will be acknowledged by the person skilled in the art that any embodiments, use and aspects of or related to the medicament of the present invention is also applicable to the pharmaceutical composition of the present invention and vice versa.

The indication, diseases and disorders for the treatment and/or prevention of which the nucleic acids, the pharmaceutical compositions and medicaments in accordance with or prepared in accordance with the present invention result from the involvement, either direct or indirect, of MCP-1 in the respective pathogenetic mechanism. However, also those indications, diseases and disorders can be treated and prevented in the pathogenetic mechanism of which MCP-2, MCP-3, MCP-4 and/or eotaxin are either directly or indirectly involved. It is obvious for the ones skilled in the art that particularly those nucleic acids according to the present invention can be used insofar, i.e. for the diseases involving in the broader sense MCP-2, MCP-3, MCP-4 and eotaxin, which interact and bind, respectively, to or with MCP-2, MCP-3, MCP-4 and eotaxin, respectively.

More specifically, such uses arise, among others, from the expression pattern of MCP-1 which suggests that it plays important roles in human diseases that are characterized by mononuclear cell infiltration. Such cell infiltration is present in many inflammatory and autoimmune diseases. In animal models, MCP-1 has been shown to be expressed in the brain after focal ischemia (Kim 1995; Wang 1995) and during experimental autoimmune encephalomyelitis (Hulkower 1993; Ransohoff 1993; Banisor 2005). MCP-1 may be an important chemokine that targets mononuclear cells in the disease process illustrated by these animal models, such as stroke and multiple sclerosis.

A large body of evidence argues in favor of a unique role of the MCP-1/CCR2 axis in monocyte chemoattraction and thus chronic inflammation: (i) MCP-1- or CCR2-deficient mice show markedly reduced macrophage chemotactic response while otherwise appearing normal (Kuziel 1997; Kurihara 1997; Boring 1997; Lu 1998). (ii), despite functional redundancy with other chemokines in vitro, loss of MCP-1 effector function alone is sufficient to impair monocytic trafficking in several inflammatory models (Lloyd 1997; Furuichi 2003; Egashira 2002; Galasso 2000; Ogata 1997; Kennedy 1998; Gonzalo 1998; Kitamoto 2003). (iii), MCP-1 levels are elevated in many inflammatory diseases. In fact, MCP-1 is thought to play a role in many diseases with and without an obvious inflammatory component such as rheumatoid arthritis (Koch 1992; Hosaka 1994; Akahoshi 1993; Harigai 1993; Rollins 1996), renal disease (Wada 1996; Viedt 2002), restenosis after angioplasty (Economou 2001), allergy and asthma (Alam 1996; Holgate 1997; Gonzalo 1998), cancer (Salcedo 2000; Gordillo 2004), atherosclerosis (Nelken 1991; Yla-Herttuala 1991; Schwartz 1993; Takeya 1993; Boring 1998), psoriasis (Vestergaard 2004), inflammation of the nervous system (Huang 2001), atopic dermatitis (Kaburagi 2001), colitis (Okuno 2002), endometriosis (Jolicoeur 2001), uveitis (Tuaillon 2002), retinal disorders (Nakazawa 2007), idiopathic pulmonary fibrosis and sarcoidosis (Iyonaga 1994) and polymyositis/dermatomyositis (De Bleecker 2002).

Therapeutic intervention with anti-MCP-1 agents—or CCR2 antagonists—would affect the excess inflammatory monocyte trafficking but may spare basal trafficking of phagocytes, thereby avoiding general immunosuppression and increased risk of infections (Dawson 2003).

Additionally, based on the increasing knowledge on the molecular mechanisms of the inflammatory process and the interplay of locally secreted mediators of inflammation, new targets for the therapy of kidney diseases have been identified (Holdsworth 2000; Segerer 2000). One of those targets, for which robust data on expression and interventional studies with specific antagonists in appropriate animal models exist is MCP-1. This protein has a widely non-redundant role for immune-cell recruitment to sites of renal inflammation. Infiltration of immune cells to the kidney is thought to be a major mechanism of structural renal damage and decline of renal function in the development of various forms of kidney disease.

All types of renal cells can express chemokines including MCP-1 upon stimulation in vitro (Segerer 2000); there is a long list of stimuli that trigger MCP-1 expression in vitro including cytokines, oxygen radicals, immune complexes, and lipid mediators.

In healthy kidneys of rats and mice, MCP-1 is not expressed, but is readily upregulated during the course of acute and chronic rodent models of renal inflammation including immune complex glomerulonephritis, rapid progressive glomerulonephritis, proliferative glomerulonephritis, diabetic nephropathy, obstructive nephropathy, or acute tubular necrosis (Segerer 2000; Anders 2003). The expression data for MCP-1 in rodents do correlate well with the respective expression found in human renal biopsies (Rovin 1994; Cockwell 1998; Wada 1999). Furthermore, renal expression in human kidneys is associated with disease activity and declines when appropriate therapy induced disease remission (Amann 2003).

Glomerular mononuclear cell infiltration is associated with the development of a diffuse glomerulosclerosis in patients with diabetic nephropathy. MCP-1 plays an important role in the recruitment and accumulation of monocytes and lymphocytes within the glomerulus (Banba 2000; Morii 2003).

Locally produced MCP-1 seems to be particularly involved in the initiation and progression of tubulointerstitial damage, as documented in experiments using transgenic mice with nephrotoxic serum-induced nephritis (NSN). MCP-1 was mainly detected in vascular endothelial cells, tubular epithelial cells and infiltrated mononuclear cells in the interstitial lesions. The MCP-1 mediated activation of tubular epithelial cells is consistent with the notion that MCP-1 contributes to tubulointerstitial inflammation, a hallmark of progressive renal disease (Wada 2001; Viedt 2002)

Due to the homology between MCP-1 on the one hand and MCP-2, MCP-3, MCP-4 and eotaxin on the other hand, the nucleic acids according to the present invention, at least those of them which interact with or bind to MCP-2, MCP-3, MCP-4 and eotaxin, respectively, can typically be used for the treatment, prevention and/or diagnosis of any disease where MCP-2, MCP-3, MCP-4 and eotaxin, respectively, is either directly or indirectly involved. Involved as preferably used herein, means that if the respective molecule which is involved in the disease, is prevented from exerting one, several or all of its functions in connection with the pathogenetic mechanism underlying the disease, the disease will be cured or the extent thereof decreased or the outbreak thereof prevented; at least the symptoms or any indicator of such disease will be relieved and improved, respectively, such that the symptoms and indicator, respectively, is identical or closer to the one(s) observed in a subject not suffering from the disease or not being at risk to develop such disease.

Of course, because the MCP-1 binding nucleic acids according to the present invention interact with or bind to human or murine MCP-1, a skilled person will generally understand that the MCP-1 binding nucleic acids according to the present invention can easily be used for the treatment, prevention and/or diagnosis of any disease as described herein of humans and animals.

These members of the monocyte chemoattractant protein (MCP) family, i.e. MCP-2, MCP-3, MCP-4 and eotaxin thus share a high degree of sequence similarity with MCP-1. Although not exclusively, eotaxin, MCP-2, -3, and -4 interact via CCR3, the characteristic chemokine receptor on human eosinophils (Heath 1997). The CCR3 receptor is upregulated in neoplastic conditions, such as cutaneous T-cell lymphoma (Kleinhans 2003), glioblastoma (Kouno 2004), or renal cell carcinoma (Johrer 2005).

More specifically, increased levels of eotaxin are directly associated with asthma diagnosis and compromised lung function (Nakamura 1999). Elevated expression of eotaxin at sites of allergic inflammation has been observed in both atopic and nonatopic asthmatics (Ying 1997; Ying 1999). Also, mRNAs coding for MCP-2 and -4 are constitutively expressed in a variety of tissues; their physiological functions in these contexts, however, are unknown. Plasma MCP-2 levels are elevated in sepsis together with MCP-1 (Bossink 1995); MCP-3 expression occurs in asthmatics (Humbert 1997). Finally, MCP-4 can be found at the luminal surface of atherosclerotic vessels (Berkhout 1997).

Accordingly, disease and/or disorders and/or diseased conditions for the treatment and/or prevention of which the medicament according to the present invention may be used include, but are not limited to inflammatory diseases, autoimmune diseases, autoimmune encephalomyelitis, stroke, acute and chronic multiple sclerosis, chronic inflammation, rheumatoid arthritis, renal diseases, restenosis, restenosis after angioplasty, acute and chronic allergic reactions, primary and secondary immunologic or allergic reactions, asthma, conjunctivitis, bronchitis, cancer, atherosclerosis, artheriosclerotic cardiovasular heart failure or stroke, psoriasis, psoriatic arthritis, inflammation of the nervous system, atopic dermatitis, colitis, endometriosis, uveitis, retinal disorders including macular degeneration, retinal detachment, diabetic retinopathy, retinopathy of prematurity, retinitis pigmentosa, proliferative vitreoretinopathy, and central serous chorioretinopathy; idiopathic pulmonary fibrosis, sarcoidosis, polymyositis, dermatomyositis, avoidance of immunosuppression, reducing the risk of infection, sepsis, renal inflammation, glomerulonephritis, rapid progressive glomerulonephritis, proliferative glomerulonephritis, diabetic nephropathy, obstructive nephropathy, acute tubular necrosis, and diffuse glomerulosclerosis, systemic lupus erythematosus, chronic bronchitis, Behçet's disease, amyotrophic lateral sclerosis (ALS), premature atherosclerosis after Kawasaki's disease, myocardial infarction, obesity, chronic liver disease, peyronie's disease; acute spinal chord injury, lung or kidney transplantation, myocarditis, Alzheimer's disease, and neuropathy, breast carcinoma, gastric carcinoma, bladder cancer, ovarian cancer, hamartoma, colorectal carcinoma, colonic adenoma, pancreatitis, chronic obstructive pulmonary disease (COPD) and inflammatory bowel diseases such as Crohn's disease or ulcerative colitis.

In a further embodiment, the medicament comprises a further pharmaceutically active agent. Such further pharmaceutically active compounds are, among others but not limited thereto, those known to control blood pressure and diabetes such as angiotensin converting enzyme (ACE) inhibitors and angiotensin receptor blockers. The further pharmaceutically active compound can be, in a further embodiment, also one of those compounds which reduce infiltration of immune cells to sites of chronic inflammation or generally suppress the exuberant immune response that is present in chronic inflammatory settings and that leads to tissue damage. Such compounds can be, but are not limited to, steroids or immune suppressants and are preferably selected from the group comprising corticosteroids like prednisone, methylprednisolone, hydrocortisone, dexamethasone and general immunosuppressants such as cyclophosphamide, cyclosporine, chlorambucil, azathioprine, tacrolimus or mycophenolate mofetil. Additionally, more specific blockers of T-cell costimulation, e.g. blockers of CD 154 or CD40 or CD28 or CD86 or CD80; or T- and/or B-cell depleting agents like an anti-CD20 agent are useful in further embodiments. Finally, the further pharmaceutically active agent may be a modulator of the activity of any other chemokine which can be a chemokine agonist or antagonist or a chemokine receptor agonist or antagonist. Alternatively, or additionally, such further pharmaceutically active agent is a further nucleic acid according to the present invention. Alternatively, the medicament comprises at least one more nucleic acid which binds to a target molecule different from MCP-1 or exhibits a function which is different from the one of the nucleic acids according to the present invention.

It is within the present invention that the medicament is alternatively or additionally used, in principle, for the prevention of any of the diseases disclosed in connection with the use of the medicament for the treatment of said diseases. Respective markers therefore, i.e. for the respective diseases are known to the ones skilled in the art. Preferably, the respective marker is MCP-1. Alternatively and/or additionally, the respective marker is selected from the group comprising MCP-2, MCP-3, MCP-4 and eotaxin. A still further group of markers is selected from the group comprising autoreactive antibodies in the plasma, such as, for example, anti-dsDNA antibodies or rheumatoid factor.

In one embodiment of the medicament of the present invention, such medicament is for use in combination with other treatments for any of the diseases disclosed herein, particularly those for which the medicament of the present invention is to be used.

"Combination therapy" (or "co-therapy") includes the administration of a medicament of the invention and at least a second agent as part of a specific treatment regimen intended to provide the beneficial effect from the co-action of these therapeutic agents, i.e. the medicament of the present invention and said second agent. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to a subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As outlined in general terms above, the medicament according to the present invention can be administered, in principle, in any form known to the ones skilled in the art. A preferred route of administration is systemic administration, more preferably by parenteral administration, preferably by injunction. Alternatively, the medicament may be administered locally. Other routes of administration comprise intramuscular, intraperitoneal, and subcutaneous, per orum, intranasal, intratracheal or pulmonary with preference given to the route of administration that is the least invasive, while ensuring efficiency.

Parenteral administration is generally used for subcutaneous, intramuscular or intravenous injections and infusions. Additionally, one approach for parenteral administration employs the implantation of a slow-release or sustained-released systems, which assures that a constant level of dosage is maintained, that are well known to the ordinary skill in the art.

Furthermore, preferred medicaments of the present invention can be administered in intranasal form via topical use of suitable intranasal vehicles, inhalants, or via transdermal routes, using those forms of transdermal skin patches well blown to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

The medicament of the present invention will generally comprise an effective amount of the active component(s) of the therapy, including, but not limited to, a nucleic acid molecule of the present invention, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the medicament of the present invention.

In a further aspect the present invention is related to a pharmaceutical composition. Such pharmaceutical composition comprises at least one of the nucleic acids according to the present invention and preferably a pharmaceutically acceptable vehicle. Such vehicle can be any vehicle or any binder used and/or known in the art. More particularly such binder or vehicle is any binder or vehicle as discussed in connection with the manufacture of the medicament disclosed herein. In a further embodiment, the pharmaceutical composition comprises a further pharmaceutically active agent.

The preparation of a medicament and a pharmaceutical composition will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, a medicament will be administered in a manner compatible with the dosage formulation, and in such amount as is pharmacologically effective. The formulations are easily administered in a variety of dosage forms, such as the type of injectable solutions described above, but drug release capsules and the like can also be employed.

In this context, the quantity of active ingredient and volume of composition to be administered depends on the individual or the subject to be treated. Specific amounts of active compound required for administration depend on the judgment of the practitioner and are peculiar to each individual.

A minimal volume of a medicament required to disperse the active compounds is typically utilized. Suitable regimes for administration are also variable, but would be typified by initially administering the compound and monitoring the results and then giving further controlled doses at further intervals.

For instance, for oral administration in the form of a tablet or capsule (e.g., a gelatin capsule), the active drug component, i.e. a nucleic acid molecule of the present invention and/or any further pharmaceutically active agent, also referred to herein as therapeutic agent(s) or active compound(s) can be combined with an oral, non-toxic, pharmaceutically acceptable inert carrier such as ethanol, glycerol, water and the like. Moreover, when desired or necessary, suitable binders, lubricants, disintegrating agents, and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes, and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol, and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

The medicament of the invention can also be administered in such oral dosage forms as timed release and sustained release tablets or capsules, pills, powders, granules, elixirs, tinctures, suspensions, syrups and emulsions. Suppositories are advantageously prepared from fatty emulsions or suspensions.

The pharmaceutical composition or medicament may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating, or coating methods, and typically contain about 0.1% to 75%, preferably about 1% to 50%, of the active ingredient.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

For solid compositions, excipients include pharmaceutical grades of mannitol, lactose, starch, magnesium stearate, sodium saccharin, talcum, cellulose, glucose, sucrose, magnesium carbonate, and the like. The active compound defined above, may be also formulated as suppositories, using for example, polyalkylene glycols, for example, propylene glycol, as the carrier. In some embodiments, suppositories are advantageously prepared from fatty emulsions or suspensions.

The medicaments and nucleic acid molecules, respectively, of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, what is well known to the ordinary skill in the art. For example, the nucleic acid molecules described herein can be provided as a complex with a lipophilic compound or non-immunogenic, high molecular weight compound constructed using methods known in the art. Additionally, liposomes may bear such nucleic acid molecules on their surface for targeting and carrying cytotoxic agents internally to mediate cell killing. An example of nucleic-acid associated complexes is provided in U.S. Pat. No. 6,011,020.

The medicaments and nucleic acid molecules, respectively, of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the medicaments and nucleic acid molecules, respectively, of the present invention may be coupled to a class of biodegradable polymers useful in achieving controlled release of a drag, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition and medicament, respectively, to be administered may also contain minor amounts of non-toxic auxiliary substances such as wetting or emulsifying agents, pH buffering agents, and other substances such as for example, sodium acetate, and triethanolamine oleate.

The dosage regimen utilizing the nucleic acid molecules and medicaments, respectively, of the present invention is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Effective plasma levels of the nucleic acid according to the present invention preferably range from 500 fM to 500 µM in the treatment of any of the diseases disclosed herein.

The nucleic acid molecules and medicaments, respectively, of the present invention may preferably be administered in a single daily dose, every second or third day, weekly, every second week, in a single monthly dose or every third month.

It is within the present invention that the medicament as described herein constitutes the pharmaceutical composition disclosed herein.

In a further aspect the present invention is related to a method for the treatment of a subject who is need of such treatment, whereby the method comprises the administration of a pharmaceutically active amount of at least one of the nucleic acids according to the present invention. In an embodiment, the subject suffers from a disease or is at risk to develop such disease, whereby the disease is any of those disclosed herein, particularly any of those diseases disclosed in connection with the use of any of the nucleic acids according to the present invention for the manufacture of a medicament.

It is to be understood that the nucleic acid as well as the antagonists according to the present invention can be used not only as a medicament or for the manufacture of a medicament, but also for cosmetic purposes, particularly with regard to the involvement of MCP-1 in inflamed regional skin lesions. Therefore, a further condition or disease for the treatment or prevention of which the nucleic acid, the medicament and/or the pharmaceutical composition according to the present invention can be used, is inflamed regional skin lesions.

As preferably used herein a diagnostic or diagnostic agent or diagnostic means is suitable to detect, either directly or indirectly MCP-1, preferably MCP-1 as described herein and more preferably MCP-1 as described herein in connection with the various disorders and diseases described herein. However, to the extent that the nucleic acid molecules according to the present invention are also binding to any, some or all of MCP-2, MCP-3, MCP-4 and eotaxin, such nucleic acid molecules can also be used for the diagnosis of diseases and disorders, respectively, the pathogenetic mechanism is either directly or indirectly linked or associated with the over-expression or over-activity with MCP-2, MCP-3, MCP-4 and/or eotaxin. The diagnostic is suitable for the detection and/or follow-up of any of the disorders and diseases, respectively, described herein. Such detection is possible through the binding of the nucleic acids according to the present invention to MCP-1. Such binding can be either directly or indirectly be detected. The respective methods and means are known to the ones skilled in the art. Among others, the nucleic acids according to the present invention may comprise a label which allows the detection of the nucleic acids according to the present invention, preferably the nucleic acid bound to MCP-1. Such a label is preferably selected from the group comprising radioactive, enzymatic and fluorescent labels. In principle, all known assays developed for antibodies can be adopted for the nucleic acids according to the present invention whereas the target-binding antibody is substituted to a target-binding nucleic acid. In antibody-assays using unlabeled target-binding antibodies the detection is preferably done by a secondary antibody which is modified with radioactive, enzymatic and fluorescent labels and bind to the target-binding antibody at its Fc-fragment. In the case of a nucleic acid, preferably a nucleic acid according to the present invention, the nucleic acid is modified with such a label, whereby preferably such a label is selected from the group comprising biotin, Cy-3 and Cy-5, and such label is detected by an antibody directed against such label, e.g. an anti-biotin antibody, an anti-Cy3 antibody or an anti-Cy5 antibody, or—in the case that the label is biotin—the label is detected by streptavidin or avidin which naturally bind to biotin. Such antibody, streptavidin or avidin in turn is preferably modified with a respective label, e.g. a radioactive, enzymatic or fluorescent label (like an secondary antibody).

In a further embodiment the nucleic acid molecules according to the invention are detected or analysed by a second detection means, wherein the said detection means is a molecular beacon. The methodology of molecular beacon is known to persons skilled in the art. In brief, nucleic acids probes which are also referred to as molecular beacons, are a reverse complement to the nucleic acids sample to be detected and hybridise because of this to a part of the nucleic acid sample to be detected. Upon binding to the nucleic acid sample the fluorophoric groups of the molecular beacon are separated which results in a change of the fluorescence signal, preferably a change in intensity. This change correlates with the amount of nucleic acids sample present.

It will be acknowledged that the detection of MCP-1 using the nucleic acids according to the present invention will particularly allow the detection of MCP-1 as defined herein.

In connection with the detection of the MCP-1 a preferred method comprises the following steps:
 (a) providing a sample which is to be tested for the presence of MCP-1,
 (b) providing a nucleic acid according to the present invention,
 (c) reacting the sample with the nucleic acid, preferably in a reaction vessel
 whereby step (a) can be performed prior to step (b), or step (b) can be preformed prior to step (a).

In a preferred embodiment a further step d) is provided, which consists in the detection of the reaction of the sample with the nucleic acid. Preferably, the nucleic acid of step b) is immobilised to a surface. The surface may be the surface of a reaction vessel such as a reaction tube, a well of a plate, or the surface of a device contained in such reaction vessel such as, for example, a bead. The immobilisation of the nucleic acid to the surface can be made by any means known to the ones skilled in the art including, but not limited to, non-covalent or covalent linkages. Preferably, the linkage is established via a covalent chemical bond between the surface and the nucleic acid. However, it is also within the present invention that the nucleic acid is indirectly immobilised to a surface, whereby such indirect immobilisation involves the use of a further component or a pair of interaction partners. Such further component is preferably a compound which specifically interacts with the nucleic acid to be immobilised which is also referred to as interaction partner, and thus mediates the attachment of the nucleic acid to the surface. The interaction partner is preferably selected from the group comprising nucleic acids, polypeptides, proteins and antibodies. Preferably, the interaction partner is an antibody, more preferably a monoclonal antibody. Alternatively, the interaction partner is a nucleic acid, preferably a functional nucleic acid. More preferably such functional nucleic acid is selected from the group comprising aptamers, spiegelmers, and nucleic acids which are at least partially complementary to the nucleic acid. In a further alternative embodiment, the binding of the nucleic acid to the surface is mediated by a multi-partite interaction partner. Such multi-partite interaction partner is preferably a pair of interaction partners or an interaction partner consisting of a first member and a second member, whereby the first member is comprised by or attached to the nucleic acid and the second member is attached to or comprised by the surface. The multi-partite interaction partner is preferably selected from the group of pairs of interaction partners comprising biotin and avidin, biotin and streptavidin, and biotin and neutravidin. Preferably, the first member of the pair of interaction partners is biotin.

A preferred result of such method is the formation of an immobilised complex of MCP-1 and the nucleic acid, whereby more preferably said complex is detected. It is within an embodiment that from the complex the MCP-1 is detected.

A respective detection means which is in compliance with this requirement is, for example, any detection means which is specific for that/those part(s) of the MCP-1. A particularly preferred detection means is a detection means which is selected from the group comprising nucleic acids, polypeptides, proteins and antibodies, the generation of which is known to the ones skilled in the art.

The method for the detection of MCP-1 also comprises that the sample is removed from the reaction vessel which has preferably been used to perform step c).

The method comprises in a further embodiment also the step of immobilising an interaction partner of MCP-1 on a surface, preferably a surface as defined above, whereby the interaction partner is defined as herein and preferably as above in connection with the respective method and more preferably comprises nucleic acids, polypeptides, proteins and antibodies in their various embodiments. In this embodiment, a particularly preferred detection means is a nucleic acid according to the present invention, whereby such nucleic acid may preferably be labelled or non-labelled. In case such nucleic acid is labelled it can directly or indirectly be detected. Such detection may also involve the use of a second detection means which is, preferably, also selected from the group comprising nucleic acids, polypeptides, proteins and embodiments in the various embodiments described herein. Such detection means are preferably specific for the nucleic acid according to the present invention. In a more preferred embodiment, the second detection means is a molecular beacon. Either the nucleic acid or the second detection means or both may comprise in a preferred embodiment a detection label. The detection label is preferably selected from the group comprising biotin, a bromo-desoxyuridine label, a digoxigenin label, a fluorescence label, a UV-label, a radio-label, and a chelator molecule. Alternatively, the second detection means interacts with the detection label which is preferably contained by, comprised by or attached to the nucleic acid. Particularly preferred combinations are as follows:

the detection label is biotin and the second detection means is an antibody directed against biotin, or wherein
the detection label is biotin and the second detection means is an avidin or an avidin carrying molecule, or wherein
the detection label is biotin and the second detection means is a streptavidin or a stretavidin carrying molecule, or wherein
the detection label is biotin and the second detection means is a neutravidin or a neutravidin carrying molecule, or
wherein the detection label is a bromo-desoxyuridine and the second detection means is an antibody directed against bromo-desoxyuridine, or wherein
the detection label is a digoxigenin and the second detection means is an antibody directed against digoxigenin, or wherein
the detection label is a chelator and the second detection means is a radio-nuclide,
whereby it is preferred that said detection label is attached to the nucleic acid. It is to be acknowledged that this kind of combination is also applicable to the embodiment where the nucleic acid is attached to the surface. In such embodiment it is preferred that the detection label is attached to the interaction partner.

Finally, it is also within the present invention that the second detection means is detected using a third detection means, preferably the third detection means is an enzyme, more preferably showing an enzymatic reaction upon detection of the second detection means, or the third detection means is a means for detecting radiation, more preferably radiation emitted by a radio-nuclide. Preferably, the third detection means is specifically detecting and/or interacting with the second detection means.

Also in the embodiment with an interaction partner of MCP-1 being immobilised on a surface and the nucleic acid according to the present invention is preferably added to the complex formed between the interaction partner and the MCP-1, the sample can be removed from the reaction, more preferably from the reaction vessel where step c) and/or d) are preformed.

In an embodiment the nucleic acid according to the present invention comprises a fluorescence moiety and whereby the fluorescence of the fluorescence moiety is different upon complex formation between the nucleic acid and MCP-1 and free MCP-1.

In a further embodiment the nucleic acid is a derivative of the nucleic acid according to the present invention, whereby the derivative of the nucleic acid comprises at least one fluorescent derivative of adenosine replacing adenosine. In a preferred embodiment the fluorescent derivative of adenosine is ethenoadenosine.

In a further embodiment the complex consisting of the derivative of the nucleic acid according to the present invention and the MCP-1 is detected using fluorescence.

In an embodiment of the method a signal is created in step (c) or step (d) and preferably the signal is correlated with the concentration of MCP-1 in the sample.

In a preferred aspect, the assays may be performed in 96-well plates, where components are immobilized in the reaction vessels as described above and the wells acting as reaction vessels.

It will be acknowledged by the ones skilled in the art that what has been said above also applies to MCP-2, MCP-3, MCP-4 and/or eotaxin, at least to the extent that the nucleic acids according to the present invention are also binding to or with MCP-2, MCP-3, MCP-4 and/or eotaxin.

The inventive nucleic acid may further be used as starting material for drug design. Basically there are two possible approaches. One approach is the screening of compound libraries whereas such compound libraries are preferably low molecular weight compound libraries. In an embodiment, the screening is a high throughput screening. Preferably, high throughput screening is the fast, efficient, trial-and-error evaluation of compounds in a target based assay. In best case the analysis are carried by a colorimetric measurement. Libraries as used in connection therewith are known to the one skilled in the art.

Alternatively, the nucleic acid according to the present invention may be used for rational design of drugs. Preferably, rational drug design is the design of a pharmaceutical lead structure. Starting from the 3-dimensional structure of the target which is typically identified by methods such as X-ray crystallography or nuclear magnetic resonance spectroscopy, computer programs are used to search through databases containing structures of many different chemical compounds. The selection is done by a computer, the identified compounds can subsequently be tested in the laboratory.

The rational design of drugs may start from any of the nucleic acid according to the present invention and involves a structure, preferably a three dimensional structure, which is similar to the structure of the inventive nucleic acids or identical to the binding mediating parts of the structure of the inventive nucleic acids. In any case such structure still shows the same or a similar binding characteristic as the inventive nucleic acids. In either a further step or as an alternative step in the rational design of drugs the preferably three dimensional structure of those parts of the nucleic acids binding to the neurotransmitter are mimicked by chemical groups which are different from nucleotides and nucleic acids. By this mimicry a compound different from the nucleic acids can be designed. Such compound is preferably a small molecule or a peptide.

In case of screening of compound libraries, such as by using a competitive assay which are known to the one skilled in the arts, appropriate MCP-1 analogues, MCP-1 agonists or MCP-1 antagonists may be found. Such competitive assays may be set up as follows. The inventive nucleic acid, preferably a spiegelmer which is a target binding L-nucleic acid, is coupled to a solid phase. In order to identify MCP-1 analogues labelled MCP-1 may be added to the assay. A potential analogue would compete with the MCP-1 molecules binding to the spiegelmer which would go along with a decrease in the signal obtained by the respective label. Screening for agonists or antagonists may involve the use of a cell culture assay as known to the ones skilled in the art.

The kit according to the present invention may comprise at least one or several of the inventive nucleic acids. Additionally, the kit may comprise at least one or several positive or negative controls. A positive control may, for example, be MCP-1, particularly the one against which the inventive nucleic acid is selected or to which it binds, preferably, in liquid form. A negative control may, e.g., be a peptide which is defined in terms of biophysical properties similar to MCP-1, but which is not recognized by the inventive nucleic acids. Furthermore, said kit may comprise one or several buffers. The various ingredients may be contained in the kit in dried or lyophilised form or solved in a liquid. The kit may comprise one or several containers which in turn may contain one or several ingredients of the kit. In a further embodiment, the kit comprises an instruction or instruction leaflet which provides to the user information on how to use the kit and its various ingredients.

The pharmaceutical and bioanalytical determination of the nucleic acid according to the present invention is elementarily for the assessment of its pharmacokinetic and biodynamic profile in several humours, tissues and organs of the human and non-human body. For such purpose, any of the detection methods disclosed herein or known to a person skilled in the art may be used. In a further aspect of the present invention a sandwich hybridisation assay for the detection of the nucleic acid according to the present invention is provided. Within the detection assay a capture probe and a detection probe are used. The capture probe is complementary to the first part and the detection probe to the second part of the nucleic acid according to the present invention. Both, capture and detection probe, can be formed by DNA nucleotides, modified DNA nucleotides, modified RNA nucleotides, RNA nucleotides, LNA nucleotides and/or PNA nucleotides.

Hence, the capture probe comprise a sequence stretch complementary to the 5'-end of the nucleic acid according to the present invention and the detection probe comprise a sequence stretch complementary to the 3'-end of the nucleic acid according to the present invention. In this case the capture probe is immobilised to a surface or matrix via its 5'-end whereby the capture probe can be immobilised directly at its 5'-end or via a linker between of its 5'-end and the surface or matrix. However, in principle the linker can be linked to each nucleotide of the capture probe. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

Alternatively, the capture probe comprises a sequence stretch complementary to the 3'-end of the nucleic acid according to the present invention and the detection probe comprise a sequence stretch complementary to the 5'-end of the nucleic acid according to the present invention. In this case the capture probe is immobilised to a surface or matrix via its 3'-end whereby the capture probe can be immobilised directly at its 3'-end or via a linker between of its 3'-end and the surface or matrix. However, in principle, the linker can be linked to each nucleotide of the sequence stretch that is complementary to the nucleic acid according to the present invention. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The number of nucleotides of the capture and detection probe that may hybridise to the nucleic acid according to the present invention is variable and can be dependant from the number of nucleotides of the capture and/or the detection probe and/or the nucleic acid according to the present invention itself. The total number of nucleotides of the capture and the detection probe that may hybridise to the nucleic acid according to the present invention should be maximal the number of nucleotides that are comprised by the nucleic acid according to the present invention. The minimal number of nucleotides (2 to 10 nucleotides) of the detection and capture probe should allow hybridisation to the 5'-end or 3'-end, respectively, of the nucleic acid according to the present invention. In order to realize high specificity and selectivity between the nucleic acid according to the present invention and other nucleic acids occurring in samples that are analyzed the total number of nucleotides of the capture and detection probe should be or maximal the number of nucleotides that are comprised by the nucleic acid according to the present invention.

Moreover the detection probe preferably carries a marker molecule or label that can be detected as previously described herein. The label or marker molecule can in principle be linked to each nucleotide of the detection probe. Preferably, the label or marker is located at the 5'-end or 3'-end of the detection probe, whereby between the nucleotides within the detection probe that are complementary to the nucleic acid according to the present invention, and the label a linker can be inserted. The linker can be formed by hydrophilic linkers of skilled in the art or by D-DNA nucleotides, modified D-DNA nucleotides, D-RNA nucleotides, modified D-RNA nucleotides, D-LNA nucleotides, PNA nucleotides, L-RNA nucleotides, L-DNA nucleotides, modified L-RNA nucleotides, modified L-DNA nucleotides and/or L-LNA nucleotides.

The detection of the nucleic acid according to the present invention can be carried out as follows: The nucleic acid according to the present invention hybridises with one of its ends to the capture probe and with the other end to the detection probe. Afterwards unbound detection probe is removed by, e.g., one or several washing steps. The amount of bound detection probe which preferably carries a label or marker molecule, can be measured subsequently.

As preferably used herein, the term treatment comprises in a preferred embodiment additionally or alternatively prevention and/or follow-up.

As preferably used herein, the terms disease and disorder shall be used in an interchangeable manner, if not indicated to the contrary.

As used herein, the term comprise is preferably not intended to limit the subject matter followed or described by such term. However, in an alternative embodiment the term comprises shall be understood in the meaning of containing and thus as limiting the subject matter followed or described by such term.

The various SEQ. ID. Nos., the chemical nature of the nucleic acid molecules according to the present invention and the target molecules MCP-1 as used herein, the actual sequence thereof and the internal reference number is summarized in the following table.

| Seq.-ID | RNA/Peptide | Sequence | Internal Reference |
|---|---|---|---|
| 1 | L-protein | QPDAINAPVTCCYNFTNRKISVQRLASYRRITSSKCPKEAVIFKTIVAKEICADPKQKWV QDSMDHLDKQTQTPKT | human MCP-1, huMCP-1, CCL2 |
| 2 | L-protein | QPDAVNAPLTCCYSFTSKMIPMSRLESYKRITSSRCPKEAVVFVTKLKREVCADPKKEWV QTYIKNLDRNQMRSEPTTLFKTASALRSSAPLNVKLTRKSEANASTTFSTTTSSTSVGVT SVTVN | mouse MCP-1, mCCL2, mMCP-1, murine MCP-1 (*Mus musculus*) |
| 3 | L-protein | QPDAINAPVTCCYNFTNRKISVQRLASYRRITSSKCPKEAVIFKTIVAKEICADPKQKWV QDSMDHLDKQIQTPKP | monkey MCP-1 (*Macaca mulatta*) |
| 4 | L-protein | QPDAINSPVTCCYTLTSKKISMQRLMSYRRVTSSKCPKEAVIFKTIAGKEICAEPKQKWV QDSISHLDKKNQTPKP | pig MCP-1 (*Sus scrofa*) |
| 5 | L-protein | QPDAIISPVTCCYTLTNKKISIQRLASYKRVTSSKCPKEAVIFKTVLNKEICADPKQKWV QDSMAHLDKKSQTQTA | dog MCP-1 (*Canis familiaris*) |
| 6 | L-protein | QPDAVNSPVTCCYTFTNKTISVKRLMSYRRINSTKCPKEAVIFMTKLAKGICADPKQKWV QDAIANLDKKMQTPKTLTSYSTTQEHTTNLSSTRTPSTTTSL | rabbit MCP-1 (*Oryctolagus cuniculus*) |
| 7 | L-protein | QPVGINTSTTCCYRFINKKIPKQRLESYRRTTSSHCPREAVIFKTKLDKEICADPTQKWV QDFMKHLDKKTQTPKL | human MCP-3, CCL7, huMCP-3 |
| 8 | L-protein | GPASVPTTCCFNLANRKIPLQRLESYRRITSGKCPQKAVIFKTKLAKDICADPKKKWVQD SMKYLDQKSPTPKP | human eotaxin/CCL11 |
| 9 | L-protein | QPDSVSIPITCCFNVINRKIPIQRLESYTRITNIQCPKEAVIFKTKRGKEVCADPKERWV RDSMKHLDQIFQNLKP | human MCP-2, CCL8, huMCP-2 |
| 10 | L-RNA | AGCGUGCCCGGAGUGGCAGGGGGACGCGACCUGCAAUAAUGCACGCU | 169-B1trc |
| 11 | L-RNA | AGCGUGCCCGGAGUGGCAGGGGGACGCGACCUGCAAUUGCACGCU | 169-F3trc |
| 12 | L-RNA | AGCGUGCCCGGAGUGGCAGGGGGACGCGACCUGUAAUAAUGCACGCU | 169-C1trc |
| 13 | L-RNA | AGCGUGCCCGGUGUGGCAGGGGGACGCGACCUGCAAUAAUGCGCGCU | 169-A3trc |
| 14 | L-RNA | AGCGUGCCCGGAGUAGCAGGGGGGCGCGACCUGCAAUAAUGCACGCU | 169-B2trc |
| 15 | L-RNA | AGCGUGCCCGGUGUGGUAGGGGGCGCGAUCUACAAUUGCACGCU | 176-B12trc |
| 16 | L-RNA | AGCGUGCCCGGUGUGACAGGGGGGCGCGACCUGCAUUUGCACGCU | 176-D9trc |
| 17 | L-RNA | AGCGUGCCCGGUGUGGCAGGGGGGCGCGACCUGUAUUUGCACGCU | 176-B10trc |
| 18 | L-RNA | AGCGUGCCCGGAGUGGCAGGGGGGCGCGACCUGCAAUAAUGCACGCU | 169-F2trc |
| 19 | L-RNA | AGCGUGCCCGGUGUGGCAGGGGGGCGCGACCUGCAAUUGCACGCU | 176-B9trc |
| 20 | L-RNA | AGCAUGCCCGGUGUGGCAGGGGGGCGCGACCUGCAUUUGCAUGCU | 176-H9trc |
| 21 | L-RNA | AGCGUGCCCGGUGUGGUAGGGGGCGCGACCUACAUUUGCACGCU | 176-E10trc |
| 22 | L-RNA | AGUGUGCCAGCUGUGAUGGGGGGCGCGACCCAUUUUACACACU | 176-G9trc |
| 23 | L-RNA | AGUGUGCCAGCGUGAUGGGGGGCGCGACCCAUUUUACACACU | 176-F9trc |
| 24 | L-RNA | AGUGUGCGAGCGUGAUGGGGGGCGCGACCCAUUUUACAUACU | 176-C11trc |
| 25 | L-RNA | AGUGUGCCAGCGUGAUGGGGGGCGCGACCCAUUUUACAUACU | 176-E11trc |
| 26 | L-RNA | AGUAUGCCAGCGUGAUGGGGGGCGCGACCCAUUUUACAUACU | 176-D10trc |
| 27 | L-RNA | AGUGUGCCAGUGUGAUGGGGGGCGCGACCCAUUUUACACACU | 176-H10trc |
| 28 | L-RNA | AGCGUGCCAGUGUGAUGGGGGGCGCGACCCAUUUUACACGCU | 176-C9trc |
| 29 | L-RNA | ACGCACGUCCCUCACCGGUGCAAGUGAAGCCGCGGCUCUGCGU | 180-B1-001 |

-continued

| Seq.-ID | RNA/Peptide | Sequence | Internal Reference |
|---|---|---|---|
| 30 | L-RNA | ACGCACCUCCCUCACCGGUGCAAGUGAAGCCGUGGCUCUGCGC | 180-A4-002 |
| 31 | L-RNA | ACGCACGUCCCUCACCGGUGCAAGUGAAGCCGUGGCUCUGCGU | 180-D1-002 |
| 32 | L-RNA | GCACGUCCCUCACCGGUGCAAGUGAAGCCGUGGCUCUGCGU | 180-D1-011 |
| 33 | L-RNA | ACGCACGUCCCUCACCGGUGCAAGUGAAGCCGUGGCUCUGC | 180-D1-012 |
| 34 | L-RNA | GCACGUCCCUCACCGGUGCAAGUGAAGCCGUGGCUCUGC | 180-D1-018 |
| 35 | L-RNA | CGCACGUCCCUCACCGGUGCAAGUGAAGCCGUGGCUCUGCGU | 180-D1-034 |
| 36 | L-RNA | CGCACGUCCCUCACCGGUGCAAGUGAAGCCGUGGCUCUGCG | 180-D1-035 |
| 37 | L-RNA | GCACGUCCCUCACCGGUGCAAGUGAAGCCGUGGCUCUGCG | 180-D1-036 = NOX-E36 |
| 38 | L-RNA | GUGCUGCGUAGUGGAAGACUACCUAAUGACAGCCGAAUGCUGGCAGCAC | 178-A8 |
| 39 | L-RNA | GUGCUGCGUAGUGGAAGACUACCUAAUGACAGCCUAAUGCUGGCAGCAC | 178-F7 |
| 40 | L-RNA | GUGCUGCGUAGUGGAAGACUACCUUAUGACAGCCGAAUGCUGGCAGCAC | 178-G7 |
| 41 | L-RNA | GUGCUGCGUAGUGAAAAACUACUGCCAGUGGGUCAGAGCUAGCAGCAC | 178-C6 |
| 42 | L-RNA | GUGCUGCGGAGUUAAAAACUCCCUAAGACAGGCCAGAGCCGGCAGCAC | 178-E7 |
| 43 | L-RNA | GUGCUGCGGAGUUGAAAACUCCCUAAGACAGGCCAGAGCCGGCAGCAC | 178-G6 |
| 44 | L-RNA | GUGCUGCGUAGUGGAAGACUACCUAAUGACAGCCUAAUGCUGGCAGCAC | 178-A7 |
| 45 | L-RNA | GUGCUGCGGAGUUAAAAACUCCCUAAGACAGGCUAGAGCCGGCAGCAC | 178-C7 |
| 46 | L-RNA | GUGCUGCGGCUGAAAAACGCCCUGCGACUGCCCUUUAUGCAGGCAGCAC | 178-E5 |
| 47 | L-RNA | GUGCUGCGUAGUGAAAAACUACCAACGACUGGCUAGAGCCGGCAGCAC | 181-F1 |
| 48 | L-RNA | GUGCUGCGUAGUGAAAGACUACCUGUGACAGCCGAAUGCUGGCAGCAC | 181-B2 |
| 49 | L-RNA | GUACUGCGUAGUUAAAAACUACCAACGACUGGCUAGAGCCGGCAGCAC | 181-C2 |
| 50 | L-RNA | GUGCUGCGUAGUUAAAAACUACCAACGACUGGCUAGAGCCGGCAGCAC | 178-A6 |
| 51 | L-RNA | GUGCUGCGUAGUUAAAAACUACCAGCGACAGGCUAGAGCCGGCAGCAC | 178-D6 |
| 52 | L-RNA | GUGCUGCGUAGUUAAAAACUACCAGCGACUGGCUAGAGCCGGCAGCAC | 178-D5 |
| 53 | L-RNA | GUGCUGCGUAGUGAGAAACUACCAACGACUGGCUAGAGCCGGCAGCAC | 181-A2 |
| 54 | L-RNA | GGCUGCGUAGUUAAAAACUACCAGCGACUGGCUAGAGCCGGCAGCC | 178-D5-020 |
| 55 | L-RNA | GGCGCGUAGUUAAAAACUACCAGCGACUGGCUAGAGCCGGCGCC | 178-D5-027 |
| 56 | L-RNA | GUGCGCGUAGUUAAAAACUACCAGCGACUGGCUAGAGCCGGCGCAC | 178-D5-030 |
| 57 | L-RNA | GUGCGCGUAGUGAGAAACUACCAACGACUGGCUAGAGCCGGCGCAC | 181-A2-002 |
| 58 | L-RNA | GUGCCGUAGUGAGAAACUACCAACGACUGGCUAGAGCCGGGCAC | 181-A2-004 |
| 59 | L-RNA | GUGGCGUAGUGAGAAACUACCAACGACUGGCUAGAGCCGGCCAC | 181-A2-005 |
| 60 | L-RNA | GUCGCGUAGUGAGAAACUACCAACGACUGGCUAGAGCCGGCGAC | 181-A2-006 |
| 61 | L-RNA | UGCGCGUAGUGAGAAACUACCAACGACUGGCUAGAGCCGGCGCA | 181-A2-007 |
| 62 | L-RNA | GCUGCGUAGUGAGAAACUACCAACGACUGGCUAGAGCCGGCAGC | 181-A2-008 |
| 63 | L-RNA | GCUGCGUAGUGAGAAACUACCAACGACUGGCUAGAGCCGGCAGC | 181-A2-011 |
| 64 | L-RNA | GGUGCGUAGUGAGAAACUACCAACGACUGGCUAGAGCCGGCACC | 181-A2-012 |
| 65 | L-RNA | UGGCGUAGUGAGAAACUACCAACGACUGGCUAGAGCCGGC-CA | 181-A2-015 |
| 66 | L-RNA | GCGCGUAGUGAGAAACUACCAACGACUGGCUAGAGCCGGCGC | 181-A2-016 |
| 67 | L-RNA | GUGCGUAGUGAGAAACUACCAACGACUGGCUAGAGCCGGCAC | 181-A2-017 |
| 68 | L-RNA | GG-GCGUAGUGAGAAACUACCAACGACUGGCUAGAGCCGGCCC | 181-A2-018 |

| Seq.-ID | RNA/Peptide | Sequence | Internal Reference |
|---|---|---|---|
| 69 | L-RNA | GAGCGUAGUGAGAAACUACCAACGACUGGCUAGAGCCGGCUC | 181-A2-019 |
| 70 | L-RNA | CGGCGUAGUGAGAAACUACCAACGACUGGCUAGAGCCGGCCG | 181-A2-020 |
| 71 | L-RNA | CCGCGUAGUGAGAAACUACCAACGACUGGCUAGAGCCGGCGG | 181-A2-021 |
| 72 | L-RNA | CAGCGUAGUGAGAAACUACCAACGACUGGCUAGAGCCGGCUG | 181-A2-022 |
| 73 | L-RNA | CUGCGUAGUGAGAAACUACCAACGACUGGCUAGAGCCGGCAG | 181-A2-023 |
| 74 | L-RNA | AGCGUGUUAGUGAAGUGGGUGGCAGGUAAAGGACACGCU | 184-B8trc |
| 75 | L-RNA | AGCGUGGUAGCGGUGUGGGUGGUAGGUAAAGGCCACGCU | 184-C6trc |
| 76 | L-RNA | AGCGUGAUAGAAGAGCGGGUGGUAGGUAAAGGUCAGGCU | 184-H5trc |
| 77 | L-RNA | AGCGUGUUAGGUAGGGUGGUAGUAAGUAAAGGACACGCU | 184-A7trc |
| 78 | L-RNA | AGCGUGUUAGGUGGGUGGUAGUAAGUAAAGGACACGCU | 187-A5trc |
| 79 | L-RNA | AGCGUGUUAGGUGGGUGGUAGUAAGUAAAGGGCACGCU | 187-H5trc |
| 80 | L-RNA | CCGCUUAGGUGGGUGGUAGUAAGUAAAGGGCGG | 174-D4-004 |
| 81 | L-RNA | GCGCGAGCAGGUGGGUGGUAGAAUGUAAAGACUCGCGUC | 166-A4-002 |
| 82 | L-RNA | CGUGUUAGGUGGGUGGUAGUAAGUAAAGGACACG | 187-A5trc-001 |
| 83 | L-RNA | GUGUUAGGUGGGUGGUAGUAAGUAAAGGACAC | 187-A5trc-002 |
| 84 | L-RNA | CGUGUUAGGUGGGUGGUAGUAAGUAAAGGGCACG | 187-H5trc-002 |
| 85 | L-RNA | GUGUUAGGUGGGUGGUAGUAAGUAAAGGGCAC | 187-H5trc-003 |
| 86 | L-RNA | UGUUAGGUGGGUGGUAGUAAGUAAAGGGCA | 187-H5trc-004 |
| 87 | L-RNA | GGACGAGAGUGACAAAUGAUAUAACCUCCUGACUAACGCUGCGGGCGACAGG | 177-B3 |
| 88 | L-RNA | GGACCUAUCGCUAAGACAACGCGCAGUCUACGGGACAUUCUCCGCGGACAGG | 177-C1 |
| 89 | L-RNA | GGACAAUUGUUACCCCCGAGAGAGACAAAUGAGACAACCUCCUGAAGACAGG | 177-C2 |
| 90 | L-RNA | GGACGAAAGUGAGAAAUGAUACAACCUCCUGUUGCUGCGAAUCCGGACAGG | 177-E3 |
| 91 | L-RNA | GGACGUAAAAGACGCUACCCGAAAGAAUGUCAGGAGGGUAGACCGACAGG | 177-D1 |
| 92 | L-RNA | GGACUAGAAACUACAAUAGCGGCCAGUUGCACCGCGUUAUCAACGACAGG | 177-E1 |
| 93 | L-RNA | GGACUAGUCAGCCAGUGUGUAUAUCGGACGCGGGUUUAUUUACUGACAGG | 177-A1 |
| 94 | L-RNA | GGACUGUCCGGAGUGUGAAACUCCCCGAGACCGCCAGAAGCGGGACAGG | 177-G3 |
| 95 | L-RNA | GGACUUCUAUCCAGGUGGGUGGUAGUAUGUAAAGAGAUAGAAGUGACAGG | 177-C3 |
| 96 | L-RNA | GGACGAGAGCGAACAAUGAUAUAACCUCCUGACGGAAAGAGAUCGACAGG | 177-A2 |
| 97 | L-RNA | CCUGUGCUACACGCAGUAAGAAGUGAACGUUCAGUAUGUGUGCACAGG | 170-E4trc |
| 98 | L-RNA | CGUGAGCCAGGCACCGAGGGCGUUAACUGGCUGAUUGGACACGACACG | 166-D2trc |
| 99 | L-RNA | CGUGAACAUGCAAGCUAAGCGGGGCUGUUGGUUGCUUGGCCCGCCACG | 174-A2trc |
| 100 | L-RNA | CGUGCAGAGAGACCAACCACGUAAAAUCAACCUAAUGGGCCGCACG | 174-E2trc |
| 101 | L-RNA | CGUGCAGAGAGACCAACCACGUAAAAUCAACCUAAUGGGCCGCACG | 183-G3trc |
| 102 | L-RNA | CGUGAACAUUCAAGCUAAGCGGGGCUGUUGGUUGCUUGGCCCGCCACG | 183-B2trc |
| 103 | L-RNA | CGUGCCGAGGCGGCGACCAGCGUUACUUAGAGAGGCUUUGGCACCACG | 166-B2trc |
| 104 | L-RNA | CGUGAUAACAGCCGUCGGUCAAGAAAACAAAGUUCGGGCGGCGCACG | 166-G3trc |
| 105 | L-RNA | CGUGGGUGGCGCACCGAGGGCGAAAAGCCACCAGUAAAGAUAGACCG | 166-D1trc |
| 106 | L-RNA | CGUGUGAUCUCCUUUGGGGUGAUUAGCUUAGAGACUUCCCACACG | 183-H2trc |

-continued

| Seq.-ID | RNA/Peptide | Sequence | Internal Reference |
|---|---|---|---|
| 107 | L-RNA | GCACCUUCGCCUAAUACACGUGCCGGCUAGCUAAUACUCGUCCGC | 167-A7trc |
| 108 | L-RNA | GCACGACUUGGGCGACCAGUGAUACUUAGAGAGCAAGUCGUCGG | 167-C7trc |
| 109 | L-RNA | GCGCGCGCUCAGUAAGAAAUUGAAAGUUCAGAAUGUCGUCGCGC | 167-B5trc |
| 110 | L-RNA | AGUGUGUGGCAGGCUAAGGAGAUAUUCCGAGACCACGCU | 184-D7trc |
| 111 | L-RNA | AGUGUGUGGCAGACUAUGGAUAGACUCCGAGACCACGCU | 184-D6trc |
| 112 | L-RNA | AGCGUGAGGCGACCAGCGGAUUACUUAGAGAGUCACGCU | 184-E5trc |
| 113 | L-RNA | AGCGUGAAGGGGACCAGCGUUACUUACAGAGUUCACGCU | 184-G6trc |
| 114 | L-RNA | AGCGUGUGAUGUAUGUAGCACCGUAUCAGAGGACACGCU | 184-B7trc |
| 115 | L-RNA | AGCGUGAGGCGACCCGUGUUUCGUAGAGAGUCACGCU | 184-B6trc |
| 116 | L-RNA | 5'PEG-GCACGUCCCUCACCGGUGCAAGUGAAGCCGUGGCUCUGCG | NOX-E36-5'PEG |
| 117 | L-RNA | GCACGUCCCUCACCGGUGCAAGUGAAGCCGUGGCUCUGCG-3'PEG | NOX-E36-3'PEG |
| 118 | L-RNA | GAGAUGGCGACAUUGGUUGGGCAUGAGGCGAGGCCCUUUGAUGAAUCCGCGGCCAUUC | 188-A3-001 |
| 119 | L-RNA | GAUGGCGACAUUGGUUGGGCAUGAGGCGAGGCCCUUUGAUGAAUCCGCGGCCAUUC | 188-A3-004 |
| 120 | L-RNA | GGCGACAUUGGUUGGGCAUGAGGCGAGGCCCUUUGAUGAAUCCGCGGCCAUUC | 188-A3-005 |
| 121 | L-RNA | GGCGACAUUGGUUGGGCAUGAGGCGAGGCCCUUUGAUGAAUCCGCGGCCAUU | 188-A3-006 |
| 122 | L-RNA | GGCGACAUUGGUUGGGCAUGAGGCGAGGCCCUUUGAUGAAUCCGCGGCCA | 188-A3-007 = mNOX-E36 |
| 123 | L-RNA | GCUGGUUACCGAGGGGGCGUCGUUGGAGUUUGGUUGGUUGUCACCAGC | 189-G7-001 |
| 124 | L-RNA | CUGGUUACCGAGGGGGCGUCGUUGGAGUUUGGUUGGUUGUCACCAG | 189-G7-002 |
| 125 | L-RNA | UGGUUACCGAGGGGGCGUCGUUGGAGUUUGGUUGGUUGUCACCA | 189-G7-003 |
| 126 | L-RNA | GCCGGUUACCGAGGGGGCGUCGUUGGAGUUUGGUUGGUUGUCACCGGC | 189-G7-007 |
| 127 | L-RNA | GCCGGCUACCGAGGGGGCGUCGUUGGAGUUUGGUUGGUUGUCGCCGGC | 189-G7-008 |
| 128 | L-RNA | GCGCGUACCGAGGGGGCGUCGUUGGAGUUUGGUUGGUUGUCCGCGC | 189-G7-010 |
| 129 | L-RNA | GGGCCUACCGAGGGGGCGUCGUUGGAGUUUGGUUGGUUGUCGGCCC | 189-G7-012 |
| 130 | D-protein | Biotin-QPDAINAPVTCCYNFTNRKISVQRLASYRRITSSKCPKEAVIFKTIVAKEICADPKQKWVQDSMDHLDKQTQTPKT | biotinylated human D-MCP-1 |
| 131 | D-protein | Biotin-QPDAVNAPLTCCYSFTSKMIPMSRLESYKRITSSRCPKEAVVFVTKLKREVCADPKKEWVQTYIKNLDRNQMRSEP-Biotin | biotinylated mouse D-MCP-1 |
| 132 | D-RNA | AGCGUGCCCGGAGUGGCAGGGGGACGCGACCUGCAAUAAUGCACGCU | 169-B1trc |
| 133 | D-RNA | AGCGUGCCCGGAGUGGCAGGGGGACGCGACCUGCAAUUGCACGCU | 169-F3trc |
| 134 | D-RNA | AGCGUGCCCGGAGUGGCAGGGGGACGCGACCUGUAAUAAUGCACGCU | 169-C1trc |
| 135 | D-RNA | AGCGUGCCCGGUGUGGCAGGGGGACGCGACCUGCAAUAAUGCGCGCU | 169-A3trc |
| 136 | D-RNA | AGCGUGCCCGGAGUAGCAGGGGGCGCGACCUGCAAUAAUGCACGCU | 169-B2trc |
| 137 | D-RNA | AGCGUGCCCGGUGUGGUAGGGGGCGCGAUCUACAAUUGCACGCU | 176-B12trc |
| 138 | D-RNA | AGCGUGCCCGGUGUGACAGGGGGCGCGACCUGCAUUUGCACGCU | 176-D9trc |
| 139 | D-RNA | AGCGUGCCCGGUGUGGCAGGGGGCGCGACCUGUAUUUGCACGCU | 176-B10trc |
| 140 | D-RNA | AGCGUGCCCGGAGUGGCAGGGGGCGCGACCUGCAAUAAUGCACGCU | 169-F2trc |
| 141 | D-RNA | AGCGUGCCCGGUGUGGCAGGGGGCGCGACCUGCAAUUGCACGCU | 176-B9trc |
| 142 | D-RNA | AGCAUGCCCGGUGUGGCAGGGGGCGCGACCUGCAUUUGCAUGCU | 176-H9trc |
| 143 | D-RNA | AGCGUGCCCGGUGUGGUAGGGGGCGCGACCUACAUUUGCACGCU | 176-E10trc |

-continued

| Seq.-ID | RNA/Peptide | Sequence | Internal Reference |
|---|---|---|---|
| 144 | D-RNA | AGUGUGCCAGCUGUGAUGGGGGGGCGCGACCCAUUUUACACACU | 176-G9trc |
| 145 | D-RNA | AGUGUGCCAGCGUGAUGGGGGGGCGCGACCCAUUUUACACACU | 176-F9trc |
| 146 | D-RNA | AGUGUGCGAGCGUGAUGGGGGGGCGCGACCCAUUUUACAUACU | 176-C11trc |
| 147 | D-RNA | AGUGUGCCAGCGUGAUGGGGGGGCGCGACCCAUUUUACAUACU | 176-E11trc |
| 148 | D-RNA | AGUAUGCCAGCGUGAUGGGGGGGCGCGACCCAUUUUACAUACU | 176-D10trc |
| 149 | D-RNA | AGUGUGCCAGUGUGAUGGGGGGGCGCGACCCAUUUUACACACU | 176-H10trc |
| 150 | D-RNA | AGCGUGCCAGUGUGAUGGGGGGGCGCGACCCAUUUUACACGCU | 176-C9trc |
| 151 | D-RNA | ACGCACGUCCCUCACCGGUGCAAGUGAAGCCGCGGCUCUGCGU | 180-81-001 |
| 152 | D-RNA | ACGCACCUCCCUCACCGGUGCAAGUGAAGCCGUGGCUCUGCGC | 180-A4-002 |
| 153 | D-RNA | ACGCACGUCCCUCACCGGUGCAAGUGAAGCCGUGGCUCUGCGU | 180-D1-002 |
| 154 | D-RNA | GCACGUCCCUCACCGGUGCAAGUGAAGCCGUGGCUCUGCGU | 180-D1-011 |
| 155 | D-RNA | ACGCACGUCCCUCACCGGUGCAAGUGAAGCCGUGGCUCUGC | 180-D1-012 |
| 156 | D-RNA | GCACGUCCCUCACCGGUGCAAGUGAAGCCGUGGCUCUGC | 180-D1-018 |
| 157 | D-RNA | CGCACGUCCCUCACCGGUGCAAGUGAAGCCGUGGCUCUGCGU | 180-D1-034 |
| 158 | D-RNA | CGCACGUCCCUCACCGGUGCAAGUGAAGCCGUGGCUCUGCG | 180-D1-035 |
| 159 | D-RNA | GCACGUCCCUCACCGGUGCAAGUGAAGCCGUGGCUCUGCG | (D-)180-D1-036, (D-)NOX-E36 |
| 160 | D-RNA | GUGCUGCGUAGUGGAAGACUACCUAAUGACAGCCGAAUGCUGGCAGCAC | 178-A8 |
| 161 | D-RNA | GUGCUGCGUAGUGGAAGACUACCUAAUGACAGCCUAAUGCUGGCAGCAC | 178-F7 |
| 162 | D-RNA | GUGCUGCGUAGUGGAAGACUACCUUAUGACAGCCGAAUGCUGGCAGCAC | 178-G7 |
| 163 | D-RNA | GUGCUGCGUAGUGAAAAACUACUGCCAGUGGGUCAGAGCUAGCAGCAC | 178-C6 |
| 164 | D-RNA | GUGCUGCGGAGUUAAAAACUCCCUAAGACAGGCCAGAGCCGGCAGCAC | 178-E7 |
| 165 | D-RNA | GUGCUGCGGAGUUGAAAAACUCCCUAAGACAGGCCAGAGCCGGCAGCAC | 178-G6 |
| 166 | D-RNA | GUGCUGCGUAGUGGAAGACUACCUAUGACAGCCUAAUGCUGGCAGCAC | 178-A7 |
| 167 | D-RNA | GUGCUGCGGAGUUAAAAACUCCCUAAGACAGGCUAGAGCCGGCAGCAC | 178-C7 |
| 168 | D-RNA | GUGCUGCGGCGUGAAAAACGCCCUGCGACUGCCCUUUAUGCAGGCAGCAC | 178-E5 |
| 169 | D-RNA | GUGCUGCGUAGUGAAAAACUACCAACGACUGGCUAGAGCCGGCAGCAC | 181-F1 |
| 170 | D-RNA | GUGCUGCGUAGUGAAAGACUACCUGUGACAGCCGAAUGCUGGCAGCAC | 181-B2 |
| 171 | D-RNA | GUACUGCGUAGUUAAAAACUACCAACGACUGGCUAGAGCCGGCAGCAC | 181-C2 |
| 172 | D-RNA | GUGCUGCGUAGUUAAAAACUACCAACGACUGGCUAGAGCCGGCAGCAC | 178-A6 |
| 173 | D-RNA | GUGCUGCGUAGUUAAAAACUACCAGCGACAGGCUAGAGCCGGCAGCAC | 178-D6 |
| 174 | D-RNA | GUGCUGCGUAGUUAAAAACUACCAGCGACUGGCUAGAGCCGGCAGCAC | 178-D5 |
| 175 | D-RNA | GUGCUGCGUAGUGAGAAACUACCAACGACUGGCUAGAGCCGGCAGCAC | 181-A2 |
| 176 | D-RNA | GGCUGCGUAGUUAAAAACUACCAGCGACUGGCUAGAGCCGGCAGCC | 178-D5-020 |
| 177 | D-RNA | GGCGCGUAGUUAAAAACUACCAGCGACUGGCUAGAGCCGGCGCC | 178-D5-027 |
| 178 | D-RNA | GUGCGCGUAGUUAAAAACUACCAGCGACUGGCUAGAGCCGGCGCAC | 178-D5-030 |
| 179 | D-RNA | GUGCGCGUAGUGAGAAACUACCAACGACUGGCUAGAGCCGGCGCAC | 181-A2-002 |
| 180 | D-RNA | GUGCCGUAGUGAGAAACUACCAACGACUGGCUAGAGCCGGGCAC | 181-A2-004 |
| 181 | D-RNA | GUGGCGUAGUGAGAAACUACCAACGACUGGCUAGAGCCGGCCAC | 181-A2-005 |

-continued

| Seq.-ID | RNA/Peptide | Sequence | Internal Reference |
|---|---|---|---|
| 182 | D-RNA | GUCGCGUAGUGAGAAACUACCAACGACUGGCUAGAGCCGGCGAC | 181-A2-006 |
| 183 | D-RNA | UGCGCGUAGUGAGAAACUACCAACGACUGGCUAGAGCCGGCGCA | 181-A2-007 |
| 184 | D-RNA | GCUGCGUAGUGAGAAACUACCAACGACUGGCUAGAGCCGGCAGC | 181-A2-008 |
| 185 | D-RNA | GCUGCGUAGUGAGAAACUACCAACGACUGGCUAGAGCCGGCAGC | 181-A2-011 |
| 186 | D-RNA | GGUGCGUAGUGAGAAACUACCAACGACUGGCUAGAGCCGGCACC | 181-A2-012 |
| 187 | D-RNA | UGGCGUAGUGAGAAACUACCAACGACUGGCUAGAGCCGGC-CA | 181-A2-015 |
| 188 | D-RNA | GCGCGUAGUGAGAAACUACCAACGACUGGCUAGAGCCGGCGC | 181-A2-016 |
| 189 | D-RNA | GUGCGUAGUGAGAAACUACCAACGACUGGCUAGAGCCGGCAC | 181-A2-017 |
| 190 | D-RNA | GG-GCGUAGUGAGAAACUACCAACGACUGGCUAGAGCCGGCCC | 181-A2-018 |
| 191 | D-RNA | GAGCGUAGUGAGAAACUACCAACGACUGGCUAGAGCCGGCUC | 181-A2-019 |
| 192 | D-RNA | CGGCGUAGUGAGAAACUACCAACGACUGGCUAGAGCCGGCCG | 181-A2-020 |
| 193 | D-RNA | CCGCGUAGUGAGAAACUACCAACGACUGGCUAGAGCCGGCGG | 181-A2-021 |
| 194 | D-RNA | CAGCGUAGUGAGAAACUACCAACGACUGGCUAGAGCCGGCUG | 181-A2-022 |
| 195 | D-RNA | CUGCGUAGUGAGAAACUACCAACGACUGGCUAGAGCCGGCAG | 181-A2-023 |
| 196 | D-RNA | AGCGUGUUAGUGAAGUGGGUGGCAGGUAAAGGACACGCU | 184-B8trc |
| 197 | D-RNA | AGCGUGGUAGCGGUGUGGGUGGUAGGUAAAGGCCACGCU | 184-C6trc |
| 198 | D-RNA | AGCGUGAUAGAAGAGCGGGUGGUAGGUAAAGGUCAGGCU | 184-H5trc |
| 199 | D-RNA | AGCGUGUUAGGUAGGGUGGUAGUAAGUAAAGGACACGCU | 184-A7trc |
| 200 | D-RNA | AGCGUGUUAGGUGGGUGGUAGUAAGUAAAGGACACGCU | 187-A5trc |
| 201 | D-RNA | AGCGUGUUAGGUGGGUGGUAGUAAGUAAAGGGCACGCU | 187-H5trc |
| 202 | D-RNA | CCGCUUAGGUGGGUGGUAGUAAGUAAAGGGCGG | 174-D4-004 |
| 203 | D-RNA | GCGCGAGCAGGUGGGUGGUAGAAUGUAAAGACUCGCGUC | 166-A4-002 |
| 204 | D-RNA | CGUGUUAGGUGGGUGGUAGUAAGUAAAGGACACG | 187-A5trc-001 |
| 205 | D-RNA | GUGUUAGGUGGGUGGUAGUAAGUAAAGGACAC | 187-A5trc-002 |
| 206 | D-RNA | CGUGUUAGGUGGGUGGUAGUAAGUAAAGGGCACG | 187-H5trc-002 |
| 207 | D-RNA | GUGUUAGGUGGGUGGUAGUAAGUAAAGGGCAC | 187-H5trc-003 |
| 208 | D-RNA | UGUUAGGUGGGUGGUAGUAAGUAAAGGGCA | 187-H5trc-004 |
| 209 | D-RNA | GGACGAGAGUGACAAAUGAUAUAACCUCCUGACUAACGCUGCGGGCGACAGG | 177-B3 |
| 210 | D-RNA | GGACCUAUCGCUAAGACAACGCGCAGUCUACGGGACAUUCUCCGCGGACAGG | 177-C1 |
| 211 | D-RNA | GGACAAUUGUUACCCCCGAGAGAGACAAAUGAGACAACCUCCUGAAGACAGG | 177-C2 |
| 212 | D-RNA | GGACGAAAGUGAAAUGAUACAACCUCCUGUUGCUGCGAAUCCGGACAGG | 177-E3 |
| 213 | D-RNA | GGACGUAAAGACGCUACCCGAAAGAAUGUCAGGAGGGUAGACCGACAGG | 177-D1 |
| 214 | D-RNA | GGACUAGAAACUACAAUAGCGGCCAGUUGCACCGCGUUAUCAACGACAGG | 177-E1 |
| 215 | D-RNA | GGACUAGUCAGCCAGUGUGUAUAUCGGACGCGGGUUUAUUUACUGACAGG | 177-A1 |
| 216 | D-RNA | GGACUGUCCGGAGUGUGAAACUCCCCGAGACCGCCAGAAGCGGGGACAGG | 177-G3 |
| 217 | D-RNA | GGACUUCUAUCCAGGUGGGUGGUAGUAUGUAAAGAGAUAGAAGUGACAGG | 177-C3 |
| 218 | D-RNA | GGACGAGAGCGAACAAUGAUAUAACCUCCUGACGGAAAGAGAUCGACAGG | 177-A2 |
| 219 | D-RNA | CCUGUGCUACACGCAGUAAGAAGUGAACGUUCAGUAUGUGUGCACAGG | 170-E4trc |

-continued

| Seq.-ID | RNA/Peptide | Sequence | Internal Reference |
|---|---|---|---|
| 220 | D-RNA | CGUGAGCCAGGCACCGAGGGCGUUAACUGGCUGAUUGGACACGACACG | 166-D2trc |
| 221 | D-RNA | CGUGAACAUGCAAGCUAAGCGGGGCUGUUGGUUGCUUGGCCCGCCACG | 174-A2trc |
| 222 | D-RNA | CGUGCAGAGAGAGACCAACCACGUAAAAUCAACCUAAUGGGCCGCACG | 174-E2trc |
| 223 | D-RNA | CGUGCAGAGAGAGACCAACCACGUAAAAUCAACCUAAUGGGCCGCACG | 183-G3trc |
| 224 | D-RNA | CGUGAACAUUCAAGCUAAGCGGGGCUGUUGGUUGCUUGGCCCGCCACG | 183-B2trc |
| 225 | D-RNA | CGUGCCGAGGCGGCGACCAGCGUUACUUAGAGAGGCUUUGGCACCACG | 166-B2trc |
| 226 | D-RNA | CGUGAUAACAGCCGUCGGUCAAGAAAACAAAGUUCGGGCGGCGCACG | 166-G3trc |
| 227 | D-RNA | CGUGGGUGGCGCACCGAGGGCGAAAAGCCACCAGUAAAGAUAGACCG | 166-D1trc |
| 228 | D-RNA | CGUGUGAUCUCCUUUGGGGUGAUUAGCUUAGAGACUUCCCACACG | 183-H2trc |
| 229 | D-RNA | GCACCUUCGCCUAAUACACGUGCCGGCUAGCUAAUACUCGUCCGC | 167-A7trc |
| 230 | D-RNA | GCACGACUUGGGCGACCAGUGAUACUUAGAGAGCAAGUCGUCGGC | 167-C7trc |
| 231 | D-RNA | GCGCGCGCUCAGUAAGAAAUUGAAAGUUCAGAAUGUCGUCGCGC | 167-B5trc |
| 232 | D-RNA | AGUGUGUGGCAGGCUAAGGAGAUAUUCCGAGACCACGCU | 184-D7trc |
| 233 | D-RNA | AGUGUGUGGCAGACUAUGGAUAGACUCCGAGACCACGCU | 184-D6trc |
| 234 | D-RNA | AGCGUGAGGCGACCAGCGGAUUACUUAGAGAGUCACGCU | 184-E5trc |
| 235 | D-RNA | AGCGUGAAGGGGACCAGCGUUACUUACAGAGUUCACGCU | 184-G6trc |
| 236 | D-RNA | AGCGUGUGAUGUAUGUAGCACCGUAUCAGAGGACACGCU | 184-B7trc |
| 237 | D-RNA | AGCGUGAGGCGACCCGUGUUUCGUAGAGAGUCACGCU | 184-B6trc |
| 238 | D-RNA | 5'PEG-GCACGUCCCUCACCGGUGCAAGUGAAGCCGUGGCUCUGCG | NOX-E36-5'PEG |
| 239 | D-RNA | GCACGUCCCUCACCGGUGCAAGUGAAGCCGUGGCUCUGCG-3'PEG | NOX-E36-3'PEG |
| 240 | D-RNA | GAGAUGGCGACAUUGGUUGGGCAUGAGGCGAGGCCCUUUGAUGAAUCCGCGGCCAUUC | 188-A3-001 |
| 241 | D-RNA | GAUGGCGACAUUGGUUGGGCAUGAGGCGAGGCCCUUUGAUGAAUCCGCGGCCAUUC | 188-A3-004 |
| 242 | D-RNA | GGCGACAUUGGUUGGGCAUGAGGCGAGGCCCUUUGAUGAAUCCGCGGCCAUUC | 188-A3-005 |
| 243 | D-RNA | GGCGACAUUGGUUGGGCAUGAGGCGAGGCCCUUUGAUGAAUCCGCGGCCAUU | 188-A3-006 |
| 244 | D-RNA | GGCGACAUUGGUUGGGCAUGAGGCGAGGCCCUUUGAUGAAUCCGCGGCCA | (D-)188-A3-007 = (D-)mNOX-E36 |
| 245 | D-RNA | GCUGGUUACCGAGGGGGCGUCGUUGGAGUUUGGUUGGUUGUCACCAGC | 189-G7-001 |
| 246 | D-RNA | CUGGUUACCGAGGGGGCGUCGUUGGAGUUUGGUUGGUUGUCACCAG | 189-G7-002 |
| 247 | D-RNA | UGGUUACCGAGGGGGCGUCGUUGGAGUUUGGUUGGUUGUCACCA | 189-G7-003 |
| 248 | D-RNA | GCCGGUUACCGAGGGGGCGUCGUUGGAGUUUGGUUGGUUGUCACCGGC | 189-G7-007 |
| 249 | D-RNA | GCCGGCUACCGAGGGGGCGUCGUUGGAGUUUGGUUGGUUGUCGCCGGC | 189-G7-008 |
| 250 | D-RNA | GCGCGUACCGAGGGGGCGUCGUUGGAGUUUGGUUGGUUGUCCGCGC | 189-G7-010 |
| 251 | D-RNA | GGGCCUACCGAGGGGGCGUCGUUGGAGUUUGGUUGGUUGUCGGCCC | 189-G7-012 |
| 252 | L-protein | QPDAVNAPLTCCYSFTGKMIPMSRLENYKRITSSRCPKEAVVFVTKLKREICAD PNKEWVQKYIRKLDQNQVRSET | rat MCP-1 |
| 253 | L-RNA | 5'PEG-GGCGACAUUGGUUGGGCAUGAGGCGAGGCCCUUUGAUGAAUCCGCGGCCA | mNOX-E36-5'PEG |
| 254 | L-RNA | GGCGACAUUGGUUGGGCAUGAGGCGAGGCCCUUUGAUGAAUCCGCGGCCA-3'PEG | mNOX-E36-3'PEG |
| 255 | L-DNA | 5'-GAGGGACGTGC-(Spacer18)$_2$-NH$_4^+$-3' | NOX-E36 Capture probe |
| 256 | L-DNA | 5'-Biotin-(Spacer18)$_2$-CGCAGAGCC | NOX-E36 Detect (-ion) probe |

-continued

| Seq.-ID | RNA/Peptide | Sequence | Internal Reference |
|---|---|---|---|
| 257 | L-Protein | KSMQVPFSRCCFSFAEQEIPLRAILCYRNTSSICSNEGLIFKLKRGKEACALDTVGWVQRHRKMLRHCPSKRK | CCL1/I-309 |
| 258 | L-Protein | SLAADTPTACCFSYTSRQIPQNFIADYFETSSQCSKPGVIFLTKRSRQVCADPSEEWVQKYVSDLELSA | CCL3/MIP-1α |
| 259 | L-Protein | APMGSDPPTACCFSYTARKLPRNFVVDYYETSSLCSQPAVVFQTKRSKQVCADPSESWVQEYVYDLELN | CCL4/MIP-1β |
| 260 | L-Protein | SPYSSDTTPCCFAYIARPLPRAHIKEYFYTSGKCSNPAVVFVTRKNRQVCANPEKKWVREYINSLEMS | CCL5/RANTES |
| 261 | L-Protein | FNPQGLAQPDALNVPSTCCFTFSSKKISLQRLKSYVITTSRCPQKAVIFRTKLGKEICADPKEKWVQNYMKHLGRKAHTLKT | CCL13/MCP-4 |
| 262 | L-Protein | TKTESSSRGPYHPSECCFTYTTYKIPRQRIMDYYETNSQCSKPGIVFITKRGHSVCTNPSDKWVQDYIKDMKEN | CCL14/HCC-1 |
| 263 | L-Protein | ASVATELRCQCLQTLQGIHPKNIQSVNVKSPGPHCAQTEVIATLKNGRKACLNPASPIVKKIIEKMLNSDKSN | CXCL1/GROα |
| 264 | L-Protein | APLATELRCQCLQTLQGIHLKNIQSVKVKSPGPHCAQTEVIATLKNGQKACLNPASPMVKKIIEKMLKNGKSN | CXCL2/GROβ |
| 265 | L-Protein | ASVVTELRCQCLQTLQGIHLKNIQSVNVRSPGPHCAQTEVIATLKNGKKACLNPASPMVQKIIEKILNKGSTN | CXCL3/GROγ |
| 266 | L-Protein | EAEEDGDLQCLCVKTTSQVRPRHITSLEVIKAGPHCPTAQLIATLKNGRKICLDLQAPLYKKIIKKLLES | CXCL4/PF4 |
| 267 | L-Protein | GPAAAVLRELRCVCLQTTQGVHPKMISNLQVFAIGPQCSKVEVVASLKNGKEICLDPEAPFLKKVIQKILDGGNKEN | CXCL5/ENA-78 |
| 268 | L-Protein | GPVSAVLTELRCTCLRVTLRVNPKTIGKLQVFPAGPQCSKVEVVASLKNGKQVCLDPEAPFLKKVIQKILDSGNKKN | CXCL6/GCP-2 |
| 269 | L-Protein | SSTKGQTKRNLAKGKEESLDSDLYAELRCMCIKTTSGIHPKNIQSLEVIGKGTHCNQVEVIATLKDGRKICLDPDAPRIKKIVQKKLAGDESAD | CXCL7/NAP-2 |
| 270 | L-Protein | EGAVLPRSAKELRCQCIKTYSKPFHPKFIKELRVIESGPHCANTEIIVKLSDGRELCLDPKENWVQRVVEKFLKRAENS | CXCL8/IL-8 |
| 271 | L-Protein | TPVVRKGRCSCISTNQGTIHLQSLKDLKQFAFSPSCEKIEIIATLKNGWICLNPDSADVKELIKKWEKQVSQKKKQKNGKKHQKKKVLKVRKSQRSRQKKTT | CXCL9/MIG |
| 272 | L-Protein | VPLSRTVRCTCISISNQPVNPRSLEKLEIIPASQFCPRVEIIATMKKKGEKRCLNPESKAIKNLLKAVSKERSKRSP | CXCL10/IP-10 |
| 273 | L-Protein | FPMFKRGRCLCIGPGVKAVKVADIEKASIMYPSNNCDKIEVIITLKENKGQRCLNPKSKQARLIIKKVERKNF | CXCL11/I-TAC |
| 274 | L-Protein | KPVSLSYRCPCRFFESHVARANVKHLKILNTPNCALQIVARLKNNNRQVCIDPKLKWIQEYLEKALNKRFKM | CXCL12α/SDF-1α |
| 275 | L-Protein | KPVSLSYRCPCRFFESHVARANVKHLKILNTPNCALQIVARLKNNNRQVCIDPKLKWIQEYLEKALNKRFKM | CXCL12β/SDF-1β |
| 276 | L-Protein | QHHGVTKCNITCSKMTSKIPVALLIHYQQNQASCGKRAIILETRQHRLFCADPKEQWVKDAMQHLDRQAAALTRNG | CX$_3$CL1/Fractalkine |
| 277 | L-Protein | VGSEVSDKRTCVSLTTQRLPVSRIKTYTITEGSLRAVIFITKRGLKVCADPQATWVRDVVRSMDRKSNTRNNMIQTKPTGTQQSTNTAVTLTG | XCL1/Lymphotactin |
| 278 | L-RNA | 5'-Biotin-GCACGUCCCUCACCGGUGCAAGUGAAGCCGUGGCUCUGCG | biotinylated NOX-E36 |
| 279 | L-RNA | 5'-UAAGGAAACUCGGUCUGAUGCGGU AGCGCUGUGCAGAGCU | POC |
| 280 | L-RNA | 5'-PEG-UAAGGAAACUCGGUCUGAUGCGGU AGCGCUGUGCAGAGCU-3' | POC-PEG |
| 281 | L-DNA | 5'-CCAATGTCGCC-(Spacer18)$_2$-NH$_4^+$-3' | mNOX-E36 Capture probe |
| 282 | L-DNA | 5'-Biotin-(Spacer18)$_2$-CGCAGAGCC | mNOX-E36 Detect (-ion) probe |

-continued

| Seq.-ID | RNA/Peptide | Sequence | Internal Reference |
|---|---|---|---|
| 283 | L-protein | QPDAINSPVTCCYTFTGKKISSQRLGSYKRVTSSKCPKEAVIFKTILAKEIC ADPEQKWVQDAVKQLDKKAQTPKP | horse MCP-1 (Equus caballus) |
| 284 | L-protein | QPDAINSQVACCYTFNSKKISMQRLMNYRRVTSSKCPKEAVIFKTILGKELC ADPKQKWVQDSINYLNKKNQTPKP | bovine MCP-1 (Bos Taurus) |
| 285 | L-protein | QPDAVNAPLTCCYSFTGKMIPMSRLENYKRITSSRCPKEAVVFVTKLKREIC ADPNKEWVQKYIRKLDQNQVRSETTVFYKIASTLRTSAPLNVNLTHKSEANA STLFSTTTSSTSVEVTSMTEN | rat MCP-1 (Rattus norvegicus) |

The present invention is further illustrated by the figures, examples and the sequence listing from which further features, embodiments and advantages may be taken wherein FIG. 1 shows an alignment of sequences of related RNA ligands binding to human MCP-1 indicating the sequence motif ("Type 1A") that is in a preferred embodiment in its entirety essential for binding to human MCP-1 (L-RNA sequences as SEQ ID NOs: 10-21, respectively, in order of appearance, and the corresponding D-RNA sequences as SEQ ID NOs: 132-143, respectively);

FIG. 2 shows an alignment of sequences of related RNA ligands binding to human MCP-1 indicating the sequence motif ("Type 1B") that is in a preferred embodiment in its entirety essential for binding to human MCP-1 and derivatives of RNA ligands 180-D1-002 (L-RNA sequences as SEQ ID NOs:22-28, respectively, in order of appearance, and the corresponding D-RNA sequences as SEQ ID NOs: 144-150, respectively);

FIG. 3 shows an alignment of sequences of related RNA ligands binding to human MCP-1 indicating the sequence motif ("Type 2") that is in a preferred embodiment in its entirety essential for binding to human MCP-1 (L-RNA sequences as SEQ ID NOs:29-37, respectively, in order of appearance, and the corresponding D-RNA sequences as SEQ ID NOs: 151-159, respectively);

FIG. 4 shows an alignment of sequences of related RNA ligands binding to human MCP-1 indicating the sequence motif ("Type 3") that is in a preferred embodiment in its entirety essential for binding to human MCP-1 (L-RNA sequences as SEQ ID NOs:38-53, respectively, in order of appearance, and the corresponding D-RNA sequences as SEQ ID NOs:160-175, respectively);

FIG. 5 shows derivatives of RNA ligands 178-D5 and 181-A2 (human MCP-1 RNA ligands of sequence motif "Type 3") (L-RNA sequences as SEQ ID NOs:54-56, 53, 57-73, respectively, in order of appearance, and the corresponding D-RNA sequences as SEQ NOs: 176-178, 175, 179-195, respectively);

Figure 6:
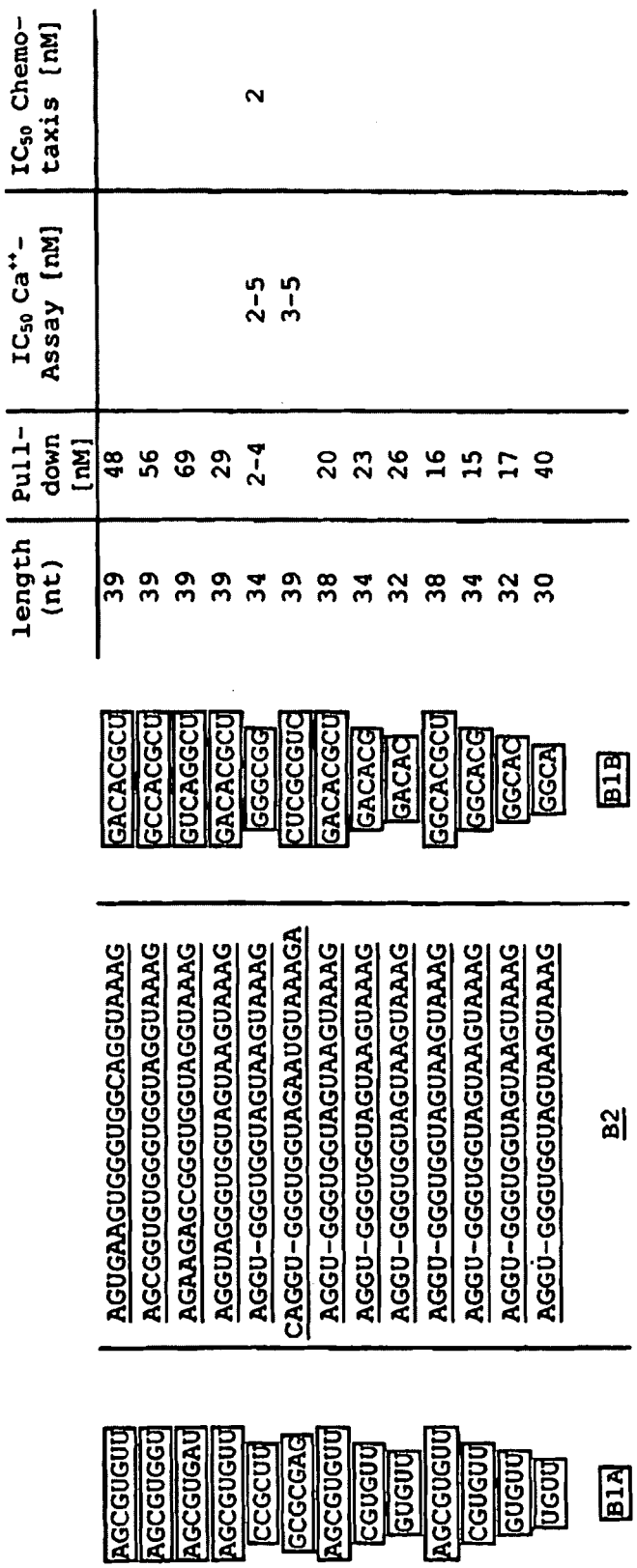
Figure 9:
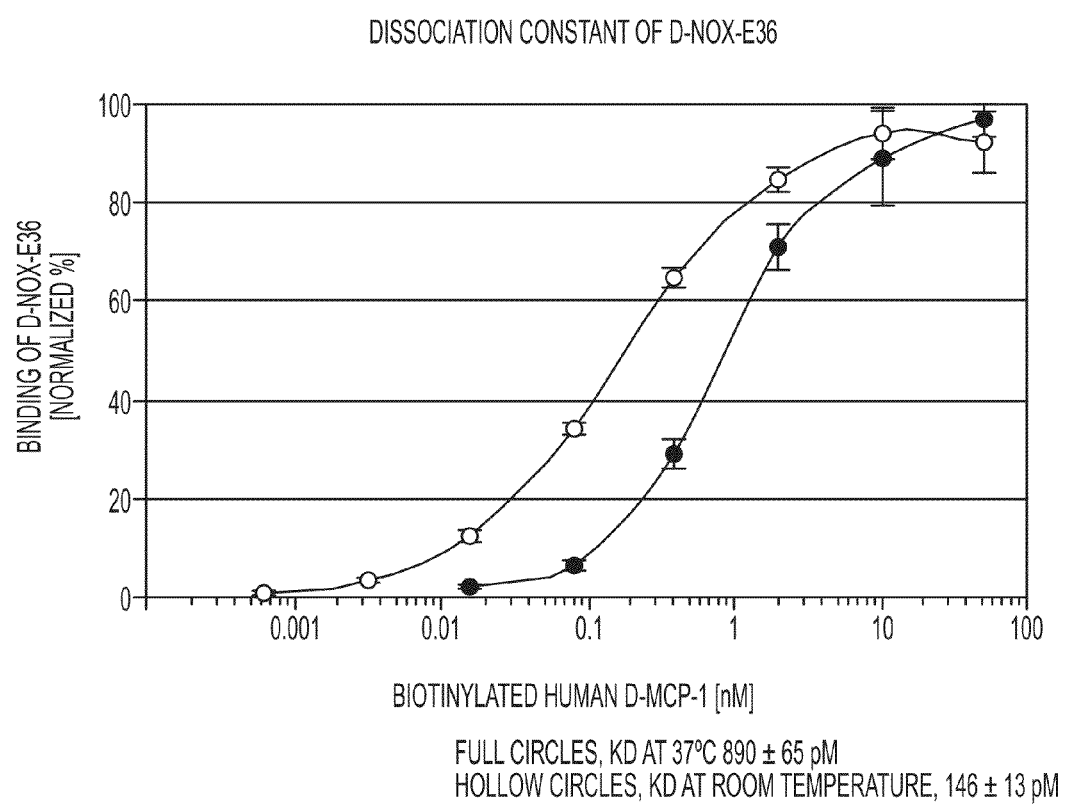
Figure 10:
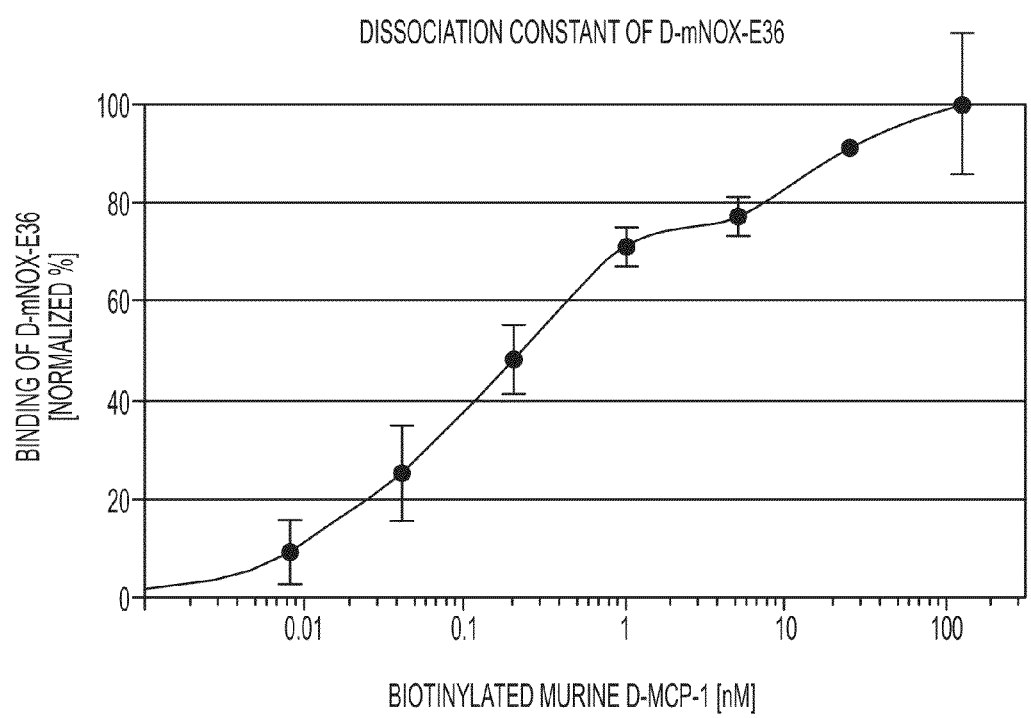
Figure 11:
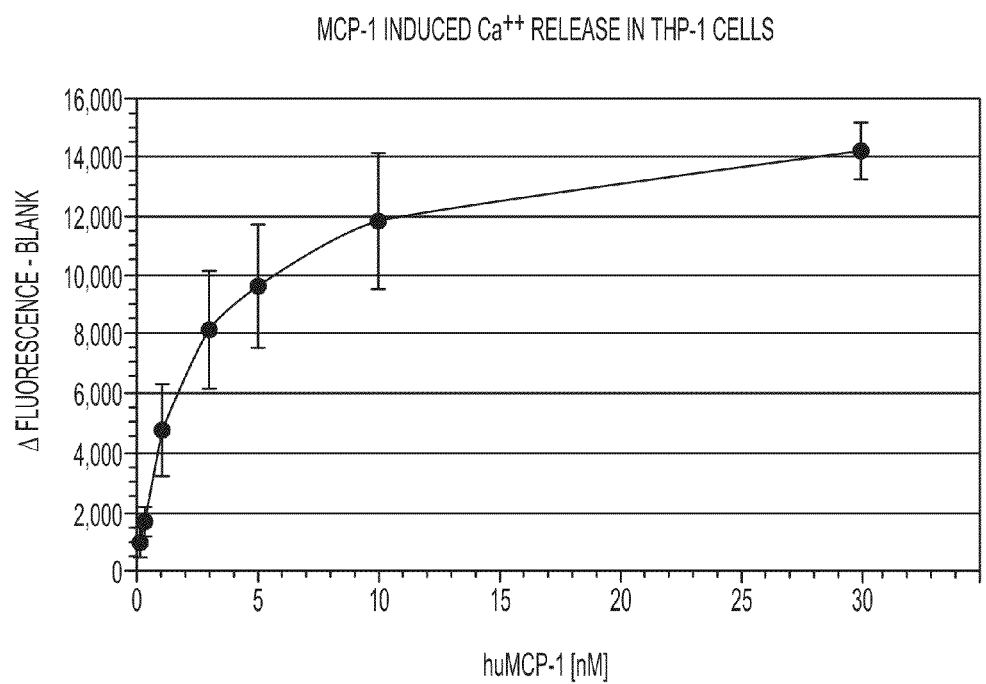
Figure 12:
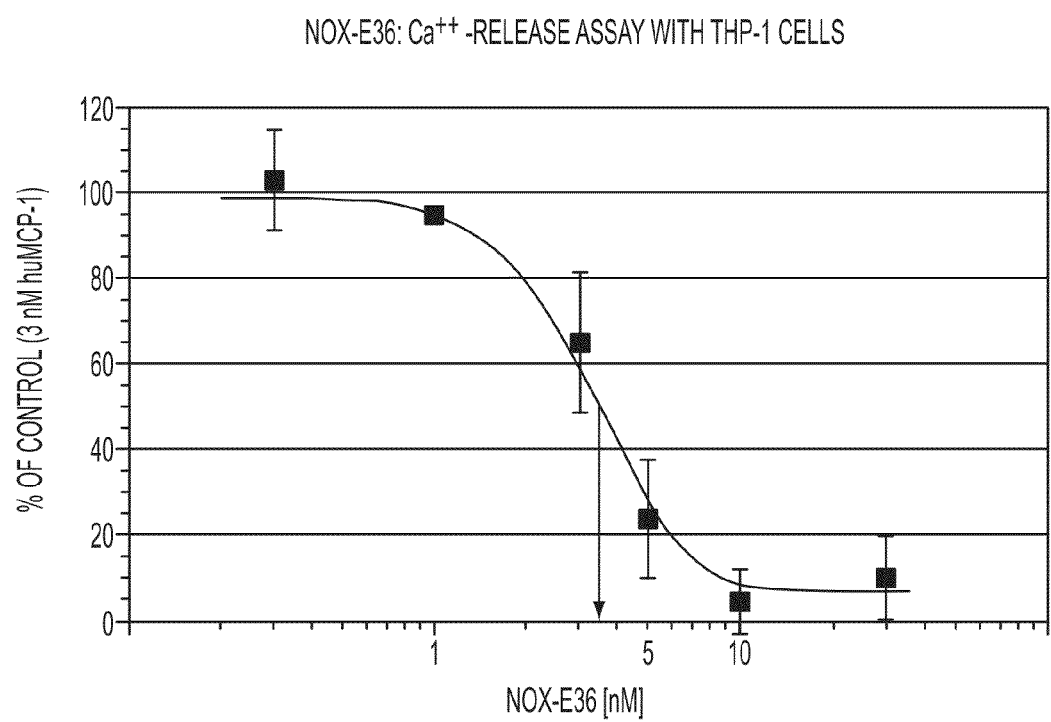
Figure 13:
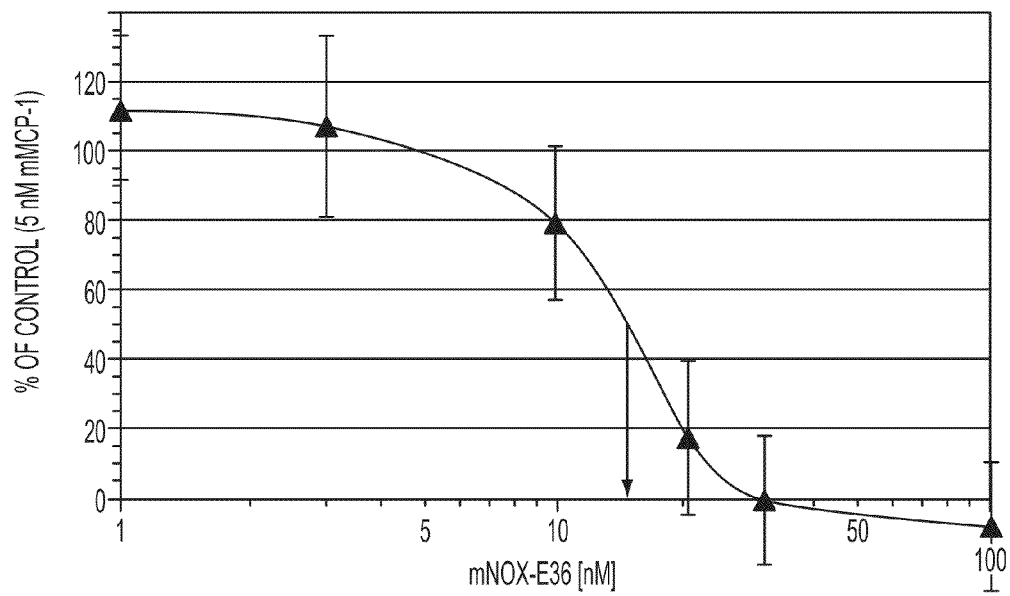
Figure 14:
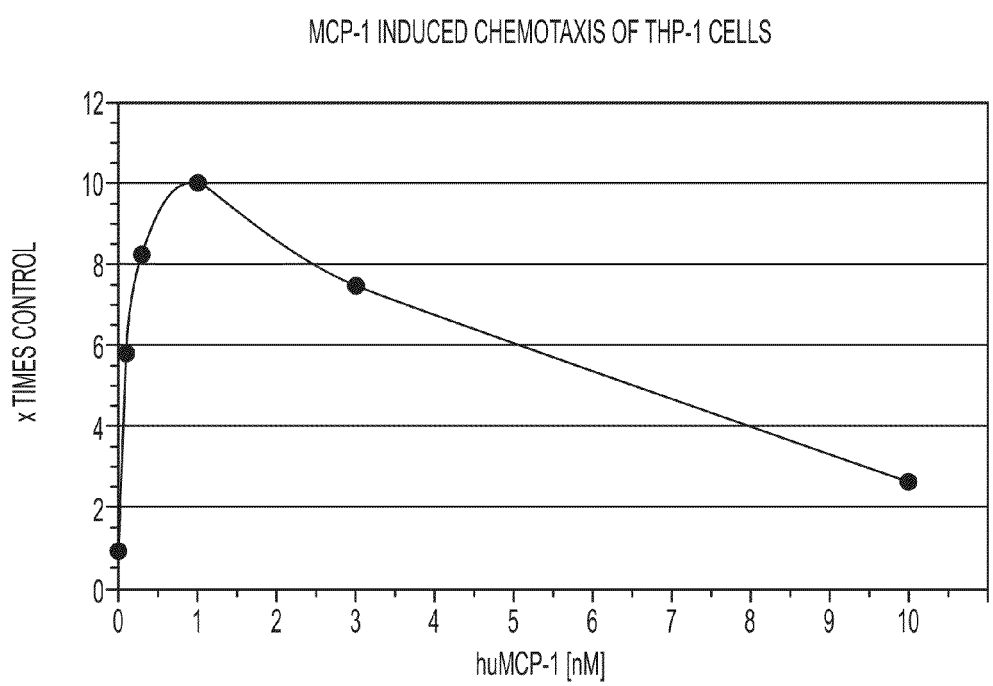
Figure 15:
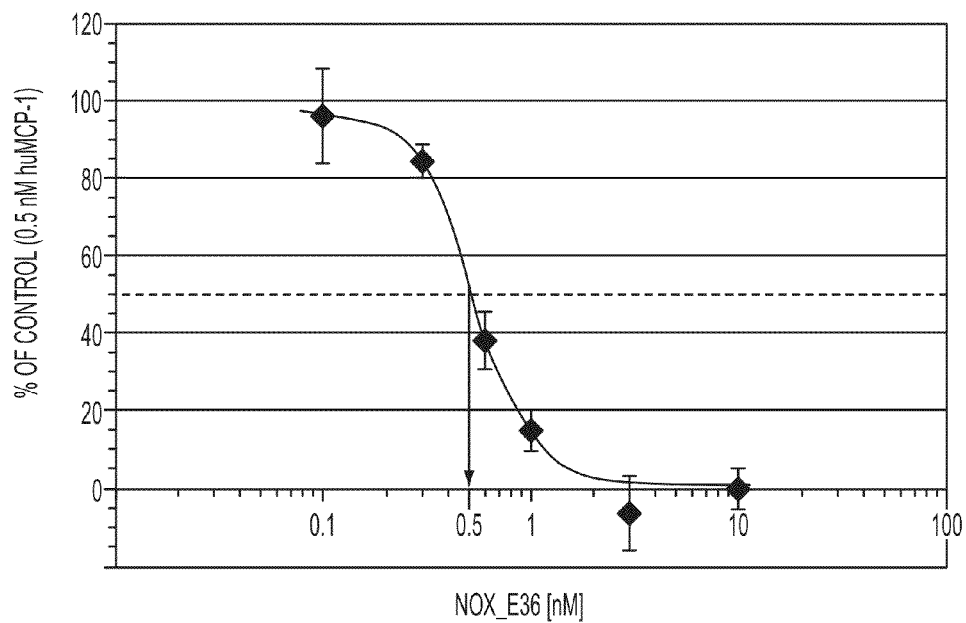
Figure 16:
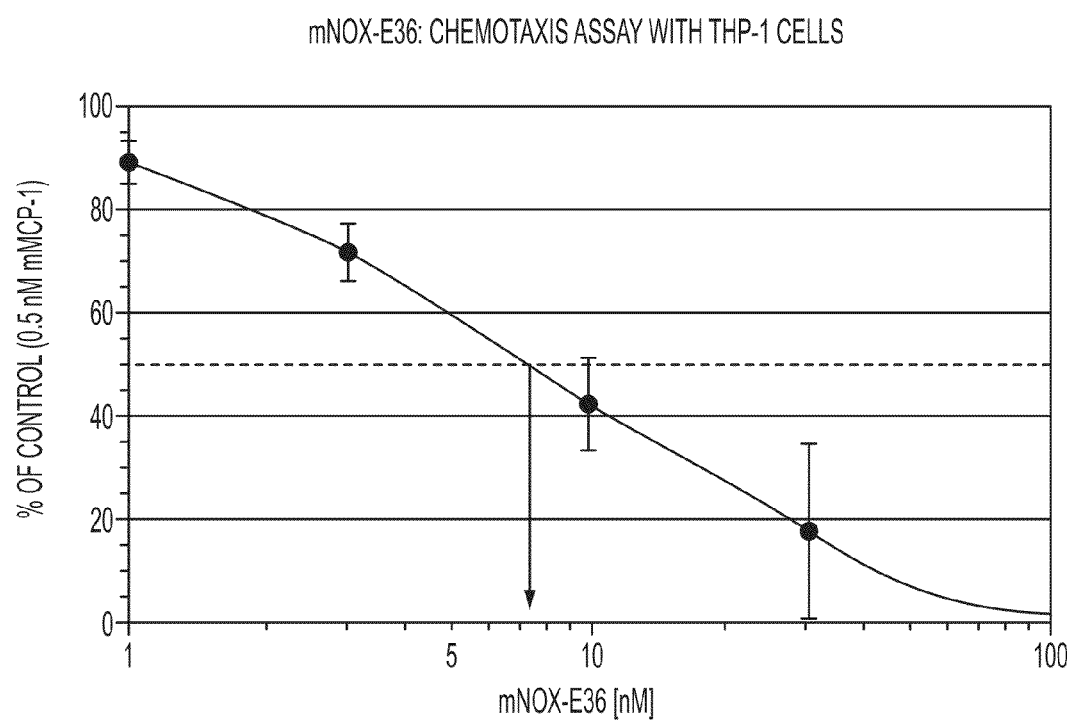
Figure 17:
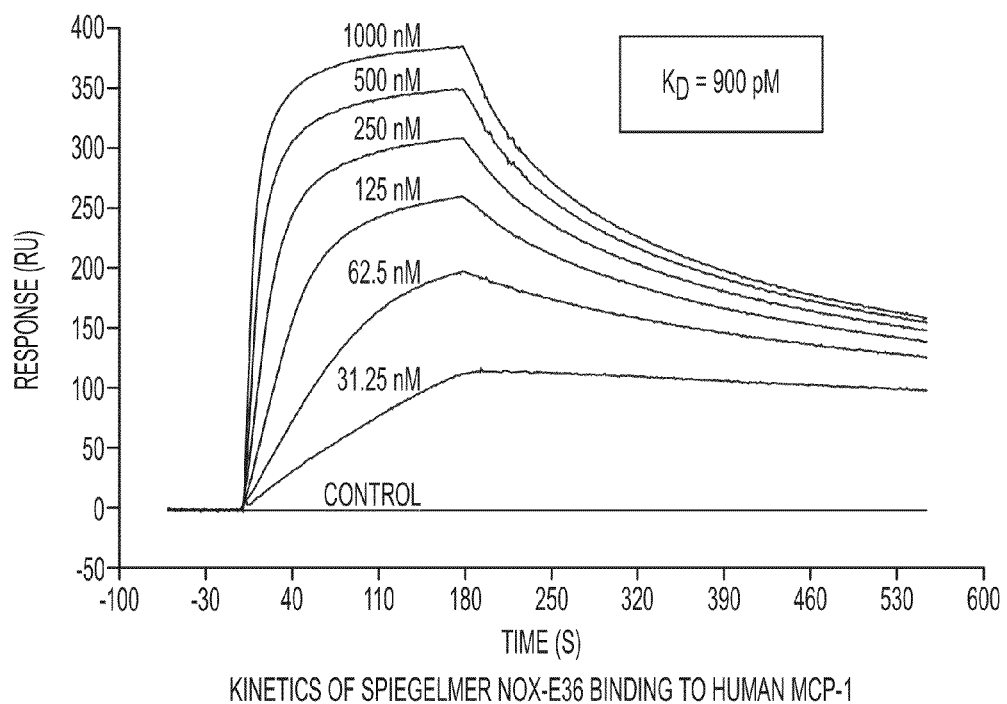
Figure 18:
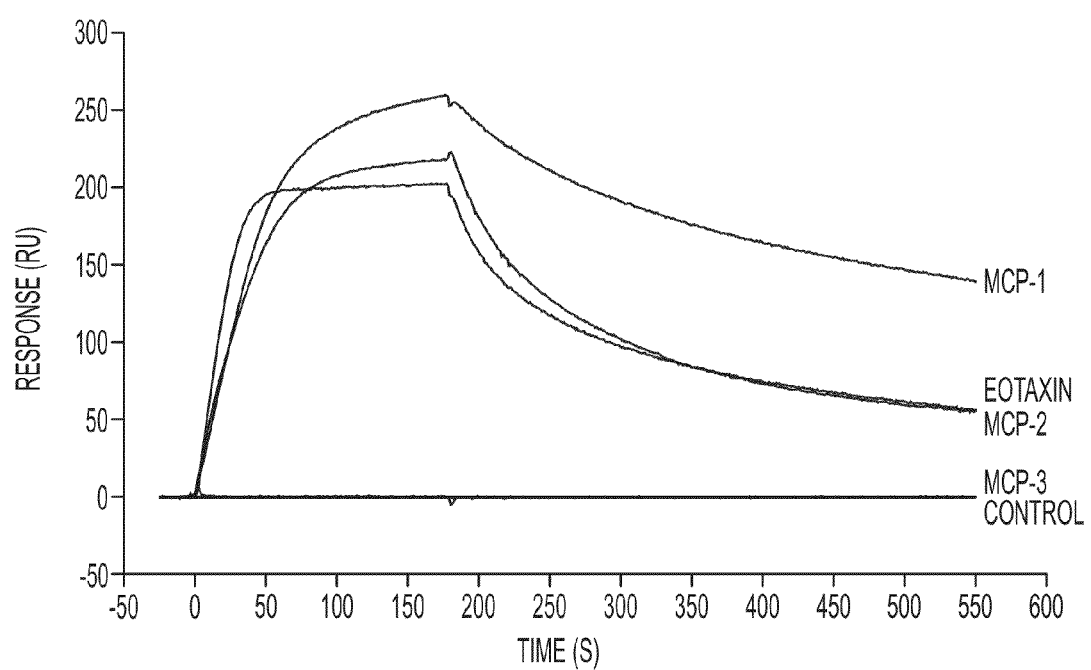
Figure 19:
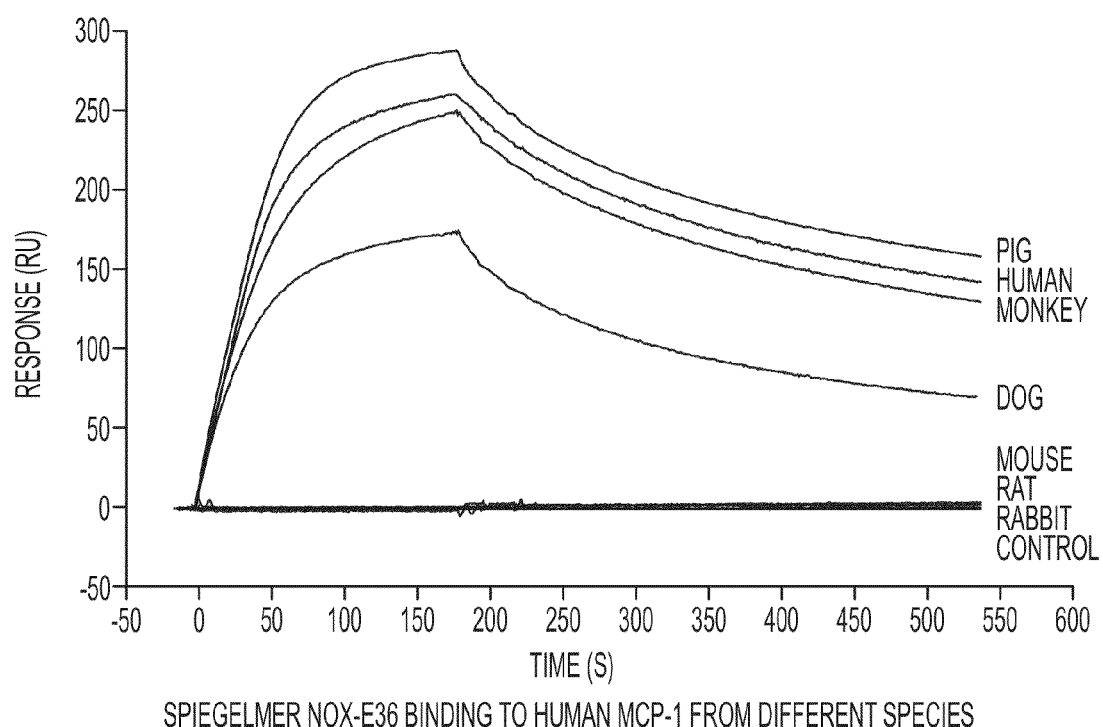
Figure 20:
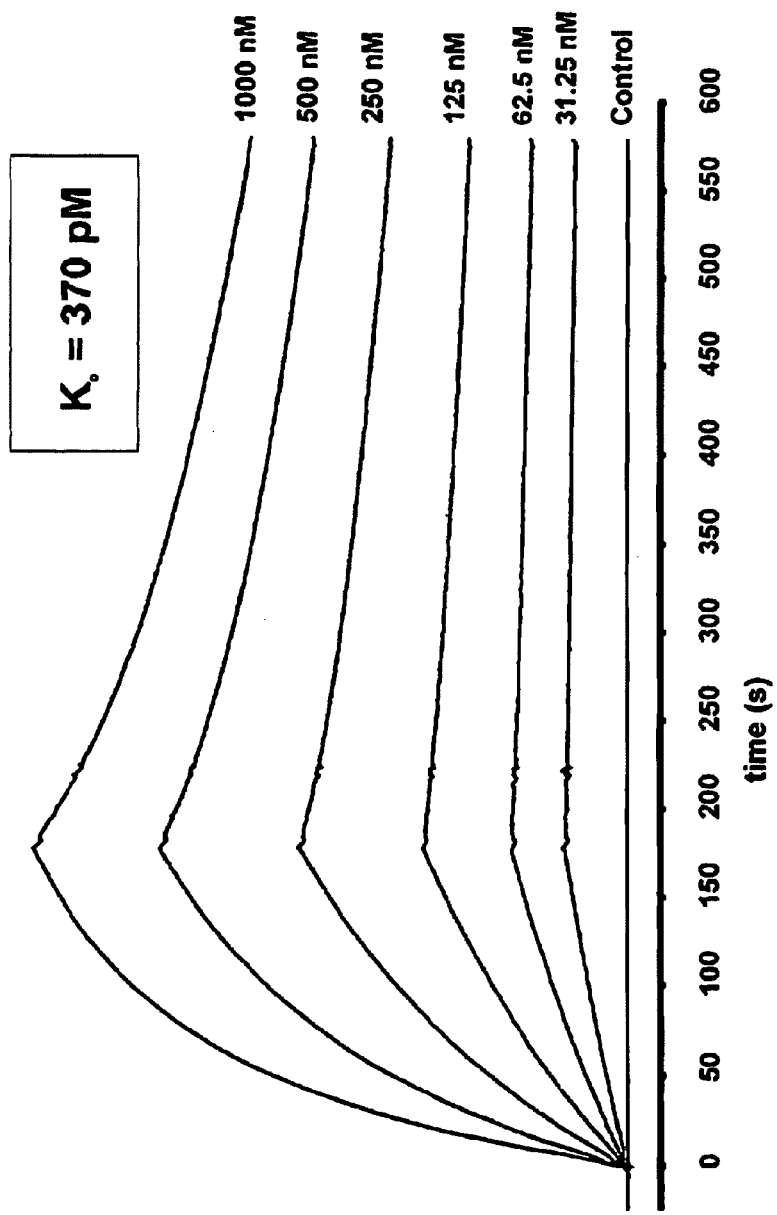
Figure 21:
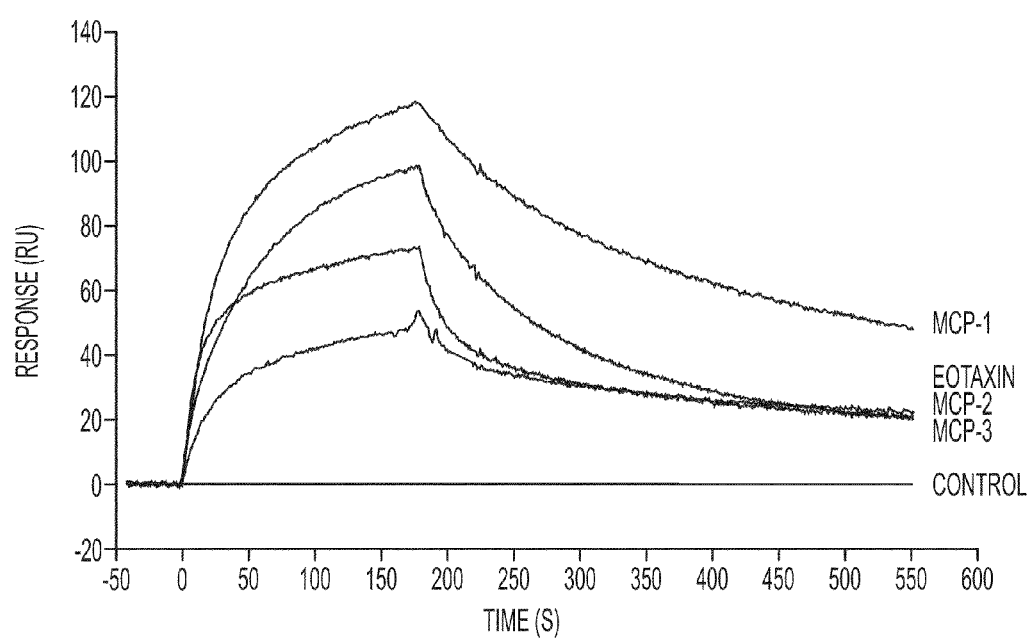
Figure 22:
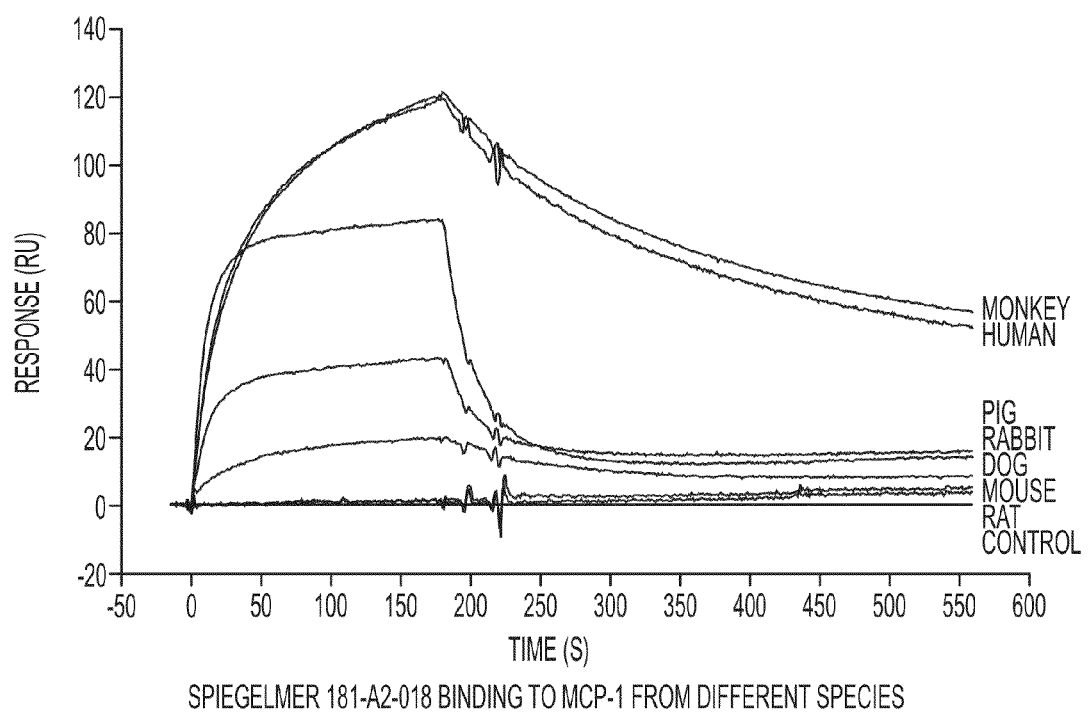
Figure 24:
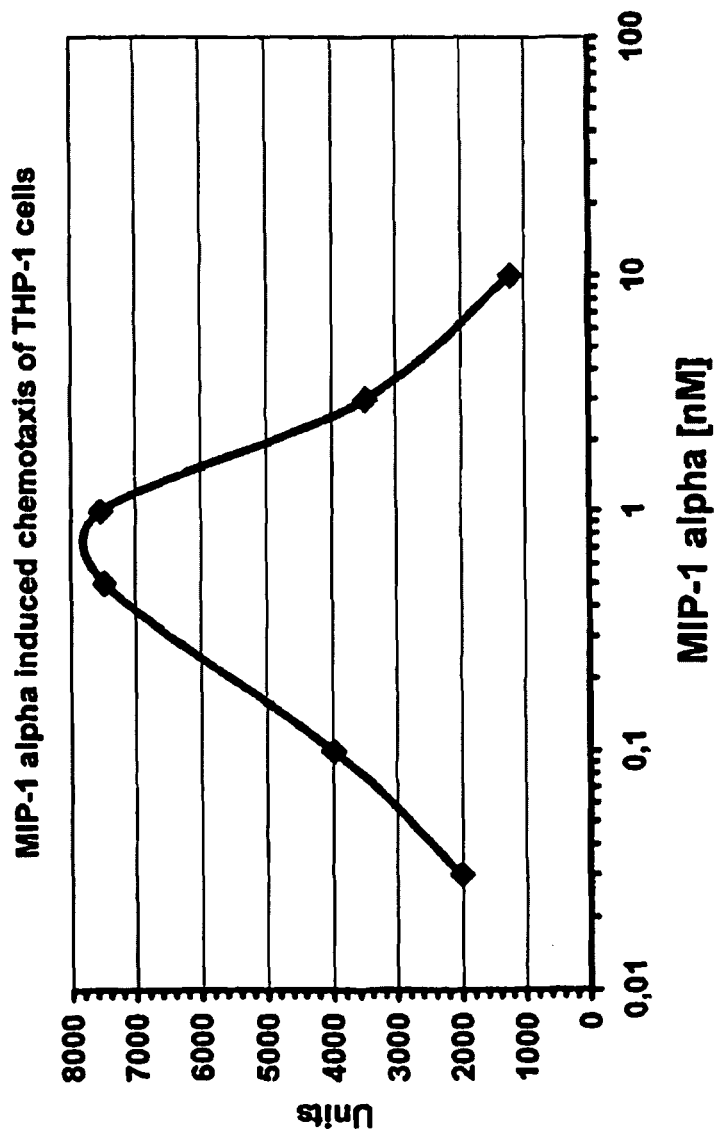
Figure 24:
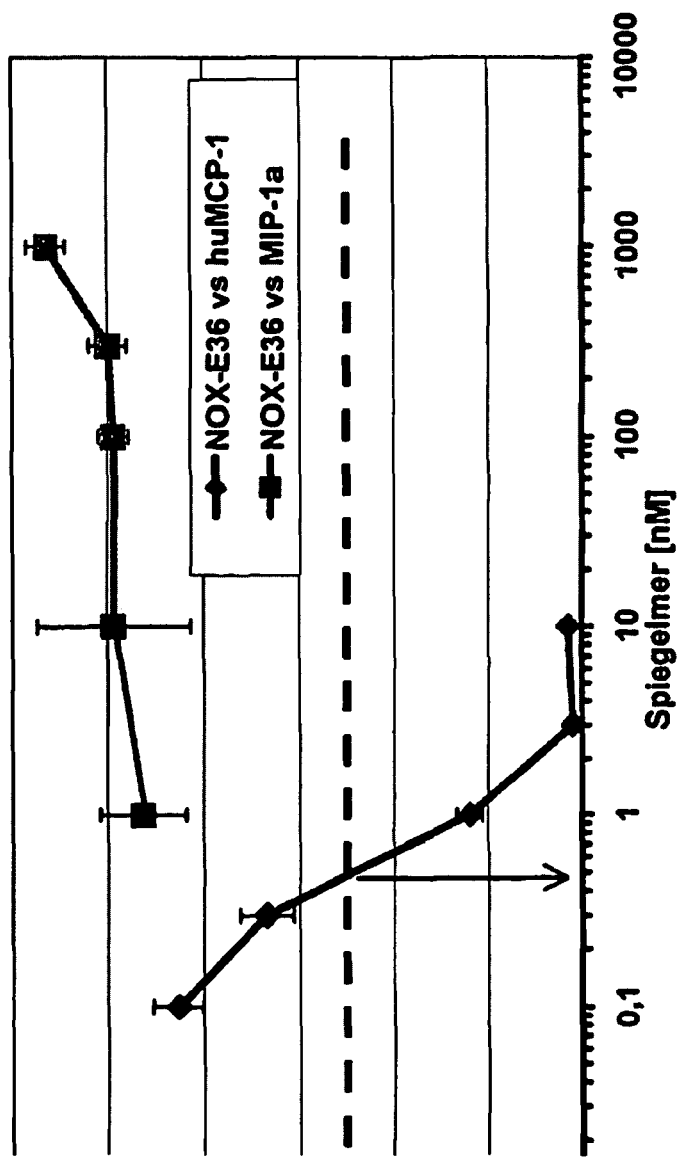
Figure 25:
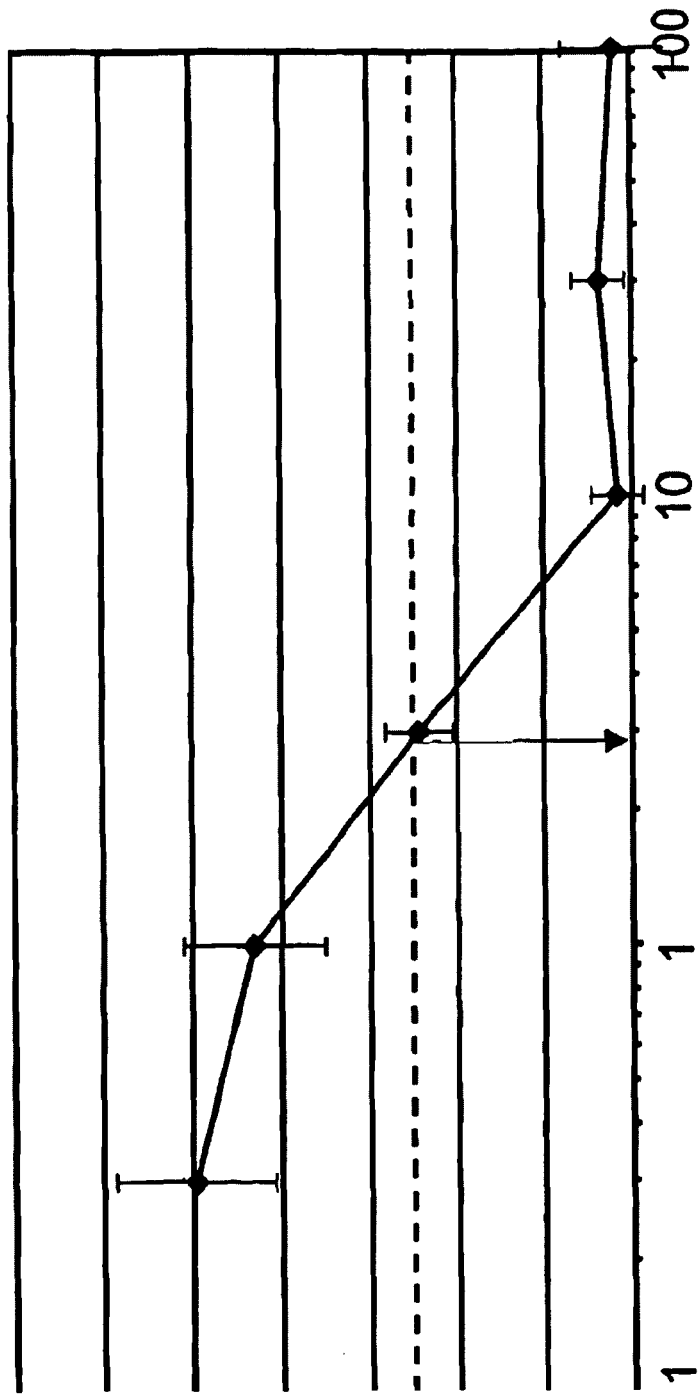
Figure 26:
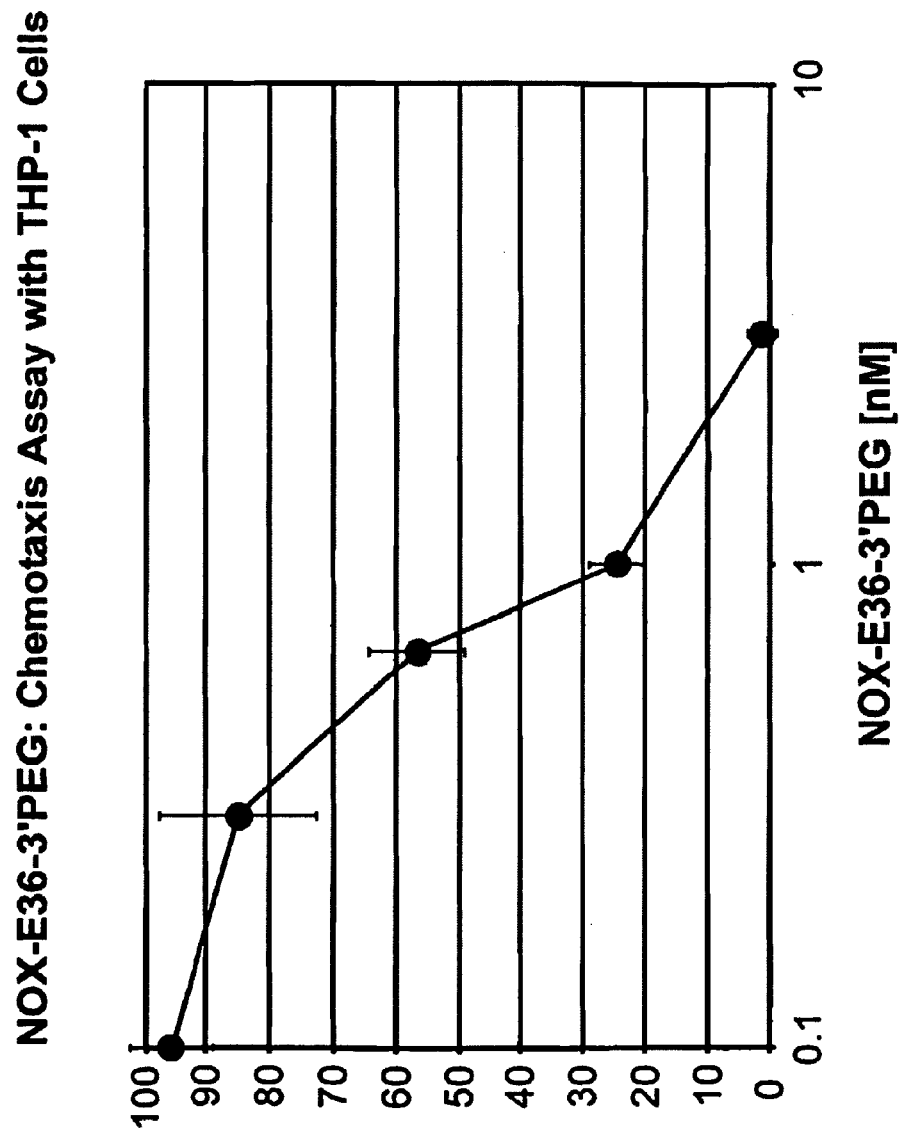
Figure 27A:
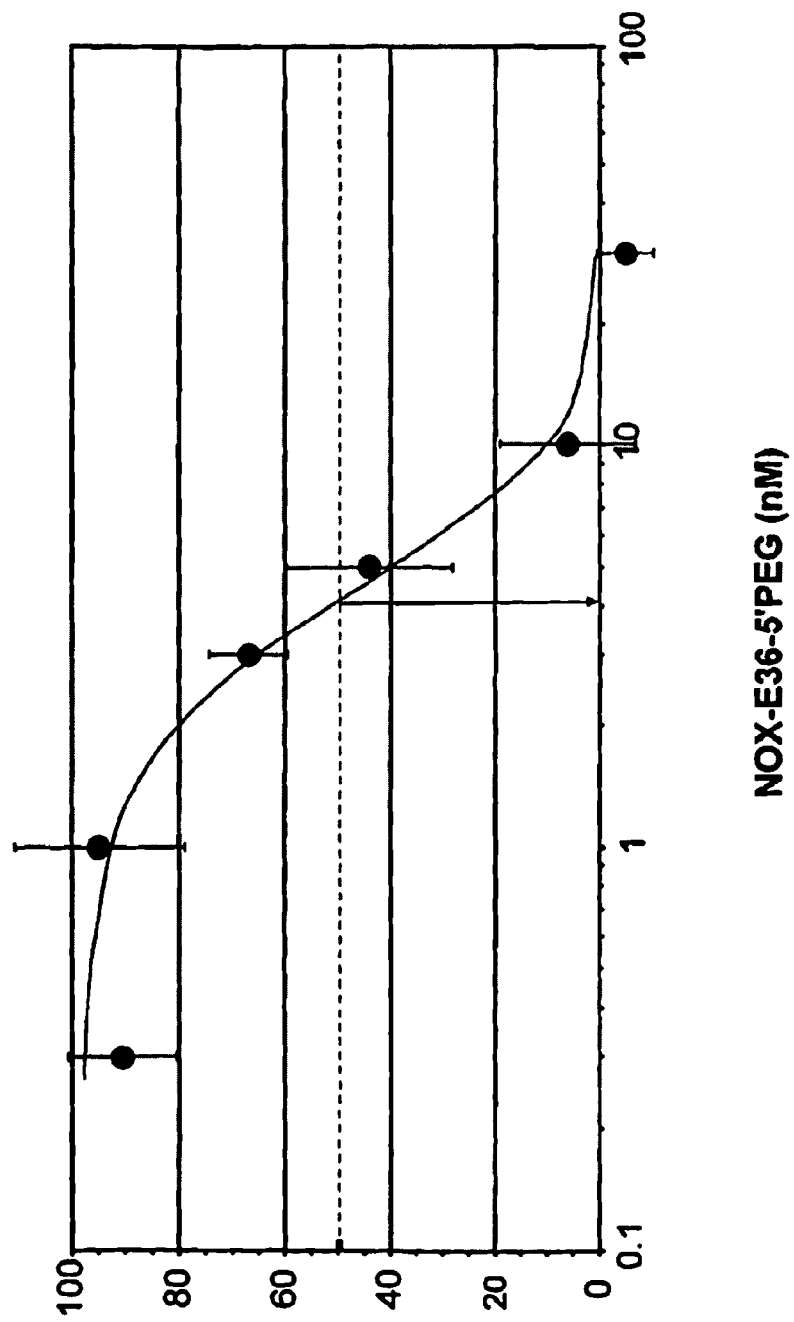
Figure 27B:
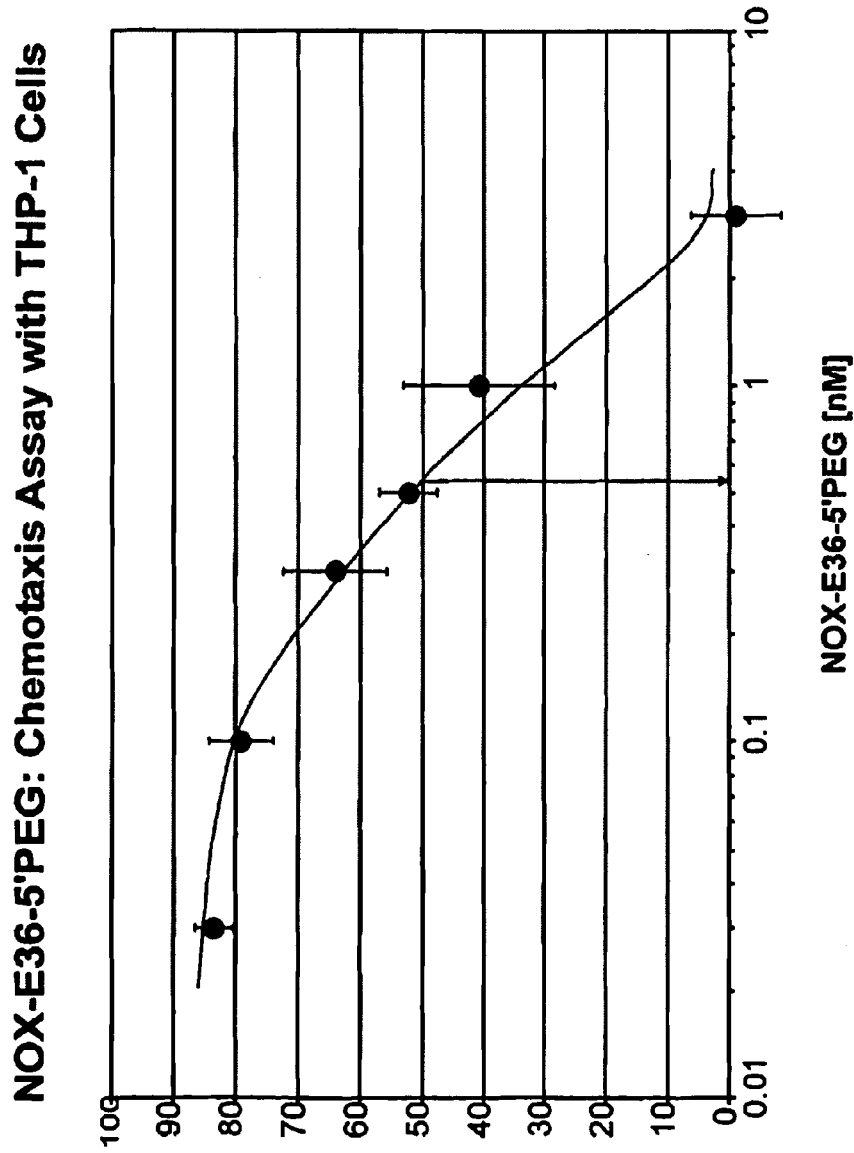
Figure 28:
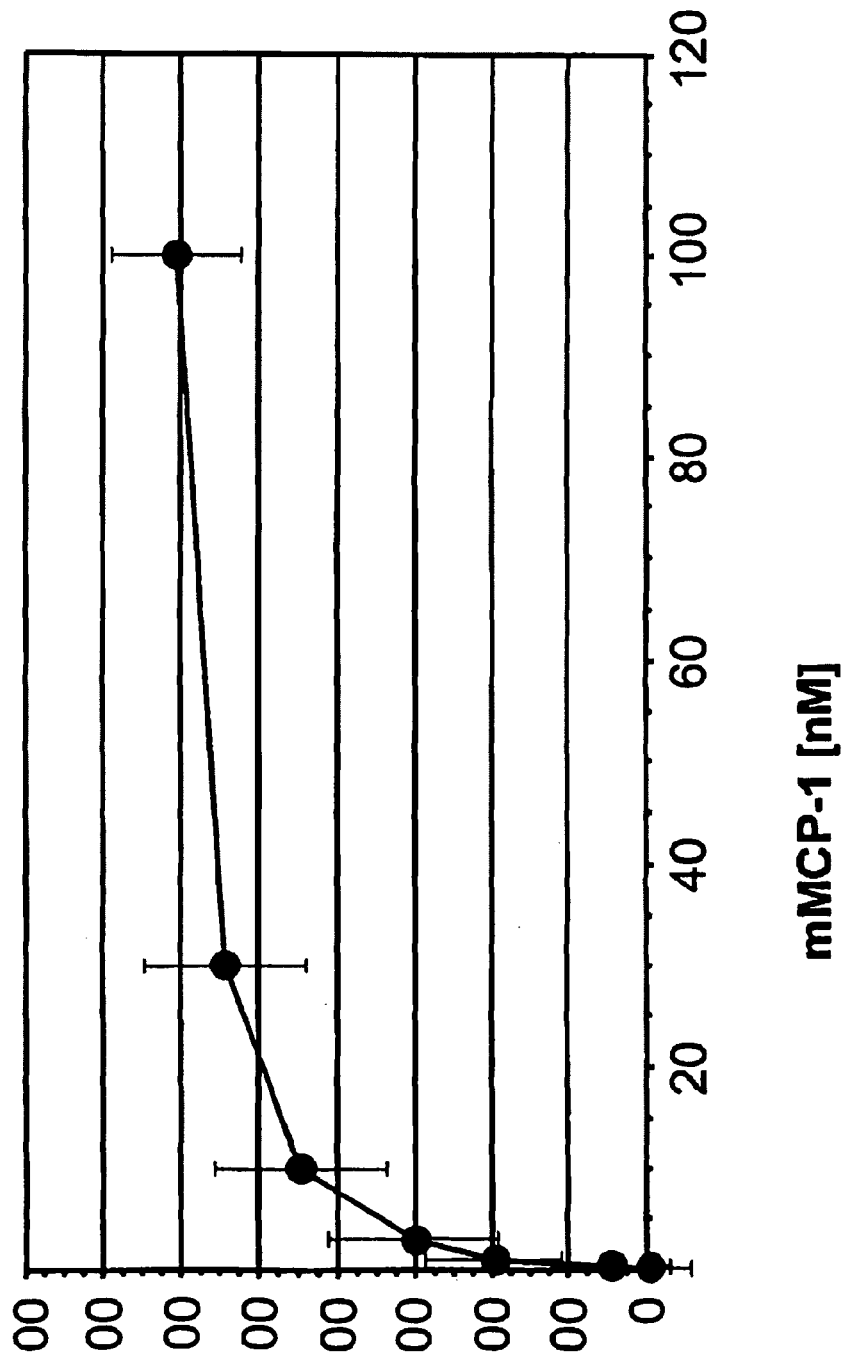
Figure 29:
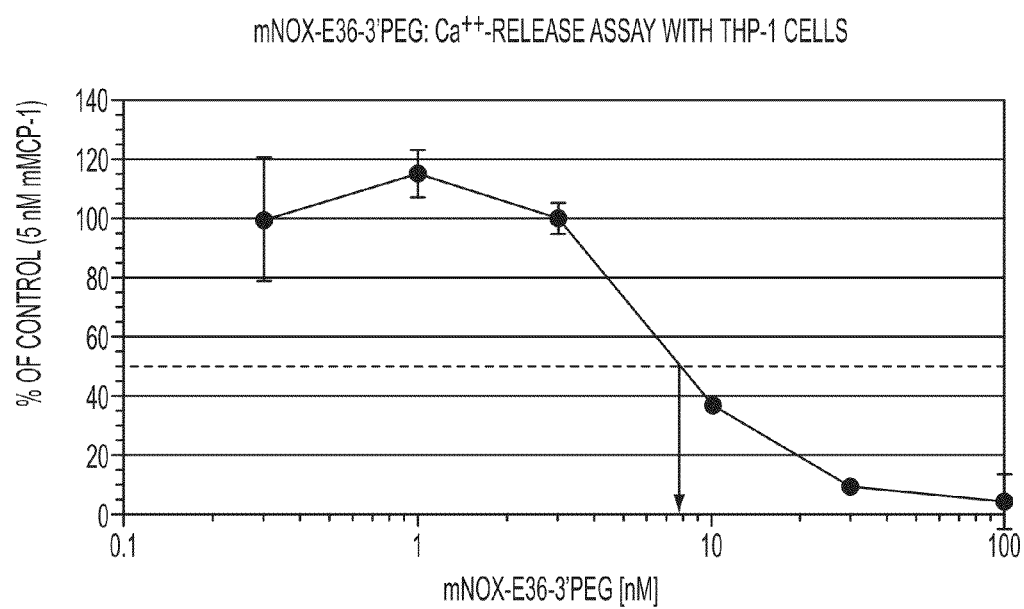
Figure 30:
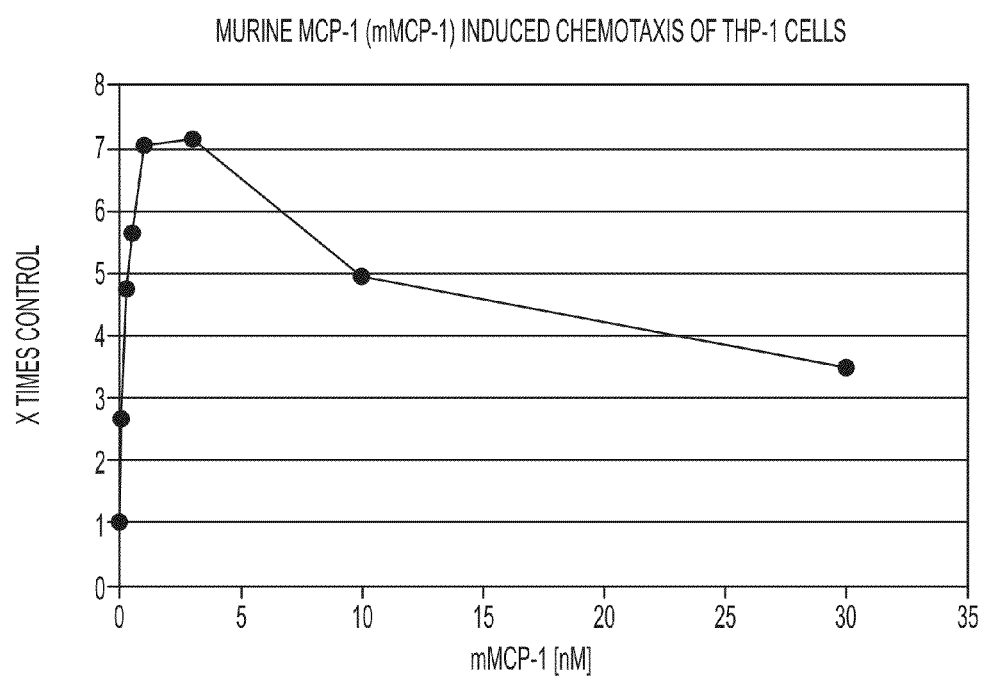
Figure 31:
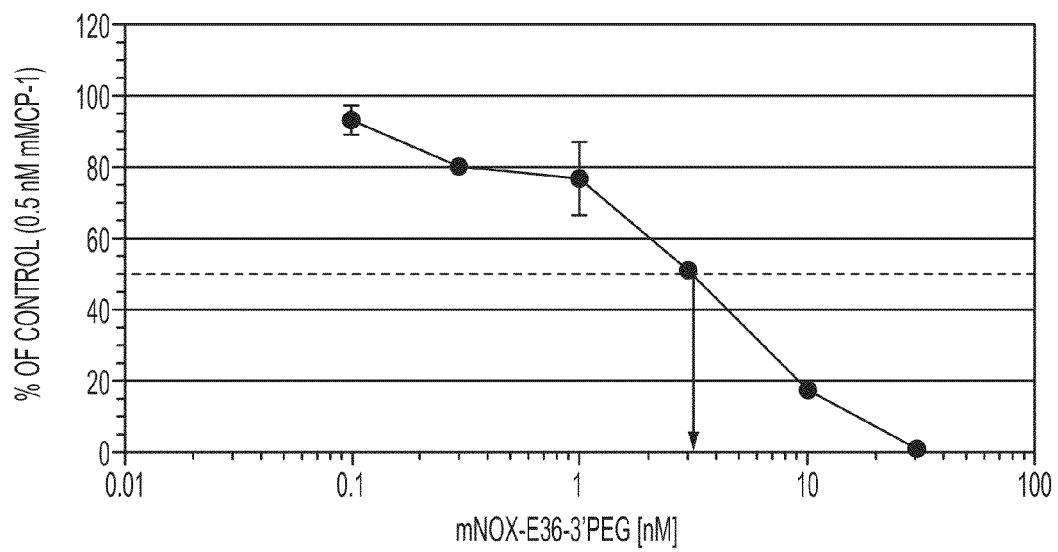
Figure 36:
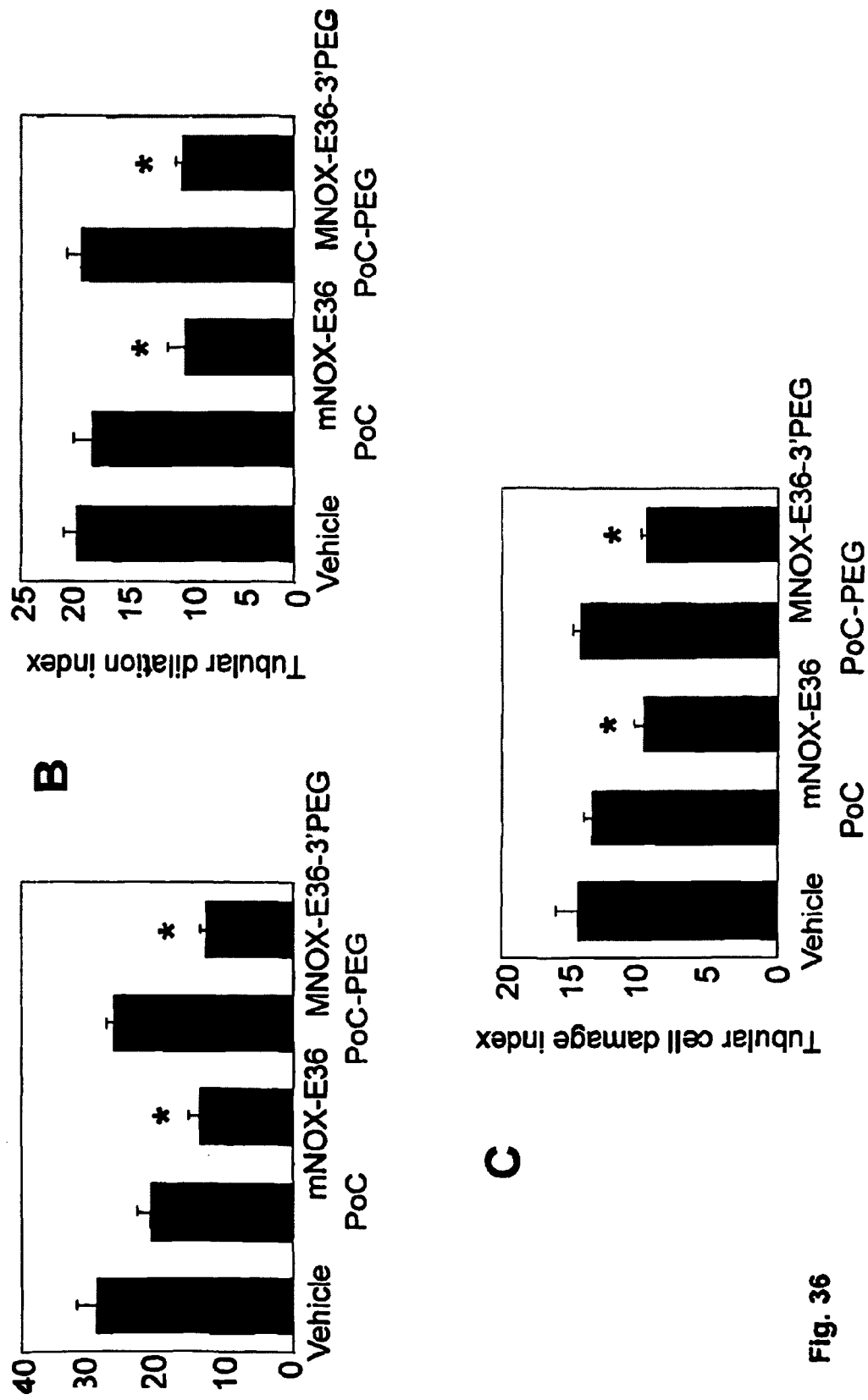
Figure 37:
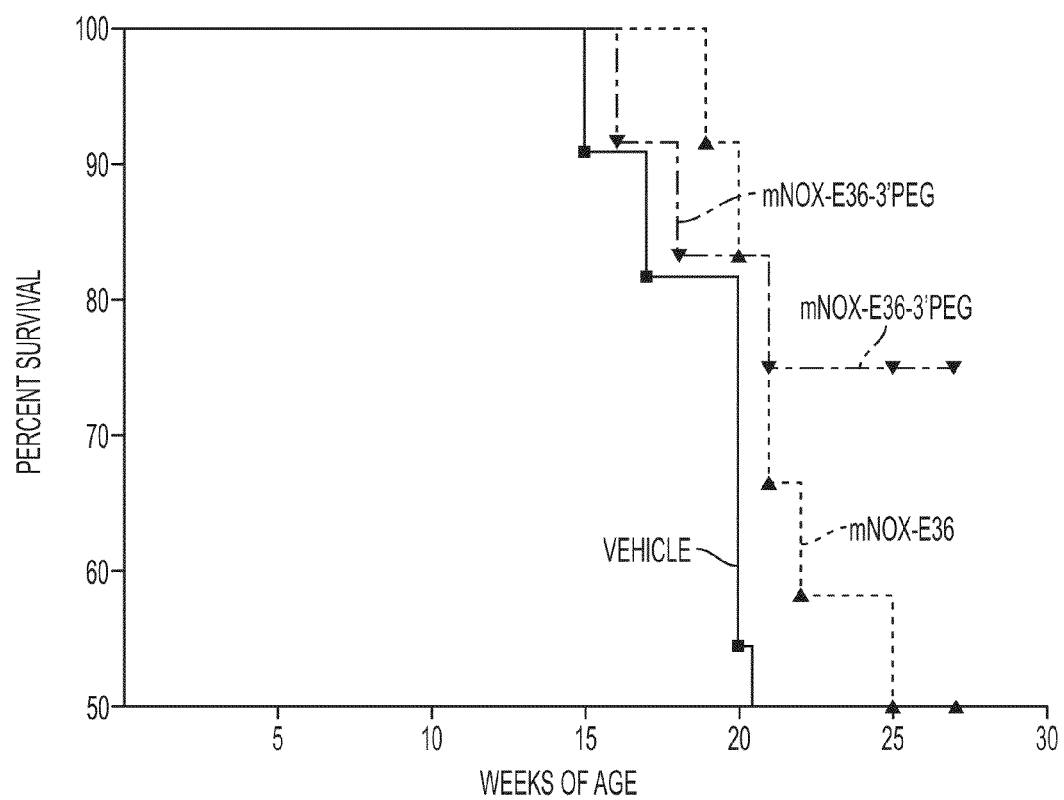
Figure 38A:
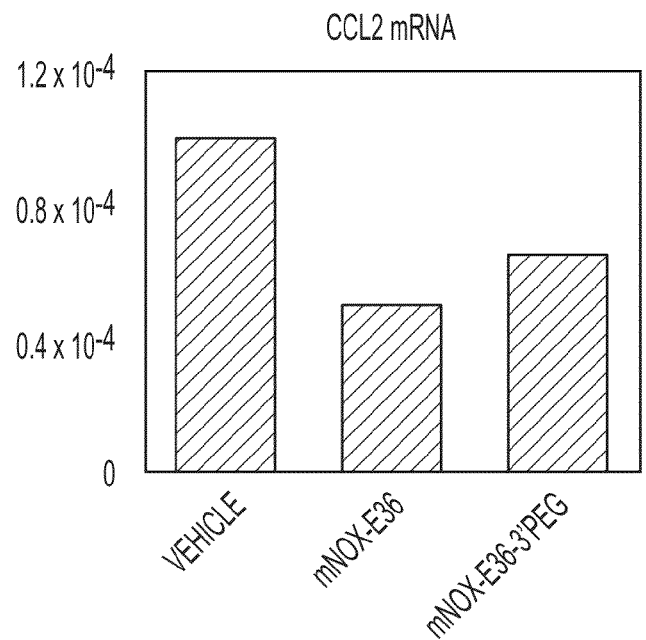
Figure 38B:
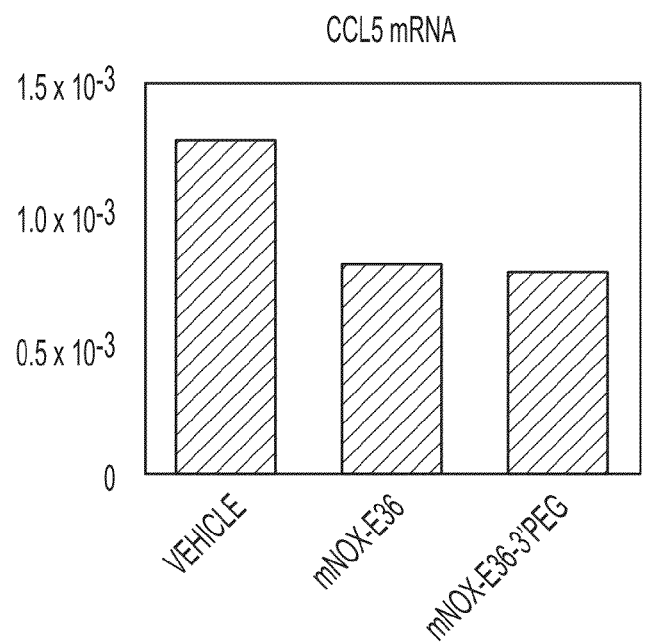
Figure 39A:
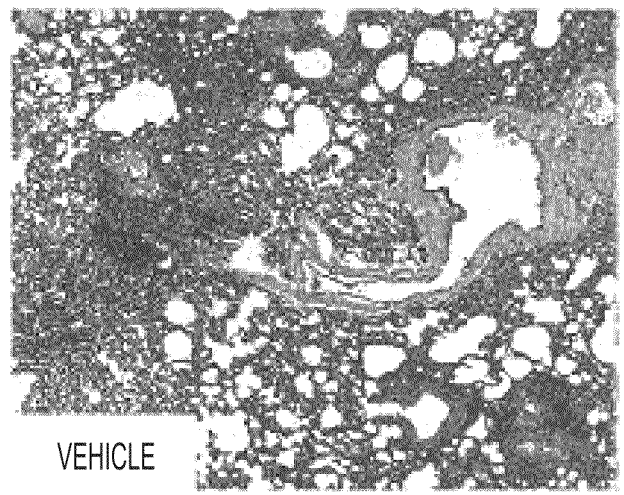
Figure 39B:
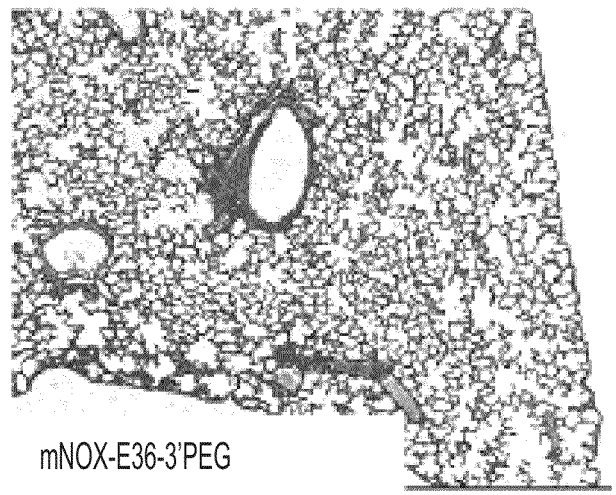
Figure 40:
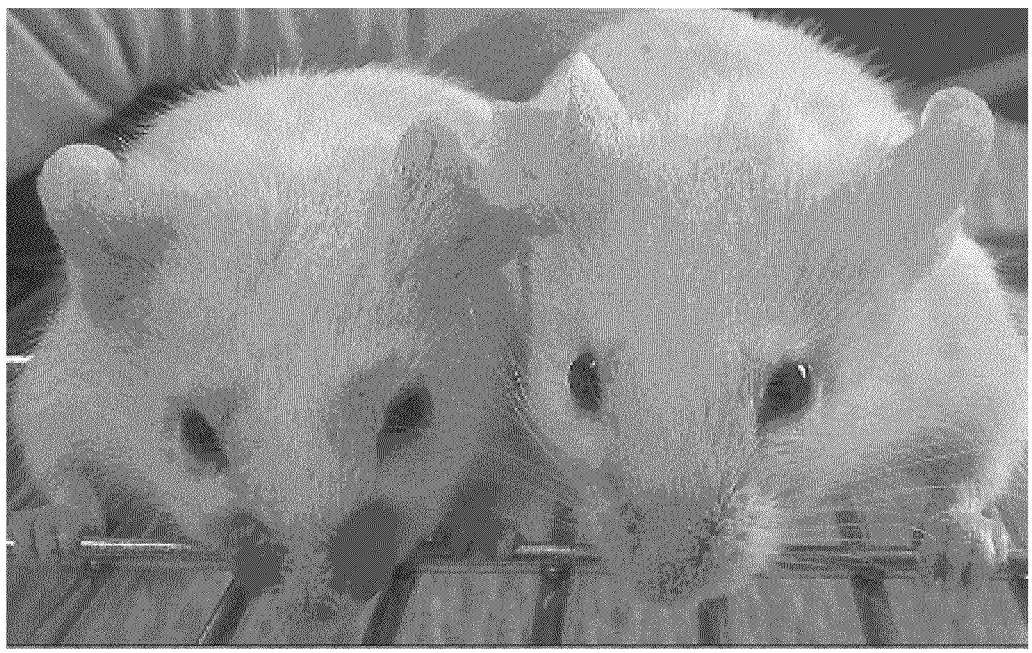
Figure 42:
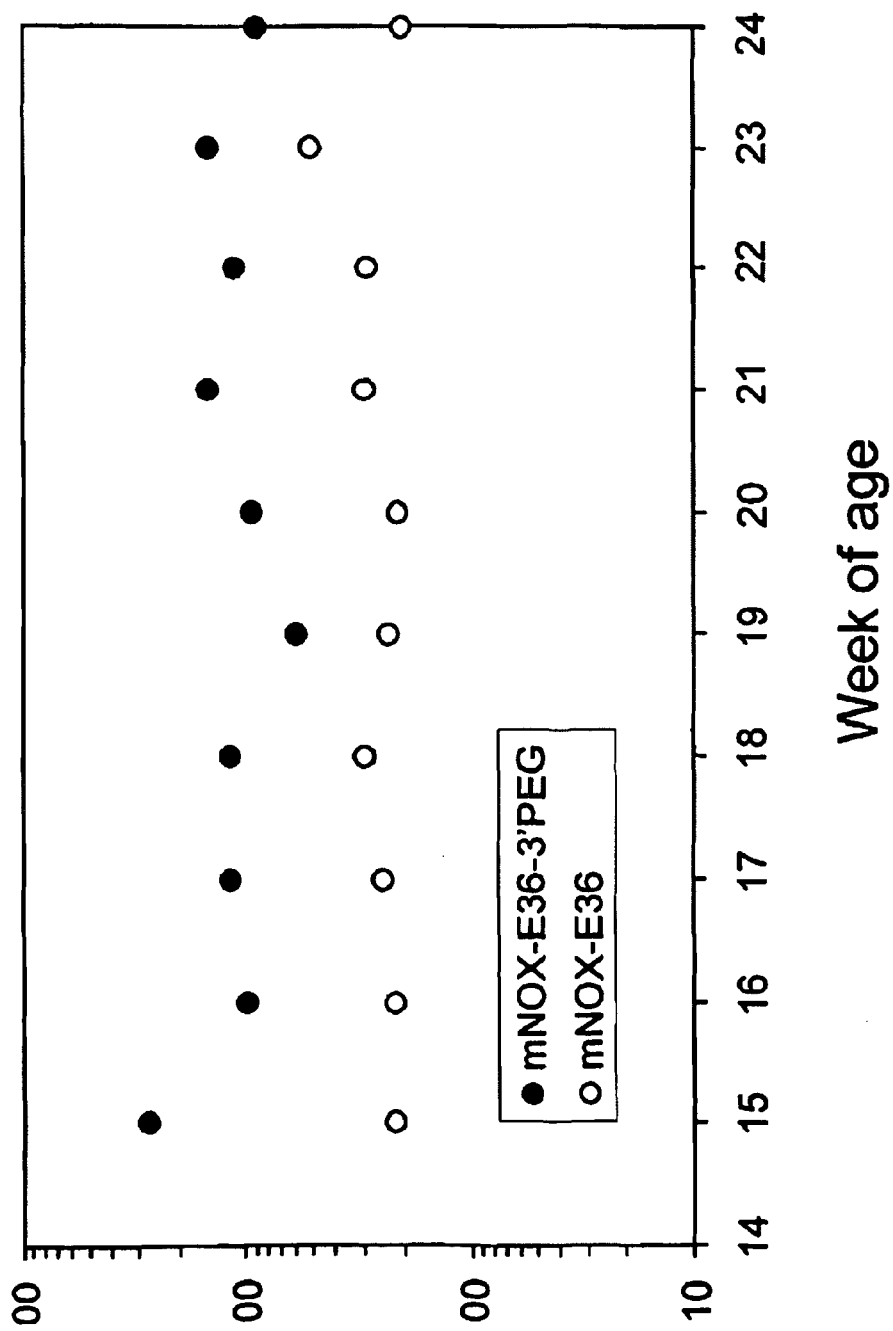
Figure 43:
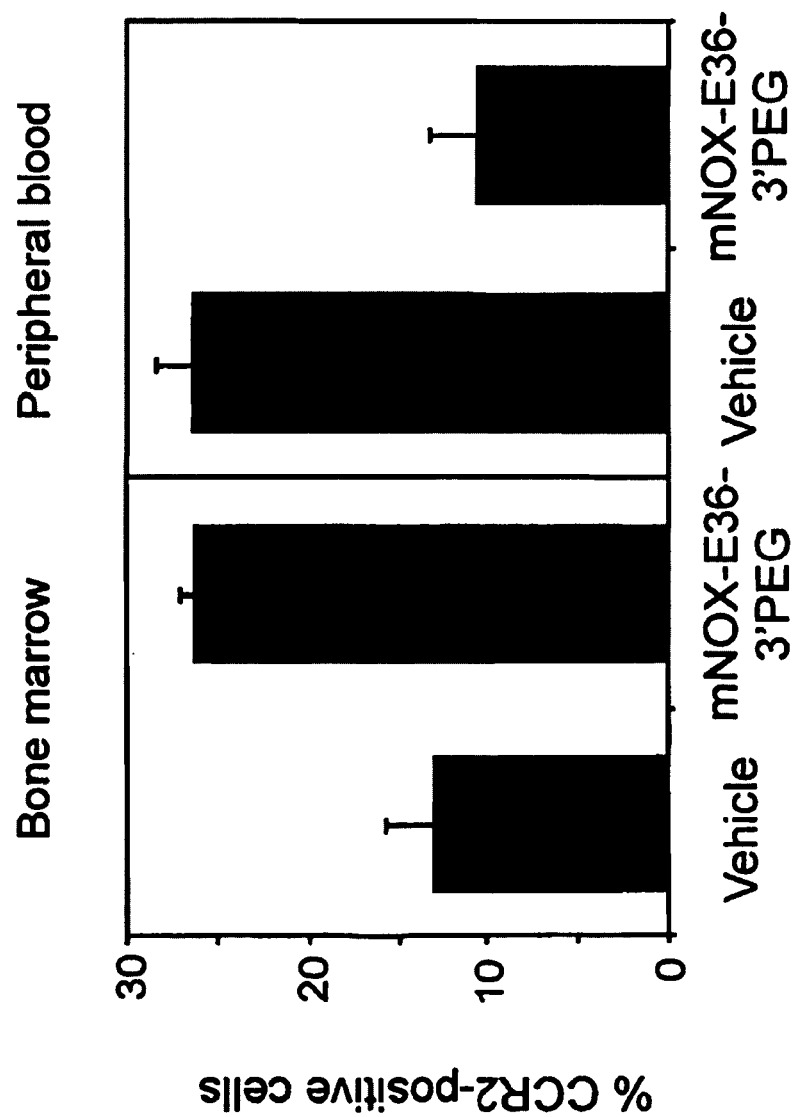
Figure 44:
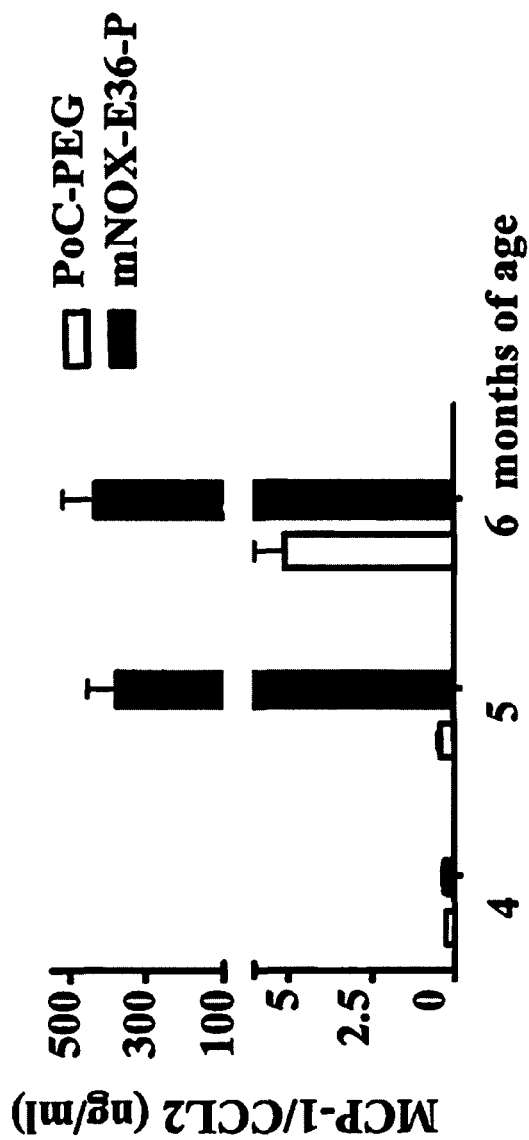
Figure 46:
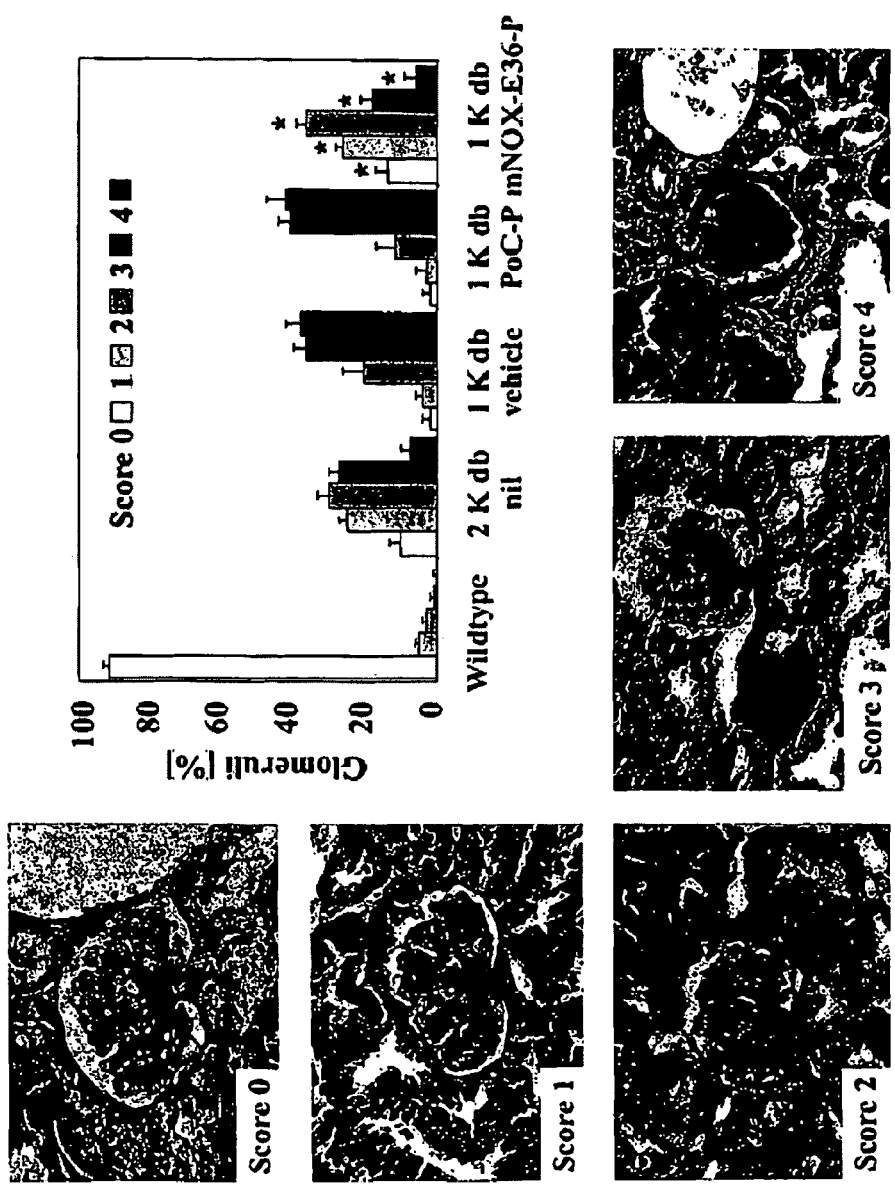
Figure 47:
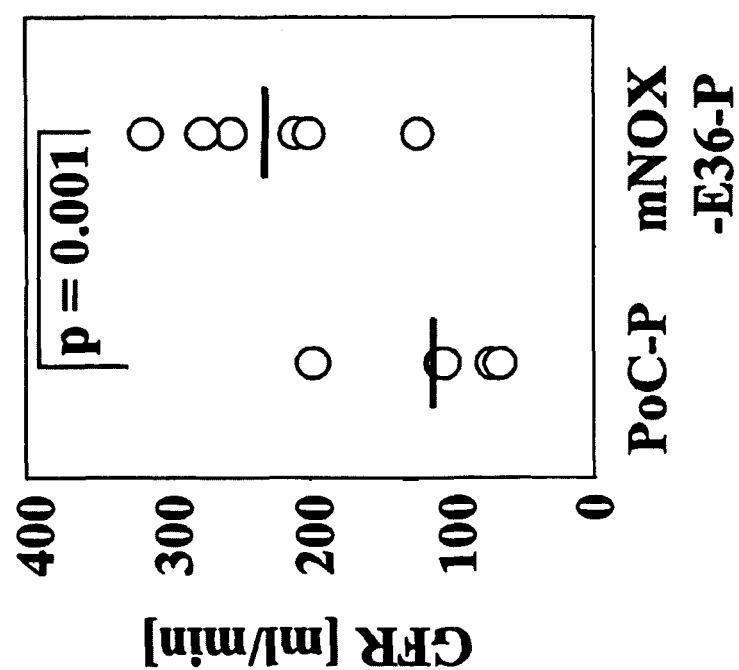
Figure 48:
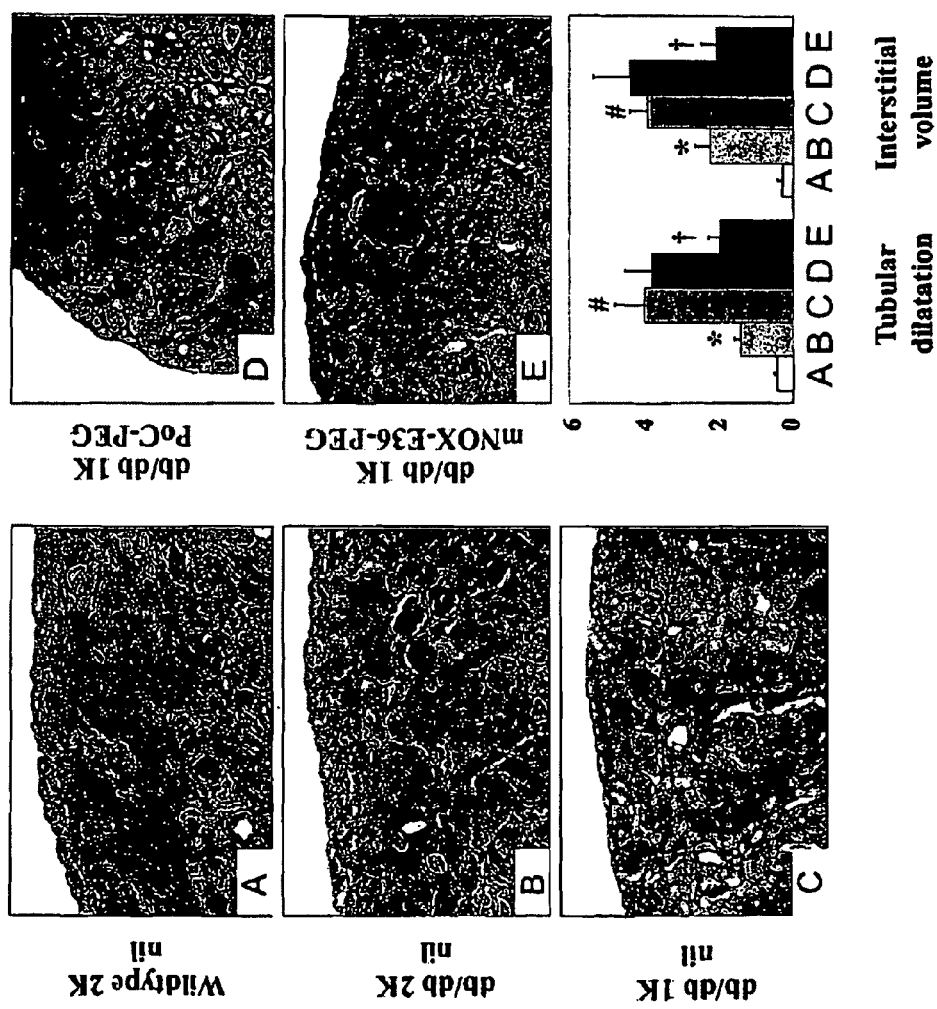
Figure 49:
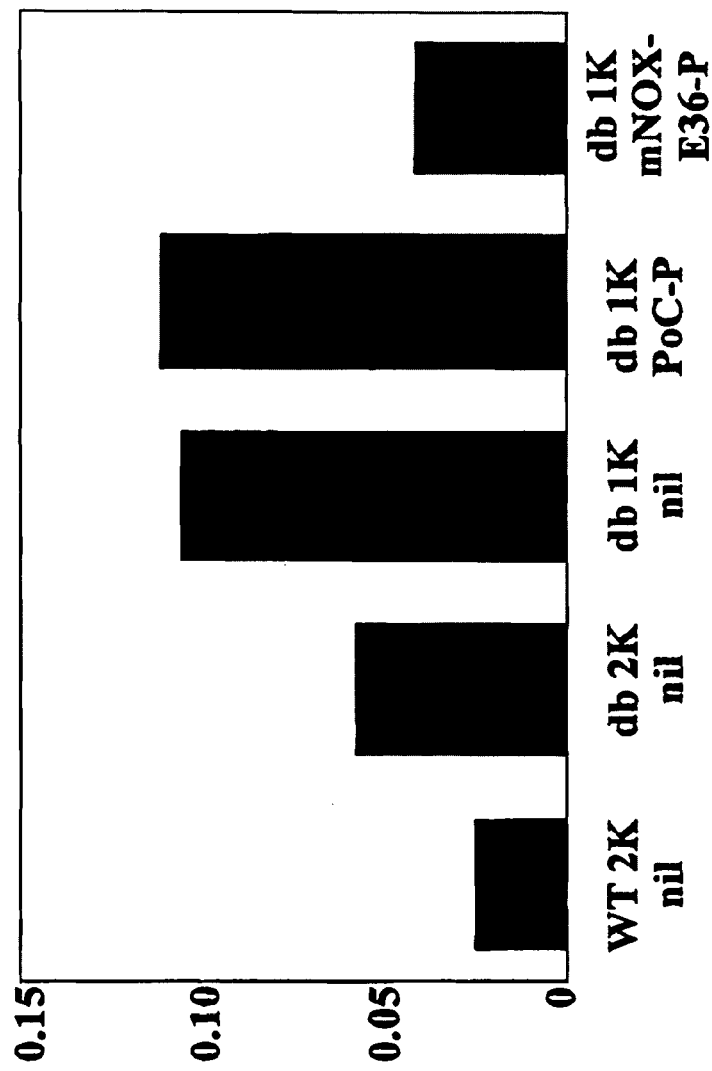
Figure 50:
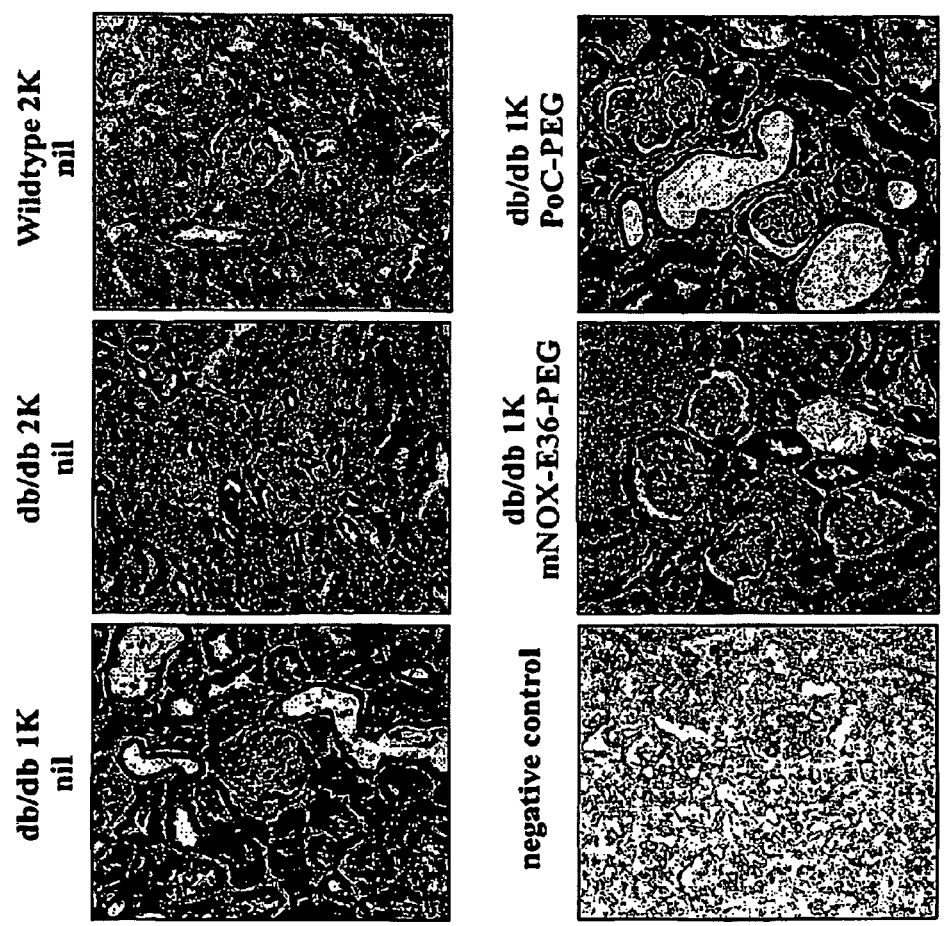

FIG. 6 shows an alignment of sequences of related RNA ligands binding to human MCP-1 indicating the sequence motif ("Type 4") that is in a preferred embodiment in its entirety essential for binding to human MCP-1 (other sequences) (L-RNA sequences as SEQ ID NOs:74-77, 80, 81, 78, 82, 83, 79, 84-86, respectively, in order of appearance and the corresponding D-RNA sequences as SEQ ID NOs:196-199, 202-203, 200, 204, 205, 201, 206-208, respectively);

FIG. 7 shows a table of sequences of several different RNA ligands binding to human MCP-1 which can not be related to the MCP-1 binding sequence motifs "Type 1A", "Type 1B"; "Type 2", "Type 3" or "Type 4" (L-RNA sequences as SEQ ID NOs:87-115, respectively, in order of appearance, and the corresponding D-RNA sequences as SEQ ID NOs:209-237 respectively);

FIG. 8 shows alignments of derivatives (SEQ ID NOs:118-129, respectively) of RNA ligand 188-A3-001 and of 189-G7-001 that bind to murine MCP-1 (L-RNA sequences as SEQ ID NOs:118-129, respectively, in order of appearance, and the corresponding D-RNA sequences as SEQ ID NOs: 240-251, respectively);

FIG. 9 shows the result of a binding analysis of the aptamer D-NOX-E36 to biotinylated human D-MCP-1 at room temperature and 37° C., represented as binding of the aptamer over concentration of biotinylated human D-MCP-1;

FIG. 10 shows the result of a binding analysis of the aptamer D-mNOX-E36 to biotinylated murine D-MCP-1 at 37° C., represented as binding of the aptamer over concentration of biotinylated murine D-MCP-1;

FIG. 11 shows MCP-1-induced $Ca^{++}$-release in THP-1 cells, whereas a dose-response curve for human MCP-1 was obtained, indicating a half effective concentration ($EC_{50}$) of approximately 3 nM, represented as difference in fluorescence to blank over concentration of human MCP-1;

FIG. 12 shows the efficacy of Spiegelmer NOX-E36 in a calcium release assay; cells were stimulated with 3 nM human MCP-1 preincubated at 37° C. with various amounts of Spiegelmer NOX-E36, represented as percentage of control over concentration of NOX-E36;

FIG. 13 shows the efficacy of Spiegelmer mNOX-E36 in a calcium release assay; cells were stimulated with 5 nM murine MCP-1 preincubated at 37° C. with various amounts of Spiegelmer mNOX-E36, represented as percentage of control over concentration of mNOX-E36;

FIG. 14 shows the human MCP-1-induced chemotaxis of THP-1 cells whereas after 3 hours migration of THP-1 cells towards various MCP-1 concentrations a dose-response curve for MCP-1 was obtained, represented as X-fold increase compared to control over concentration of human MCP-1;

FIG. 15 shows the efficacy of Spiegelmer NOX-E36 in a chemotaxis assay; cells were allowed to migrate towards 0.5 nM human MCP-1 preincubated at 37° C. with various amounts of Spiegelmer NOX-E36, represented as percentage of control over concentration of Spiegelmer NOX-E36;

FIG. 16 shows the efficacy of Spiegelmer mNOX-E36 in a chemotaxis assay; cells were allowed to migrate towards 0.5 nM murine MCP-1 preincubated at 37° C. with various amounts of Spiegelmer NOX-E36, represented as percentage of control over concentration of Spiegelmer mNOX-E36;

FIG. 17 shows the Biacore 2000 sensorgram indicating the $K_D$ value of Spiegelmer NOX-E-36 binding to human MCP-1 which was immobilized on a PioneerF1 sensor chip by amine coupling procedure, represented as response (RU) over time;

FIG. 18 shows the Biacore 2000 sensorgram indicating binding of Spiegelmer NOX-E36 to human MCP-family proteins (huMCP-1, huMCP-2, huMCP-3) and human eotaxin, which were immobilized by amine coupling procedure on a PioneerF1 and a CM4 sensor chip, respectively, represented as response (RU) over time;

FIG. 19 shows the Biacore 2000 sensorgram indicating binding of Spiegelmer NOX-E36 to MCP-1 from different species (canine MCP-1, monkey MCP-1, human MCP-1, porcine MCP-1, rabbit MCP-1, mouse MCP-1, rat MCP-1) whereas different forms of MCP-1 were immobilized by amine coupling procedure on PioneerF1 and a CM4 sensor chips, respectively, represented as response (RU) over time;

FIG. 20 shows the Biacore 2000 sensorgram indicating the $K_D$ value of Spiegelmer 181-A2-018 binding to human MCP-1 which was immobilized on a CM4 sensor Chip by amine coupling procedure, represented as response (RU) over time;

FIG. 21 shows the Biacore 2000 sensorgram indicating binding of Spiegelmer 181-A2-018 to human MCP-family proteins (huMCP-1, huMCP-2, huMCP-3) and human eotaxin which were immobilized by amine coupling procedure on a PioneerF1 and a CM4 sensor chip, respectively, represented as response (RU) over time;

FIG. 22 shows the Biacore 2000 sensorgram indicating binding of Spiegelmer 181-A2-018 to MCP-1 from different species (canine MCP-1, monkey MCP-1, human MCP-1, porcine MCP-1, rabbit MCP-1, mouse MCP-1, rat MCP-1) whereas different forms of MCP-1 were immobilized by amine coupling procedure on PioneerF1 and a CM4 sensor chips, respectively, represented as response (RU) over time;

FIG. 23 shows a Clustal W alignment of MCP-1 from different mammalian species (SEQ ID Nos:1, 3, 4, 283, 5, 6, 284, 7-9, 131, 252, respectively, in order of appearance) as well as human MCP-2, MCP-3, and eotaxin (Positions 1-76 only);

FIG. 24A shows a table summarizing the binding specificity of NOX-E36 and 181-A2-018 regarding MCP-1 from different mammalian species as well as human MCP-2, MCP-3, and eotaxin;

FIG. 24B shows a table summarizing the selectivity of NOX-E36 as determined by Biacore analysis whereby biotinylated NOX-E36 was immobilized on a sensor chip surface and binding of a panel of various CC and CXC chemokines to NOX-E36 was analyzed;

FIG. 24C shows the kinetic analysis of NOX-E36 interacting with chemokines as determined by Biacore analysis whereby the chemokines were immobilized covalently on a CM5 sensor chip surface and various concentrations of the NOX-E36 were injected and NOX-E36s binding behaviour was analyzed using the BiaEvaluation software;

FIG. 24D shows the chemotaxis dose-response curve of THP-1 cell stimulation with MIP-1α with a half-effective concentration of about 0.2 nM;

FIG. 24E shows the Inhibition of MIP-1α induced chemotaxis by NOX-E36. NOX-E36 had no influence on the MIP1α induced chemotaxis of THP-1 cells;

FIG. 25 shows the efficacy of Spiegelmer NOX-E36-3'-PEG in a calcium release assay; cells were stimulated with 3 nM human MCP-1 preincubated at 37° C. with various amounts of Spiegelmer NOX-E36-3'-PEG, represented as percentage of control over concentration of Spiegelmer NOX-E36-3'-PEG;

FIG. 26 shows the efficacy of Spiegelmer NOX-E36-3'-PEG in a chemotaxis assay; cells were allowed to migrate towards 0.5 nM human MCP-1 preincubated at 37° C. with various amounts of Spiegelmer NOX-E36-3'-PEG, represented as percentage of control over concentration of NOX-E36-3'-PEG;

FIG. 27A shows the efficacy of Spiegelmer NOX-E36-5'-PEG in a calcium release assay; cells were stimulated with 3 nM human MCP-1 preincubated at 37° C. with various amounts of Spiegelmer NOX-E36-5'-PEG, represented as percentage of control over concentration of Spiegelmer NOX-E36-5'-PEG;

FIG. 27B shows the efficacy of Spiegelmer NOX-E36-5'-PEG in a chemotaxis assay; cells were allowed to migrate towards 0.5 nM human MCP-1 preincubated at 37° C. with various amounts of Spiegelmer NOX-E36-5'-PEG, represented as percentage of control over concentration of Spiegelmer NOX-E36-5'-PEG;

FIG. 28 shows murine MCP-1-induced $Ca^{++}$-release in THP-1 cells, whereas a dose-response curve for murine MCP-1 was obtained, indicating a half effective concentration ($EC_{50}$) of approximately 5 nM, represented as difference in fluorescence to blank over concentration of murine MCP-1;

FIG. 29 shows the efficacy of anti-murine MCP-1 Spiegelmer mNOX-E36-3'-PEG in a calcium release assay; cells were stimulated with 3 nM murine MCP-1 preincubated at 37° C. with various amounts of Spiegelmer mNOX-E36-3'-PEG, represented as percentage of control over concentration of Spiegelmer mNOX-E36-3'-PEG;

FIG. 30 shows the murine MCP-1-induced chemotaxis of THP-1 cells whereas after 3 hours migration of THP-1 cells towards various mMCP-1 concentrations a dose-response curve for mMCP-1 was obtained, represented as X-fold increase compared to control over concentration of murine MCP-1;

FIG. 31 shows the efficacy of anti-murine MCP-1 Spiegelmer mNOX-E36-3'-PEG in a chemotaxis assay; cells were allowed to migrate towards 0.5 nM murine MCP-1 preincubated at 37° C. with various amounts of Spiegelmer mNOX-E36-3'-PEG, represented as percentage of control over concentration of anti-murine Spiegelmer mNOX-E36-3'-PEG;

FIG. 32 shows the Biacore 2000 sensorgram indicating the $K_D$ value of aptamer D-mNOX-E36 binding to murine D-MCP-1 which was immobilized on a PioneerF1 sensor chip by amine coupling procedure, represented as response (RU) over time;

FIG. 33 shows the Biacore 2000 sensorgram indicating binding of aptamer D-mNOX-E36 to human D-MCP-1 and murine D-MCP-1 whereas the two different forms of D-MCP-1 were immobilized, by amine coupling procedure on PioneerF1 and a CM4 sensor chips, respectively, represented as response (RU) over time;

FIGS. 34A-I show renal sections of 24-week old MRL$^{lpr/lpr}$ mice, stained with periodic acid Schiff (PAS), antibodies for Mac-2 (macrophages) and CD3 (T cells) as indicated; images are representative for 7-12 mice in each group (original magnification PAS: ×100, PAS inserts: ×400, Mac2: ×400, CD3: ×100;

FIG. 35 shows a table illustrating renal function parameters and histological findings in the different groups of 24-week old MRL$^{lpr/lpr}$ mice;

FIG. 36 shows the quantification of histological changes by morphometry performed on silver stained sections of mice from all groups; A, interstitial volume index; B, tubular dilation index, and C, tubular cell damage index were calculated as percentage of high power field and are expressed as means±SEM;

FIG. 37 shows the survival of MRL$^{lpr/lpr}$ mice of the various treatment groups as calculated by Kaplan-Meier analysis;

FIGS. 38A-B show renal mRNA expression for the CC-chemokines CCL2 and CCL5 as determined by real-time RT-PCR using total renal RNA pooled from 5 mice of each group whereby RNA levels for each group of mice are expressed per respective 18S rRNA expression;

FIGS. 39A-B show reduction of lung pathology by treatment with mNOX-E36-3'PEG; lung tissue was prepared from of all groups at age 24 weeks and scored semiquantitatively; treatment with mNOX-E36 and mNOX-E36-3'PEG reduced peribronchiolar inflammation in MRL$^{lpr/lpr}$ mice; images are representative for 7-11 mice in each group; original magnification ×100;

FIG. 40 shows cutaneous lupus manifestations of MRL$^{lpr/lpr}$ mice at age 24 weeks which typically occur at the facial or neck area (left mouse) which were less common in anti-mCCL2 Spiegelmer-treated mice (right mouse);

FIG. 41 shows serum and histological findings in MRL$^{lpr/lpr}$ mice at age 24 weeks;

FIG. 42 shows the pharmacokinetics of pegylated and unpegylated anti-mCCL2 Spiegelmers in plasma during the study, indicated as plasma concentration of Spiegelmer mNOX-E36 as a function of time;

FIG. 43 shows flow cytometry for CCR2 on bone marrow and peripheral blood in 24 week old vehicle- or mNOX-E36-3'PEG-treated MRL$^{lpr/lpr}$ mice; data are shown as mean percentage of CCR2 positive cells±SEM in either bone marrow or peripheral blood in 5 mice of each group;

FIG. 44 shows serum CCL2 levels in PoC-PEG- (white bars) and mNOX-E36-3'PEG (mNOX-E36-P)-treated (black bars) 1K db/db mice as determined by ELISA at different time points as indicated; data are means±SEM; *, $p<0.05$ mNOX-E36-3'PEG (mNOX-E36-P) vs. PoC-PEG;

FIG. 45 shows the infiltrated number of Mac-2 and Ki-67 positive cells in the glomeruli and the interstitium of untreated or POC-PEG or rather mNOX-E36-3'PEG treated db/db mice;

FIG. 46 shows the diabetic glomerulosclerosis in 6 months old db/db mice; renal sections from mice of the different groups were stained with periodic acid Schiff and 15 glomeruli from each renal section were scored for the extent of glomerulosclerosis; images show representative glomeruli graded to the respective scores as indicated, original magnification 400×; the graph illustrates the mean percentage of each score±SEM from all mice in each group (n=7-10); *, $p<0.05$ for mNOX-E36-3'PEG (mNOX-E36-P) vs. PoC-PEG (PoC-P)-treated 1K db/db mice;

FIG. 47 shows the glomerular filtration rate (GFR) in 6 months old mNOX-E36-3'PEG (mNOX-E36-P)- and PoC-PEG(PoC-P)-treated 1K db/db mice; GFR was determined by FITC-inulin clearance kinetics in the groups of PoC-PEG- and mNOX-E36-3'PEG-treated 1K db/db mice at the end of the study;

FIG. 48 shows tubular atrophy and interstitial volume of 6 months old db/db mice; images of silver-stained renal sections illustrate representative kidneys from the respective groups (original magnification 100×); values represent means±SEM of the respective morphometric analysis index from 7-10 mice in each group; *, $p<0.05$ 2K db/db vs. BKS wild-type mice; #, $p<0.05$ 1K vs. 2K db/db mice; t, $p<0.05$ mNOX-E36-3'PEG (mNOX-E36-PEG)- vs. PoC-PEG-treated 1K db/db mice;

FIG. 49 shows renal CCL2 mRNA expression db/db mice as determined by real-time RT-PCR using total renal RNA pooled from 6-10 mice of each group; mRNA levels for each group of mice are expressed per respective 18 S rRNA expression; and FIG. 50 shows spatial CCL2 expression in kidneys of db/db mice as determined by immunostaining; images illustrate representative sections of kidneys from 6 months old mice of the respective groups as indicated (original magnification, 200×).

EXAMPLE 1

Nucleic Acids that Bind Human MCP-1

Using biotinylated human D-MCP-1 as a target, several nucleic acids that bind to human MCP-1 could be generated the nucleotide sequences of which are depicted in FIGS. 1 through 7. The nucleic acids were characterized on the aptamer, i.e. D-nucleic acid level using competitive or direct pull-down assays with biotinylated human D-MCP-1 (Example 4) or on the Spiegelmer level, i.e. L-nucleic acid with the natural configuration of MCP-1 (L-MCP) by surface plasmon resonance measurement using a Biacore 2000 instrument (Example 7), an in vitro cell culture Ca$^{++}$-release assay (Example 5), or an in vitro chemotaxis assay (Example 6).

The nucleic acid molecules thus generated exhibit different sequence motifs, four main types are defined in FIGS. 1 and 2 (Type 1A/1B), FIG. 3 (Type 2), FIGS. 4 and 5 (Type 3), and FIG. 6 (Type 4). Additional MCP-1 binding nucleic acids which can not be related to each other and to the different sequence motifs described herein, are listed in FIG. 7. For definition of nucleotide sequence motifs, the IUPAC abbreviations for ambiguous nucleotides is used:

| S | strong | G or C; |
| W | weak | A or U; |
| R | purine | G or A; |
| Y | pyrimidine | C or U; |
| K | keto | G or U; |
| M | imino | A or C; |
| B | not A | C or U or G; |
| D | not C | A or G or U; |
| H | not G | A or C or U; |
| V | not U | A or C or G; |
| N | all | A or G or C or U |

If not indicated to the contrary, any nucleic acid sequence or sequence of stretches and boxes, respectively, is indicated in the 5'→3' direction.

Type 1A MCP-1 Binding Nucleic Acids (FIG. 1)

As depicted in FIG. 1 all sequences of MCP-1 binding nucleic acids of Type 1A comprise several sequences stretches or boxes whereby boxes B1A and B1B are the 5'- and 3' terminal stretches that can hybridize with each other. However, such hybridization is not necessarily given in the molecule as actually present under physiological conditions. Boxes B2, B3, B4, B5 and box B6 are flanked by box B1A and box B1B.

The nucleic acids were characterized on the aptamer level using direct and competitive pull-down assays with biotinylated human D-MCP-1 in order to rank them with respect to their binding behaviour (Example 4). Selected sequences were synthesized as Spiegelmer (Example 3) and were tested using the natural configuration of MCP-1 (L-MCP) in an in vitro cell culture Ca$^{++}$-release assay (Example 5).

The sequences of the defined boxes may be different between the MCP-1 binding nucleic acids of Type 1A which influences the binding affinity to MCP-1. Based on binding analysis of the different MCP-1 binding nucleic acids summarized as Type 1A MCP-1 binding nucleic acids, the boxes B1A, B2, B3, B4, B5, B6 and B1B and their nucleotide sequences as described in the following are individually and more preferably in their entirety essential for binding to MCP-1:

boxes B1A and B1B are the 5'- and 3' terminal stretches can hybridize with each other; where B1A is AGCRUG, preferably AGCGUG; and where B1B is CRYGCU, preferably CACGCU,
box B2, which is CCCGGW, preferably CCCGGU;
box B3, which is GUR, preferably GUG;
box B4, which is RYA, preferably GUA;
box B5, which is GGGGGRCGCGAYC (SEQ ID NO: 292), preferably GGGGGGCGCGACC (SEQ ID NO: 294);
box B6, which is UGCAAUAAUG (SEQ ID NO: 293) or URYAWUUG, preferably UACAUUUG;

As depicted in FIG. 1, the nucleic acid molecule referred to as 176-E10trc has the best binding affinity to MCP-1 (as aptamer in the pull-assay with a $K_D$ of 5 nM as well as Spiegelmer with an $IC_{50}$ of 4-5 nM in in vitro cell culture $Ca^{++}$-release assay) and therefore may constitute the optimal sequence and the optimal combination of sequence elements B1A, B2, B3, B4, B5, B6 and B1B.

Type 1B MCP-1 Binding Nucleic Acids (FIG. 2)

As depicted in FIG. 2, all sequences of Type 1B comprise several sequences stretches or boxes whereby boxes B1A and B1B are the 5'- and 3' terminal stretches that can hybridize with each other and boxes B2, B3, B4, B5 and box B6 are flanked by box B1A and box B1B. However, such hybridization is not necessarily given in the molecule as actually present under physiological conditions.

The nucleic acids were characterized on the aptamer level using direct and competitive pull-down assays with biotinylated human D-MCP-1 in order to rank them with respect to their binding behaviour (Example 4). Selected sequences were synthesized as Spiegelmer (Example 3) and were tested using the natural configuration of MCP-1 (L-MCP) in an in vitro cell culture $Ca^{++}$-release assay (Example 5).

The sequences of the defined boxes may be different between the MCP-1 binding nucleic acids of Type 1B which influences the binding affinity to MCP-1. Based on binding analysis of the different MCP-1 binding nucleic acids summarized as Type 1B MCP-1 binding nucleic acids, the boxes B1A, B2, B3, B4, B5, B6 and B1B and their nucleotide sequences as described in the following are individually and more preferably in their entirety essential for binding to MCP-1:

boxes B1A and B1B that can hybridize with each other; where B1A is AGYRUG, preferably AGCGUG; and where B1B is CAYRCU, preferably CACGCU;
box B2, which is CCAGCU or CCAGY, preferably CCAGU;
box B3, which is GUG;
box B4, which is AUG; box B5, which is GGGGGGCGCGACC (SEQ ID NO:294);
box B6, which is CAUUUUA or CAUUUA, preferably CAUUUUA;

As depicted in FIG. 2, the nucleic acid referred to as 176-C9trc has the best binding affinity to MCP-1 (as aptamer in the pull-down assay with a $K_D$ of 5 nM as well as Spiegelmer with an $IC_{50}$ of 4-5 nM in in vitro cell culture $Ca^{++}$-release assay) and therefore may constitute the optimal sequence and the optimal combination of sequence elements B1A, B2, B3, B4, B5, B6 and B1B.

Type 2 MCP-1 Binding Nucleic Acids (FIG. 3)

As depicted in FIG. 3, all sequences of Type 2 comprise several sequences stretches or boxes whereby boxes B1A and B1B are the 5'- and 3' terminal stretches that can hybridize with each other and box B2 is the central sequence element. However, such hybridization is not necessarily given in the molecule as actually present under physiological conditions.

The nucleic acids were characterized on the aptamer level using direct and competitive pull-down assays with biotinylated human D-MCP-1 in order to rank them with respect to their binding behaviour (Example 4). Selected sequences were synthesized as Spiegelmer (Example 3) and were tested using the natural configuration of MCP-1 (L-MCP) in in vitro cell culture $C^{++}$-release (Example 5) or in vitro chemotaxis assays (Example 6).

The sequences of the defined boxes may be different between the MCP-1 binding nucleic acids of Type 3 which influences the binding affinity to MCP-1. Based on binding analysis of the different MCP-1 binding nucleic acids summarized as Type 2 MCP-1 binding nucleic acids, the boxes B1A, B2, and B1B and their nucleotide sequences as described in the following are individually and more preferably in their entirety essential for binding to MCP-1:

boxes B1A and B1B, 5'- and 3' terminal stretches that can hybridize with each other; where B1A is ACGCA and B1B is UGCGU, or B1A is CGCA and B1B is UGCG, or B1A is GCA and B1B is UGCG or UGC; preferably B1A is GCA and B1B is UGCG;
box B2, CSUCCCUCACCGGUGCAAGUGAAGCC-GYGGCUC (SEQ ID NO:287), preferably C GUCCCUCACCGGUGCAAGUGAAGCCGUGG-CUC (SEQ ID NO:288)

As depicted in FIG. 3, the nucleic acid referred to as 180-D1-002 as well as the derivatives of 180-D1-002 like 180-D1-011, 180-D1-012, 180-D1-035, and 180-D1-036 (=NOX-E36) have the best binding affinity to MCP-1 as aptamer in the pull-down or competitive pull-down assay with an $K_D$ of <1 nM and therefore may constitute the optimal sequence and the optimal combination of sequence elements B1A, B2, and B1B.

For nucleic acid molecule D-NOX-E36 (D-180-D1-036; SEQ. ID No. 159), a dissociation constant ($K_D$) of 890±65 pM at room temperature (RT) and of 146±13 pM at 37° C. was determined (Example 4; FIG. 9). The respective Spiegelmer NOX-E36 (180-D1-036; SEQ. ID No. 37) exhibited an inhibitory concentration ($IC_{50}$) of 3-4 nM in an in vitro $Ca^{++}$-release assay (Example 5; FIG. 12) and of ca. 0.5 nM in an in vitro chemotaxis assay (Example 6; FIG. 15). For the PEGylated derivatives of NOX-E36, NOX-E36-3'PEG and NOX-E36-5'PEG, $IC_{50}$s of ca. 3 nM were determined in the $Ca^{++}$-release assay (Example 5, FIG. 25 and FIG. 27A) and <1 nM in the chemotaxis assay (Example 6; FIG. 26 and FIG. 27B).

Type 3 MCP-1 Binding Nucleic Acids (FIGS. 4+5)

As depicted in FIGS. 4 and 5, all sequences of Type 3 comprise several sequence stretches or boxes whereby three pairs of boxes are characteristic for Type 3 MCP-1 binding nucleic acids. Both boxes B1A and B1B as well as boxes B2A and B2B as well as boxes B5A and B5B bear the ability to hybridize with each other. However, such hybridization is not necessarily given in the molecule as actually present under physiological conditions. Between these potentially hybridized sequence elements, non-hybridizing nucleotides are located, defined as box B3, box B4 and box B6.

The nucleic acids were characterized on the aptamer level using direct and competitive pull-down assays with biotinylated human D-MCP-1 in order to rank them with respect to their binding behavior (Example 4). Selected sequences were synthesized as Spiegelmer (Example 3) and were tested using the natural configuration of MCP-1 (L-MCP) in in vitro chemotaxis assays (Example 6) or via Biacore measurements (Example 7).

The sequences of the defined boxes may be different between the MCP-1 binding nucleic acids of Type 3 which influences the binding affinity to MCP-1. Based on binding analysis of the different MCP-1 binding nucleic acids summarized as Type 3 MCP-1 binding nucleic acids, the boxes B1A, B2A, B3, B2B, B4, B5A, B6, B5B, B1B and their nucleotide sequences as described in the following are individually and more preferably in their entirety essential for binding to MCP-1:

boxes B1A and B1B, 5'- and 3' terminal stretches that can hybridize with each other; where B1A is GURCUGC and B1B is GCAGCAC; preferably B1A is GUGCUGC and B1B is GCAGCAC;
or B1A is GKSYGC and B1B is GCRSMC; preferably B1A is GUGCGC and B1B is GCGCAC;
or B1A is KBBSC and B1B is GSVVM; preferably B1A is KKSSC and B1B is GSSMM;
or B1A is BNGC and B1B is GCNV; preferably B1A is SNGC and B1B is GCNS; most preferably B1A is GGGC and B1B is GCCC;

boxes B2A and B2B, stretches that can hybridize with each other; where B2A is GKMGU and B2B is ACKMC; preferably B2A is GUAGU and B2B is ACUAC;

box B3, which is KRRAR, preferably UAAAA or GAGAA;

box B4, which is CURYGA or CUWAUGA or CWRMGACW or UGCCAGUG, preferably CAGCGACU or CAACGACU;

B5A and B5B, stretches that can hybridize with each other; where B5A is GGY and B5B is GCYR whereas GCY can hybridize with the nucleotides of B5A; or B5A is CWGC and B5B is GCWG; preferably B5A is GGC and B5B is GCCG;

box B6, which is: YAGA or CKAAU or CCUUUAU, preferably UAGA.

As depicted in FIGS. 4 and 5, the nucleic acid referred to as 178-D5 and its derivative 178-D5-030 as well as 181-A2 with its derivatives 181-A2-002, 181-A2-004, 181-A2-005, 181-A2-006, 181-A2-007, 181-A2-017, 181-A2-018, 181-A2-019, 181-A2-020, 181-A2-021, and 181-A2-023 have the best binding affinity to MCP-1. 178-D5 and 178-D5-030 were evaluated as aptamers in direct or competitive pull-down assays (Example 4) with an $K_D$ of approx. 500 pM. In the same experimental set-up, 181-A2 was determined with an $K_D$ of approx. 100 pM. By Biacore analysis (Example 7), the $K_D$ of 181-A2 and its derivatives towards MCP-1 was determined to be 200-300 pM. In $Ca^{++}$ release and chemotaxis assays with cultured cells (Example 5 and 6, respectively), for both 178-D5 and 181-A2, an $IC_{50}$ of approx. 500 pM was measured. Therefore, 178-D5 as well as 181-A2 and their derivatives may constitute the optimal sequence and the optimal combination of sequence elements B1A, B2A, B3, B2B, B4, B5A, B6, B5B and B1B.

Type 4 MCP-1 Binding Nucleic Acids (FIG. 6)

As depicted in FIG. 6, all sequences of Type 4 comprise several sequences, stretches or boxes whereby boxes B1A and B1B are the 5'- and 3' terminal stretches that can hybridize with each other and box B2 is the central sequence element.

The nucleic acids were characterized on the aptamer level using direct pull-down assays with biotinylated human D-MCP-1 in order to rank them with respect to their binding behavior (Example 4). Selected sequences were synthesized as Spiegelmer (Example 3) and were tested using the natural configuration of MCP-1 (L-MCP) in an in vitro cell culture $Ca^{++}$-release (Example 5) and/or chemotaxis assay (Example 6).

The sequences of the defined boxes may differ among the MCP-1 binding nucleic acids of Type 4 which influences the binding affinity to MCP-1. Based on binding analysis of the different MCP-1 binding nucleic acids summarized as Type 4 MCP-1 binding nucleic acids, the boxes B1A, B2, and B1B their nucleotide sequences as described in the following are individually and more preferably in their entirety essential for binding to MCP-1:

boxes B1A and B1B, 5'- and 3' terminal stretches that can hybridize with each other; where B1A is AGCGUGDU and B1B is GNCASGCU; or B1A is GCGCGAG and B1B is CUCGCGUC; or B1A is CSKSUU and B1B is GRSMSG; or B1A is GUGUU and B1B is GRCAC; or B1A is UGUU and B1B is GGCA; preferably B1A is CSKSUU and B1B is GRSMSG; mostly preferred B1A is CCGCUU and B1B is GGGCGG; and box B2, which is AGNDRDGBKGGURGYARGUAAAG (SEQ ID NO:289) or AGGUGGGUGGUAGU-AAGUAAAG (SEQ ID NO:290) or CAGGUGGGUGGUAGAAUGUAAAGA, (SEQ ID NO:291 preferably AGGUGGGUGGUAG-UAAGUAAAG (SEQ ID NO:290)

As depicted in FIG. 6, the nucleic acid referred to as 174-D4-004 and 166-A4-002 have the best binding affinity to MCP-1 (as Spiegelmer with an $IC_{50}$ of 2-5 nM in in vitro cell culture $Ca^{++}$ release assay) and may, therefore, constitute the optimal sequence and the optimal combination of sequence elements B1A, B2, and B1B.

Additionally, 29 other MCP-1 binding nucleic acids were identified which cannot be described by a combination of nucleotide sequence elements as has been shown for Types 1-4 of MCP-1 binding nucleic acids. These sequences are listed in FIG. 7.

It is to be understood that any of the sequences shown in FIGS. 1 through 7 are nucleic acids according to the present invention, including those truncated forms thereof but also including those extended forms thereof under the proviso, however, that the thus truncated and extended, respectively, nucleic acid molecules are still capable of binding to the target.

EXAMPLE 2

Nucleic Acids that Bind Murine MCP-1

Using biotinylated murine D-MCP-1 as a target, several nucleic acid molecules binding thereto could be generated. The result of a sequence analysis of these nucleic acid molecules can be taken from FIG. 8.

The nucleic acids were characterized on the aptamer level using a pull-down assay using biotinylated murine D-MCP-1 in order to in order to rank them with respect to their binding behavior (Example 4). Selected sequences were synthesized as Spiegelmer (Example 3) and were tested using the natural configuration of MCP-1 (L-MCP) in an in vitro cell culture $Ca^{++}$-release (Example 5) and chemotaxis assay (Example 6).

As depicted in FIG. 8, D-188-A3-001 and D-189-G7-001 and their derivatives bind D-MCP-1 with subnanomolar $K_D$ in the pull-down assay (FIG. 8).

For D-mNOX-E36 (=D-188-A3-007; SEQ. ID No. 244), a dissociation constant ($K_D$) of 0.1-0.2 nM at 37° C. was determined (Example 4; FIG. 10). The respective Spiegelmer mNOX-E36 (188-A3-007; SEQ. ID No. 122) exhibited an inhibitory concentration ($IC_{50}$) of approx. 12 nM in an in vitro $Ca^{++}$-release assay (Example 5; FIG. 13) and of approx. 7 nM in an in vitro chemotaxis assay (Example 6; FIG. 16). For the PEGylated derivative of mNOX-E36, mNOX-E36-3'PEG (SEQ. ID No. 254), $IC_{50}$'s of approx. 8 nM were determined in the $Ca^{++}$-release assay (Example 5, FIG. 29) and approx. 3 nM in the chemotaxis assay (Example 6; FIG. 31).

It is to be understood that any of the sequences shown in FIGS. 1 through 7 are nucleic acids according to the present invention, including those truncated forms thereof but also including those extended forms thereof under the proviso, however, that the thus truncated and extended, respectively, nucleic acid molecules are still capable of binding to the target.

EXAMPLE 3

Synthesis and Derivatization of Aptamers and Spiegelmers

Small Scale Synthesis

Aptamers and Spiegelmers were produced by solid-phase synthesis with an ABI 394 synthesizer (Applied Biosystems, Foster City, Calif., USA) using 2'TBDMS RNA phosphoramidite chemistry (M. J. Damha, K. K. Ogilvie, Methods in Molecular Biology, Vol. 20 Protocols for oligonucleotides and analogs, ed. S. Agrawal, p. 81-114, Humana Press Inc. 1993). rA(N-Bz)-, rC(Ac)-, rG(N-ibu)-, and rU-phosphoramidites in the D- and L-configuration were purchased from ChemGenes, Wilmington, Mass. Aptamers and Spiegelmers were purified by gel electrophoresis.

Large Scale Synthesis Plus Modification

Spiegelmer NOX-E36 was produced by solid-phase synthesis with an ÄktaPilot100 synthesizer (Amersham Biosciences; General Electric Healthcare, Freiburg) using 2'TBDMS RNA phosphoramidite chemistry (M. J. Damha, K. K. Ogilvie, Methods in Molecular Biology, Vol. 20 Protocols for oligonucleotides and analogs, ed. S. Agrawal, p. 81-114, Humana Press Inc. 1993). L-rA(N-Bz)-, L-rC(Ac)-, L-rG(N-ibu)-, and L-rU-phosphoramidites were purchased from ChemGenes, Wilmington, Mass. The 5'-amino-modifier was purchased from American International Chemicals Inc. (Framingham, Mass., USA). Synthesis of the unmodified Spiegelmer was started on L-riboG modified CPG pore size 1000 Å (Link Technology, Glasgow, UK); for the 3'—$NH_2$-modified Spiegelmer, 3'-Aminomodifier-CPG, 1000 Å (ChemGenes, Wilmington, Mass.) was used. For coupling (15 min per cycle), 0.3 M benzylthiotetrazole (CMS-Chemicals, Abingdon, UK) in acetonitrile, and 3.5 equivalents of the respective 0.1 M phosphoramidite solution in acetonitrile was used. An oxidation-capping cycle was used. Further standard solvents and reagents for oligonucleotide synthesis were purchased from Biosolve (Valkenswaard, NL). The Spiegelmer was synthesized DMT-ON; after deprotection, it was purified via preparative RP-HPLC (Wincott F. et al. (1995) *Nucleic Acids Res* 23:2677) using Source 15RPC medium (Amersham). The 5'DMT-group was removed with 80% acetic acid (30 min at RT). Subsequently, aqueous 2 M NaOAc solution was added and the Spiegelmer was desalted by tangential-flow filtration using a 5 K regenerated cellulose membrane (Millipore, Bedford, Mass.).

PEGylation of NOX-E36

In order to prolong the Spiegelmer's plasma residence time in vivo, Spiegelmer NOX-E36 was covalently coupled to a 40 kDa polyethylene glycol (PEG) moiety at the 3'-end or 5'-end.

3'-PEGylation of NOX-E36

For PEGylation (for technical details of the method for PEGylation see European patent application EP 1 306 382), the purified 3'-amino modified Spiegelmer was dissolved in a mixture of $H_2O$ (2.5 ml), DMF (5 ml), and buffer A (5 ml; prepared by mixing citric acid.$H_2O$ [7 g], boric acid [3.54 g], phosphoric acid [2.26 ml], and 1 M NaOH [343 ml] and adding H2O to a final volume of 1 l; pH=8.4 was adjusted with 1 M HCl).

The pH of the Spiegelmer solution was brought to 8.4 with 1 M NaOH. Then, 40 kDa PEG-NHS ester (Nektar Therapeutics, Huntsville, Ala.) was added at 37° C. every 30 min in four portions of 0.6 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), 4 ml buffer A, and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C, 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC: The PEGylated Spiegelmer was desalted by tangential-flow filtration (5 K regenerated cellulose membrane, Millipore, Bedford Mass.).

5'-PEGylation of NOX-E36

For PEGylation (for technical details of the method for PEGylation see European patent application EP 1 306 382), the purified 5'-amino modified Spiegelmer was dissolved in a mixture of $H_2O$ (2.5 ml), DMF (5 ml), and buffer A (5 ml; prepared by mixing citric acid.$H_2O$ [7 g], boric acid [3.54 g], phosphoric acid [2.26 ml], and 1 M NaOH [343 ml] and adding water to a final volume of 1 l; pH=8.4 was adjusted with 1 M HCl).

The pH of the Spiegelmer solution was brought to 8.4 with 1 M NaOH. Then, 40 kDa PEG-NHS ester (Nektar Therapeutics, Huntsville, Ala.) was added at 37° C. every 30 min in six portions of 0.25 equivalents until a maximal yield of 75 to 85% was reached. The pH of the reaction mixture was kept at 8-8.5 with 1 M NaOH during addition of the PEG-NHS ester.

The reaction mixture was blended with 4 ml urea solution (8 M), and 4 ml buffer B (0.1 M triethylammonium acetate in $H_2O$) and heated to 95° C. for 15 min. The PEGylated Spiegelmer was then purified by RP-HPLC with Source 15RPC medium (Amersham), using an acetonitrile gradient (buffer B; buffer C, 0.1 M triethylammonium acetate in acetonitrile). Excess PEG eluted at 5% buffer C, PEGylated Spiegelmer at 10-15% buffer C. Product fractions with a purity of >95% (as assessed by HPLC) were combined and mixed with 40 ml 3 M NaOAC. The PEGylated Spiegelmer was desalted by tangential-flow filtration (5 K regenerated cellulose membrane, Millipore, Bedford Mass.).

EXAMPLE 4

Determination of Binding Constants (Pull-Down Assay)

Direct Pull-Down Assay

The affinity of aptamers to D-MCP-1 was measured in a pull down assay format at 20 or 37° C., respectively. Aptamers were 5'-phosphate labeled by T4 polynucleotide kinase (Invitrogen, Karlsruhe, Germany) using [$\gamma$-$^{32}$P]-labeled ATP (Hartmann Analytic, Braunschweig, Germany). The specific radioactivity of labeled aptamers was 200,000-800,000 cpm/pmol. Aptamers were incubated after de- and renaturation at 20 pM concentration at 37° C. in selection buffer (20 mM Tris-HCl pH 7.4; 137 mM NaCl; 5 mM KCl; 1 mM MgCl$_2$; 1 mM CaCl$_2$; 0.1% [w/vol] Tween-20) together with varying amounts of biotinylated D-MCP-1 for 4-12 hours in order to reach equilibrium at low concentrations. Selection buffer was supplemented with 10 µg/ml human serum albumin (Sigma-Aldrich, Steinheim, Germany), and 10 µg/ml yeast RNA (Ambion, Austin, USA) in order to prevent adsorption of binding partners with surfaces of used plasticware or the immobilization matrix. The concentration range of biotinylated D-MCP-1 was set from 8 pM to 100 nM; total reaction volume was 1 ml. Peptide and peptide-aptamer complexes were immobilized on 1.5 µl Streptavidin Ultralink Plus particles (Pierce Biotechnology, Rockford, USA) which had been preequilibrated with selection buffer and resuspended in a total volume of 6 µl. Particles were kept in suspension for 30 min at the respective temperature in a thermomixer. Immobilized radioactivity was quantitated in a scintillation counter after detaching the supernatant and appropriate washing. The percentage of binding was plotted against the concentration of biotinylated D-MCP-1 and dissociation constants were obtained by using software algorithms (GRAFIT; Erithacus Software; Surrey U.K.) assuming a 1:1 stoichiometry.

Competitive Pull-Down Assay

In order to compare different D-MCP-1 binding aptamers, a competitive ranking assay was performed. For this purpose the most affine aptamer available was radioactively labeled (see above) and served as reference. After de- and renaturation it was incubated at 37° C. with biotinylated D-MCP-1 in 1 ml selection buffer at conditions that resulted in around 5-10% binding to the peptide after immobilization and washing on NeutrAvidin agarose or Streptavidin Ultralink Plus (both from Pierce) without competition. An excess of de- and renatured non-labeled D-RNA aptamer variants was added to different concentrations (e.g. 2, 10, and 50 nM) with the labeled reference aptamer to parallel binding reactions. The aptamers to be tested competed with the reference aptamer for target binding, thus decreasing the binding signal in dependence of their binding characteristics. The aptamer that was found most active in this assay could then serve as a new reference for comparative analysis of further aptamer variants.

EXAMPLE 5

Determination of Inhibitory Concentration in a Ca$^{++}$-Release Assay

THP-1-cells (DSMZ, Braunschweig) were cultivated overnight at a cell density of 0.3×10$^6$/ml at 37° C. and 5% CO$_2$ in RPMI 1640 medium with GlutaMAX (Invitrogen) which contained in addition 10% fetal calf serum, 50 units/ml penicillin, 50 µg/ml streptomycin and 50 µM $\beta$-mercaptoethanol.

The Spiegelmers were incubated together with recombinant human MCP-1 (Bachem) in Hanks balanced salt solution (HBSS), containing 1 mg/ml bovine serum albumin, 5 mM probenecid and 20 mM HEPES (HBSS+) for 15 to 60 min at 37° C. in a 0.2 ml low profile 96-tube plate ("stimulation solution").

For loading with the calcium indicator dye, cells were centrifuged at 300×g for 5 min, resuspended in 4 ml indicator dye solution (10 µM fluo-4 [Molecular Probes], 0.08% pluronic 127 [Molecular Probes] in HBSS+) and incubated for 60 min at 37° C. Thereafter, 11 ml HBSS+ were added and the cells were centrifuged as above, washed once with 15 ml HBSS+ and then resuspended in HBSS+ to give a cell density of 1.1×10$^6$/ml. 90 µl of this cell suspension were added to each well of a black 96-well plate.

Measurement of fluorescence signals was done at an excitation wavelength of 485 nm and an emission wavelength of 520 nm in a Fluostar Optima multidetection plate reader (BMG). For parallel measurement of several samples, wells of one (perpendicular) row of a 96-well plate were recorded together. First three readings with a time lag of 4 sec were done for determination of the base line. Then the recording was interrupted and the plate was moved from the instrument. Using a multi-channel pipette, 10 µl of the stimulation solution was added to the wells, then the plate was moved into the instrument again and the measurement was continued. In total, 20 recordings with time intervals of 4 seconds were performed.

For each well the difference between maximal fluorescence and base line value was determined and plotted against MCP-1 concentration or, in the experiments on the inhibition of calcium release by Spiegelmers, against concentration of Spiegelmer.

Determination of Half-Maximal Effective Concentration (EC$_{50}$) for Human MCP-1

After stimulation of THP-1 cells with various hMCP-1 concentrations and plotting the difference between the maximal and the baseline signals, a dose-response curve for human MCP-1 was obtained, indicating a half effective concentration (EC$_{50}$) of about 2-4 nM (FIG. 11). This concentration was used for the further experiments on inhibition of Ca$^{++}$-release by Spiegelmers.

Determination of Half-Maximal Effective Concentration (EC$_{50}$) for Murine MCP-1

After stimulation of THP-1 cells with various mMCP-1 concentrations and plotting the difference between the maximal and the baseline signals, a dose-response curve for murine MCP-1 was obtained, indicating a half effective concentration (EC$_{50}$) of about 5 nM (FIG. 28).

This concentration was used for the further experiments on inhibition of Ca$^{++}$-release by Spiegelmers.

EXAMPLE 6

Determination of Inhibitory Concentration in a Chemotaxis Assay

THP-1 cells grown as described above were centrifuged, washed once in HBH (HBSS, containing 1 mg/ml bovine serum albumin and 20 mM HEPES) and resuspended at 3×10$^6$ cells/ml. 100 µl of this suspension were added to Transwell inserts with 5 µm pores (Corning, #3421). In the lower compartments MCP-1 was preincubated together with Spiegelmers in various concentrations in 600 µl HBH at 37° C. for 20 to 30 min prior to addition of cells. Cells were allowed to migrate at 37° C. for 3 hours. Thereafter the inserts were removed and 60 µl of 440 µM resazurin (Sigma) in phosphate buffered saline was added to the lower compartments. After incubation at 37° C. for 2.5 hours; fluorescence was measured at an excitation wavelength of 544 nm and an emission wavelength of 590 nm in a Fluostar Optima multidetection plate reader (BMG).

Determination of Half-Maximal Effective Concentration ($EC_{50}$) for Human MCP-1

After 3 hours migration of THP-1 cells towards various human MCP-1 concentrations, a dose-response curve for human MCP-1 was obtained, indicating a maximal effective concentration of about 1 nM and reduced activation at higher concentrations (FIG. 14). For the further experiments on inhibition of chemotaxis by Spiegelmers a MCP-1 concentration of 0.5 nM was used.

Determination of Half-Maximal Effective Concentration ($EC_{50}$) for Murine MCP-1

After 3 hours migration of THP-1 cells towards various murine MCP-1 concentrations, a dose-response curve for murine MCP-1 was obtained, indicating a maximal effective concentration of about 1-3 nM and reduced activation at higher concentrations (FIG. 30). For the further experiments on inhibition of chemotaxis by Spiegelmers a murine MCP-1 concentration of 0.5 nM was used.

EXAMPLE 7

Binding Analysis by Surface Plasmon Resonance Measurement 7.1 Specificity Assessment of NOX-E36, 181-A2-018 and mNOX-E36

The Biacore 2000 instrument (Biacore AB, Uppsala, Sweden) was used to analyze binding of nucleic acids to human MCP-1 and related proteins. When coupling was to be achieved via amine groups, the proteins were dialyzed against water for 1-2 h (Millipore VSWP mixed cellulose esters; pore size, 0.025 µM) to remove interfering amines. PioneerF1 or CM4 sensor chips (Biacore AB) were activated before protein coupling by a 35-µl injection of a 1:1 dilution of 0.4 M NHS and 0.1 M EDC at a flow of 5 µl/min. Chemokine was then injected in concentrations of 0.1-1.5 mg/ml at a flow of 2 µl/min until the instrument's response was in the range of 1000-2000 RU (relative units). Unreacted NHS esters were deactivated by injection of 35 µl ethanolamine hydrochloride solution (pH 8.5) at a flow of 5 µl/min. The sensor chip was primed twice with binding buffer and equilibrated at 10 µl/min for 1-2 hours until the baseline appeared stable. For all proteins, kinetic parameters and dissociation constants were evaluated by a series of Spiegelmer injections at concentrations of 1000, 500, 250, 125, 62.5, 31.25, and 0 nM in selection buffer (Tris-HCl, 20 mM; NaCl, 137 mM; KCl, 5 mM; $CaCl_2$, 1 mM; $MgCl_2$, 1 mM; Tween20, 0.1% [w/v]; pH 7.4). In all experiments, the analysis was performed at 37° C. using the Kinject command defining an association time of 180 and a dissociation time of 360 seconds at a flow of 10 µl/min. Data analysis and calculation of dissociation constants ($K_D$) was done with the BIAevaluation 3.0 software (BIACORE AB, Uppsala, Sweden) using the Langmuir 1:1 stoichiometric fitting algorithm.

7.1.1 NOX-E36 and 181-A2-018 (Human-MCP-1 Specific Nucleic Acids)

Only for human MCP-1 all sensorgrams are depicted (FIGS. 17 and 20, respectively); for the other proteins, only the sensorgram obtained with 125 nM Spiegelmer concentration is shown for sake of clarity (FIGS. 18/19 and 21/22).

Analysis of the NOX-E36.hMCP-1 interaction: recombinant human MCP-1 was immobilized on a PioneerF1 sensor chip following the manufacturer's recommendations (amine coupling procedure) until an instrument response of 1381 RU (relative units) was established. The determined dissociation constant ($K_D$) for NOX-E36 binding to human MCP-1 was ca. 890 pM (FIG. 17).

Analysis of the 181-A2-018.hMCP-1 interaction: recombinant human MCP-1 was immobilized on a CM4 sensor chip following the manufacturer's recommendations (amine coupling procedure) until an instrument response of 3111 RU (relative units) was established. The determined dissociation constant ($K_D$) for 181-A2-018 binding to human MCP-1 was ca. 370 pM (FIG. 20).

To determine the specificity of NOX-E36 and 181-A2-018, various human MCP-1 family proteins as well as human eotaxin were immobilized on a PioneerF1 and a CM4 sensor chip (hMCP-1, 1754 RU; hMCP-2, 1558 RU; hMCP-3, 1290 RU; eotaxin, 1523 RU). Kinetic analysis revealed that NOX-E36 binds to eotaxin and hMCP-2 with dissociation constants ($K_D$) of 5-10 nM; hMCP-3 was not recognized (FIGS. 18 and 24A). 181-A2-018, in contrast, binds eotaxin, hMCP-2 and hMCP-3, but with slightly lower affinity (10-20 nM; FIGS. 21 and 24A).

Interspecies cross-reactivity of NOX-E36 and 181-A2-018 was assessed using amino-coupling immobilized MCP-1 from human (1460 RU), monkey (1218 RU), pig (1428 RU), dog (1224 RU), rabbit (1244 RU), rat (1267 RU), and mouse (1361 RU) on a PioneerF1 and a CM4 sensor chip. Kinetic analysis revealed that NOX-E36 binds to human, monkey, porcine, and canine MCP-1 with comparable dissociation constants ($K_D$) of 0.89-1.2 nM whereas MCP-1 from mouse, rat and rabbit were not recognized (FIGS. 19 and 24A). 181-A2-018 binds to human and monkey MCP-1 with comparable dissociation constants ($K_D$) of 0.5-0.6 nM, whereas porcine, rabbit and canine MCP-1 are bound with much lower affinity. Rat and mouse MCP-1 were not recognized by NOX-A2-018 (FIGS. 22 and 24A).

Sequences as well as degree of homology in percent identical amino acids between the MCP-1 protein from different species and closely related human proteins are depicted in FIG. 23; calculated KD values for NOX-E36 and 181-A2-018 are displayed in tabular format in FIG. 24A.

7.1.2 mNOX-E36 (Murine MCP-1 Specific Nucleic Acid)

To analyze the binding behaviour of mNOX-E36, 3759 RU of synthetic biotinylated murine D-MCP-1 (flow cell 3) and 3326 RU of biotinylated human D-MCP-1 (flow cell 4) were immobilized on a Streptavidin conjugated sensor chip (Biacore AB, Freiburg, Germany), respectively. mNOX-E36 aptamer (D-RNA) solutions of 500, 250, 125, 62.5, 31.25, and 0 nM were injected using the Kinject command defining an association time of 180 sec and a dissociation time of 360 sec. Flow cell 1 was used as buffer and dextran matrix control (Biacore SA-Chip surface) whereas on flow cell 2, an unspecific D-peptide was immobilized to determine unspecific binding of the aptamer. FIG. 32 shows a sensorgram of the D-NOX-E36 kinetic for binding to murine D-MCP-1 with a calculated dissociation constant ($K_D$) of 200-300 pM. mNOX-E36 does not bind human D-MCP-1 (FIG. 33); for sake of clarity, only the sensorgram obtained with 125 nM Spiegelmer is shown.

7.2 Selectivity Assessment of NOX-E36

Selectivity of NOX-E36 was assessed by surface plasmon resonance analysis by immobilizing 5' biotinylated NOX-E36 on a Streptavidin (SA-Chip). 352 RU of NOX-E36 on flowcell (FC) 1 and equal amount of 5'-terminal biotinylated non-functional control Spiegelmer (POC) on FC 2 were immobilized by streptavidin/biotin binding. FC3 was used as surface control to determine unspecific binding to the dextran-SA sensor surface.

100 nM of a panel of human chemokines from all four subgroups (CC, CXC, CX$_3$C, and XC) were injected for 360 s and complexes were allowed to dissociate for 360 s at a flow of 10 µl/min and 37° C. Response units after association (Resp. 1; degree of interaction) and after dissociation (Resp. 2, affinity of interaction) were plotted. After each injection the chip surface was regenerated with a 240 s of 1 M sodium chloride with 0.1% Tween; immobilized Spiegelmers were subsequently allowed to refold for 2 minutes at physiological conditions (running buffer). Injection of each chemokine was repeated 3 times. CXCL1, CXCL2, CXCL6 and CXCL9 showed unspecific binding to ribonucleic acids and chip dextran surface. Specific high-affinity binding to immobilized NOX-E36 could only be detected for CCL2/MCP-1, CCL8/MCP-2, CCL11/eotaxin, CCL3/MIP1α, and CXCL7/NAP-2 (FIG. 24B). The finding that MCP-2 and eotaxin are bound by NOX-E36 is not surprising due to the relatively high homology between these chemokines and MCP-1 of 62 and 70%, for the unexpected positives CCL3/MIP-1α and CXCL7/NAP-2, in vitro tests for functional inhibition have been performed or are currently being established, respectively.

Finally, the kinetic parameters of interaction between NOX-E36 and CCL2/MCP-1, CCL8/MCP-2, CCL11/eotaxin, CCL3/MIP1α, CXCL7/NAP-2, CCL7/MCP-3 and CCL13/MCP-4 were determined in the "inverted" system. Here, the chemokines were immobilized and free NOX-E36 was injected (for the detailed protocol, see 7.1). Kinetic data are summarized in FIG. 24C.

7.3 Assessment of Anti-MIP-1α Functionality In Vitro

Biacore measurements had shown cross reactivity of NOX-E36 with MIP-1□. By employing a functional, cell culture-based in vitro assay it should be checked if mere Biacore binding of NOX-E36 to MIP-1□ also translates to functionality, e.g. antagonism.

To achieve this, chemotaxis experiments with THP-1 cells were performed that can be stimulated by MIP-1α. THP-1 cells grown as described above were centrifuged, washed once in HBH (HBSS, containing 1 mg/ml bovine serum albumin and 20 mM HEPES) and resuspended at 3×10$^6$ cells/ml. 100 µl of this suspension were added to Transwell inserts with 5 µm pores (Corning, #3421). In the lower compartments MIP-1□ was preincubated together with Spiegelmers in various concentrations in 600 µl HBH at 37° C. for 20 to 30 min prior to addition of cells. Cells were allowed to migrate at 37° C. for 3 hours. Thereafter the inserts were removed and 60 µl of 440 µM resazurin (Sigma) in phosphate buffered saline was added to the lower compartments. After incubation at 37° C. for 2.5 hours, fluorescence was measured at an excitation wavelength of 544 nm and an emission wavelength of 590 nm in a Fluostar Optima multidetection plate reader (BMG).

After 3 hours migration of THP-1 cells towards various human MIP-1□ concentrations, a dose-response curve for human MIP-1α was obtained, indicating a half-maximal effective concentration of about 1 nM and reduced activation at higher concentrations (FIG. 24D). For the further experiments on inhibition of chemotaxis by Spiegelmers a MIP-1α concentration of 0.5 nM was used.

Experiments for determination of chemotaxis inhibition by NOX-E36 were performed with a stimulus of 0.5 nM MIP-1α. It could be clearly shown that NOX-E36 does not inhibit MIP-1α induced chemotaxis up to the highest tested concentration of 1 µM MIP-1α. As positive control, the respective experiment with MCP-1 as stimulus was performed in parallel (FIG. 24E).

EXAMPLE 8

Therapy of Lupus-Like Disease in MRL$^{lpr/lpr}$ Mice with Anti-mMCP-1 Spiegelmer Blocking proinflammatory mediators has become a successful approach for the treatment of chronic inflammation (Steinman 2004). In addition to TNF and interleukins, CC-chemokines are important candidates for specific antagonism because CC-chemokines mediate leukocyte recruitment from the intravascular space to sites of inflammation (Baggiolini 1998, Luster 2005). There is very strong evidence that MCP-1 (=CCL2) and its respective chemokine receptor CCR2 play a crucial role in autoimmune tissue injury such as the clinical manifestations of systemic lupus erythematosus (Gerard & Rollins 2001). For example, MRL$^{lpr/lpr}$ mice deficient either for the Ccl2 or the Ccr2 gene are protected from lupus-like autoimmunity (Perez de Lema 2005, Tesch 1999). Hence, the CCL2/CCR2 axis may represent a promising therapeutic target, e.g. for lupus nephritis. In fact, delayed gene therapy or transfer of transfected cells, both resulting in in situ production of an NH$_2$-truncated MCP-1, markedly reduced autoimmune tissue injury in MRL$^{lpr/lpr}$ mice. However, such experimental approaches cannot be used in humans because of irrepressible antagonist production and tumor formation (Hasegawa 2003, Shimizu 2004). Therefore, it remains necessary to develop novel CCL2 antagonists with favorable pharmacokinetic profiles in vivo. In this example it is shown that blockade of murine CCL2 with the anti-mCCL2 Spiegelmer mNOX-E36 or mNOX-E36-3'PEG would be suitable for the treatment of lupus nephritis and other disease manifestations of systemic lupus erythematosus. Late onset of mCCL2 Spiegelmer therapy effectively improves lupus nephritis, autoimmune peribronchitis, and lupus-like skin disease in MRL$^{lpr/lpr}$ mice, independent of any previous problem associated with therapeutic CCL2/CCR2 blockade.

Animals and Experimental Protocol

Ten week old female MRL$^{lpr/lpr}$ mice were obtained from Harlan Winkelmann (Borchen, Germany) and kept under normal housing conditions in a 12 hour light and dark cycle. Water and standard chow (Ssniff, Soest, Germany) were available ad libitum. At age 14 weeks, groups of 12 mice received subcutaneous injections of Spiegelmers in 5% glucose (injection volume, 4 ml/kg) three times per week as follows: mNOX-E36, 1.5 µmol/kg; mNOX-E36-3'PEG, 0.9 µmol/kg, nonfunctional control Spiegelmer PoC (5'-UAAG-GAAACUCGGUCUGAUGCGGU AGCGCUGUGCA-GAGCU-3'), 1.9 µmol/kg; PoC-PEG, 0.9 µmol/kg; vehicle (5% glucose). The plasma levels of mNOX-E36 and mNOX-E36-3'PEG were determined from blood samples taken weekly from the retroorbital sinus 3 or 24 hours after injection, respectively. Spiegelmer levels in plasma samples were determined by a modification of the sandwich hybridization method as described in Example 8. Mice were sacrificed by cervical dislocation at the end of week 24 of age.

Evaluation of Systemic Lupus

Skin lesions were recorded by a semiquantitative score (Schwarting 2005). The weight ratio of spleen and the bulk of mesenterial lymphnodes to total body weight were calculated as markers of the lupus-associated lymphoproliferative syndrome. Blood and urine samples were collected from each animal at the end of the study period by bleeding from the retro-orbital venous plexus under general anesthesia with inhaled ether. Blood and urine samples were collected from each animal at the end of the study and urine albumin/creatinine ratio and serum dsDNA autoantibody IgG isotype titers were determined as previously described (Pawar 2006).

Glomerular filtration rate (GFR) was determined at 24 weeks by clearance kinetics of plasma FITC-inulin (Sigma-Aldrich, Steinheim, Germany) 5, 10, 15, 20, 35, 60, and 90 minutes after a single bolus injection (Qi 2004). Fluorescence was determined with 485 nm excitation and read at 535 nm emission. GFR was calculated based on a two-compartment model using a non-linear regression curve-fitting software (Graph-Pad Prism, GraphPad Software Inc., San Diego, Calif.). Serum cytokine levels were determined using commercial ELISA kits for IL-6, IL-12p40 (OptEiA, BD Pharmingen), and IFN-α (PBL Biomedical Labs, USA). From all mice, kidneys and lungs were fixed in 10% buffered formalin, processed, and embedded in paraffin. 5-μm sections for silver and periodic acid-Schiff stains were prepared following routine protocols (Anders 2002). The severity of the renal lesions was graded using the indices for activity and chronicity as described for human lupus nephritis (Austin 1984), and morphometry of renal interstitial injury was conducted as previously described (Anders 2002). The severity of the peribronchial inflammation was graded semiquantitatively from 0-4. For immunostaining, sections of formalin-fixed and paraffin-embedded tissues were dewaxed and rehydrated. Endogenous peroxidase was blocked by 3% hydrogen peroxide and antigen retrieval was performed in Antigen Retrieval Solution (Vector, Burlingame, Calif.) in an autoclave oven. Biotin was blocked using the Avidin/Biotin blocking Kit (Vector). Slides were incubated with the primary antibodies for one hour, followed by biotinylated secondary antibodies (anti-rat IgG, Vector), and the ABC reagent (Vector). Slides were washed in phosphate buffered saline between the incubation steps. 3'3'Diaminobenzidine (DAB, Sigma, Taufkirchen, Germany) with metal enhancement was used as detection system, resulting in a black colour product. Methyl green was used as counterstain, slides were dehydrated and mounted in Histo-mount (Zymed Laboratories, San Francisco, Calif.). The following primary antibodies were used: rat anti-Mac2 (macrophages, Cederlane, Ontario, Canada, 1:50), anti-mouse CD3 (1:100, clone 500A2, BD), anti-mouse $IgG_1$ (1:100, M32015, Caltag Laboratories, Burlingame, Calif., USA), anti-mouse $IgG_{2a}$ (1:100, M32215, Caltag), anti-mouse C3 (1:200, GAM/C3c/FITC, Nordic Immunological Laboratories, Tilburg, Netherlands). Negative controls included incubation with a respective isotype antibody. For quantitative analysis glomerular cells were counted in 15 cortical glomeruli per section. Glomerular Ig and C3c deposits were scored from 0-3 on 15 cortical glomerular sections.

RNA Preparation and Real-Time Quantitative (TaqMan) RT-PCR

Renal tissue from each mouse was snap frozen in liquid nitrogen and stored at −80° C. From each animal, total renal RNA preparation and reverse transcription were performed as described (Anders 2002). Primers and probes were from PE Biosystems, Weiterstadt, Germany. The used primers (300 nM) used for detection of Ccl2, Ccl5 and 18S rRNA, predeveloped TaqMan assay reagent from PE Biosystems.

Flow Cytometry

Total blood and bone marrow samples were obtained from mice of all groups at the end of the study. Flow cytometry was performed using a FACScalibur machine and the previously characterized MC21 anti-mCCR2 antibody (Mack 2001). A biotinylated anti-rat IgG antibody (BD Biosciences) was used for detection. A rat $IgG_{2b}$ (BD Biosciences) was used as isotype control.

Statistical Analysis

Data were expressed as mean±standard error of the mean (SEM). Comparison between groups were performed using univariate ANOVA. Posthoc Bonferroni's correction was used for multiple comparisons. A value of $p<0.05$ was considered to indicate statistical significance.

Sandwich Hybridisation Assay

Amount of Spiegelmer in the samples was quantified by a sandwich hybridisation assay based on an assay as described by Drolet et al. 2000 (*Pharm Res* 17:1503). Blood samples were collected in parallel to follow the plasma clearance of NOX-E36. Selected tissues were prepared to determine Spiegelmer concentrations.

Hybridisation Plate Preparation

Spiegelmer mNOX-E36 was quantified by using a non-validated sandwich hybridisation assay. Briefly, the mNOX-E36 capture probe (Seq. ID.: 281) was immobilized to white DNA-BIND 96well plates (Corning Costar, Wiesbaden, Germany) at 0.75 mM in 0.5 M sodium phosphate, 1 mM EDTA, pH 8.5 over night at 4° C. Wells were washed twice and blocked with 0.5% w/v BSA in 0.25 M sodium phosphate, 1 mM EDTA, pH 8.5 for 3 h at 37° C., washed again and stored at 4° C. until use. Prior to hybridisation, wells were pre-warmed to 37° C. and washed twice with pre-warmed wash buffer (3×SSC, 0.5% [w/v] sodium dodecyl sarcosinate, pH 7.0; in advance a 20× stock [3 M NaCl, 0.3 M $Na_3$Citrate) is prepared without sodium lauroylsarcosine and diluted accordingly).

Sample Preparation

All samples were assayed in duplicates. Plasma samples were thawed on ice, vortexed and spun down briefly in a cooled tabletop centrifuge. Tissue homogenates were thawed at RT and centrifuged 5 min at maximum speed and RT. Only 5 μl each sample were removed for the assay, and afterwards returned to the freezer for storage. Samples were diluted with hybridisation buffer (8 nM mNOX-E36 detection probe [Seq. ID:282] in wash buffer) at RT according to the following scheme:

| | |
|---|---|
| 1:30 | 5 μl sample + 145 μl hybridisation buffer |
| 1:300 | 20 μl 1:30 + 180 μl hybridisation buffer |
| 1:3000 | 20 μl 1:300 + 180 μl hybridisation buffer |
| 1:30000 | 20 μl 1:3000 + 180 μl hybridisation buffer |

All sample dilutions were assayed. mNOX-E36 standard was serial diluted to a 8-point calibration curve spanning the 0-4 nM range. No QC samples were prepared and assayed. Calibration standard was identical to that of the in-study samples.

Hybridisation and Detection

Samples were heated for 10 min at 95° C. and cooled to 37° C. Spiegelmer/detection probe complexes were annealed to immobilized capture probes for 30 min at 37° C. Unbound spiegelmers were removed by washing twice with wash buffer and 1×TBST (20 mM Tris-Cl, 137 mM NaCl, 0.1% Tween 20, pH 7.5), respectively. Hybridized complexes were detected by streptavidin alkaline phosphatase diluted 1:5000 in 1×TBST for 1 h at room temperature. To remove unbound conjugate, wells were washed again with 1×TBST and 20 mM Tris-Cl, 1 mM MgCl2, pH 9.8 (twice each). Wells were finally filled with 100 ml CSDP substrate (Applied Biosystems, Darmstadt, Germany) and incubated for 45 min at room temperature. Chemiluminescence was measured on a FLU-Ostar Optima microplate reader (BMG Labtechnologies, Offenburg, Germany).

Data Analysis

The following assayed sample dilutions were used for quantitative data analysis: rat EDTA plasma 1:2000

The data obtained from the vehicle group (no Spiegelmer was adminstered) was subtracted as background signal.

The sandwich hybridisation assay as described herein also works in similar fashion for Spiegelmer NOX-36, NOX-E36-5'-PEG and NOX-E36-3'-PEG whereby the respective NOX-E36 capture probe (Seq. ID:255) and the respective NOX-E36 detection probe (Seq. ID:256) has to be used (data not shown).

Results mNOX-E36-3'PEG Improves Survival and Kidney Disease of MRL$^{lpr/lpr}$ Mice Female MRL$^{lpr/lpr}$ mice develop and subsequentially die from proliferative immune complex glomerulonephritis with striking similarities to diffuse proliferative lupus nephritis in humans. In this therapeutic study design, treated MRL$^{lpr/lpr}$ mice were treated with pegylated and unpegylated anti-mCCL2 Spiegelmer, pegylated and unpegylated control ("PoC")-Spiegelmer or vehicle from week 14 to 24 of age. At this time point vehicle, PoC or PoC-PEG-treated MRL$^{lpr/lpr}$ mice showed diffuse proliferative glomerulonephritis characterized by glomerular macrophage infiltration and a mixed periglomerular and interstitial inflammatory cell infiltrate consisting of glomerular and interstitial Mac2-positive macrophages and interstitial CD3-positive lymphocytes (FIGS. 34 and 35). mNOX-E36-3'PEG improved the activity and chronicity index of lupus nephritis as well as the forementioned markers of renal inflammation (FIG. 35). The unpegylated molecule mNOX-E36 was less effective on the chronicity index and interstitial macrophage and T cell counts (FIG. 35). Advanced chronic kidney disease was further illustrated by tubular atrophy and confluent areas of interstitial fibrosis in vehicle-, PoC-, and PoC-PEG-treated mice (FIG. 34). Applying morphometry to quantify these changes, it was found that pegylated and unpegylated mNOX-E36 reduced interstitial volume, tubular cell damage, and tubular dilation, all being markers of the severity and prognosis of chronic kidney disease (FIG. 36). mNOX-E36-3'PEG but not unpegylated mNOX-E36 improved 50% mortality (FIG. 37). Thus, mNOX-E36-3'PEG can reduce the number of renal macrophage and T cell infiltrates and improve lupus nephritis and (renal) survival of MRL$^{lpr/lpr}$ mice. In order to study whether treatment with mNOX-E36 and mNOX-E36-3'PEG affects intrarenal inflammation in MRL$^{lpr/lpr}$ mice, real-time RT-PCR was performed to assess the expression levels of the proinflammatory chemokines CCL2 and CCL5 which were previously shown to be progressively upregulated in kidneys of MRL$^{lpr/lpr}$ mice during progression of renal disease (Perez de Lema 2001). Treatment with mNOX-E36 and mNOX-E36-3'PEG from week 14 to 24 of age reduced renal expression of CCL2 and CCL5 mRNA compared to vehicle-treated controls (FIG. 38).

Anti-CCL2 Spiegelmers Reduce Extrarenal Autoimmune Tissue Injury in MRL$^{lpr/lpr}$ Mice Skin and lungs are also commonly affected from autoimmune tissue injury in MRL$^{lpr/lpr}$ mice. In vehicle-treated mice autoimmune lung disease was characterized by moderate peribronchiolar and perivascular inflammatory cell infiltrates and skin lesions were observed in 60% of mice (FIGS. 39, 40 and 35). mNOX-E36 and mNOX-E36-3'PEG both reduced peribronchial inflammation and skin disease as compared to vehicle-, PoC-, and PoC-PEG-treated MRL$^{lpr/lpr}$ mice, respectively (FIGS. 39, 40 and 35). Hence, the effects of CCL2-specific Spiegelmers are not limited to lupus nephritis but extend to other manifestations of autoimmune tissue injury in MRL$^{lpr/lpr}$ mice.

mNOX-E36 and the Lymphoproliferative Syndrome, dsDNA Autoantibodies, and Serum Cytokine Levels in MRL$^{lpr/lpr}$ Mice Female MRL$^{lpr/lpr}$ mice develop a lymphoproliferative syndrome characterized by massive splenomegaly and bulks of cervical, axillary, inguinal, and mesenterial lymph nodes. mNOX-E36 and mNOX-E36-3'PEG both had no effect on the weight of spleens and lymph nodes in MRL$^{lpr/lpr}$ mice (FIG. 41). Autoimmunity in MRL$^{lpr/lpr}$ mice is characterized by the production of autoantibodies against multiple nuclear antigens including dsDNA. In 24 week old MRL$^{lpr/lpr}$ mice serum dsDNA IgG, IgG$_1$, IgG$_2$, IgG$_{2b}$ autoantibodies were present at high levels. mNOX-E36 and mNOX-E36-3'PEG both had no effect on either of these DNA autoantibodies (FIG. 41). Lupus-like disease in vehicle-treated MRL$^{lpr/lpr}$ mice was characterized by elevated serum levels of IFN-α, IL-12p40, and IL-6. mNOX-E36 and mNOX-E36-3'PEG both had no effect on either of these inflammatory mediators (FIG. 41). Thus, both mNOX-E36 variants do not affect lymphoproliferation, anti-dsDNA IgG production, and serum cytokine levels in MRL$^{lpr/lpr}$ mice.

Plasma Levels of mNOX-E36 and mNOX-E36-3'PEG in MRL$^{lpr/lpr}$ Mice mNOX-E36 and mNOX-E36-3'PEG plasma levels were determined at weekly intervals in order to monitor drug exposure during progressive kidney disease of MRL$^{lpr/lpr}$ mice. The median plasma levels of mNOX-E36 3 h after injection and mNOX-E36-3'PEG 24 h after injection were approximately 300 nM and 1 μM throughout the study, respectively (FIG. 42). Thus, pegylation increased the plasma levels of mNOX-E36 and the progressive kidney disease of MRL$^{lpr/lpr}$ mice did not modulate the pharmacokinetics of both Spiegelmers.

mNOX-E36-3'PEG Blocks the Emigration of Monocytes from the Bone Marrow

Monocyte emigration from bone marrow during bacterial infection was shown to involve chemokine receptor CCR2 (Serbina 2006), but the role of CCL2 in the context of autoimmunity remains hypothetical. Therefore, the CCR2-positive monocyte population in peripheral blood and bone marrows in mice of mNOX-E36-3'PEG- and vehicle-treated groups of 24 week old MRL$^{lpr/lpr}$ mice was examined. Treatment with mNOX-E36-3'PEG increased the percentage of CCR2 positive cells in the bone marrow from 13% to 26% whereas it reduced this population in the peripheral blood from 26% to 11% (FIG. 43). These data support a role of CCL2 for the evasion of CCR2 positive cells from the bone marrow during autoimmune disease of MRL$^{lpr/lpr}$ mice.

Summary

Applying the Spiegelmer technology, a novel and specific mCCL2 antagonist was created which potently blocks mCCL2 in vitro and in vivo. In fact, late onset of treatment with the CCL2 Spiegelmer markedly improved advanced lupus-like autoimmune tissue injury in MRL$^{lpr/lpr}$ mice. These data support a central role for CCL2 in chronic inflammatory tissue damage and identify CCL2 Spiegelmers as a novel therapeutic for autoimmune tissue injury.

EXAMPLE 9

Therapy of Diabetic Nephropathy in Unilaterally Nephrectomized Diabetic Mice with Anti-mMCP-1 Spiegelmer Diabetic nephropathy remains a leading cause of end-stage renal disease because targeting the angiotensin-dependent pathomechanisms does not always prevent disease progression (Zimmet 2001; Ritz 1999; United States Renal Data System 2004; Svensson 2003). Hence, other treatment strategies are required to add on to the therapeutic armament for diabetic nephropathy.

Data from recent experimental studies relate the progression of diabetic nephropathy to intrarenal inflammation (Galkina 2006; Mora 2005; Meyer 2003; Tuttle 2005). For example, mycophenolate mofetil, methotrexate or irradiation reduce urinary albumin excretion, and glomerulosclerosis in rats with streptozotocin-induced diabetic nephropathy (Yozai 2005; Utimura 2003). Yet, the molecular and cellular mechanisms of intrarenal inflammation in diabetic nephropathy remain poorly characterized. Patients with diabetic nephropathy have increased serum levels of acute phase markers of inflammation but this may not represent intrarenal inflammation (Dalla Vestra 2005; Navarro 2003). Patients with diabetic nephropathy excrete high levels of the CC-chemokine monocyte chemoattractant protein 1 (MCP-1/CCL2) in the urine which may be more specific for intrarenal inflammation (Morii 2003; Tashiro 2002; Takebayashi 2006). In fact, MCP-1/CCL2 is expressed by human mesangial cells exposed to either high glucose concentrations or advanced glycation end products (Ihm 1998; Yamagishi 2002). CCL2 is involved in the complex multistep process of leukocyte recruitment from intravascular to extravascular compartments, i.e. glomeruli and the renal interstitium (Baggiolini 1998). In fact, macrophage infiltrates are a common finding in human and experimental diabetic glomerulosclerosis and tubulointerstitial injury (Bohle 1991; Furuta 1993; Chow 2007). Ccl2-deficient type 1 or type 2 diabetic mice have lower glomerular macrophage counts which is associated with less glomerular injury (Chow 2004; Chow 2006). In these studies the functional role of CCL2 for glomerular pathology of type 1 and type 2 diabetic nephropathy was also demonstrated. Hence, CCL2 may represent a potential therapeutic target for diabetic nephropathy, and suitable CCL2 antagonists with favourable pharmacokinetic profiles should be validated in this disease context. In this example we report the effects of the PEGylated anti-CCL2 Spiegelmer mNOX-E36-3'PEG in type 2 diabetic db/db mice with advanced diabetic nephropathy. We shown that an anti-CCL2-Spiegelmer would be suitable for the treatment of diabetic nephropathy.

Animals and Experimental Protocol

Male 5 week old C57BLKS db/db or C57BLKS wild-type mice were obtained from Taconic (Ry, Denmark) and housed in filter top cages with a 12 hour dark/light cycle and unlimited access to food and water for the duration of the study. Cages, bedding, nestlets, food, and water were sterilized by autoclaving before use. At the age of 6 weeks uninephrectomy ("1K" mice) or sham surgery ("2K" mice) was performed through a 1 cm flank incision as previously described in db/db and wild-type mice (Bower 1980). In mice of the sham surgery groups the kidney was left in situ. 10 weeks later, at the age of 4 months, 1K db/db mice were divided in two groups that received three times per week subcutaneous injections with either mNOX-E36-3'PEG or PoC-PEG in 5% glucose (dose, 0.9 µmol/kg; injection volume, 1 ml/kg). Treatment was continued for 8 weeks (until the age 6 months) when the animals were sacrificed and the tissues were obtained for histopathological evaluation. All experimental procedures had been approved by the local government authorities.

Evaluation of Diabetic Nephropathy

All immunohistological studies were performed on paraffin-embedded sections as described (Anders 2002). The following antibodies were used as primary antibodies: rat anti-Mac2 (glomerular macrophages, Cederlane, Ontario, Canada, 1:50), anti-Ki-67 (cell proliferation, Dianova, Hamburg, Germany, 1:25). For histopathological evaluation, from each mouse parts of the kidneys were fixed in 10% formalin in phosphate-buffered saline and embedded in paraffin. 3 µm-sections were stained with periodic acid-Schiff reagent or silver following the instructions of the supplier (Bio-Optica, Milano, Italy). Glomerular sclerotic lesions were assessed using a semiquantitative score by a blinded observer as follows: 0=no lesion, 1=<25% sclerotic, 2=25-49% sclerotic, 3=50-74% sclerotic, 4=75-100% sclerotic, respectively. 15 glomeruli were analysed per section. The indices for interstitial volume and tubular dilatation were determined by superimposing a grid of 100 points on 10 non-overlapping cortical fields as described previously (Anders 2002). Interstitial cell counts were determined in 15 high power fields (hpf, 400×) by a blinded observer. RNA preparation and real-time quantitative (TaqMan) RT-PCR was done from deparaffinized glomeruli. After incubation in lysing buffer (10 mM Tris-HCl, 0.1 mM EDTA, 2% SDS and 20 µg/ml proteinase K) for 16 h at 60° C., phenol-chloroform-based RNA extraction was performed. Glomerular RNA was dissolved in 10 µl RNAse free water. Reverse transcription and real time RT-PCR from total organ and glomerular RNA was performed as described (Anders 2002, Cohen 2002). Controls consisting of ddH$_2$O were negative for target and housekeeper genes. Oligonucleotide primer (300 nM) and probes (100 nM) for mCcl2, Gapdh, and 18 S rRNA were predeveloped TaqMan assay reagents from PE. Primers and probes were from ABI Biosystems, Weiterstadt, Germany. Glomerular filtration rate (GFR) was determined by clearance kinetics of plasma FITC-inulin (Sigma-Aldrich, Steinheim, Germany) 5, 10, 15, 20, 35, 60, and 90 minutes after a single bolus injection (Qi 2004). Fluorescence was determined with 485 nm excitation and read at 535 nm emission. GFR was calculated based on a two-compartment model using a non-linear regression curve-fitting software (GraphPad Prism, GraphPad Software Inc., San Diego, Calif.). All data are presented as mean±SEM. Comparison of groups was performed using ANOVA and post-hoc Bonferroni's correction was used for multiple comparisons. A value of $p<0.05$ was considered to indicate statistical significance.

Results mNOX-E36-3'PEG Reduces Glomerular Macrophage Counts and Global Glomerulosclerosis in Unilaterally Nephrectomized db/db Mice When lack of functional CCL2 is associated with decreased glomerular macrophage recruitment in db/db mice (Chow 2007) and mNOX-E36-3'PEG is able to block CCL2-mediated macrophage recruitment in vitro and in vivo, mNOX-E36-3'PEG should impair renal macrophage recruitment in db/db mice with advanced type 2 diabetic nephropathy. To test this hypothesis, we initiated subcutaneous injections with mNOX-E36-3'PEG or PoC-PEG at age of 4 months in unilaterally nephrectomized ("1K") db/db mice. Treatment was continued for 8 weeks when tissues were collected for the assessment of diabetic nephropathy. During that period, mNOX-E36-3'PEG treatment did not significantly affect white blood or platelet counts, blood glucose levels or body weight which were both markedly elevated in all groups of db/db mice as compared to non-diabetic BLKS mice (data not shown). Interestingly, mNOX-E36-3'PEG increased the serum levels of CCL2 in 1K db/db mice, indicating that the CCL2 antagonist retains CCL2 in the circulation (FIG. 44). Consistent with our hypothesis mNOX-E36-3'PEG significantly reduced the number of glomerular macrophages by 40% as compared to PoC-PEG- or vehicle-treated db/db mice, associated with lower numbers of Ki-67 positive proliferating cells within the glomerulus in mNOX-E36-3'PEG-treated db/db mice (FIG. 45). These findings were associated with a significant improvement of global diabetic glomerulosclerosis in 1K db/db mice (FIG. 46). In fact, mNOX-E36-3'PEG treatment reduced diabetic glomerulosclerosis in 1K db/db mice to the extent of glomerulosclerosis present in age-matched non-nephrectomized ("2K") db/db mice (FIG. 46). These findings show that delayed blockade of CCL2-dependent glomerular macrophage recruitment with mNOX-E36-3'PEG prevents global diabetic glomerulosclerosis in type 2 diabetic db/db mice.

mNOX-E36-3'PEG Improves GFR in 1K db/db Mice

The beneficial effects of mNOX-E36-3'PEG treatment on diabetic glomerulosclerosis in 1K db/db mice should be associated with a better GFR. We analyzed FITC-inulin clearance kinetics as a marker of GFR in db/db mice (Qi 2004). As compared to a normal GFR of about 250 ml/min in db/db mice (Qi 2004), we found a reduced GFR of was 112±23 ml/min in 6 months old 1K db/db mice injected with PoC-PEG (FIG. 47). mNOX-E36-3'PEG treatment significantly improved the GFR to 231±30 ml/min in 1K db/db mice ($p<0.001$) suggesting that blocking CCL2-dependent glomerular macrophage recruitment can also improve renal function in type 2 diabetic mice.

mNOX-E36-3'PEG Reduces Interstitial Macrophage Counts and Tubulointerstitial Injury in 1K db/db Mice Advanced diabetic nephropathy in humans is associated with significant numbers of interstitial macrophages and tubulointerstitial injury (Bohle 1991). In 2K db/db mice interstitial macrophage infiltrates and significant tubulointerstitial injury does not occur before 8 months of age (Chow 2007). Early uninephrectomy accelerates the development of tubulointerstitial pathology in db/db mice (Ninichuk 2005), thus we quantified interstitial macrophages, tubular dilatation and interstitial volume as markers of tubulointerstitial damage in mice of all groups at 6 months of age. At this time point 1K db/db mice revealed increased numbers of interstitial macrophages and significant elevations of tubular dilatation and interstitial volume as compared to 2K db/db mice (FIG. 45, FIG. 48). mNOX-E36-3'PEG treatment reduced the numbers of interstitial macrophages by 53% as well as tubular dilatation and interstitial volume in 1K db/db mice (FIG. 45, FIG. 48). Thus, blocking CCL2-dependent renal macrophage recruitment also prevents tubulointerstitial injury in type 2 diabetic db/db mice.

mNOX-E36-3'PEG Reduces Renal Expression of Ccl2 in 1K db/db Mice

Macrophage infiltrates amplify inflammatory responses in tissue injury, e.g. local CCL2 expression. We therefore hypothesized that the mNOX-E36-3'PEG-related decrease in renal macrophages would be associated with less renal CCL2 expression. We used real-time RT-PCR to quantify the mRNA expression of CCL2 in db/db mice. mNOX-E36-3'PEG reduced the mRNA levels of CCL2 in kidneys of 6 months old 1K db/db mice as compared to age-matched PoC-PEG-treated mice (FIG. 49). To further assess the spatial expression of CCL2 we performed immunostaining for CCL2 protein on renal sections. In 1K db/db mice the expression of CCL2 was markedly enhanced in glomeruli, tubuli, and interstitial cells as compared to 2K db/db or 2K wild-type mice (FIG. 50). mNOX-E36-3'PEG markedly reduced the staining for CCL2 in all these compartments as compared to vehicle- or PoC-PEG-treated 1K db/db mice. These data indicate that blocking CCL2-dependent renal macrophage recruitment with mNOX-E36-3'PEG reduces the local expression of CCL2 in 1K db/db mice.

Summary

The concept that inflammation contributes to the progression of human diabetic nephropathy becomes increasingly accepted (Tuttle 2005), bringing MCP-1/CCL2 as a potential target to treat this disease into the focus. In this example, we have shown that treatment of unilaterally nephrectomized diabetic mice with mNOX-E36-3'PEG reduced the numbers of glomerular (and interstitial) macrophages at 6 months of age, associated with less proliferating glomerular cells. In addition, renal/glomerular expression of CCL2 mRNA was markedly reduced with mNOX-E36-3'PEG treatment. Furthermore, lower numbers of glomerular macrophages and glomerular proliferating cells in the therapy group were associated with protection from global glomerulosclerosis and with a significant improvement of the glomerular filtration rate. The beneficial effects of mNOX-E36-3'PEG on glomerular pathology and renal function in diabetic mice are consistent with those studies that have used other CCL2 antagonists in other models of glomerular injury (Lloyd 1997, Hasegawa 2003, Tang 1996, Wenzel 1997, Fujinaka 1997, Schneider 1999). Remarkably, delayed onset of CCL2 blockade also reduced the numbers of interstitial macrophages being associated with less tubulointerstitial pathology in 1K db/db mice.

Together, these data validate CCL2 as a promising therapeutic target for diabetic nephropathy and suggest that initiating CCL2 blockade with a Spiegelmer—even at an advanced stage of the disease—may still be protective.

This application is a 371 national stage application of PCT Ser. No. EP2007/001294 (WO2007/093409), the content of which is incorporated by reference herein in entirety.

REFERENCES

The complete bibliographic data of the documents recited herein the disclosure of which is incorporated by reference is, if not indicated to the contrary, as follows.

Akahoshi T, Wada C, Endo H, Hirota K, Hosaka S, Takagishi K, Kondo H, Kashiwazaki S, Matsushima K (1993). Expression of monocyte chemotactic and activating factor in rheumatoid arthritis. Regulation of its production in synovial cells by interleukin-1 and tumor necrosis factor. *Arthritis Rheum.* 36:762

Alam R, York J, Moyars M, Stafford S, Grant J A, Lee J, Forsythe P, Sim T, Ida N (1996). Increased MCP-1, RANTES, and MIP-1α in bronchoalveolar lavage fluid of allergic asthmatic patients. *Am. J. Respir. Crit. Care Med.* 153:1398

Altschul S F, Gish W, Miller W, Myers E W, Lipman D J (1990), Basic local alignment search tool. *J Mol. Biol.* 215(3):403-10.

Altschul S F, Madden T L, Schaffer A A, Zhang J, Zhang Z, Miller W, Lipman D J (1997). Gapped BLAST and PSI-BLAST: a new generation of protein database search programs. Nucleic Acids Res. September 1; 25(17):3389-402.

Amann B, Tinzmann R, Angelkort B (2003). ACE inhibitors improve diabetic nephropathy through suppression of renal MCP-1. *Diabetes Care* 26:2421

Anders H J, Vielhauer V, Frink M, Linde Y, Cohen C D, Blattner S M, Kretzler M, Strutz F, Mack M, Grone H J, Onuffer J, Horuk R, Nelson P J, Schlöndorff D (2002). A chemokine receptor CCR-1 antagonist reduces renal fibrosis after unilateral ureter ligation. *J. Clin. Invest.* 109:251

Anders H J, Vielhauer V, Schlöndorff D (2003). Chemokines and chemokine receptors are involved in the resolution or progression of renal disease. *Kidney Int.* 63:401

Aurup H et al. (1994). *Nucleic Acids Res* 22:20

Austin H A 3rd, Muenz L R, Joyce K M, Antonovych T T, Balow J E (1984). Diffuse proliferative lupus nephritis: identification of specific pathologic features affecting renal outcome. *Kidney Int.* 25:689

Baggiolini M, Dewald B, Moser B (1994). Interleukin-8 and related chemotactic cytokines—CXC and CC chemokines. *Adv. Immunol.* 55:97

Baggiolini M (1998). Chemokines and leukocyte traffic. *Nature* 392:565

Banba N, Nakamura T, Matsumura M, Kuroda H, Hattori Y, Kasai K (2000). Possible relationship of monocyte chemoattractant protein-1 with diabetic nephropathy. *Kidney Int.* 58:684

Banisor I, Leist T P, Kalman B (2005). Involvement of β-chemokines in the development of inflammatory demyelination. *J. Neuroinflammation* 2:7

Bazan J F, Bacon K B, Hardiman G, Wang W, Soo K, Rossi D, Greaves D R, Zlotnik A, Schall T J (1997). A new class of membrane-bound chemokine with a CX3C motif. *Nature* 385:640

Berkhout T A (1997). *J Biol Chem* 272:16404

Bohle A, Wehrmann M, Bogenschutz O, Batz C, Muller C A, Muller G A (1991). The pathogenesis of chronic renal failure in diabetic nephropathy. Investigation of 488 cases of diabetic glomerulosclerosis. *Pathol. Res. Pract.* 187:251

Boring L, Gosling J, Chensue S W, Kunkel S L, Farese R V Jr, Broxmeyer H E, Charo I F (1997). Impaired monocyte migration and reduced type 1 (Th1) cytokine responses in C—C chemokine receptor 2 knockout mice. *J. Clin. Invest.* 100:2552

Boring L, Gosling J, Cleary M, Charo I F (1998). Decreased lesion formation in CCR2−/− mice reveals a role for chemokines in the initiation of atherosclerosis. *Nature* 394:894

Boring L, Gosling J, Monteclaro F S, Lusis A J, Tsou C L, Charo I F (1996). Molecular cloning and functional expression of murine JE (monocyte chemoattractant protein 1) and murine macrophage inflammatory protein 1 alpha receptors: evidence for two closely linked C—C chemokine receptors on chromosome 9. *J. Biol. Chem.* 271:7551

Bossink A W, Paemen L, Jansen P M, Hack C E, Thijs L G, Van Damme J (1995). Plasma levels of the chemokines monocyte chemotactic proteins-1 and -2 are elevated in human sepsis. *Blood* 86:3841

Bower G, Brown D M, States M W, Vernier R L, Mauer S M (1980). Studies of the glomerular mesangium and the juxtaglomerular apparatus in the genetically diabetic mouse. *Lab. Invest.* 43:333

Charo I F, Myers S J, Herman A, Franci C, Connolly A J, Coughlin S R (1994). Molecular cloning and functional expression of two monocyte chemoattractant protein 1 receptors reveals alternative splicing of the carboxyl-terminal tails. *Proc. Natl Acad. Sci. USA* 91:2752

Chow F Y, Nikolic-Paterson D J, Ma F Y, Ozols E, Rollins B J, Tesch G H (2007). Monocyte chemoattractant protein-1-induced tissue inflammation is critical for the development of renal injury but not type 2 diabetes in obese db/db mice. *Diabetologica* 50:471

Chow F Y, Nikolic-Paterson D J, Ozols E, Atkins R C, Rollin B J, Tesch G H (2006). Monocyte chemoattractant protein-1 promotes the development of diabetic renal injury in streptozotocin-treated mice. *Kidney Int.* 69:73

Chow F, Ozols E, Nikolic-Paterson D J, Atkins R C, Tesch G H (2004). Macrophages in mouse type 2 diabetic nephropathy: Correlation with diabetic state and progressive renal injury. *Kidney Int.* 65:116

Cockwell P, Howie A J, Adu D, Savage C O (1998). In situ analysis of C—C chemokine mRNA in human glomerulonephritis. *Kidney Int.* 54:827

Cohen C D, Gröne H J, Grone E F, Nelson P J, Schlöndorff D, Kretzler M (2002). Laser microdissection and gene expression analysis on formaldehyde-fixed archival tissue. *Kidney Int.* 61:125

Cummins L L et al. (1995). *Nucleic Acids Res* 23:2019

Dalla Vestra M, Mussap M, Gallina P, Bruseghin M, Cernigoi A M, Sailer A, Plebani M, Fioretto P (2005). Acute-phase markers of inflammation and glomerular structure in patients with type 2 diabetes. *J. Am. Soc. Nephrol.* 16 Suppl 1:S78

Dawson J, Miltz W, Mir A K, Wiessner C (2003). Targeting monocyte chemoattractant protein-1 signalling in disease. *Expert Opin. Ther. Targets* 7:35

De Bleecker J L, De Paepe B, Vanwalleghem I E, Schroder J M (2002). Differential expression of chemokines in inflammatory myopathies. *Neurology* 58:1779

Drolet D W, Nelson J, Tucker C E, Zack P M, Nixon K, Bolin R, Judkins M B, Farmer J A, Wolf J L, Gill S C, Bendele R A (2000). Pharmacokinetics and safety of an anti-vascular endothelial growth factor aptamer (NX1838) following injection into the vitreous humor of rhesus monkeys. *Pharm. Res.* 17:1503

Eaton B E et al. (1995). *Chem Biol* 2:633

Eaton B E, Gold L, Hicke B J, Janjic N, Jucker F M, Sebosta D P, Tarasow T M, Willis M C, Zichi D A (1997). *Bioorg Med Chem* 5:1087

Economou E, Tousoulis D, Katinioti A, Stefanadis C, Trikas A, Pitsavos C, Tentolouris C, Toutouza M G, Toutouzas P (2001). Chemokines in patients with ischaemic heart disease and the effect of coronary angioplasty. *Int. J. Cardiol.* 80:55

Egashira K, Zhao Q, Kataoka C, Ohtani K, Usui M, Charo I F, Nishida K, Inoue S, Katoh M, Ichiki T, Takeshita A (2002). Importance of monocyte chemoattractant protein-1 pathway in neointimal hyperplasia after periarterial injury in mice and monkeys. *Circ. Res.* 90:1167

Fujinaka H, Yamamoto T, Takeya M, Feng L, Kawasaki K, Yaoita E, Kondo D, Wilson C B, Uchiyama M, Kihara I (1997). Suppression of anti-glomerular basement membrane nephritis by administration of anti-monocyte chemoattractant protein-1 antibody in WKY rats. *J. Am. Soc. Nephrol.* 8:1174

Furuichi K, Wada T, Iwata Y, Kitagawa K, Kobayashi K-1, Hashimoto H, Ishiwata Y, Tomosugi N, Mukaida N, Matsushima K, Egashira K, Yokoyama H (2003). Gene therapy expressing amino-terminal truncated monocyte chemoattractant protein-1 prevents renal ischemia-reperfusion injury. *J. Am. Soc. Nephrol.* 14:1066

Furuta T, Saito T, Ootaka T, Soma J, Obara K, Abe K, Yoshinaga K (1993). The role of macrophages in diabetic glomerulosclerosis. *Am. J. Kidney Dis.* 21:480

Galasso J M, Liu Y, Szaflarski J, Warren J S, Silverstein F S (2000). Monocyte chemoattractant protein-1 is a mediator of acute excitotoxic injury in neonatal rat brain. *Neuroscience* 101:737

Galkina E, Ley K (2006). Leukocyte recruitment and vascular injury in diabetic nephropathy. *J. Am. Soc. Nephrol.* 17:368-377

Gao J L, Kuhns D B, Tiffany H L, McDermott D, Li X, Francke U, Murphy P M (1993). Structure and functional expression of the human macrophage inflammatory protein 1 alpha/RANTES receptor. *J. Exp. Med.* 177:1421

Garcia-Zepeda E A, Combadiere C, Rothenberg M E, Sarafi M N, Lavigne F, Hamid Q, Murphy P M, Luster A D (1996). Human monocyte chemoattractant protein (MCP)-4 is a novel CC chemokine with activities on monocytes, eosinophils, and basophils induced in allergic and nonallergic inflammation that signals through the CC chemokine receptors (CCR)-2 and -3. *J. Immunol.* 157: 5613

Gerard C, Rollins, B J. Chemokines and disease. *Nat. Immunol.* 6:1182

Gong X, Gong W, Kuhns D B, Ben-Baruch A, Howard O M, Wang J M (1997). Monocyte chemotactic protein-2 (MCP-2) uses CCR1 and CCR2B as its functional receptors. *J. Biol. Chem.* 272:11682

Gonzalo J A, Lloyd C M, Wen D, Albar J P, Wells T N C, Proudfoot A, Martinez-A C, Dorf M, Bjerke T, Coyle A J, Gutierrez-Ramos J C (1998). The coordinated action of CC chemokines in the lung orchestrates allergic inflammation and airway hyperresponsiveness. *J. Exp. Med.* 188:157

Gordillo G M, Onat D, Stockinger M, Roy S, Atalay M, Beck F M, Sen C K (2004). A key angiogenic role of monocyte chemoattractant protein-1 in hemangioendothelioma proliferation. Am. J. Physiol. Cell Physiol. 287:C866

Green L S et al. (1995). *Chem Biol* 2:683

Handel T M, Domaille P J (1996). Heteronuclear (1H, 13C, 15N) NMR assignments and solution structure of the monocyte chemoattractant protein-1 (MCP-1) dimer. *Biochemistry* 35:6569

Harigai M, Hara M, Yoshimura T, Leonard E J, Inoue K, Kashiwazaki S (1993). Monocyte chemoattractant protein-1 (MCP-1) in inflammatory joint diseases and its involvement in the cytokine network of rheumatoid synovium. *Clin. Immunol. Immunopathol.* 69:83

Hasegawa H, Kohno M, Sasaki M, Inoue A, Ito M R, Terada M, Hieshima K, Maruyama H, Miyazaki J, Yoshie O, Nose M, Fujita S (2003). Antagonist of monocyte chemoattractant protein 1 ameliorates the initiation and progression of lupus nephritis and renal vasculitis in MRL/lpr mice. *Arthritis Rheum.* 48:2555

Heath H, Qin S et al. (1997). Chemokine receptor usage by human eosinophils. The importance of CCR3 demonstrated using an antagonistic monoclonal antibody. *J Clin Invest* 99:178

Holdsworth S R, Kitching A R, Tipping P G (2000). Chemokines as therapeutic targets in renal disease. *Curr. Opin. Nephrol. Hypertens.* 9:505

Holgate S T, Bodey K S, Janezic A, Frew A J, Kaplan A P, Teran L M (1997). Release of RANTES, MIP-1α, and MCP-1 into asthmatic airways following endobronchial allergen challenge. *Am. J. Respir. Crit. Care Med.* 156:1377

Hosaka S et al. (1994). *Clin Exp Immunol* 97:451

Huang D R, Wang J, Kivisakk P, Rollins B J, Ransohoff R M (2001). Absence of monocyte chemoattractant protein 1 in mice leads to decreased local macrophage recruitment and antigen-specific T helper cell type 1 immune response in experimental autoimmune encephalomyelitis. *J. Exp. Med.* 193:713

Hulkower K, Brosnan C F, Aquino D A, Cammer W, Kulshrestha S, Guida M P, Rapoport D A, Berman J W (1993). Expression of CSF-1, c-fms, and MCP-1 in the central nervous system of rats with experimental allergic encephalomyelitis. *J. Imiminol.* 150:2525

Humbert M, Ying S, Corrigan C, Menz G, Barkans J, Pfister R, Meng Q, Van Damme J, Opdenakker G, Durham S R, Kay A B (1997). Bronchial mucosal expression of the genes encoding chemokines RANTES and MCP-3 in symptomatic atopic and nonatopic asthmatics: relationship to the eosinophil-active cytokines interleukin (IL)-5, granulocyte macrophage-colony-stimulating factor, and IL-3. *Am J Respir Cell Mol Biol* 16:1

Ihm C G, Park J K, Hong S P, Lee T W, Cho B S, Kim M J, Cha D R, Ha H (1998). A high glucose concentration stimulates the expression of monocyte chemotactic peptide 1 in human mesangial cells. *Nephron* 79:33

Iyonaga K, Takeya M, Saita N, Sakamoto O, Yoshimura T, Ando M, Takahashi K (1994). Monocyte chemoattractant protein-1 in idiopathic pulmonary fibrosis and other interstitial lung diseases. *Hum. Pathol.* 25:455

Johrer K, Zelle-Rieser C, Perathoner A, Moser P, Hager M, Ramoner R, Gander H, Hold L, Bartsch G, Greil R, Thurnher M (2005). Up-regulation of functional chemokine receptor CCR3 in human renal cell carcinoma. *Clin Cancer Res* 11:2459

Jolicoeur C, Lemay A, Akoum A (2001). Comparative effect of danazol and a GnRH agonist on monocyte chemotactic protein-1 expression by endometriotic cells. *Am. J. Reprod. Immunol.* 45:86

Jose P J, Griffiths-Johnson D A, Collins P D, Walsh D T, Moqbel R, Totty N F, Truong O, Hsuan J J, Williams T J. Eotaxin: a potent eosinophil chemoattractant cytokine detected in a guinea pig model of allergic airways inflammation. *J. Exp. Med.* 179:881

Kaburagi Y, Shimada Y, Nagaoka T, Hasegawa M, Takehara K, Sato S (2001). Enhanced production of CC-chemokines (RANTES, MCP-1, MIP-1α, MIP-1β, and eotaxin) in patients with atopic dermatitis. *Arch. Dermatol. Res.* 293:350

Kawasaki A M et al. (1993). *J Med Chem* 36:831

Kennedy K J, Strieter R M, Kunkel S L, Lukacs N W, Karpus W J (1998). Acute and relapsing experimental autoimmune encephalomyelitis are regulated by differential expression of the CC chemokines macrophage inflammatory protein-1α and monocyte chemotactic protein-1. *J. Neuroimmunol.* 91:98

Kim J S, Gautam S C, Chopp M, Zaloga C, Jones M L, Ward P A, Welch K M (1995). Expression of monocyte chemoattractant protein-1 and macrophage inflammatory protein-1 after focal cerebral ischemia in the rat. *J. Neuroimmunol.* 56:127

Kitamoto S, Egashira K (2003). Anti-monocyte chemoattractant protein-1 gene therapy for cardiovascular diseases. *Expert Rev. Cardiovasc. Ther.* 1:393

Kleinhans M, Tun-Kyi A, Gilliet M, Kadin M E, Dummer R, Burg G, and Nestle F O (2003). Functional expression of the eotaxin receptor CCR3 in CD30+ cutaneous T-cell lymphoma. *Blood* 101:1487

Koch A E, Kunkel S L, Harlow L A, Johnson B, Evanoff H L, Haines G K, Burdick M D, Pope R M, Strieter R M (1992). Enhanced production of monocyte chemoattractant protein-1 in rheumatoid arthritis. *J. Clin. Invest.* 90:772

Kouno J, Nagai H, Nagahata T, Onda M, Yamaguchi H, Adachi K, Takahashi H, Teramoto A, and Emi M (2004). Up-regulation of CC chemokine, CCL3L1, and receptors, CCR3, CCR5 in human glioblastoma that promotes cell growth. *J Neurooncol* 70:301

Kurihara T, Warr G, Loy J, Bravo R (1997). Defects in macrophage recruitment and host defense in mice lacking the CCR2 chemokine receptor. *J. Exp. Med.* 186:1757

Kusser W (2000). *J Biotechnol* 74:27-38

Kuziel W A, Morgan S J, Dawson T C, Griffin S, Smithies O, Ley K, Maeda N (1997). Severe reduction in leukocyte adhesion and monocyte extravasation in mice deficient in CC chemokine receptor 2. *Proc. Natl Acad. Sci. USA* 94:12053

Lesnik E A et al. (1993). *Biochemistry* 32:7832

Lloyd C M, Minto A W, Dorf M E, Proudfoot A, Wells T N C, Salant D J, Gutierrez-Ramos J C (1997). RANTES and monocyte chemoattractant protein-1 (MCP-1) play an important role in the inflammatory phase of crescentic nephritis, but only MCP-1 is involved in crescent formation and interstitial fibrosis. *J. Exp. Med.* 185:1371

Lu B B, Rutledge B J, Gu L, Fiorillo J, Lukacs N W, Kunkel S L, North R, Gerard C, Rollins B J (1998). Abnormalities in monocyte recruitment and cytokine expression in monocyte chemoattractant protein-1 deficient mice. *J. Exp. Med.* 187:601

Lubkowski J, Bujacz G, Boque L, Domaille P J, Handel T M, Wlodawer A (1997). The structure of MCP-1 in two crystal forms provides a rare example of variable quaternary interactions. *Nat Struct Biol* 4:64

Mack M, Cihak J, Simonis C, Luckow B, Proudfoot A E, Plachy J, Bruhl H, Frink M, Anders H J, Vielhauer V, Pfirstinger J, Stangassinger M, Schlöndorff D (2001). Expression and characterization of the chemokine receptors CCR2 and CCR5 in mice. *J. Immunol.* 166:4697

Martinelli R, Sabroe I, LaRosa G, Williams T J, Pease J E. The CC chemokine eotaxin (CCL11) is a partial agonist of CC chemokine receptor 2b. *J Biol Chem* 276:42957

Matsushima K, Morishita K, Yoshimura T, Lavu S, Kobayashi Y, Lew W, Appella E, Kung H F, Leonard E J, Oppenheim J J (1989). Molecular cloning of a human monocyte-derived neutrophil chemotactic factor (MDNCF) and the induction of MDNCF mRNA by interleukin 1 and tumor necrosis factor. *J. Exp. Med.* 167:1883

McGinnis S, Madden T L (2004). BLAST: at the core of a powerful and diverse set of sequence analysis tools. *Nucleic Acids Res.* 32 (Web Server issue):W20-5.

Meyer T W (2003). Immunosuppression for diabetic glomerular disease? *Kidney Int.* 63:377

Miller M D, Krangel M S (1992). Biology and biochemistry of the chemokines: a family of chemotactic and inflammatory cytokines. *Crit. Rev. Immunol.* 12:17

Miller L E et al. (1993). *J Physiol* 469:213

Mora C, Navarro J F (2005). The role of inflammation as a pathogenic factor in the development of renal disease in diabetes. *Curr. Diab. Rep.* 5:399

Morii T, Fujita H, Narita T, Shimotomai T, Fujishima H, Yoshioka N, Imai H, Kakei M, Ito S (2003). Association of monocyte chemoattractant protein-1 with renal tubular damage in diabetic nephropathy. *J. Diabetes Complications* 17:11

Murphy P M, Baggiolini M, Charo I F, Hebert C A, Horuk R, Matsushima K, Miller L H, Oppenheim J J, Power C A (2000). International union of pharmacology. XXII. Nomenclature for chemokine receptors. *Pharmacol. Rev.* 52:145

Nakamura H, Weiss S T, Israel E, Luster A D, Drazen J M, Lilly C M (1999). Eotaxin and impaired lung function in asthma. *Am J Respir Crit. Care Med* 160:1952

Nakazawa T, Hisatomi T, Nakazawa C, Noda K, Maruyama K, She H, Matsubara A, Miyahara S, Nakao S, Yin Y, Benowitz L, Hafezi-Moghadam A, Miller J W (2007). Monocyte chemoattractant protein 1 mediated retinal detachment-induced photoreceptor apoptosis. *Proc Natl. Acad. Sci. USA* 104:2425

Navarro J F, Mora C, Maca M, Garca J (2003). Inflammatory parameters are independently associated with urinary albumin in type 2 diabetes mellitus. *Am. J. Kidney Dis.* 42:53

Myers S J, Wong L M, Charo I F (1995). Signal transduction and ligand specificity of the human monocyte chemoattractant protein-1 receptor in transfected embryonic kidney cells. *J. Biol. Chem.* 270:5786

Needleman & Wunsch (1970), A general method applicable to the search for similarities in the amino acid sequence of two proteins. *J Mol. Biol.* 48(3):443-53.

Nelken N A, Coughlin S R, Gordon D, Wilcox J N (1991). Monocyte chemoattractant protein-1 in human atheromatous plaques. *J. Clin. Invest.* 88:1121

Neote K, DiGregorio D, Mak J Y, Horuk R, Schall T J (1993). Molecular cloning, functional expression, and signaling characteristics of a C—C chemokine receptor. *Cell* 72:415

Ninichuk V, Gross O, Reichel C, Khandoga A, Pawar R D, Ciubar R, Segerer S, Belemezova E, Radomska E, Luckow B, de Lema G P, Murphy P M, Gao J L, Henger A, Kretzler M, Horuk R, Weber M, Krombach F, Schlondorff D, Anders H J (2005). Delayed chemokine receptor 1 blockade prolongs survival in collagen 4A3-deficient mice with Alport disease. *J. Am. Soc. Nephrol.* 16:977

Ogata H, Takeya M, Yoshimura T, Takagi K, Takahashi K (1997). The role of monocyte chemoattractant protein-1 (MCP-1) in the pathogenesis of collagen-induced arthritis in rats. *J. Pathol.* 182:106

Okuno T, Andoh A, Bamba S, Araki Y, Fujiyama Y, Fujiyama M, Bamba T (2002). Interleukin-1β and tumor necrosis factor-α induce chemokine and matrix metalloproteinase gene expression in human colonic subepithelial myofibroblasts. *Scand. J. Gastroenterol.* 37:317

Oppenheim J J, Zachariae C O, Mukaida N, Matsushima K (1991). Properties of the novel proinflammatory supergene "intercrine" cytokine family. *Annu. Rev. Immunol.* 9:617

Pawar R D, Patole P S, Zecher D, Segerer S, Kretzler M, Schlöndorff D, Anders H J (2006). Toll-like receptor-7 modulates immune complex glomerulonephritis. *J. Am. Soc. Nephrol.* 17:141

Pearson & Lipman (1988), Improved tools for biological sequence comparison. *Proc. Nat'l. Acad. Sci. USA* 85:2444

Perez de Lema G, Maier H, Franz T J, Escribese M; Chilla mS, Segerer S, Camarasa N, Schmid H, Banas B, Kalaydjiev S, Busch D H, Pfeffer K, Mampaso F, Schlöndorff D, Luckow B (2005). Chemokine receptor CCR2 deficiency reduces renal disease and prolongs survival in MRL/lpr lupus-prone mice. *J. Am. Soc. Nephrol.* 16:3592

Perez de Lema G, Maier H, Nieto E, Vielhauer V, Luckow B, Mampaso F, Schlöndorff D. Chemokine expression precedes inflammatory cell infiltration and chemokine receptor and cytokine expression during the initiation of murine lupus nephritis. *J. Am. Soc. Nephrol.* 12:1369

Ponath P D, Qin S, Ringler D J, Clark-Lewis I, Wang J, Kassam N, Smith H, Shi X, Gonzalo J A, Newman W, Gutierrez-Ramos J C, Mackay C R (1996a). Cloning of the human eosinophil chemoattractant, eotaxin. Expression, receptor binding, and functional properties suggest a mechanism for the selective recruitment of eosinophils. *J. Clin. Invest.* 97:604

Ponath P D, Qin S, Post T W, Wang J, Wu L, Gerard N P, Newman W, Gerard C, Mackay C R (1996b). Molecular cloning and characterization of a human eotaxin receptor expressed selectively on eosinophils. *J. Exp. Med.* 183:2437

Power C A, Meyer A, Nemeth K, Bacon K B, Hoogewerf A J, Proudfoot A E, Wells T N (1995). Molecular cloning and functional expression of a novel CC chemokine receptor cDNA from a human basophilic cell line. *J. Biol. Chem.* 270:19495

Qi Z, Whitt I, Mehta A, Jin J, Zhao M, Harris R C, Fogo A B, Breyer M D (2004). Serial determination of glomerular filtration rate in conscious mice using FITC-inulin clearance. *Am. J. Physiol. Renal Physiol.* 286:F590

Qin S, LaRosa G, Campbell J J, Smith-Heath H, Kassam N, Shi X, Zeng L, Buthcher E C, Mackay C R (1996). Expression of monocyte chemoattractant protein-1 and interleukin-8 receptors on subsets of T cells: correlation with transendothelial chemotactic potential. *Eur. J. Immunol.* 26:640

Ransohoff R M et al. (1993). *FASEB J* 7:592

Raport C J, Gosling J, Schweickart V L, Gray P W, Charo I F (1996). Molecular cloning and functional characterization of a novel human CC chemokine receptor (CCR5) for RANTES, MIP-1β, and MIP-1α. *J. Biol. Chem.* 271:17161

Ritz E, Rychlik I, Locatelli F, Halimi S (1999). End-stage renal failure in type 2 diabetes: A medical catastrophe of worldwide dimensions. *Am. J. Kidney Dis.* 34:795-808

Rollins B J, Stier P, Ernst T, Wong G G (1989). The human homolog of the JE gene encodes a monocyte secretory protein. *Mol. Cell. Biol.* 9:4687

Rollins B J (1996). Monocyte chemoattractant protein 1: a potential regulator of monocyte recruitment in inflammatory disease. *Mol. Med. Today* 2:198

Rovin B H, Rumancik M, Tan L, Dickerson J (1994). Glomerular expression of monocyte chemoattractant protein-1 in experimental and human glomerulonephritis. *Lab. Invest.* 71:536

Ruffing N, Sullivan N, et al. (1998). CCR5 has an expanded ligand-binding repertoire and is the primary receptor used by MCP-2 on activated T cells. *Cell Immunol* 189:160

Salcedo R, Ponce M L, Young H A, Wasserman K, Ward J M, Keinman H K, Oppenheim J J, Murphy W J (2000). Human endothelial cells express CCR2 and respond to MCP-1: direct role of MCP-1 in angiogenesis and tumor progression. *Blood* 96:34

Samson M, Labbe O, Mollereau C, Vassart G, Parmentier M (1996). Molecular cloning and functional expression of a new human CC-chemokine receptor gene. *Biochemistry* 35:3362

Schall T J, Bacon K B (1994). Chemokines, leukocyte trafficking, and inflammation. *Curr. Opin. Immunol.* 6:865

Schneider A, Panzer U, Zahner G, Wenzel U, Wolf G, Thaiss F, Helmchen U, Stahl R A (1999). Monocyte chemoattractant protein-1 mediates collagen deposition in experimental glomerulonephritis by transforming growth factor-beta. *Kidney Int.* 56:135

Schwarting A, Paul K, Tschirner S, Menke J, Hansen T, Brenner W, Kelly V R, Relle M, Galle P R (2005). Interferon-beta: a therapeutic for autoimmune lupus in MRL-Faslpr mice. *J. Am. Soc. Nephrol.* 16:3264

Schwartz C J, Valente A J, Sprague E A (1993). A modern view of atherogenesis. *Am. J. Cardiol.* 71:9B Segerer S, Nelson P J, Schlöndorff D (2000). Chemokines, chemokine receptors, and renal disease: from basic science to pathophysiologic and therapeutic studies. *J. Am. Soc. Nephrol.* 11:152

Shimizu S, Nakashima H, Masutani K, Inoue Y, Miyake K, Akahoshi M, Tanaka Y, Egashira K, Hirakata H, Otsuka T, Harada M (2004). Anti-monocyte chemoattractant protein-1 gene therapy attenuates nephritis in MRL/lpr mice. *Rheumatology* (Oxford) 43:1121

Smith & Waterman (1981), *Adv. Appl. Math.* 2: 482

Springer T A (1995). Traffic signals on endothelium for lymphocyte recirculation and leukocyte emigration. *Annu. Rev. Physiol.* 57:827

Steinman L (2004). Immune therapy for autoimmune diseases. *Science* 305:212

Svensson M, Sundkvist G, Amqvist H J, Bjork E, Blohme G, Bolinder J, Henricsson M, Nystrom L, Torffvit O, Waembaum I, Ostman J, Eriksson J W (2003). Signs of nephropathy may occur early in young adults with diabetes despite modern diabetes management: Results from the nationwide population-based Diabetes Incidence Study in Sweden (DISS). *Diabetes Care* 26:2903

Takebayashi K, Matsumoto S, Aso Y, Inukai T (2006). Association between circulating monocyte chemoattractant protein-1 and urinary albumin excretion in nonobese Type 2 diabetic patients. *J. Diabetes Complications* 20:98

Takeya M, Yoshimura T, Leonard E T, Takahashi K (1993). Detection of monocyte chemoattractant protein-1 in human atherosclerotic lesions by an anti-monocyte chemoattractant protein-1 monoclonal antibody. *Hum. Pathol.* 24:534

Tang W W, Qi M, Warren J S (1996). Monocyte chemoattractant protein 1 mediates glomerular macrophage infiltration in anti-GBM Ab G N. *Kidney Int.* 50:665

Tashiro K, Koyanagi I, Saitoh A, Shimizu A, Shike T, Ishiguro C, Koizumi M, Funabiki K, Horikoshi S, Shirato I, Tomino Y (2002). Urinary levels of monocyte chemoattractant protein-1 (MCP-1) and interleukin-8 (IL-8), and renal injuries in patients with type 2 diabetic nephropathy. *J. Clin. Lab. Anal.* 16:1

Tesch G H, Maifert S, Schwarting A, Rollins B J, Kelley V R (1999). Monocyte chemoattractant protein 1-dependent leukocytic infiltrates are responsible for autoimmune disease in MRL-Fas(lpr) mice. *J. Exp. Med.* 190:1813

Tuaillon N, Shen de F, Berger R B, Lu B, Rollins B J, Chan C C (2002). MCP-1 expression in endotoxin-induced uveitis. *Invest. Ophthalmol. Vis. Sci.* 43:1493

Tuttle K R (2005). Linking metabolism and immunology: diabetic nephropathy is an inflammatory disease. *J. Am. Soc. Nephrol.* 16:1537

Uguccioni M, Mackay C R et al. (1997). High expression of the chemokine receptor CCR3 in human blood basophils. Role in activation by eotaxin, MCP-4, and other chemokines. *J Clin Invest* 100:1137

United States Renal Data System (2004). Annual data report: Incidence and prevalence 2004. *Am. J. Kidney Dis.* 45:S77

Utimura R, Fujihara C K, Mattar A L, Malheiros D M, Noronha I L, Zatz R (2003). Mycophenolate mofetil prevents the development of glomerular injury in experimental diabetes. *Kidney Int.* 63:209

Van Riper G, Siciliano S, Fischer P A, Meurer R, Springer M S, Rosen H (1993). Characterization and species distribution of high affinity GTP-coupled receptors for human rantes and monocyte chemoattractant protein 1. *J. Exp. Med.* 177:851

Venkatesan N et al. (2003). *Curr Med Chem* 10:1973

Vestergaard C, Just H, Baumgartner Nielsen J, Thestrup-Pedersen K, Delman M (2004). Expression of CCR2 on monocytes and macrophages in chronically inflamed skin in atopic dermatitis and psoriasis. *Acta Derm. Venereol.* 84:353

Viedt C, Orth S R (2002). Monocyte chemoattractant protein-1 (MCP-1) in the kidney: does it more than simply attract monocytes? *Nephrol. Dial. Transplant.* 17:2043

Wada T, Furuichi K, Segada-Takaeda C, Ahimizu M, Sakai N, Takeda S I, Takasawa K, Kida H, Kobayashi K I, Mukaida N, Ohmoto Y, Matsushima K, Yokoyama H (1999). MIP-1α and MCP-1 contribute to crescents and interstitial lesions in human crescentic glomerulonephritis. *Kidney Int.* 56:995

Wada T, Yokoyama H, Matsushima K, Kobayashi K I (2001). Chemokines in renal diseases. *Int. Immunopharmacol.* 1:637

Wada T, Yokoyama H, Furuichi K, Kobayashi K I, Harada K, Naruto M, Su S B, Akiyama M, Mukaida N, Matsushima K (1996). Intervention of crescentic glomerulonephritis by antibodies to monocyte chemotactic and activating factor (MCAF/MCP-1). *FASEB J.* 10:1418

Wang X, Yue T L, Barone F C, Feuerstein G Z (1995). Monocyte chemoattractant protein-1 messenger RNA expression in rat ischemic cortex. *Stroke* 26:661

Wenzel U, Schneider A, Valente A J, Abboud H E, Thaiss F, Helmchen U M, Stahl R A (1997). Monocyte chemoattractant protein-1 mediates monocyte/macrophage influx in anti-thymocyte antibody-induced glomerulonephritis. *Kidney Int.* 51:770

Yamagishi S, Inagaki Y, Okamoto T, Amano S, Koga K, Takeuchi M, Makita Z (2002). Advanced glycation end product-induced apoptosis and overexpression of vascular endothelial growth factor and monocyte chemoattractant protein-1 in human-cultured mesangial cells. *J. Biol. Chem.* 277:20309

Ying S, Robinson D S, Meng Q, Rottman J, Kennedy R, Ringler D J, Mackay C R, Daugherty B L, Springer M S, Durham S R, Williams T J, Kay A B (1997). Enhanced expression of eotaxin and CCR3 mRNA and protein in atopic asthma. Association with airway hyperresponsiveness and predominant co-localization of eotaxin mRNA to bronchial epithelial and endothelial cells. *Eur Immunol* 27:3507

Ying S, Meng Q, Zeibecoglou K, Robinson D S, Macfarlane A, Humbert M, Kay A B (1999). Eosinophil chemotactic chemokines (eotaxin, eotaxin-2, RANTES, monocyte chemoattractant protein-3 (MCP-3), and MCP-4), and C—C chemokine receptor 3 expression in bronchial biopsies from atopic and nonatopic (Intrinsic) asthmatics. *J Immunol* 163:6321

Yla-Herttuala S, Lipton B A, Rosenfeld M E, Sarkioja T, Yoshimura T, Leonard E J, Witztum J L, Steinberg D (1991). Expression of monocyte chemoattractant protein 1 in macrophage-rich areas of human and rabbit atherosclerotic lesions. *Proc. Natl. Acad. Sci. USA* 88:5252

Yoshimura T, Robinson E A, Tanaka S, Appella E, Leonard E J (1989). Purification and amino acid analysis of two human monocyte chemoattractants produced by phytohemagglutinin-stimulated human blood mononuclear leukocytes. *J. Immunol.* 142:1956

Yozai K, Shikata K, Sasaki M, Tone A, Ohga S, Usui H, Okada S, Wada J, Nagase R, Ogawa D, Shikata Y, Makino H (2005). Methotrexate prevents renal injury in experimental diabetic rats via anti-inflammatory actions. *J. Am. Soc. Nephrol.* 16:3326

Zimmet P, Alberti K G, Shaw J (2001). Global and societal implications of the diabetes epidemic. *Nature* 414:782

The features of the present invention disclosed in the specification, the claims and/or the drawings may both separately and in any combination thereof be material for realizing the invention in various forms thereof.

The invention claimed is:

1. An L-nucleic acid that binds a chemokine, wherein the nucleic acid comprises in direction a first stretch Box B1A, a second stretch Box B2, and a third stretch Box B1B, wherein the first stretch Box B1A comprises a nucleotide sequence selected from the group consisting of ACGCA, CGCA and GCA, the second stretch Box B2 comprises CSUCCCUCAC-CGGUGCAAGUGAAGCCGYGGCUC (SEQ ID NO:287), and the third stretch Box B1B comprises a nucleotide sequence selected from the group consisting of UGCG and UGC.

2. The nucleic acid according to claim 1, wherein the second stretch Box B2 comprises CGUCCCUCACCGGUG-CAAGUGAAGCCGUGGCUC (SEQ ID NO:288).

3. The nucleic acid according to claim 1, wherein
   a) the first stretch Box B1A comprises ACGCA, and the third stretch Box B1B comprises UGCGU;
   b) the first stretch Box B1A comprises CGCA, and the third stretch Box B1B comprises UGCG; or
   c) the first stretch Box B1A comprises GCA, and the third stretch Box B1B comprises UGC or UGCG.

4. The nucleic acid according to claim 1, wherein the first stretch Box B1A comprises GCA.

5. The nucleic acid according to claim 1, wherein the third stretch Box B1B comprises UGCG.

6. The nucleic acid according to claim 1, wherein the chemokine is selected from the group consisting of eotaxin, MCP-1, MCP-2 and MCP-3.

7. The nucleic acid according to claim 1, wherein the chemokine is human MCP-1.

8. The nucleic acid according to claim 1, comprising a modification.

9. The nucleic acid according to claim 8, wherein the modification comprises hydroxyethyl starch (HES) moiety or a polyethylene glycol (PEG) moiety.

10. The nucleic acid according to claim 8, wherein the modification comprises a straight or a branched PEG.

11. The nucleic acid according to claim 10, wherein said straight or branched PEG has a molecular weight from about 20 kD to about 120 kD.

12. The nucleic acid according to claim 9, wherein said HES moiety has a molecular weight from about 10 kD to about 130 kD.

13. The nucleic acid according to claim 1, wherein the first stretch Box B1A and the third stretch Box B1B optionally hybridize with each other to form a double-stranded structure.

14. A pharmaceutical composition comprising a nucleic acid according to claim 1 and a pharmaceutically acceptable excipient, carrier, pharmaceutically active agent or combination thereof.

15. A method for treating a disease associated with a chemokine comprising exposing a subject suspected of having said disease with the nucleic acid of claim 1.

16. The method of claim 15, wherein said chemokine comprises human MCP-1.

17. A method for detecting a chemokine comprising exposing a sample suspected of comprising said chemokine with the nucleic acid of claim 1 and determining presence of complexes of said nucleic acid and said chemokine, wherein presence of complexes correlates with presence of chemokine in said sample.

18. The method of claim 17, wherein said chemokine comprises eotaxin, MCP-1, MCP-2 or MCP-3.

19. A method for identifying a chemokine antagonist or agonist comprising the steps:
   providing a candidate chemokine antagonist and/or a candidate chemokine agonist,
   providing the nucleic acid according to claim 1,
   providing a test system which provides a signal in the presence of complexes of the chemokine and said nucleic acid, Wherein a chemokine antagonist and/or chemokine agonist interferes with formation of said complexes, and
   determining whether an antagonist and/or an agonist identified in the test system is an antagonist and/or agonist of said chemokine.

20. The method of claim 19, wherein said chemokine is selected from the group consisting of eotaxin, MCP-1, MCP-2 and MCP-3.

21. The method of claim 19, wherein said test system comprises a solid phase, and said chemokine is immobilized on said solid phase.

* * * * *

SEQUENCE LISTING

```
<160> NUMBER OF SEQ ID NOS: 294

<210> SEQ ID NO 1
<211> LENGTH: 76
<212> TYPE: PRT
<213> ORGANISM: Homo sapiens

<400> SEQUENCE: 1

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75

<210> SEQ ID NO 2
<211> LENGTH: 125
<212> TYPE: PRT
<213> ORGANISM: Mus musculus

<400> SEQUENCE: 2

Gln Pro Asp Ala Val Asn Ala Pro Leu Thr Cys Cys Tyr Ser Phe Thr
1               5                   10                  15

Ser Lys Met Ile Pro Met Ser Arg Leu Glu Ser Tyr Lys Arg Ile Thr
            20                  25                  30

Ser Ser Arg Cys Pro Lys Glu Ala Val Val Phe Val Thr Lys Leu Lys
        35                  40                  45

Arg Glu Val Cys Ala Asp Pro Lys Lys Glu Trp Val Gln Thr Tyr Ile
    50                  55                  60
```

```
Lys Asn Leu Asp Arg Asn Gln Met Arg Ser Glu Pro Thr Thr Leu Phe
 65                  70                  75                  80

Lys Thr Ala Ser Ala Leu Arg Ser Ser Ala Pro Leu Asn Val Lys Leu
             85                  90                  95

Thr Arg Lys Ser Glu Ala Asn Ala Ser Thr Thr Phe Ser Thr Thr Thr
            100                 105                 110

Ser Ser Thr Ser Val Gly Val Thr Ser Val Thr Val Asn
        115                 120                 125

<210> SEQ ID NO 3
<211> LENGTH: 76
<212> TYPE: PRT
<213> ORGANISM: Maca mulatta

<400> SEQUENCE: 3

Gln Pro Asp Ala Ile Asn Ala Pro Val Thr Cys Cys Tyr Asn Phe Thr
  1               5                  10                  15

Asn Arg Lys Ile Ser Val Gln Arg Leu Ala Ser Tyr Arg Arg Ile Thr
             20                  25                  30

Ser Ser Lys Cys Pro Lys Glu Ala Val Ile Phe Lys Thr Ile Val Ala
         35                  40                  45

Lys Glu Ile Cys Ala Asp Pro Lys Gln Lys Trp Val Gln Asp Ser Met
 50                  55                  60

Asp His Leu Asp Lys Gln Ile Gln Thr Pro Lys Pro
 65                  70                  75

<210> SEQ ID NO 4
<211> LENGTH: 76
<212> TYPE: PRT
<213> ORGANISM: Sus scrofa

<400> SEQUENCE: 4

Gln Pro Asp Ala Ile Asn Ser Pro Val Thr Cys Cys Tyr Thr Leu Thr
  1               5                  10                  15

Ser Lys Lys Ile Ser Met Gln Arg Leu Met Ser Tyr Arg Arg Val Thr
             20                  25                  30

Ser Ser Lys Cys Pro Lys Glu Ala Val Ile Phe Lys Thr Ile Ala Gly
         35                  40                  45

Lys Glu Ile Cys Ala Glu Pro Lys Gln Lys Trp Val Gln Asp Ser Ile
 50                  55                  60

Ser His Leu Asp Lys Lys Asn Gln Thr Pro Lys Pro
 65                  70                  75

<210> SEQ ID NO 5
<211> LENGTH: 76
<212> TYPE: PRT
<213> ORGANISM: Canis familiaris

<400> SEQUENCE: 5

Gln Pro Asp Ala Ile Ile Ser Pro Val Thr Cys Cys Tyr Thr Leu Thr
  1               5                  10                  15

Asn Lys Lys Ile Ser Ile Gln Arg Leu Ala Ser Tyr Lys Arg Val Thr
             20                  25                  30

Ser Ser Lys Cys Pro Lys Glu Ala Val Ile Phe Lys Thr Val Leu Asn
         35                  40                  45

Lys Glu Ile Cys Ala Asp Pro Lys Gln Lys Trp Val Gln Asp Ser Met
 50                  55                  60

Ala His Leu Asp Lys Lys Ser Gln Thr Gln Thr Ala
```

<210> SEQ ID NO 6
<211> LENGTH: 102
<212> TYPE: PRT
<213> ORGANISM: Oryctolagus cuniculus

<400> SEQUENCE: 6

```
Gln Pro Asp Ala Val Asn Ser Pro Val Thr Cys Cys Tyr Thr Phe Thr
1               5                   10                  15

Asn Lys Thr Ile Ser Val Lys Arg Leu Met Ser Tyr Arg Arg Ile Asn
            20                  25                  30

Ser Thr Lys Cys Pro Lys Glu Ala Val Ile Phe Met Thr Lys Leu Ala
        35                  40                  45

Lys Gly Ile Cys Ala Asp Pro Lys Gln Lys Trp Val Gln Asp Ala Ile
    50                  55                  60

Ala Asn Leu Asp Lys Lys Met Gln Thr Pro Lys Thr Leu Thr Ser Tyr
65                  70                  75                  80

Ser Thr Thr Gln Glu His Thr Thr Asn Leu Ser Ser Thr Arg Thr Pro
                85                  90                  95

Ser Thr Thr Thr Ser Leu
            100
```

<210> SEQ ID NO 7
<211> LENGTH: 76
<212> TYPE: PRT
<213> ORGANISM: Homo sapiens

<400> SEQUENCE: 7

```
Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75
```

<210> SEQ ID NO 8
<211> LENGTH: 74
<212> TYPE: PRT
<213> ORGANISM: Homo sapiens

<400> SEQUENCE: 8

```
Gly Pro Ala Ser Val Pro Thr Thr Cys Cys Phe Asn Leu Ala Asn Arg
1               5                   10                  15

Lys Ile Pro Leu Gln Arg Leu Glu Ser Tyr Arg Arg Ile Thr Ser Gly
            20                  25                  30

Lys Cys Pro Gln Lys Ala Val Ile Phe Lys Thr Lys Leu Ala Lys Asp
        35                  40                  45

Ile Cys Ala Asp Pro Lys Lys Lys Trp Val Gln Asp Ser Met Lys Tyr
    50                  55                  60

Leu Asp Gln Lys Ser Pro Thr Pro Lys Pro
65                  70
```

<210> SEQ ID NO 9
<211> LENGTH: 76

-continued

```
<212> TYPE: PRT
<213> ORGANISM: Homo sapiens

<400> SEQUENCE: 9

Gln Pro Asp Ser Val Ser Ile Pro Ile Thr Cys Cys Phe Asn Val Ile
1               5                   10                  15

Asn Arg Lys Ile Pro Ile Gln Arg Leu Glu Ser Tyr Thr Arg Ile Thr
                20                  25                  30

Asn Ile Gln Cys Pro Lys Glu Ala Val Ile Phe Lys Thr Lys Arg Gly
            35                  40                  45

Lys Glu Val Cys Ala Asp Pro Lys Glu Arg Trp Val Arg Asp Ser Met
        50                  55                  60

Lys His Leu Asp Gln Ile Phe Gln Asn Leu Lys Pro
65                  70                  75

<210> SEQ ID NO 10
<211> LENGTH: 47
<212> TYPE: RNA
<213> ORGANISM: Artificial
<220> FEATURE:
<223> OTHER INFORMATION: synthetic

<400> SEQUENCE: 10
agcgugcccg gaguggcagg gggacgcgac cugcaauaau gcacgcu          47

<210> SEQ ID NO 11
<211> LENGTH: 45
<212> TYPE: RNA
<213> ORGANISM: Artificial
<220> FEATURE:
<223> OTHER INFORMATION: synthethic

<400> SEQUENCE: 11
agcgugcccg gaguggcagg gggacgcgac cugcaauugc acgcu            45

<210> SEQ ID NO 12
<211> LENGTH: 47
<212> TYPE: RNA
<213> ORGANISM: Artificial
<220> FEATURE:
<223> OTHER INFORMATION: synthethic

<400> SEQUENCE: 12
agcgugcccg gaguggcagg gggacgcgac cuguaauaau gcacgcu          47

<210> SEQ ID NO 13
<211> LENGTH: 47
<212> TYPE: RNA
<213> ORGANISM: Artificial
<220> FEATURE:
<223> OTHER INFORMATION: synthetic

<400> SEQUENCE: 13
agcgugcccg guguggcagg gggacgcgac cugcaauaau gcgcgcu          47

<210> SEQ ID NO 14
<211> LENGTH: 47
<212> TYPE: RNA
<213> ORGANISM: Artificial
<220> FEATURE:
<223> OTHER INFORMATION: synthethic

<400> SEQUENCE: 14
agcgugcccg gaguagcagg ggggcgcgac cugcaauaau gcacgcu          47
```

<210> SEQ ID NO 15
<211> LENGTH: 45
<212> TYPE: RNA
<213> ORGANISM: Artificial
<220> FEATURE:
<223> OTHER INFORMATION: synthetic

<400> SEQUENCE: 15
agcgugcccg gugugguagg ggggcgcgau cuacaauugc acgcu        45

<210> SEQ ID NO 16
<211> LENGTH: 45
<212> TYPE: RNA
<213> ORGANISM: Artificial
<220> FEATURE:
<223> OTHER INFORMATION: synthetic

<400> SEQUENCE: 16
agcgugcccg gugugacagg ggggcgcgac cugcauuugc acgcu        45

<210> SEQ ID NO 17
<211> LENGTH: 45
<212> TYPE: RNA
<213> ORGANISM: Artificial
<220> FEATURE:
<223> OTHER INFORMATION: synthetic

<400> SEQUENCE: 17
agcgugcccg guguggcagg ggggcgcgac cuguauuugc acgcu        45

<210> SEQ ID NO 18
<211> LENGTH: 47
<212> TYPE: RNA
<213> ORGANISM: Artificial
<220> FEATURE:
<223> OTHER INFORMATION: synthetic

<400> SEQUENCE: 18
agcgugcccg gaguggcagg ggggcgcgac cugcaauaau gcacgcu      47

<210> SEQ ID NO 19
<211> LENGTH: 45
<212> TYPE: RNA
<213> ORGANISM: Artificial
<220> FEATURE:
<223> OTHER INFORMATION: synthetic

<400> SEQUENCE: 19
agcgugcccg guguggcagg ggggcgcgac cugcaauugc acgcu        45

<210> SEQ ID NO 20
<211> LENGTH: 45
<212> TYPE: RNA
<213> ORGANISM: Artificial
<220> FEATURE:
<223> OTHER INFORMATION: synthetic

<400> SEQUENCE: 20
agcaugcccg guguggcagg ggggcgcgac cugcauuugc augcu        45

<210> SEQ ID NO 21
<211> LENGTH: 45
<212> TYPE: RNA
<213> ORGANISM: Artificial
<220> FEATURE:
<223> OTHER INFORMATION: synthetic

<400> SEQUENCE: 21
agcgugcccg gugugguagg ggggcgcgac cuacauuugc acgcu                        45

<210> SEQ ID NO 22
<211> LENGTH: 44
<212> TYPE: RNA
<213> ORGANISM: Artificial
<220> FEATURE:
<223> OTHER INFORMATION: synthetic

<400> SEQUENCE: 22
agugugccag cugugauggg ggggcgcgac ccauuuuaca cacu                         44

<210> SEQ ID NO 23
<211> LENGTH: 43
<212> TYPE: RNA
<213> ORGANISM: Artificial
<220> FEATURE:
<223> OTHER INFORMATION: synthetic

<400> SEQUENCE: 23
agugugccag cgugaugggg gggcgcgacc cauuuacac acu                           43

<210> SEQ ID NO 24
<211> LENGTH: 43
<212> TYPE: RNA
<213> ORGANISM: Artificial
<220> FEATURE:
<223> OTHER INFORMATION: synthetic

<400> SEQUENCE: 24
agugugcgag cgugaugggg gggcgcgacc cauuuacau acu                           43

<210> SEQ ID NO 25
<211> LENGTH: 43
<212> TYPE: RNA
<213> ORGANISM: Artificial
<220> FEATURE:
<223> OTHER INFORMATION: synthetic

<400> SEQUENCE: 25
agugugccag cgugaugggg gggcgcgacc cauuuacau acu                           43

<210> SEQ ID NO 26
<211> LENGTH: 42
<212> TYPE: RNA
<213> ORGANISM: Artificial
<220> FEATURE:
<223> OTHER INFORMATION: synthetic

<400> SEQUENCE: 26
aguaugccag cgugaugggg gggcgcgacc cauuuacaua cu                           42

<210> SEQ ID NO 27
<211> LENGTH: 43
<212> TYPE: RNA
<213> ORGANISM: Artificial
<220> FEATURE:
<223> OTHER INFORMATION: synthetic

<400> SEQUENCE: 27
agugugccag ugugaugggg gggcgcgacc cauuuacac acu                           43

<210> SEQ ID NO 28
<211> LENGTH: 43
<212> TYPE: RNA

-continued

<213> ORGANISM: Artificial
<220> FEATURE:
<223> OTHER INFORMATION: synthetic

<400> SEQUENCE: 28
agcgugccag ugugaugggg gggcgcgacc cauuuuacac gcu                43

<210> SEQ ID NO 29
<211> LENGTH: 43
<212> TYPE: RNA
<213> ORGANISM: Artificial
<220> FEATURE:
<223> OTHER INFORMATION: synthetic

<400> SEQUENCE: 29
acgcacgucc cucaccggug caagugaagc cgcggcucug cgu                43

<210> SEQ ID NO 30
<211> LENGTH: 43
<212> TYPE: RNA
<213> ORGANISM: Artificial
<220> FEATURE:
<223> OTHER INFORMATION: synthetic

<400> SEQUENCE: 30
acgcaccucc cucaccggug caagugaagc cguggcucug cgc                43

<210> SEQ ID NO 31
<211> LENGTH: 43
<212> TYPE: RNA
<213> ORGANISM: Artificial
<220> FEATURE:
<223> OTHER INFORMATION: synthetic

<400> SEQUENCE: 31
acgcacgucc cucaccggug caagugaagc cguggcucug cgu                43

<210> SEQ ID NO 32
<211> LENGTH: 41
<212> TYPE: RNA
<213> ORGANISM: Artificial
<220> FEATURE:
<223> OTHER INFORMATION: synthetic

<400> SEQUENCE: 32
gcacgucccu caccggugca agugaagccg uggcucugcg u                  41

<210> SEQ ID NO 33
<211> LENGTH: 41
<212> TYPE: RNA
<213> ORGANISM: Artificial
<220> FEATURE:
<223> OTHER INFORMATION: synthetic

<400> SEQUENCE: 33
acgcacgucc cucaccggug caagugaagc cguggcucug c                  41

<210> SEQ ID NO 34
<211> LENGTH: 39
<212> TYPE: RNA
<213> ORGANISM: Artificial
<220> FEATURE:
<223> OTHER INFORMATION: synthetic

<400> SEQUENCE: 34
gcacgucccu caccggugca agugaagccg uggcucugc                     39

```
<210> SEQ ID NO 35
<211> LENGTH: 42
<212> TYPE: RNA
<213> ORGANISM: Artificial
<220> FEATURE:
<223> OTHER INFORMATION: synthetic

<400> SEQUENCE: 35
cgcacguccc ucaccggugc aagugaagcc guggcucugc gu                    42

<210> SEQ ID NO 36
<211> LENGTH: 41
<212> TYPE: RNA
<213> ORGANISM: Artificial
<220> FEATURE:
<223> OTHER INFORMATION: synthetic

<400> SEQUENCE: 36
cgcacguccc ucaccggugc aagugaagcc guggcucugc g                     41

<210> SEQ ID NO 37
<211> LENGTH: 40
<212> TYPE: RNA
<213> ORGANISM: Artificial
<220> FEATURE:
<223> OTHER INFORMATION: synthetic

<400> SEQUENCE: 37
gcacgucccu caccggugca agugaagccg uggcucugcg                       40

<210> SEQ ID NO 38
<211> LENGTH: 49
<212> TYPE: RNA
<213> ORGANISM: Artificial
<220> FEATURE:
<223> OTHER INFORMATION: synthetic

<400> SEQUENCE: 38
gugcugcgua guggaagacu accuaaugac agccgaaugc uggcagcac             49

<210> SEQ ID NO 39
<211> LENGTH: 49
<212> TYPE: RNA
<213> ORGANISM: Artificial
<220> FEATURE:
<223> OTHER INFORMATION: synthetic

<400> SEQUENCE: 39
gugcugcgua guggaagacu accuaaugac agccuaaugc uggcagcac             49

<210> SEQ ID NO 40
<211> LENGTH: 49
<212> TYPE: RNA
<213> ORGANISM: Artificial
<220> FEATURE:
<223> OTHER INFORMATION: synthetic

<400> SEQUENCE: 40
gugcugcgua guggaagacu accuuaugac agccgaaugc uggcagcac             49

<210> SEQ ID NO 41
<211> LENGTH: 48
<212> TYPE: RNA
<213> ORGANISM: Artificial
<220> FEATURE:
<223> OTHER INFORMATION: synthetic
```

<400> SEQUENCE: 41
gugcugcgua gugaaaaacu acugccagug ggucagagcu agcagcac        48

<210> SEQ ID NO 42
<211> LENGTH: 48
<212> TYPE: RNA
<213> ORGANISM: Artificial
<220> FEATURE:
<223> OTHER INFORMATION: synthetic

<400> SEQUENCE: 42
gugcugcgga guuaaaaacu cccuaagaca ggccagagcc ggcagcac        48

<210> SEQ ID NO 43
<211> LENGTH: 48
<212> TYPE: RNA
<213> ORGANISM: Artificial
<220> FEATURE:
<223> OTHER INFORMATION: synthetic

<400> SEQUENCE: 43
gugcugcgga guugaaaacu cccuaagaca ggccagagcc ggcagcac        48

<210> SEQ ID NO 44
<211> LENGTH: 48
<212> TYPE: RNA
<213> ORGANISM: Artificial
<220> FEATURE:
<223> OTHER INFORMATION: synthetic

<400> SEQUENCE: 44
gugcugcgua guggaagacu accuaugaca gccuaaugcu ggcagcac        48

<210> SEQ ID NO 45
<211> LENGTH: 48
<212> TYPE: RNA
<213> ORGANISM: Artificial
<220> FEATURE:
<223> OTHER INFORMATION: synthetic

<400> SEQUENCE: 45
gugcugcgga guuaaaaacu cccuaagaca ggcuagagcc ggcagcac        48

<210> SEQ ID NO 46
<211> LENGTH: 50
<212> TYPE: RNA
<213> ORGANISM: Artificial
<220> FEATURE:
<223> OTHER INFORMATION: synthetic

<400> SEQUENCE: 46
gugcugcggc gugaaaaacg cccugcgacu gcccuuuaug caggcagcac        50

<210> SEQ ID NO 47
<211> LENGTH: 48
<212> TYPE: RNA
<213> ORGANISM: Artificial
<220> FEATURE:
<223> OTHER INFORMATION: synthetic

<400> SEQUENCE: 47
gugcugcgua gugaaaaacu accaacgacu ggcuagagcc ggcagcac        48

<210> SEQ ID NO 48
<211> LENGTH: 48
<212> TYPE: RNA

```
<213> ORGANISM: Artificial
<220> FEATURE:
<223> OTHER INFORMATION: synthetic

<400> SEQUENCE: 48
gugcugcgua gugaaagacu accugugaca gccgaaugcu ggcagcac        48

<210> SEQ ID NO 49
<211> LENGTH: 48
<212> TYPE: RNA
<213> ORGANISM: Artificial
<220> FEATURE:
<223> OTHER INFORMATION: synthetic

<400> SEQUENCE: 49
guacugcgua guuaaaaacu accaacgacu ggcuagagcc ggcagcac        48

<210> SEQ ID NO 50
<211> LENGTH: 48
<212> TYPE: RNA
<213> ORGANISM: Artificial
<220> FEATURE:
<223> OTHER INFORMATION: synthetic

<400> SEQUENCE: 50
gugcugcgua guuaaaaacu accaacgacu ggcuagagcc ggcagcac        48

<210> SEQ ID NO 51
<211> LENGTH: 48
<212> TYPE: RNA
<213> ORGANISM: Artificial
<220> FEATURE:
<223> OTHER INFORMATION: synthetic

<400> SEQUENCE: 51
gugcugcgua guuaaaaacu accagcgaca ggcuagagcc ggcagcac        48

<210> SEQ ID NO 52
<211> LENGTH: 48
<212> TYPE: RNA
<213> ORGANISM: Artificial
<220> FEATURE:
<223> OTHER INFORMATION: synthetic

<400> SEQUENCE: 52
gugcugcgua guuaaaaacu accagcgacu ggcuagagcc ggcagcac        48

<210> SEQ ID NO 53
<211> LENGTH: 48
<212> TYPE: RNA
<213> ORGANISM: Artificial
<220> FEATURE:
<223> OTHER INFORMATION: synthetic

<400> SEQUENCE: 53
gugcugcgua gugagaaacu accaacgacu ggcuagagcc ggcagcac        48

<210> SEQ ID NO 54
<211> LENGTH: 46
<212> TYPE: RNA
<213> ORGANISM: Artificial
<220> FEATURE:
<223> OTHER INFORMATION: synthetic

<400> SEQUENCE: 54
ggcugcguag uuaaaaacua ccagcgacug gcuagagccg gcagcc          46
```

<210> SEQ ID NO 55
<211> LENGTH: 44
<212> TYPE: RNA
<213> ORGANISM: Artificial
<220> FEATURE:
<223> OTHER INFORMATION: synthetic

<400> SEQUENCE: 55
ggcgcguagu uaaaaacuac cagcgacugg cuagagccgg cgcc                    44

<210> SEQ ID NO 56
<211> LENGTH: 46
<212> TYPE: RNA
<213> ORGANISM: Artificial
<220> FEATURE:
<223> OTHER INFORMATION: synthetic

<400> SEQUENCE: 56
gugcgcguag uuaaaaacua ccagcgacug gcuagagccg gcgcac                  46

<210> SEQ ID NO 57
<211> LENGTH: 46
<212> TYPE: RNA
<213> ORGANISM: Artificial
<220> FEATURE:
<223> OTHER INFORMATION: synthetic

<400> SEQUENCE: 57
gugcgcguag ugagaaacua ccaacgacug gcuagagccg gcgcac                  46

<210> SEQ ID NO 58
<211> LENGTH: 44
<212> TYPE: RNA
<213> ORGANISM: Artificial
<220> FEATURE:
<223> OTHER INFORMATION: synthetic

<400> SEQUENCE: 58
gugccguagu gagaaacuac caacgacugg cuagagccgg gcac                    44

<210> SEQ ID NO 59
<211> LENGTH: 44
<212> TYPE: RNA
<213> ORGANISM: Artificial
<220> FEATURE:
<223> OTHER INFORMATION: synthetic

<400> SEQUENCE: 59
guggcguagu gagaaacuac caacgacugg cuagagccgg ccac                    44

<210> SEQ ID NO 60
<211> LENGTH: 44
<212> TYPE: RNA
<213> ORGANISM: Artificial
<220> FEATURE:
<223> OTHER INFORMATION: synthetic

<400> SEQUENCE: 60
gucgcguagu gagaaacuac caacgacugg cuagagccgg cgac                    44

<210> SEQ ID NO 61
<211> LENGTH: 44
<212> TYPE: RNA
<213> ORGANISM: Artificial
<220> FEATURE:
<223> OTHER INFORMATION: synthetic

```
<400> SEQUENCE: 61
ugcgcguagu gagaaacuac caacgacugg cuagagccgg cgca          44

<210> SEQ ID NO 62
<211> LENGTH: 44
<212> TYPE: RNA
<213> ORGANISM: artificial sequence
<220> FEATURE:
<223> OTHER INFORMATION: synthetic

<400> SEQUENCE: 62
gcugcguagu gagaaacuac caacgacugg cuagagccgg cagc          44

<210> SEQ ID NO 63
<211> LENGTH: 44
<212> TYPE: RNA
<213> ORGANISM: Artificial
<220> FEATURE:
<223> OTHER INFORMATION: synthetic

<400> SEQUENCE: 63
gcugcguagu gagaaacuac caacgacugg cuagagccgg cagc          44

<210> SEQ ID NO 64
<211> LENGTH: 44
<212> TYPE: RNA
<213> ORGANISM: Artificial
<220> FEATURE:
<223> OTHER INFORMATION: synthetic

<400> SEQUENCE: 64
ggugcguagu gagaaacuac caacgacugg cuagagccgg cacc          44

<210> SEQ ID NO 65
<211> LENGTH: 42
<212> TYPE: RNA
<213> ORGANISM: Artificial
<220> FEATURE:
<223> OTHER INFORMATION: synthetic

<400> SEQUENCE: 65
uggcguagug agaaacuacc aacgacuggc uagagccggc ca            42

<210> SEQ ID NO 66
<211> LENGTH: 42
<212> TYPE: RNA
<213> ORGANISM: Artificial
<220> FEATURE:
<223> OTHER INFORMATION: synthetic

<400> SEQUENCE: 66
gcgcguagug agaaacuacc aacgacuggc uagagccggc gc            42

<210> SEQ ID NO 67
<211> LENGTH: 42
<212> TYPE: RNA
<213> ORGANISM: Artificial
<220> FEATURE:
<223> OTHER INFORMATION: synthetic

<400> SEQUENCE: 67
gugcguagug agaaacuacc aacgacuggc uagagccggc ac            42

<210> SEQ ID NO 68
<211> LENGTH: 42
<212> TYPE: RNA
```

```
<213> ORGANISM: Artificial
<220> FEATURE:
<223> OTHER INFORMATION: synthetic

<400> SEQUENCE: 68
gggcguagug agaaacuacc aacgacuggc uagagccggc cc                          42

<210> SEQ ID NO 69
<211> LENGTH: 42
<212> TYPE: RNA
<213> ORGANISM: Artificial
<220> FEATURE:
<223> OTHER INFORMATION: synthetic

<400> SEQUENCE: 69
gagcguagug agaaacuacc aacgacuggc uagagccggc uc                          42

<210> SEQ ID NO 70
<211> LENGTH: 42
<212> TYPE: RNA
<213> ORGANISM: Artificial
<220> FEATURE:
<223> OTHER INFORMATION: synthetic

<400> SEQUENCE: 70
cggcguagug agaaacuacc aacgacuggc uagagccggc cg                          42

<210> SEQ ID NO 71
<211> LENGTH: 42
<212> TYPE: RNA
<213> ORGANISM: Artificial
<220> FEATURE:
<223> OTHER INFORMATION: synthetic

<400> SEQUENCE: 71
ccgcguagug agaaacuacc aacgacuggc uagagccggc gg                          42

<210> SEQ ID NO 72
<211> LENGTH: 42
<212> TYPE: RNA
<213> ORGANISM: Artificial
<220> FEATURE:
<223> OTHER INFORMATION: synthetic

<400> SEQUENCE: 72
cagcguagug agaaacuacc aacgacuggc uagagccggc ug                          42

<210> SEQ ID NO 73
<211> LENGTH: 42
<212> TYPE: RNA
<213> ORGANISM: Artificial
<220> FEATURE:
<223> OTHER INFORMATION: synthetic

<400> SEQUENCE: 73
cugcguagug agaaacuacc aacgacuggc uagagccggc ag                          42

<210> SEQ ID NO 74
<211> LENGTH: 39
<212> TYPE: RNA
<213> ORGANISM: Artificial
<220> FEATURE:
<223> OTHER INFORMATION: synthetic

<400> SEQUENCE: 74
agcguguuag ugaagugggu ggcagguaaa ggacacgcu                              39
```

```
<210> SEQ ID NO 75
<211> LENGTH: 39
<212> TYPE: RNA
<213> ORGANISM: Artificial
<220> FEATURE:
<223> OTHER INFORMATION: synthetic

<400> SEQUENCE: 75
agcgugguag cggugugggu gguagguaaa ggccacgcu                    39

<210> SEQ ID NO 76
<211> LENGTH: 39
<212> TYPE: RNA
<213> ORGANISM: Artificial
<220> FEATURE:
<223> OTHER INFORMATION: synthetic

<400> SEQUENCE: 76
agcgugauag aagagcgggu gguagguaaa ggucaggcu                    39

<210> SEQ ID NO 77
<211> LENGTH: 39
<212> TYPE: RNA
<213> ORGANISM: Artificial
<220> FEATURE:
<223> OTHER INFORMATION: synthetic

<400> SEQUENCE: 77
agcguguuag guaggguggu aguaaguaaa ggacacgcu                    39

<210> SEQ ID NO 78
<211> LENGTH: 38
<212> TYPE: RNA
<213> ORGANISM: Artificial
<220> FEATURE:
<223> OTHER INFORMATION: synthetic

<400> SEQUENCE: 78
agcguguuag gugggguggua guaaguaaag gacacgcu                    38

<210> SEQ ID NO 79
<211> LENGTH: 38
<212> TYPE: RNA
<213> ORGANISM: Artificial
<220> FEATURE:
<223> OTHER INFORMATION: synthetic

<400> SEQUENCE: 79
agcguguuag gugggguggua guaaguaaag ggcacgcu                    38

<210> SEQ ID NO 80
<211> LENGTH: 34
<212> TYPE: RNA
<213> ORGANISM: Artificial
<220> FEATURE:
<223> OTHER INFORMATION: synthetic

<400> SEQUENCE: 80
ccgcuuaggu gggugguagu aaguaaaggg gcgg                         34

<210> SEQ ID NO 81
<211> LENGTH: 39
<212> TYPE: RNA
<213> ORGANISM: Artificial
<220> FEATURE:
<223> OTHER INFORMATION: synthetic
```

-continued

<400> SEQUENCE: 81
gcgcgagcag guggguggua gaauguaaag acucgcguc                    39

<210> SEQ ID NO 82
<211> LENGTH: 34
<212> TYPE: RNA
<213> ORGANISM: Artificial
<220> FEATURE:
<223> OTHER INFORMATION: synthetic

<400> SEQUENCE: 82
cguguuaggu ggugguagu aaguaaagga cacg                          34

<210> SEQ ID NO 83
<211> LENGTH: 32
<212> TYPE: RNA
<213> ORGANISM: Artificial
<220> FEATURE:
<223> OTHER INFORMATION: synthetic

<400> SEQUENCE: 83
guguuaggug ggugguagua aguaaaggac ac                           32

<210> SEQ ID NO 84
<211> LENGTH: 34
<212> TYPE: RNA
<213> ORGANISM: Artificial
<220> FEATURE:
<223> OTHER INFORMATION: synthetic

<400> SEQUENCE: 84
cguguuaggu ggugguagu aaguaaaggg cacg                          34

<210> SEQ ID NO 85
<211> LENGTH: 32
<212> TYPE: RNA
<213> ORGANISM: Artificial
<220> FEATURE:
<223> OTHER INFORMATION: synthetic

<400> SEQUENCE: 85
guguuaggug ggugguagua aguaaagggc ac                           32

<210> SEQ ID NO 86
<211> LENGTH: 30
<212> TYPE: RNA
<213> ORGANISM: Artificial
<220> FEATURE:
<223> OTHER INFORMATION: synthetic

<400> SEQUENCE: 86
uguuaggugg gugguaguaa guaaagggca                              30

<210> SEQ ID NO 87
<211> LENGTH: 52
<212> TYPE: RNA
<213> ORGANISM: Artificial
<220> FEATURE:
<223> OTHER INFORMATION: synthetic

<400> SEQUENCE: 87
ggacgagagu gacaaaugau auaaccuccu gacuaacgcu gcgggcgaca gg     52

<210> SEQ ID NO 88
<211> LENGTH: 52
<212> TYPE: RNA

<213> ORGANISM: Artificial
<220> FEATURE:
<223> OTHER INFORMATION: synthetic

<400> SEQUENCE: 88
ggaccuaucg cuaagacaac gcgcagucua cgggacauuc uccgcggaca gg    52

<210> SEQ ID NO 89
<211> LENGTH: 52
<212> TYPE: RNA
<213> ORGANISM: Artificial
<220> FEATURE:
<223> OTHER INFORMATION: synthetic

<400> SEQUENCE: 89
ggacaauugu uaccccgag agagacaaau gagacaaccu ccugaagaca gg    52

<210> SEQ ID NO 90
<211> LENGTH: 51
<212> TYPE: RNA
<213> ORGANISM: Artificial
<220> FEATURE:
<223> OTHER INFORMATION: synthetic

<400> SEQUENCE: 90
ggacgaaagu gagaaaugau acaaccuccu guugcugcga auccggacag g    51

<210> SEQ ID NO 91
<211> LENGTH: 50
<212> TYPE: RNA
<213> ORGANISM: Artificial
<220> FEATURE:
<223> OTHER INFORMATION: synthetic

<400> SEQUENCE: 91
ggacguaaaa gacgcuaccc gaaagaaugu caggagggua gaccgacagg    50

<210> SEQ ID NO 92
<211> LENGTH: 50
<212> TYPE: RNA
<213> ORGANISM: Artificial
<220> FEATURE:
<223> OTHER INFORMATION: synthetic

<400> SEQUENCE: 92
ggacuagaaa cuacaauagc ggccaguugc accgcguuau caacgacagg    50

<210> SEQ ID NO 93
<211> LENGTH: 50
<212> TYPE: RNA
<213> ORGANISM: Artificial
<220> FEATURE:
<223> OTHER INFORMATION: synthetic

<400> SEQUENCE: 93
ggacuaguca gccagugugu auaucggacg cggguuuauu uacugacagg    50

<210> SEQ ID NO 94
<211> LENGTH: 50
<212> TYPE: RNA
<213> ORGANISM: Artificial
<220> FEATURE:
<223> OTHER INFORMATION: synthetic

<400> SEQUENCE: 94
ggacuguccg gagugugaaa cuccccgaga ccgccagaag cggggacagg    50

<210> SEQ ID NO 95
<211> LENGTH: 50
<212> TYPE: RNA
<213> ORGANISM: Artificial
<220> FEATURE:
<223> OTHER INFORMATION: synthetic

<400> SEQUENCE: 95
ggacuucuau ccaggugggu gguaguaugu aaagagauag aagugacagg         50

<210> SEQ ID NO 96
<211> LENGTH: 50
<212> TYPE: RNA
<213> ORGANISM: Artificial
<220> FEATURE:
<223> OTHER INFORMATION: synthetic

<400> SEQUENCE: 96
ggacgagagc gaacaaugau auaaccuccu gacggaaaga gaucgacagg         50

<210> SEQ ID NO 97
<211> LENGTH: 48
<212> TYPE: RNA
<213> ORGANISM: Artificial
<220> FEATURE:
<223> OTHER INFORMATION: synthetic

<400> SEQUENCE: 97
ccugugcuac acgcaguaag aagugaacgu ucaguaugug ugcacagg           48

<210> SEQ ID NO 98
<211> LENGTH: 48
<212> TYPE: RNA
<213> ORGANISM: Artificial
<220> FEATURE:
<223> OTHER INFORMATION: synthetic

<400> SEQUENCE: 98
cgugagccag gcaccgaggg cguuaacugg cugauuggac acgacacg           48

<210> SEQ ID NO 99
<211> LENGTH: 48
<212> TYPE: RNA
<213> ORGANISM: Artificial
<220> FEATURE:
<223> OTHER INFORMATION: synthetic

<400> SEQUENCE: 99
cgugaacaug caagcuaagc ggggcuguug guugcuuggc ccgccacg           48

<210> SEQ ID NO 100
<211> LENGTH: 48
<212> TYPE: RNA
<213> ORGANISM: Artificial
<220> FEATURE:
<223> OTHER INFORMATION: synthetic

<400> SEQUENCE: 100
cgugcagaga gagaccaacc acguaaaauc aaccuaaugg gccgcacg           48

<210> SEQ ID NO 101
<211> LENGTH: 48
<212> TYPE: RNA
<213> ORGANISM: Artificial
<220> FEATURE:
<223> OTHER INFORMATION: synthetic

<400> SEQUENCE: 101
cgugcagaga gagaccaacc acguaaaauc aaccuaaugg gccgcacg            48

<210> SEQ ID NO 102
<211> LENGTH: 48
<212> TYPE: RNA
<213> ORGANISM: Artificial
<220> FEATURE:
<223> OTHER INFORMATION: synthetic

<400> SEQUENCE: 102
cgugaacauu caagcuaagc ggggcuguug guugcuuggc ccgccacg            48

<210> SEQ ID NO 103
<211> LENGTH: 48
<212> TYPE: RNA
<213> ORGANISM: Artificial
<220> FEATURE:
<223> OTHER INFORMATION: synthetic

<400> SEQUENCE: 103
cgugccgagg cggcgaccag cguuacuuag agaggcuuug gcaccacg            48

<210> SEQ ID NO 104
<211> LENGTH: 47
<212> TYPE: RNA
<213> ORGANISM: Artificial
<220> FEATURE:
<223> OTHER INFORMATION: synthetic

<400> SEQUENCE: 104
cgugauaaca gccgucgguc aagaaaacaa aguucgggcg gcgcacg             47

<210> SEQ ID NO 105
<211> LENGTH: 47
<212> TYPE: RNA
<213> ORGANISM: Artificial
<220> FEATURE:
<223> OTHER INFORMATION: synthetic

<400> SEQUENCE: 105
cguggguggc gcaccgaggg cgaaaagcca ccaguaaaga uagaccg             47

<210> SEQ ID NO 106
<211> LENGTH: 45
<212> TYPE: RNA
<213> ORGANISM: Artificial
<220> FEATURE:
<223> OTHER INFORMATION: synthetic

<400> SEQUENCE: 106
cgugugaucu ccuuuggggu gauuagcuua gagacuuccc acacg               45

<210> SEQ ID NO 107
<211> LENGTH: 45
<212> TYPE: RNA
<213> ORGANISM: Artificial
<220> FEATURE:
<223> OTHER INFORMATION: synthetic

<400> SEQUENCE: 107
gcaccuucgc cuaauacacg ugccggcuag cuaauacucg uccgc               45

<210> SEQ ID NO 108
<211> LENGTH: 45
<212> TYPE: RNA

```
<213> ORGANISM: Artificial
<220> FEATURE:
<223> OTHER INFORMATION: synthetic

<400> SEQUENCE: 108
gcacgacuug ggcgaccagu gauacuuaga gagcaagucg ucggc                    45

<210> SEQ ID NO 109
<211> LENGTH: 44
<212> TYPE: RNA
<213> ORGANISM: Artificial
<220> FEATURE:
<223> OTHER INFORMATION: synthetic

<400> SEQUENCE: 109
gcgcgcgcuc aguaagaaau ugaaaguuca gaaugucguc gcgc                     44

<210> SEQ ID NO 110
<211> LENGTH: 39
<212> TYPE: RNA
<213> ORGANISM: Artificial
<220> FEATURE:
<223> OTHER INFORMATION: synthetic

<400> SEQUENCE: 110
aguguguggc aggcuaagga gauauuccga gaccacgcu                           39

<210> SEQ ID NO 111
<211> LENGTH: 39
<212> TYPE: RNA
<213> ORGANISM: Artificial
<220> FEATURE:
<223> OTHER INFORMATION: synthetic

<400> SEQUENCE: 111
aguguguggc agacuaugga uagacuccga gaccacgcu                           39

<210> SEQ ID NO 112
<211> LENGTH: 39
<212> TYPE: RNA
<213> ORGANISM: Artificial
<220> FEATURE:
<223> OTHER INFORMATION: synthetic

<400> SEQUENCE: 112
agcgugaggc gaccagcgga uuacuuagag agucacgcu                           39

<210> SEQ ID NO 113
<211> LENGTH: 39
<212> TYPE: RNA
<213> ORGANISM: Artificial
<220> FEATURE:
<223> OTHER INFORMATION: synthetic

<400> SEQUENCE: 113
agcgugaagg ggaccagcgu uacuuacaga guucacgcu                           39

<210> SEQ ID NO 114
<211> LENGTH: 39
<212> TYPE: RNA
<213> ORGANISM: Artificial
<220> FEATURE:
<223> OTHER INFORMATION: synthetic

<400> SEQUENCE: 114
agcgugugau guauguagca ccguaucaga ggacacgcu                           39
```

<210> SEQ ID NO 115
<211> LENGTH: 37
<212> TYPE: RNA
<213> ORGANISM: Artificial
<220> FEATURE:
<223> OTHER INFORMATION: synthetic

<400> SEQUENCE: 115
agcgugaggc gacccguguu ucguagagag ucacgcu                                37

<210> SEQ ID NO 116
<211> LENGTH: 40
<212> TYPE: RNA
<213> ORGANISM: Artificial
<220> FEATURE:
<223> OTHER INFORMATION: synthetic

<400> SEQUENCE: 116
gcacgucccu caccggugca agugaagccg uggcucugcg                             40

<210> SEQ ID NO 117
<211> LENGTH: 40
<212> TYPE: RNA
<213> ORGANISM: Artificial
<220> FEATURE:
<223> OTHER INFORMATION: synthetic

<400> SEQUENCE: 117
gcacgucccu caccggugca agugaagccg uggcucugcg                             40

<210> SEQ ID NO 118
<211> LENGTH: 58
<212> TYPE: RNA
<213> ORGANISM: Artificial
<220> FEATURE:
<223> OTHER INFORMATION: synthetic

<400> SEQUENCE: 118
gagauggcga cauugguugg gcaugaggcg aggcccuuug augaauccgc ggccauuc         58

<210> SEQ ID NO 119
<211> LENGTH: 56
<212> TYPE: RNA
<213> ORGANISM: Artificial
<220> FEATURE:
<223> OTHER INFORMATION: synthetic

<400> SEQUENCE: 119
gauggcgaca uugguugggc augaggcgag gcccuuugau gaauccgcgg ccauuc           56

<210> SEQ ID NO 120
<211> LENGTH: 53
<212> TYPE: RNA
<213> ORGANISM: Artificial
<220> FEATURE:
<223> OTHER INFORMATION: synthetic

<400> SEQUENCE: 120
ggcgacauug guugggcaug aggcgaggcc cuuugaugaa uccgcggcca uuc              53

<210> SEQ ID NO 121
<211> LENGTH: 52
<212> TYPE: RNA
<213> ORGANISM: Artificial
<220> FEATURE:
<223> OTHER INFORMATION: synthetic -continued

<400> SEQUENCE: 121
ggcgacauug guugggcaug aggcgaggcc cuuugaugaa uccgcggcca uu    52

<210> SEQ ID NO 122
<211> LENGTH: 50
<212> TYPE: RNA
<213> ORGANISM: Artificial
<220> FEATURE:
<223> OTHER INFORMATION: synthetic

<400> SEQUENCE: 122
ggcgacauug guugggcaug aggcgaggcc cuuugaugaa uccgcggcca    50

<210> SEQ ID NO 123
<211> LENGTH: 48
<212> TYPE: RNA
<213> ORGANISM: Artificial
<220> FEATURE:
<223> OTHER INFORMATION: synthetic

<400> SEQUENCE: 123
gcugguuacc gaggggcgu cguuggaguu ugguugguug ucaccagc    48

<210> SEQ ID NO 124
<211> LENGTH: 46
<212> TYPE: RNA
<213> ORGANISM: Artificial
<220> FEATURE:
<223> OTHER INFORMATION: synthetic

<400> SEQUENCE: 124
cugguuaccg agggggcguc guuggaguuu gguugguugu caccag    46

<210> SEQ ID NO 125
<211> LENGTH: 44
<212> TYPE: RNA
<213> ORGANISM: Artificial
<220> FEATURE:
<223> OTHER INFORMATION: synthetic

<400> SEQUENCE: 125
ugguuaccga gggggcgucg uuggaguuug guugguuguc acca    44

<210> SEQ ID NO 126
<211> LENGTH: 48
<212> TYPE: RNA
<213> ORGANISM: Artificial
<220> FEATURE:
<223> OTHER INFORMATION: synthetic

<400> SEQUENCE: 126
gccgguuacc gaggggcgu cguuggaguu ugguugguug ucaccggc    48

<210> SEQ ID NO 127
<211> LENGTH: 48
<212> TYPE: RNA
<213> ORGANISM: Artificial
<220> FEATURE:
<223> OTHER INFORMATION: synthetic

<400> SEQUENCE: 127
gccggcuacc gaggggcgu cguuggaguu ugguugguug ucgccggc    48

<210> SEQ ID NO 128
<211> LENGTH: 46
<212> TYPE: RNA

```
<213> ORGANISM: Artificial
<220> FEATURE:
<223> OTHER INFORMATION: synthetic

<400> SEQUENCE: 128
gcgcguaccg aggggcguc guuggaguuu gguugguugu ccgcgc          46

<210> SEQ ID NO 129
<211> LENGTH: 46
<212> TYPE: RNA
<213> ORGANISM: Artificial
<220> FEATURE:
<223> OTHER INFORMATION: synthetic

<400> SEQUENCE: 129
gggccuaccg aggggcguc guuggaguuu gguugguugu cggccc          46

<210> SEQ ID NO 130
<211> LENGTH: 76
<212> TYPE: PRT
<213> ORGANISM: Artificial
<220> FEATURE:
<223> OTHER INFORMATION: biotinylated human D MCP-1
<220> FEATURE:
<221> NAME/KEY: D-Protein
<222> LOCATION: (1)..(76)
<223> OTHER INFORMATION: synthetic
<220> FEATURE:
<221> NAME/KEY: Biotinylation
<222> LOCATION: (1)..(1)
<223> OTHER INFORMATION: synthetic

<400> SEQUENCE: 130

Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
                20                  25                  30

Ser Ser Lys Cys Pro Lys Glu Ala Val Ile Phe Lys Thr Ile Val Ala
            35                  40                  45

Lys Glu Ile Cys Ala Asp Pro Lys Gln Lys Trp Val Gln Asp Ser Met
50                  55                  60

Asp His Leu Asp Lys Gln Thr Gln Thr Pro Lys Thr
65                  70                  75

<210> SEQ ID NO 131
<211> LENGTH: 76
<212> TYPE: PRT
<213> ORGANISM: Artificial Sequence
<220> FEATURE:
<223> OTHER INFORMATION: biotinylated mouse D MCP-1
<220> FEATURE:
<221> NAME/KEY: D-Protein
<222> LOCATION: (1)..(76)
<223> OTHER INFORMATION: synthetic
<220> FEATURE:
<221> NAME/KEY: Biotinylation
<222> LOCATION: (1)..(1)
<223> OTHER INFORMATION: synthetic
<220> FEATURE:
<221> NAME/KEY: Biotinylation
<222> LOCATION: (76)..(76)
<223> OTHER INFORMATION: synthetic

<400> SEQUENCE: 131

Gln Pro Asp Ala Val Asn Ala Pro Leu Thr Cys Cys Tyr Ser Phe Thr
1               5                   10                  15

Ser Lys Met Ile Pro Met Ser Arg Leu Glu Ser Tyr Lys Arg Ile Thr
                20                  25                  30
```

```
Ser Ser Arg Cys Pro Lys Glu Ala Val Val Phe Val Thr Lys Leu Lys
        35                  40                  45

Arg Glu Val Cys Ala Asp Pro Lys Lys Glu Trp Val Gln Thr Tyr Ile
    50                  55                  60

Lys Asn Leu Asp Arg Asn Gln Met Arg Ser Glu Pro
65                  70                  75

<210> SEQ ID NO 132
<211> LENGTH: 47
<212> TYPE: RNA
<213> ORGANISM: Artificial
<220> FEATURE:
<223> OTHER INFORMATION: synthetic

<400> SEQUENCE: 132
agcgugcccg gaguggcagg gggacgcgac cugcaauaau gcacgcu              47

<210> SEQ ID NO 133
<211> LENGTH: 45
<212> TYPE: RNA
<213> ORGANISM: Artificial
<220> FEATURE:
<223> OTHER INFORMATION: synthetic

<400> SEQUENCE: 133
agcgugcccg gaguggcagg gggacgcgac cugcaauugc acgcu                45

<210> SEQ ID NO 134
<211> LENGTH: 47
<212> TYPE: RNA
<213> ORGANISM: Artificial
<220> FEATURE:
<223> OTHER INFORMATION: synthetic

<400> SEQUENCE: 134
agcgugcccg gaguggcagg gggacgcgac cuguaauaau gcacgcu              47

<210> SEQ ID NO 135
<211> LENGTH: 47
<212> TYPE: RNA
<213> ORGANISM: Artificial
<220> FEATURE:
<223> OTHER INFORMATION: synthetic

<400> SEQUENCE: 135
agcgugcccg guguggcagg gggacgcgac cugcaauaau gcgcgcu              47

<210> SEQ ID NO 136
<211> LENGTH: 47
<212> TYPE: RNA
<213> ORGANISM: Artificial
<220> FEATURE:
<223> OTHER INFORMATION: synthetic

<400> SEQUENCE: 136
agcgugcccg gaguagcagg ggggcgcgac cugcaauaau gcacgcu              47

<210> SEQ ID NO 137
<211> LENGTH: 45
<212> TYPE: RNA
<213> ORGANISM: Artificial
<220> FEATURE:
<223> OTHER INFORMATION: synthetic

<400> SEQUENCE: 137
```

-continued

```
agcgugcccg gugugguagg ggggcgcgau cuacaauugc acgcu            45

<210> SEQ ID NO 138
<211> LENGTH: 45
<212> TYPE: RNA
<213> ORGANISM: Artificial
<220> FEATURE:
<223> OTHER INFORMATION: synthetic

<400> SEQUENCE: 138
agcgugcccg gugugacagg ggggcgcgac cugcauuugc acgcu            45

<210> SEQ ID NO 139
<211> LENGTH: 45
<212> TYPE: RNA
<213> ORGANISM: Artificial
<220> FEATURE:
<223> OTHER INFORMATION: synthetic

<400> SEQUENCE: 139
agcgugcccg guguggcagg ggggcgcgac cuguauuugc acgcu            45

<210> SEQ ID NO 140
<211> LENGTH: 47
<212> TYPE: RNA
<213> ORGANISM: Artificial
<220> FEATURE:
<223> OTHER INFORMATION: synthetic

<400> SEQUENCE: 140
agcgugcccg gaguggcagg ggggcgcgac cugcaauaau gcacgcu          47

<210> SEQ ID NO 141
<211> LENGTH: 45
<212> TYPE: RNA
<213> ORGANISM: Artificial
<220> FEATURE:
<223> OTHER INFORMATION: synthetic

<400> SEQUENCE: 141
agcgugcccg guguggcagg ggggcgcgac cugcaauugc acgcu            45

<210> SEQ ID NO 142
<211> LENGTH: 45
<212> TYPE: RNA
<213> ORGANISM: Artificial
<220> FEATURE:
<223> OTHER INFORMATION: synthetic

<400> SEQUENCE: 142
agcaugcccg guguggcagg ggggcgcgac cugcauuugc augcu            45

<210> SEQ ID NO 143
<211> LENGTH: 45
<212> TYPE: RNA
<213> ORGANISM: Artificial
<220> FEATURE:
<223> OTHER INFORMATION: synthetic

<400> SEQUENCE: 143
agcgugcccg gugugguagg ggggcgcgac cuacauuugc acgcu            45

<210> SEQ ID NO 144
<211> LENGTH: 44
<212> TYPE: RNA
<213> ORGANISM: Artificial
<220> FEATURE:
```

```
<223> OTHER INFORMATION: synthetic

<400> SEQUENCE: 144
agugugccag cugugauggg ggggcgcgac ccauuuuaca cacu          44

<210> SEQ ID NO 145
<211> LENGTH: 43
<212> TYPE: RNA
<213> ORGANISM: Artificial
<220> FEATURE:
<223> OTHER INFORMATION: synthetic

<400> SEQUENCE: 145
agugugccag cgugaugggg gggcgcgacc cauuuacac acu             43

<210> SEQ ID NO 146
<211> LENGTH: 43
<212> TYPE: RNA
<213> ORGANISM: Artificial
<220> FEATURE:
<223> OTHER INFORMATION: synthetic

<400> SEQUENCE: 146
agugugcgag cgugaugggg gggcgcgacc cauuuuacau acu            43

<210> SEQ ID NO 147
<211> LENGTH: 43
<212> TYPE: RNA
<213> ORGANISM: Artificial
<220> FEATURE:
<223> OTHER INFORMATION: synthetic

<400> SEQUENCE: 147
agugugccag cgugaugggg gggcgcgacc cauuuuacau acu            43

<210> SEQ ID NO 148
<211> LENGTH: 42
<212> TYPE: RNA
<213> ORGANISM: Artificial
<220> FEATURE:
<223> OTHER INFORMATION: synthetic

<400> SEQUENCE: 148
aguaugccag cgugaugggg gggcgcgacc cauuuacaua cu             42

<210> SEQ ID NO 149
<211> LENGTH: 43
<212> TYPE: RNA
<213> ORGANISM: Artificial
<220> FEATURE:
<223> OTHER INFORMATION: synthetic

<400> SEQUENCE: 149
agugugccag ugugaugggg gggcgcgacc cauuuuacac acu            43

<210> SEQ ID NO 150
<211> LENGTH: 43
<212> TYPE: RNA
<213> ORGANISM: Artificial
<220> FEATURE:
<223> OTHER INFORMATION: synthetic

<400> SEQUENCE: 150
agcgugccag ugugaugggg gggcgcgacc cauuuuacac gcu            43

<210> SEQ ID NO 151
```

```
<211> LENGTH: 43
<212> TYPE: RNA
<213> ORGANISM: Artificial
<220> FEATURE:
<223> OTHER INFORMATION: synthetic

<400> SEQUENCE: 151
acgcacgucc cucaccggug caagugaagc cgcggcucug cgu          43

<210> SEQ ID NO 152
<211> LENGTH: 43
<212> TYPE: RNA
<213> ORGANISM: Artificial
<220> FEATURE:
<223> OTHER INFORMATION: synthetic

<400> SEQUENCE: 152
acgcaccucc cucaccggug caagugaagc cguggcucug cgc          43

<210> SEQ ID NO 153
<211> LENGTH: 43
<212> TYPE: RNA
<213> ORGANISM: Artificial
<220> FEATURE:
<223> OTHER INFORMATION: synthetic

<400> SEQUENCE: 153
acgcacgucc cucaccggug caagugaagc cguggcucug cgu          43

<210> SEQ ID NO 154
<211> LENGTH: 41
<212> TYPE: RNA
<213> ORGANISM: Artificial
<220> FEATURE:
<223> OTHER INFORMATION: synthetic

<400> SEQUENCE: 154
gcacgucccu caccggugca agugaagccg uggcucugcg u            41

<210> SEQ ID NO 155
<211> LENGTH: 41
<212> TYPE: RNA
<213> ORGANISM: Artificial
<220> FEATURE:
<223> OTHER INFORMATION: synthetic

<400> SEQUENCE: 155
acgcacgucc cucaccggug caagugaagc cguggcucug c            41

<210> SEQ ID NO 156
<211> LENGTH: 39
<212> TYPE: RNA
<213> ORGANISM: Artificial
<220> FEATURE:
<223> OTHER INFORMATION: synthetic

<400> SEQUENCE: 156
gcacgucccu caccggugca agugaagccg uggcucugc              39

<210> SEQ ID NO 157
<211> LENGTH: 42
<212> TYPE: RNA
<213> ORGANISM: Artificial
<220> FEATURE:
<223> OTHER INFORMATION: synthetic

<400> SEQUENCE: 157
```
cgcacguccc ucaccggugc aagugaagcc guggcucugc gu                42

<210> SEQ ID NO 158
<211> LENGTH: 41
<212> TYPE: RNA
<213> ORGANISM: Artificial
<220> FEATURE:
<223> OTHER INFORMATION: synthetic

<400> SEQUENCE: 158
cgcacguccc ucaccggugc aagugaagcc guggcucugc g                 41

<210> SEQ ID NO 159
<211> LENGTH: 40
<212> TYPE: RNA
<213> ORGANISM: Artificial
<220> FEATURE:
<223> OTHER INFORMATION: synthetic

<400> SEQUENCE: 159
gcacgucccu caccggugca agugaagccg uggcucugcg                   40

<210> SEQ ID NO 160
<211> LENGTH: 49
<212> TYPE: RNA
<213> ORGANISM: Artificial
<220> FEATURE:
<223> OTHER INFORMATION: synthetic

<400> SEQUENCE: 160
gugcugcgua guggaagacu accuaaugac agccgaaugc uggcagcac         49

<210> SEQ ID NO 161
<211> LENGTH: 49
<212> TYPE: RNA
<213> ORGANISM: Artificial
<220> FEATURE:
<223> OTHER INFORMATION: synthetic

<400> SEQUENCE: 161
gugcugcgua guggaagacu accuaaugac agccuaaugc uggcagcac         49

<210> SEQ ID NO 162
<211> LENGTH: 49
<212> TYPE: RNA
<213> ORGANISM: Artificial
<220> FEATURE:
<223> OTHER INFORMATION: synthetic

<400> SEQUENCE: 162
gugcugcgua guggaagacu accuuaugac agccgaaugc uggcagcac         49

<210> SEQ ID NO 163
<211> LENGTH: 48
<212> TYPE: RNA
<213> ORGANISM: Artificial
<220> FEATURE:
<223> OTHER INFORMATION: synthetic

<400> SEQUENCE: 163
gugcugcgua gugaaaaacu acugccagug ggucagagcu agcagcac          48

<210> SEQ ID NO 164
<211> LENGTH: 48
<212> TYPE: RNA
<213> ORGANISM: Artificial
<220> FEATURE:

<223> OTHER INFORMATION: synthetic

<400> SEQUENCE: 164
gugcugcgga guuaaaaacu cccuaagaca ggccagagcc ggcagcac        48

<210> SEQ ID NO 165
<211> LENGTH: 48
<212> TYPE: RNA
<213> ORGANISM: Artificial
<220> FEATURE:
<223> OTHER INFORMATION: synthetic

<400> SEQUENCE: 165
gugcugcgga guugaaaacu cccuaagaca ggccagagcc ggcagcac        48

<210> SEQ ID NO 166
<211> LENGTH: 48
<212> TYPE: RNA
<213> ORGANISM: Artificial
<220> FEATURE:
<223> OTHER INFORMATION: synthetic

<400> SEQUENCE: 166
gugcugcgua guggaagacu accuaugaca gccuaaugcu ggcagcac        48

<210> SEQ ID NO 167
<211> LENGTH: 48
<212> TYPE: RNA
<213> ORGANISM: Artificial
<220> FEATURE:
<223> OTHER INFORMATION: synthetic

<400> SEQUENCE: 167
gugcugcgga guuaaaaacu cccuaagaca ggcuagagcc ggcagcac        48

<210> SEQ ID NO 168
<211> LENGTH: 50
<212> TYPE: RNA
<213> ORGANISM: Artificial
<220> FEATURE:
<223> OTHER INFORMATION: synthetic

<400> SEQUENCE: 168
gugcugcggc gugaaaaacg cccugcgacu gcccuuuaug caggcagcac        50

<210> SEQ ID NO 169
<211> LENGTH: 48
<212> TYPE: RNA
<213> ORGANISM: Artificial
<220> FEATURE:
<223> OTHER INFORMATION: synthetic

<400> SEQUENCE: 169
gugcugcgua gugaaaaacu accaacgacu ggcuagagcc ggcagcac        48

<210> SEQ ID NO 170
<211> LENGTH: 48
<212> TYPE: RNA
<213> ORGANISM: Artificial
<220> FEATURE:
<223> OTHER INFORMATION: synthetic

<400> SEQUENCE: 170
gugcugcgua gugaaagacu accugugaca gccgaaugcu ggcagcac        48

<210> SEQ ID NO 171

```
<211> LENGTH: 48
<212> TYPE: RNA
<213> ORGANISM: Artificial
<220> FEATURE:
<223> OTHER INFORMATION: synthetic

<400> SEQUENCE: 171
guacugcgua guuaaaaacu accaacgacu ggcuagagcc ggcagcac          48

<210> SEQ ID NO 172
<211> LENGTH: 48
<212> TYPE: RNA
<213> ORGANISM: Artificial
<220> FEATURE:
<223> OTHER INFORMATION: synthetic

<400> SEQUENCE: 172
gugcugcgua guuaaaaacu accaacgacu ggcuagagcc ggcagcac          48

<210> SEQ ID NO 173
<211> LENGTH: 48
<212> TYPE: RNA
<213> ORGANISM: Artificial
<220> FEATURE:
<223> OTHER INFORMATION: synthetic

<400> SEQUENCE: 173
gugcugcgua guuaaaaacu accagcgaca ggcuagagcc ggcagcac          48

<210> SEQ ID NO 174
<211> LENGTH: 48
<212> TYPE: RNA
<213> ORGANISM: Artificial
<220> FEATURE:
<223> OTHER INFORMATION: synthetic

<400> SEQUENCE: 174
gugcugcgua guuaaaaacu accagcgacu ggcuagagcc ggcagcac          48

<210> SEQ ID NO 175
<211> LENGTH: 48
<212> TYPE: RNA
<213> ORGANISM: Artificial
<220> FEATURE:
<223> OTHER INFORMATION: synthetic

<400> SEQUENCE: 175
gugcugcgua gugagaaacu accaacgacu ggcuagagcc ggcagcac          48

<210> SEQ ID NO 176
<211> LENGTH: 46
<212> TYPE: RNA
<213> ORGANISM: Artificial
<220> FEATURE:
<223> OTHER INFORMATION: synthetic

<400> SEQUENCE: 176
ggcugcguag uuaaaaacua ccagcgacug gcuagagccg gcagcc            46

<210> SEQ ID NO 177
<211> LENGTH: 44
<212> TYPE: RNA
<213> ORGANISM: Artificial
<220> FEATURE:
<223> OTHER INFORMATION: synthetic

<400> SEQUENCE: 177
```

-continued

```
ggcgcguagu uaaaaacuac cagcgacugg cuagagccgg cgcc          44
```

<210> SEQ ID NO 178
<211> LENGTH: 46
<212> TYPE: RNA
<213> ORGANISM: Artificial
<220> FEATURE:
<223> OTHER INFORMATION: synthetic

<400> SEQUENCE: 178

```
gugcgcguag uuaaaaacua ccagcgacug gcuagagccg gcgcac        46
```

<210> SEQ ID NO 179
<211> LENGTH: 46
<212> TYPE: RNA
<213> ORGANISM: Artificial
<220> FEATURE:
<223> OTHER INFORMATION: synthetic

<400> SEQUENCE: 179

```
gugcgcguag ugagaaacua ccaacgacug gcuagagccg gcgcac        46
```

<210> SEQ ID NO 180
<211> LENGTH: 44
<212> TYPE: RNA
<213> ORGANISM: Artificial
<220> FEATURE:
<223> OTHER INFORMATION: synthetic

<400> SEQUENCE: 180

```
gugccguagu gagaaacuac caacgacugg cuagagccgg gcac          44
```

<210> SEQ ID NO 181
<211> LENGTH: 44
<212> TYPE: RNA
<213> ORGANISM: Artificial
<220> FEATURE:
<223> OTHER INFORMATION: synthetic

<400> SEQUENCE: 181

```
guggcguagu gagaaacuac caacgacugg cuagagccgg ccac          44
```

<210> SEQ ID NO 182
<211> LENGTH: 44
<212> TYPE: RNA
<213> ORGANISM: Artificial
<220> FEATURE:
<223> OTHER INFORMATION: synthetic

<400> SEQUENCE: 182

```
gucgcguagu gagaaacuac caacgacugg cuagagccgg cgac          44
```

<210> SEQ ID NO 183
<211> LENGTH: 44
<212> TYPE: RNA
<213> ORGANISM: Artificial
<220> FEATURE:
<223> OTHER INFORMATION: synthetic

<400> SEQUENCE: 183

```
ugcgcguagu gagaaacuac caacgacugg cuagagccgg cgca          44
```

<210> SEQ ID NO 184
<211> LENGTH: 44
<212> TYPE: RNA
<213> ORGANISM: Artificial
<220> FEATURE:

```
<223> OTHER INFORMATION: synthetic

<400> SEQUENCE: 184
gcugcguagu gagaaacuac caacgacugg cuagagccgg cagc                    44

<210> SEQ ID NO 185
<211> LENGTH: 44
<212> TYPE: RNA
<213> ORGANISM: Artificial
<220> FEATURE:
<223> OTHER INFORMATION: synthetic

<400> SEQUENCE: 185
gcugcguagu gagaaacuac caacgacugg cuagagccgg cagc                    44

<210> SEQ ID NO 186
<211> LENGTH: 44
<212> TYPE: RNA
<213> ORGANISM: Artificial
<220> FEATURE:
<223> OTHER INFORMATION: synthetic

<400> SEQUENCE: 186
ggugcguagu gagaaacuac caacgacugg cuagagccgg cacc                    44

<210> SEQ ID NO 187
<211> LENGTH: 40
<212> TYPE: RNA
<213> ORGANISM: Artificial
<220> FEATURE:
<223> OTHER INFORMATION: synthetic

<400> SEQUENCE: 187
uggcguagug agaaacuacc aacgacuggc uagagccggc                         40

<210> SEQ ID NO 188
<211> LENGTH: 42
<212> TYPE: RNA
<213> ORGANISM: Artificial
<220> FEATURE:
<223> OTHER INFORMATION: synthetic

<400> SEQUENCE: 188
gcgcguagug agaaacuacc aacgacuggc uagagccggc gc                      42

<210> SEQ ID NO 189
<211> LENGTH: 42
<212> TYPE: RNA
<213> ORGANISM: Artificial
<220> FEATURE:
<223> OTHER INFORMATION: synthetic

<400> SEQUENCE: 189
gugcguagug agaaacuacc aacgacuggc uagagccggc ac                      42

<210> SEQ ID NO 190
<211> LENGTH: 42
<212> TYPE: RNA
<213> ORGANISM: Artificial
<220> FEATURE:
<223> OTHER INFORMATION: synthetic

<400> SEQUENCE: 190
gggcguagug agaaacuacc aacgacuggc uagagccggc cc                      42

<210> SEQ ID NO 191
```

```
<211> LENGTH: 42
<212> TYPE: RNA
<213> ORGANISM: Artificial
<220> FEATURE:
<223> OTHER INFORMATION: synthetic

<400> SEQUENCE: 191
gagcguagug agaaacuacc aacgacuggc uagagccggc uc                              42

<210> SEQ ID NO 192
<211> LENGTH: 42
<212> TYPE: RNA
<213> ORGANISM: Artificial
<220> FEATURE:
<223> OTHER INFORMATION: synthetic

<400> SEQUENCE: 192
cggcguagug agaaacuacc aacgacuggc uagagccggc cg                              42

<210> SEQ ID NO 193
<211> LENGTH: 42
<212> TYPE: RNA
<213> ORGANISM: Artificial
<220> FEATURE:
<223> OTHER INFORMATION: synthetic

<400> SEQUENCE: 193
ccgcguagug agaaacuacc aacgacuggc uagagccggc gg                              42

<210> SEQ ID NO 194
<211> LENGTH: 42
<212> TYPE: RNA
<213> ORGANISM: Artificial
<220> FEATURE:
<223> OTHER INFORMATION: synthetic

<400> SEQUENCE: 194
cagcguagug agaaacuacc aacgacuggc uagagccggc ug                              42

<210> SEQ ID NO 195
<211> LENGTH: 42
<212> TYPE: RNA
<213> ORGANISM: Artificial
<220> FEATURE:
<223> OTHER INFORMATION: synthetic

<400> SEQUENCE: 195
cugcguagug agaaacuacc aacgacuggc uagagccggc ag                              42

<210> SEQ ID NO 196
<211> LENGTH: 39
<212> TYPE: RNA
<213> ORGANISM: Artificial
<220> FEATURE:
<223> OTHER INFORMATION: synthetic

<400> SEQUENCE: 196
agcguguuag ugaagugggu ggcagguaaa ggacacgcu                                  39

<210> SEQ ID NO 197
<211> LENGTH: 39
<212> TYPE: RNA
<213> ORGANISM: Artificial
<220> FEATURE:
<223> OTHER INFORMATION: synthetic

<400> SEQUENCE: 197
```

```
agcguggua g cggugugggu gguagguaaa ggccacgcu                          39

<210> SEQ ID NO 198
<211> LENGTH: 39
<212> TYPE: RNA
<213> ORGANISM: Artificial
<220> FEATURE:
<223> OTHER INFORMATION: synthetic

<400> SEQUENCE: 198
agcgugauag aagagcgggu gguagguaaa ggucaggcu                          39

<210> SEQ ID NO 199
<211> LENGTH: 39
<212> TYPE: RNA
<213> ORGANISM: Artificial
<220> FEATURE:
<223> OTHER INFORMATION: synthetic

<400> SEQUENCE: 199
agcguguuag guagguggu aguaaguaaa ggacacgcu                           39

<210> SEQ ID NO 200
<211> LENGTH: 38
<212> TYPE: RNA
<213> ORGANISM: Artificial
<220> FEATURE:
<223> OTHER INFORMATION: synthetic

<400> SEQUENCE: 200
agcguguuag gugggguggua guaaguaaag gacacgcu                          38

<210> SEQ ID NO 201
<211> LENGTH: 38
<212> TYPE: RNA
<213> ORGANISM: Artificial
<220> FEATURE:
<223> OTHER INFORMATION: synthetic

<400> SEQUENCE: 201
agcguguuag gugggguggua guaaguaaag ggcacgcu                          38

<210> SEQ ID NO 202
<211> LENGTH: 34
<212> TYPE: RNA
<213> ORGANISM: Artificial
<220> FEATURE:
<223> OTHER INFORMATION: synthetic

<400> SEQUENCE: 202
ccgcuuaggu ggguggua gu aaguaaaggg gcgg                              34

<210> SEQ ID NO 203
<211> LENGTH: 39
<212> TYPE: RNA
<213> ORGANISM: Artificial
<220> FEATURE:
<223> OTHER INFORMATION: synthetic

<400> SEQUENCE: 203
gcgcgagcag guggguggua gaauguaaag acucgcguc                          39

<210> SEQ ID NO 204
<211> LENGTH: 34
<212> TYPE: RNA
<213> ORGANISM: Artificial
<220> FEATURE:
```

```
<223> OTHER INFORMATION: synthetic

<400> SEQUENCE: 204
cguguuaggu ggugguagu aaguaaagga cacg                                34

<210> SEQ ID NO 205
<211> LENGTH: 32
<212> TYPE: RNA
<213> ORGANISM: Artificial
<220> FEATURE:
<223> OTHER INFORMATION: synthetic

<400> SEQUENCE: 205
guguuaggug ggugguagua aguaaaggac ac                                 32

<210> SEQ ID NO 206
<211> LENGTH: 34
<212> TYPE: RNA
<213> ORGANISM: Artificial
<220> FEATURE:
<223> OTHER INFORMATION: synthetic

<400> SEQUENCE: 206
cguguuaggu gggugguagu aaguaaaggg cacg                               34

<210> SEQ ID NO 207
<211> LENGTH: 32
<212> TYPE: RNA
<213> ORGANISM: Artificial
<220> FEATURE:
<223> OTHER INFORMATION: synthetic

<400> SEQUENCE: 207
guguuaggug ggugguagua aguaaagggc ac                                 32

<210> SEQ ID NO 208
<211> LENGTH: 30
<212> TYPE: RNA
<213> ORGANISM: Artificial
<220> FEATURE:
<223> OTHER INFORMATION: synthetic

<400> SEQUENCE: 208
uguuaggugg gugguaguaa guaaagggca                                    30

<210> SEQ ID NO 209
<211> LENGTH: 52
<212> TYPE: RNA
<213> ORGANISM: Artificial
<220> FEATURE:
<223> OTHER INFORMATION: synthetic

<400> SEQUENCE: 209
ggacgagagu gacaaaugau auaaccuccu gacuaacgcu gcgggcgaca gg           52

<210> SEQ ID NO 210
<211> LENGTH: 52
<212> TYPE: RNA
<213> ORGANISM: Artificial
<220> FEATURE:
<223> OTHER INFORMATION: synthetic

<400> SEQUENCE: 210
ggaccuaucg cuaagacaac gcgcagucua cgggacauuc uccgcggaca gg           52

<210> SEQ ID NO 211
```

```
<211> LENGTH: 52
<212> TYPE: RNA
<213> ORGANISM: Artificial
<220> FEATURE:
<223> OTHER INFORMATION: synthetic

<400> SEQUENCE: 211
ggacaauugu uaccccgag agagacaaau gagacaaccu ccugaagaca gg        52

<210> SEQ ID NO 212
<211> LENGTH: 51
<212> TYPE: RNA
<213> ORGANISM: Artificial
<220> FEATURE:
<223> OTHER INFORMATION: synthetic

<400> SEQUENCE: 212
ggacgaaagu gagaaaugau acaaccuccu guugcugcga auccggacag g         51

<210> SEQ ID NO 213
<211> LENGTH: 50
<212> TYPE: RNA
<213> ORGANISM: Artificial
<220> FEATURE:
<223> OTHER INFORMATION: synthetic

<400> SEQUENCE: 213
ggacguaaaa gacgcuaccc gaaagaaugu caggagggua gaccgacagg           50

<210> SEQ ID NO 214
<211> LENGTH: 50
<212> TYPE: RNA
<213> ORGANISM: Artificial
<220> FEATURE:
<223> OTHER INFORMATION: synthetic

<400> SEQUENCE: 214
ggacuagaaa cuacaauagc ggccaguugc accgcguuau caacgacagg           50

<210> SEQ ID NO 215
<211> LENGTH: 50
<212> TYPE: RNA
<213> ORGANISM: Artificial
<220> FEATURE:
<223> OTHER INFORMATION: synthetic

<400> SEQUENCE: 215
ggacuaguca gccagugugu auaucggacg cggguuuauu uacugacagg           50

<210> SEQ ID NO 216
<211> LENGTH: 50
<212> TYPE: RNA
<213> ORGANISM: Artificial
<220> FEATURE:
<223> OTHER INFORMATION: synthetic

<400> SEQUENCE: 216
ggacuguccg gagugugaaa cuccccgaga ccgccagaag cggggacagg           50

<210> SEQ ID NO 217
<211> LENGTH: 50
<212> TYPE: RNA
<213> ORGANISM: Artificial
<220> FEATURE:
<223> OTHER INFORMATION: synthetic

<400> SEQUENCE: 217
```

```
ggacuucuau ccagguggu gguaguaugu aaagagauag aagugacagg         50
```

<210> SEQ ID NO 218
<211> LENGTH: 50
<212> TYPE: RNA
<213> ORGANISM: Artificial
<220> FEATURE:
<223> OTHER INFORMATION: synthetic

<400> SEQUENCE: 218

```
ggacgagagc gaacaaugau auaaccuccu gacggaaaga gaucgacagg         50
```

<210> SEQ ID NO 219
<211> LENGTH: 48
<212> TYPE: RNA
<213> ORGANISM: Artificial
<220> FEATURE:
<223> OTHER INFORMATION: synthetic

<400> SEQUENCE: 219

```
ccugugcuac acgcaguaag aagugaacgu ucaguaugug ugcacagg           48
```

<210> SEQ ID NO 220
<211> LENGTH: 48
<212> TYPE: RNA
<213> ORGANISM: Artificial
<220> FEATURE:
<223> OTHER INFORMATION: synthetic

<400> SEQUENCE: 220

```
cgugagccag gcaccgaggg cguuaacugg cugauuggac acgacacg           48
```

<210> SEQ ID NO 221
<211> LENGTH: 48
<212> TYPE: RNA
<213> ORGANISM: Artificial
<220> FEATURE:
<223> OTHER INFORMATION: synthetic

<400> SEQUENCE: 221

```
cgugaacaug caagcuaagc ggggcuguug guugcuuggc ccgccacg           48
```

<210> SEQ ID NO 222
<211> LENGTH: 48
<212> TYPE: RNA
<213> ORGANISM: Artificial
<220> FEATURE:
<223> OTHER INFORMATION: synthetic

<400> SEQUENCE: 222

```
cgugcagaga gagaccaacc acguaaaauc aaccuaaugg gccgcacg           48
```

<210> SEQ ID NO 223
<211> LENGTH: 48
<212> TYPE: RNA
<213> ORGANISM: Artificial
<220> FEATURE:
<223> OTHER INFORMATION: synthetic

<400> SEQUENCE: 223

```
cgugcagaga gagaccaacc acguaaaauc aaccuaaugg gccgcacg           48
```

<210> SEQ ID NO 224
<211> LENGTH: 48
<212> TYPE: RNA
<213> ORGANISM: Artificial
<220> FEATURE:

```
<223> OTHER INFORMATION: synthetic

<400> SEQUENCE: 224
cgugaacauu caagcuaagc ggggcuguug guugcuuggc ccgccacg        48

<210> SEQ ID NO 225
<211> LENGTH: 48
<212> TYPE: RNA
<213> ORGANISM: Artificial
<220> FEATURE:
<223> OTHER INFORMATION: synthetic

<400> SEQUENCE: 225
cgugccgagg cggcgaccag cguuacuuag agaggcuuug gcaccacg        48

<210> SEQ ID NO 226
<211> LENGTH: 47
<212> TYPE: RNA
<213> ORGANISM: Artificial
<220> FEATURE:
<223> OTHER INFORMATION: synthetic

<400> SEQUENCE: 226
cgugauaaca gccgucgguc aagaaaacaa aguucgggcg gcgcacg         47

<210> SEQ ID NO 227
<211> LENGTH: 47
<212> TYPE: RNA
<213> ORGANISM: Artificial
<220> FEATURE:
<223> OTHER INFORMATION: synthetic

<400> SEQUENCE: 227
cguggguggc gcaccgaggg cgaaaagcca ccaguaaaga uagaccg         47

<210> SEQ ID NO 228
<211> LENGTH: 45
<212> TYPE: RNA
<213> ORGANISM: Artificial
<220> FEATURE:
<223> OTHER INFORMATION: synthetic

<400> SEQUENCE: 228
cgugugaucu ccuuuggggu gauuagcuua gagacuuccc acacg           45

<210> SEQ ID NO 229
<211> LENGTH: 45
<212> TYPE: RNA
<213> ORGANISM: Artificial
<220> FEATURE:
<223> OTHER INFORMATION: synthetic

<400> SEQUENCE: 229
gcaccuucgc cuaauacacg ugccggcuag cuaauacucg uccgc           45

<210> SEQ ID NO 230
<211> LENGTH: 45
<212> TYPE: RNA
<213> ORGANISM: Artificial
<220> FEATURE:
<223> OTHER INFORMATION: synthetic

<400> SEQUENCE: 230
gcacgacuug ggcgaccagu gauacuuaga gagcaagucg ucggc           45

<210> SEQ ID NO 231
```

```
<211> LENGTH: 44
<212> TYPE: RNA
<213> ORGANISM: Artificial
<220> FEATURE:
<223> OTHER INFORMATION: synthetic

<400> SEQUENCE: 231
gcgcgcgcuc aguaagaaau ugaaaguuca gaaugucguc gcgc                    44

<210> SEQ ID NO 232
<211> LENGTH: 39
<212> TYPE: RNA
<213> ORGANISM: Artificial
<220> FEATURE:
<223> OTHER INFORMATION: synthetic

<400> SEQUENCE: 232
aguguguggc aggcuaagga gauauuccga gaccacgcu                          39

<210> SEQ ID NO 233
<211> LENGTH: 39
<212> TYPE: RNA
<213> ORGANISM: Artificial
<220> FEATURE:
<223> OTHER INFORMATION: synthetic

<400> SEQUENCE: 233
aguguguggc agacuaugga uagacuccga gaccacgcu                          39

<210> SEQ ID NO 234
<211> LENGTH: 39
<212> TYPE: RNA
<213> ORGANISM: Artificial
<220> FEATURE:
<223> OTHER INFORMATION: synthetic

<400> SEQUENCE: 234
agcgugaggc gaccagcgga uuacuuagag agucacgcu                          39

<210> SEQ ID NO 235
<211> LENGTH: 39
<212> TYPE: RNA
<213> ORGANISM: Artificial
<220> FEATURE:
<223> OTHER INFORMATION: synthetic

<400> SEQUENCE: 235
agcgugaagg ggaccagcgu uacuuacaga guucacgcu                          39

<210> SEQ ID NO 236
<211> LENGTH: 39
<212> TYPE: RNA
<213> ORGANISM: Artificial
<220> FEATURE:
<223> OTHER INFORMATION: synthetic

<400> SEQUENCE: 236
agcgugugau guauguagca ccguaucaga ggacacgcu                          39

<210> SEQ ID NO 237
<211> LENGTH: 37
<212> TYPE: RNA
<213> ORGANISM: Artificial
<220> FEATURE:
<223> OTHER INFORMATION: synthetic

<400> SEQUENCE: 237
```
agcgugaggc gacccguguu ucguagagag ucacgcu					37

<210> SEQ ID NO 238
<211> LENGTH: 40
<212> TYPE: RNA
<213> ORGANISM: Artificial
<220> FEATURE:
<223> OTHER INFORMATION: synthetic
<220> FEATURE:
<221> NAME/KEY: D-RNA
<222> LOCATION: (1)..(40)
<223> OTHER INFORMATION: 5' PEGylation

<400> SEQUENCE: 238
gcacgucccu caccggugca agugaagccg uggcucugcg					40

<210> SEQ ID NO 239
<211> LENGTH: 40
<212> TYPE: RNA
<213> ORGANISM: Artificial
<220> FEATURE:
<223> OTHER INFORMATION: synthetic
<220> FEATURE:
<221> NAME/KEY: D-RNA
<222> LOCATION: (1)..(40)
<223> OTHER INFORMATION: 3'-PEGylation

<400> SEQUENCE: 239
gcacgucccu caccggugca agugaagccg uggcucugcg					40

<210> SEQ ID NO 240
<211> LENGTH: 58
<212> TYPE: RNA
<213> ORGANISM: Artificial
<220> FEATURE:
<223> OTHER INFORMATION: synthetic

<400> SEQUENCE: 240
gagauggcga cauugguugg gcaugaggcg aggcccuuug augaauccgc ggccauuc		58

<210> SEQ ID NO 241
<211> LENGTH: 56
<212> TYPE: RNA
<213> ORGANISM: Artificial
<220> FEATURE:
<223> OTHER INFORMATION: synthetic

<400> SEQUENCE: 241
gauggcgaca uugguugggc augaggcgag gcccuuugau gaauccgcgg ccauuc		56

<210> SEQ ID NO 242
<211> LENGTH: 53
<212> TYPE: RNA
<213> ORGANISM: Artificial
<220> FEATURE:
<223> OTHER INFORMATION: synthetic

<400> SEQUENCE: 242
ggcgacauug guugggcaug aggcgaggcc cuuugaugaa uccgcggcca uuc		53

<210> SEQ ID NO 243
<211> LENGTH: 52
<212> TYPE: RNA
<213> ORGANISM: Artificial
<220> FEATURE:
<223> OTHER INFORMATION: synthetic

<400> SEQUENCE: 243

-continued ggcgacauug guugggcaug aggcgaggcc cuuugaugaa uccgcggcca uu    52

<210> SEQ ID NO 244
<211> LENGTH: 50
<212> TYPE: RNA
<213> ORGANISM: Artificial
<220> FEATURE:
<223> OTHER INFORMATION: synthetic

<400> SEQUENCE: 244
ggcgacauug guugggcaug aggcgaggcc cuuugaugaa uccgcggcca    50

<210> SEQ ID NO 245
<211> LENGTH: 48
<212> TYPE: RNA
<213> ORGANISM: Artificial
<220> FEATURE:
<223> OTHER INFORMATION: synthetic

<400> SEQUENCE: 245
gcugguuacc gagggggcgu cguuggaguu ugguugguug ucaccagc    48

<210> SEQ ID NO 246
<211> LENGTH: 46
<212> TYPE: RNA
<213> ORGANISM: Artificial
<220> FEATURE:
<223> OTHER INFORMATION: synthetic

<400> SEQUENCE: 246
cugguuaccg aggggcguc guuggaguuu gguugguugu caccag    46

<210> SEQ ID NO 247
<211> LENGTH: 44
<212> TYPE: RNA
<213> ORGANISM: Artificial
<220> FEATURE:
<223> OTHER INFORMATION: synthetic

<400> SEQUENCE: 247
ugguuaccga gggcgucg uuggaguuug guugguuguc acca    44

<210> SEQ ID NO 248
<211> LENGTH: 48
<212> TYPE: RNA
<213> ORGANISM: Artificial
<220> FEATURE:
<223> OTHER INFORMATION: synthetic

<400> SEQUENCE: 248
gccgguuacc gagggggcgu cguuggaguu ugguugguug ucaccggc    48

<210> SEQ ID NO 249
<211> LENGTH: 48
<212> TYPE: RNA
<213> ORGANISM: Artificial
<220> FEATURE:
<223> OTHER INFORMATION: synthetic

<400> SEQUENCE: 249
gccggcuacc gagggggcgu cguuggaguu ugguugguug ucgccggc    48

<210> SEQ ID NO 250
<211> LENGTH: 46
<212> TYPE: RNA
<213> ORGANISM: Artificial
<220> FEATURE:

```
-continued

<223> OTHER INFORMATION: synthetic

<400> SEQUENCE: 250
gcgcguaccg aggggggcguc guuggaguuu gguugguugu ccgcgc            46

<210> SEQ ID NO 251
<211> LENGTH: 46
<212> TYPE: RNA
<213> ORGANISM: Artificial
<220> FEATURE:
<223> OTHER INFORMATION: synthetic

<400> SEQUENCE: 251
gggccuaccg aggggggcguc guuggaguuu gguugguugu cggccc            46

<210> SEQ ID NO 252
<211> LENGTH: 76
<212> TYPE: PRT
<213> ORGANISM: Rattus rattus

<400> SEQUENCE: 252

Gln Pro Asp Ala Val Asn Ala Pro Leu Thr Cys Cys Tyr Ser Phe Thr
1               5                   10                  15

Gly Lys Met Ile Pro Met Ser Arg Leu Glu Asn Tyr Lys Arg Ile Thr
            20                  25                  30

Ser Ser Arg Cys Pro Lys Glu Ala Val Val Phe Val Thr Lys Leu Lys
        35                  40                  45

Arg Glu Ile Cys Ala Asp Pro Asn Lys Glu Trp Val Gln Lys Tyr Ile
    50                  55                  60

Arg Lys Leu Asp Gln Asn Gln Val Arg Ser Glu Thr
65                  70                  75

<210> SEQ ID NO 253
<211> LENGTH: 50
<212> TYPE: RNA
<213> ORGANISM: Artificial
<220> FEATURE:
<223> OTHER INFORMATION: synthetic

<400> SEQUENCE: 253
ggcgacauug guugggcaug aggcgaggcc cuuugaugaa uccgcggcca          50

<210> SEQ ID NO 254
<211> LENGTH: 50
<212> TYPE: RNA
<213> ORGANISM: Artificial
<220> FEATURE:
<223> OTHER INFORMATION: synthetic

<400> SEQUENCE: 254
ggcgacauug guugggcaug aggcgaggcc cuuugaugaa uccgcggcca          50

<210> SEQ ID NO 255
<211> LENGTH: 11
<212> TYPE: DNA
<213> ORGANISM: Artificial
<220> FEATURE:
<223> OTHER INFORMATION: synthetic

<400> SEQUENCE: 255
gagggacgtg c                                                   11

<210> SEQ ID NO 256
<211> LENGTH: 9
```

```
<212> TYPE: DNA
<213> ORGANISM: Artificial
<220> FEATURE:
<223> OTHER INFORMATION: synthetic

<400> SEQUENCE: 256 cgcagagcc                                                                9

<210> SEQ ID NO 257
<211> LENGTH: 73
<212> TYPE: PRT
<213> ORGANISM: Artificial Sequence
<220> FEATURE:
<223> OTHER INFORMATION: CCL1/I-309
<220> FEATURE:
<221> NAME/KEY: L-Protein
<222> LOCATION: (1)..(73)
<223> OTHER INFORMATION: synthetic

<400> SEQUENCE: 257

Lys Ser Met Gln Val Pro Phe Ser Arg Cys Cys Phe Ser Phe Ala Glu
1               5                   10                  15

Gln Glu Ile Pro Leu Arg Ala Ile Leu Cys Tyr Arg Asn Thr Ser Ser
            20                  25                  30

Ile Cys Ser Asn Glu Gly Leu Ile Phe Lys Leu Lys Arg Gly Lys Glu
        35                  40                  45

Ala Cys Ala Leu Asp Thr Val Gly Trp Val Gln Arg His Arg Lys Met
    50                  55                  60

Leu Arg His Cys Pro Ser Lys Arg Lys
65                  70

<210> SEQ ID NO 258
<211> LENGTH: 69
<212> TYPE: PRT
<213> ORGANISM: Artificial Sequence
<220> FEATURE:
<223> OTHER INFORMATION: CCL3/MIP-1?
<220> FEATURE:
<221> NAME/KEY: L-Protein
<222> LOCATION: (1)..(69)
<223> OTHER INFORMATION: synthetic

<400> SEQUENCE: 258

Ser Leu Ala Ala Asp Thr Pro Thr Ala Cys Cys Phe Ser Tyr Thr Ser
1               5                   10                  15

Arg Gln Ile Pro Gln Asn Phe Ile Ala Asp Tyr Phe Glu Thr Ser Ser
            20                  25                  30

Gln Cys Ser Lys Pro Gly Val Ile Phe Leu Thr Lys Arg Ser Arg Gln
        35                  40                  45

Val Cys Ala Asp Pro Ser Glu Glu Trp Val Gln Lys Tyr Val Ser Asp
    50                  55                  60

Leu Glu Leu Ser Ala
65

<210> SEQ ID NO 259
<211> LENGTH: 69
<212> TYPE: PRT
<213> ORGANISM: Artificial Sequence
<220> FEATURE:
<223> OTHER INFORMATION: CCL4/MIP-1beta
<220> FEATURE:
<221> NAME/KEY: L-Protein
<222> LOCATION: (1)..(69)
<223> OTHER INFORMATION: synthetic

<400> SEQUENCE: 259
```

Ala Pro Met Gly Ser Asp Pro Pro Thr Ala Cys Cys Phe Ser Tyr Thr
1               5                   10                  15

Ala Arg Lys Leu Pro Arg Asn Phe Val Val Asp Tyr Tyr Glu Thr Ser
                20                  25                  30

Ser Leu Cys Ser Gln Pro Ala Val Val Phe Gln Thr Lys Arg Ser Lys
            35                  40                  45

Gln Val Cys Ala Asp Pro Ser Glu Ser Trp Val Gln Glu Tyr Val Tyr
    50                  55                  60

Asp Leu Glu Leu Asn
65

<210> SEQ ID NO 260
<211> LENGTH: 68
<212> TYPE: PRT
<213> ORGANISM: Artificial Sequence
<220> FEATURE:
<223> OTHER INFORMATION: CCL5/RANTES
<220> FEATURE:
<221> NAME/KEY: L-Protein
<222> LOCATION: (1)..(68)
<223> OTHER INFORMATION: synthetic

<400> SEQUENCE: 260

Ser Pro Tyr Ser Ser Asp Thr Thr Pro Cys Cys Phe Ala Tyr Ile Ala
1               5                   10                  15

Arg Pro Leu Pro Arg Ala His Ile Lys Glu Tyr Phe Tyr Thr Ser Gly
                20                  25                  30

Lys Cys Ser Asn Pro Ala Val Val Phe Val Thr Arg Lys Asn Arg Gln
            35                  40                  45

Val Cys Ala Asn Pro Glu Lys Lys Trp Val Arg Glu Tyr Ile Asn Ser
    50                  55                  60

Leu Glu Met Ser
65

<210> SEQ ID NO 261
<211> LENGTH: 82
<212> TYPE: PRT
<213> ORGANISM: Artificial Sequence
<220> FEATURE:
<223> OTHER INFORMATION: CCL13/MCP-4
<220> FEATURE:
<221> NAME/KEY: L-Protein
<222> LOCATION: (1)..(82)
<223> OTHER INFORMATION: synthetic

<400> SEQUENCE: 261

Phe Asn Pro Gln Gly Leu Ala Gln Pro Asp Ala Leu Asn Val Pro Ser
1               5                   10                  15

Thr Cys Cys Phe Thr Phe Ser Ser Lys Lys Ile Ser Leu Gln Arg Leu
                20                  25                  30

Lys Ser Tyr Val Ile Thr Thr Ser Arg Cys Pro Gln Lys Ala Val Ile
            35                  40                  45

Phe Arg Thr Lys Leu Gly Lys Glu Ile Cys Ala Asp Pro Lys Glu Lys
    50                  55                  60

Trp Val Gln Asn Tyr Met Lys His Leu Gly Arg Lys Ala His Thr Leu
65                  70                  75                  80

Lys Thr

<210> SEQ ID NO 262
<211> LENGTH: 74
<212> TYPE: PRT

```
<213> ORGANISM: Artificial Sequence
<220> FEATURE:
<223> OTHER INFORMATION: CCL14/HCC-1
<220> FEATURE:
<221> NAME/KEY: L-Protein
<222> LOCATION: (1)..(74)
<223> OTHER INFORMATION: synthetic

<400> SEQUENCE: 262

Thr Lys Thr Glu Ser Ser Arg Gly Pro Tyr His Pro Ser Glu Cys
1               5                   10                  15

Cys Phe Thr Tyr Thr Thr Tyr Lys Ile Pro Arg Gln Arg Ile Met Asp
            20                  25                  30

Tyr Tyr Glu Thr Asn Ser Gln Cys Ser Lys Pro Gly Ile Val Phe Ile
        35                  40                  45

Thr Lys Arg Gly His Ser Val Cys Thr Asn Pro Ser Asp Lys Trp Val
    50                  55                  60

Gln Asp Tyr Ile Lys Asp Met Lys Glu Asn
65                  70

<210> SEQ ID NO 263
<211> LENGTH: 73
<212> TYPE: PRT
<213> ORGANISM: Artificial Sequence
<220> FEATURE:
<223> OTHER INFORMATION: CXCL1/GROalpha
<220> FEATURE:
<221> NAME/KEY: L-Protein
<222> LOCATION: (1)..(73)
<223> OTHER INFORMATION: synthetic

<400> SEQUENCE: 263

Ala Ser Val Ala Thr Glu Leu Arg Cys Gln Cys Leu Gln Thr Leu Gln
1               5                   10                  15

Gly Ile His Pro Lys Asn Ile Gln Ser Val Asn Val Lys Ser Pro Gly
            20                  25                  30

Pro His Cys Ala Gln Thr Glu Val Ile Ala Thr Leu Lys Asn Gly Arg
        35                  40                  45

Lys Ala Cys Leu Asn Pro Ala Ser Pro Ile Val Lys Lys Ile Ile Glu
    50                  55                  60

Lys Met Leu Asn Ser Asp Lys Ser Asn
65                  70

<210> SEQ ID NO 264
<211> LENGTH: 73
<212> TYPE: PRT
<213> ORGANISM: Artificial Sequence
<220> FEATURE:
<223> OTHER INFORMATION: CXCL2/GRObeta
<220> FEATURE:
<221> NAME/KEY: L-Protein
<222> LOCATION: (1)..(73)
<223> OTHER INFORMATION: synthetic

<400> SEQUENCE: 264

Ala Pro Leu Ala Thr Glu Leu Arg Cys Gln Cys Leu Gln Thr Leu Gln
1               5                   10                  15

Gly Ile His Leu Lys Asn Ile Gln Ser Val Lys Val Lys Ser Pro Gly
            20                  25                  30

Pro His Cys Ala Gln Thr Glu Val Ile Ala Thr Leu Lys Asn Gly Gln
        35                  40                  45

Lys Ala Cys Leu Asn Pro Ala Ser Pro Met Val Lys Lys Ile Ile Glu
    50                  55                  60
```

```
Lys Met Leu Lys Asn Gly Lys Ser Asn
65                  70

<210> SEQ ID NO 265
<211> LENGTH: 73
<212> TYPE: PRT
<213> ORGANISM: Artificial Sequence
<220> FEATURE:
<223> OTHER INFORMATION: CXCL3/GROgama
<220> FEATURE:
<221> NAME/KEY: L-Protein
<222> LOCATION: (1)..(73)
<223> OTHER INFORMATION: synthetic

<400> SEQUENCE: 265

Ala Ser Val Val Thr Glu Leu Arg Cys Gln Cys Leu Gln Thr Leu Gln
1               5                   10                  15

Gly Ile His Leu Lys Asn Ile Gln Ser Val Asn Val Arg Ser Pro Gly
                20                  25                  30

Pro His Cys Ala Gln Thr Glu Val Ile Ala Thr Leu Lys Asn Gly Lys
            35                  40                  45

Lys Ala Cys Leu Asn Pro Ala Ser Pro Met Val Gln Lys Ile Ile Glu
        50                  55                  60

Lys Ile Leu Asn Lys Gly Ser Thr Asn
65                  70

<210> SEQ ID NO 266
<211> LENGTH: 70
<212> TYPE: PRT
<213> ORGANISM: Artificial Sequence
<220> FEATURE:
<223> OTHER INFORMATION: CXCL4/PF4
<220> FEATURE:
<221> NAME/KEY: L-Protein
<222> LOCATION: (1)..(70)
<223> OTHER INFORMATION: synthetic

<400> SEQUENCE: 266

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
                20                  25                  30

Gly Pro His Cys Pro Thr Ala Gln Leu Ile Ala Thr Leu Lys Asn Gly
            35                  40                  45

Arg Lys Ile Cys Leu Asp Leu Gln Ala Pro Leu Tyr Lys Lys Ile Ile
        50                  55                  60

Lys Lys Leu Leu Glu Ser
65                  70

<210> SEQ ID NO 267
<211> LENGTH: 77
<212> TYPE: PRT
<213> ORGANISM: artificial sequence
<220> FEATURE:
<223> OTHER INFORMATION: CXCL5/ENA-78
<220> FEATURE:
<221> NAME/KEY: L-Protein
<222> LOCATION: (1)..(77)
<223> OTHER INFORMATION: synthetic

<400> SEQUENCE: 267

Gly Pro Ala Ala Ala Val Leu Arg Glu Leu Arg Cys Val Cys Leu Gln
1               5                   10                  15

Thr Thr Gln Gly Val His Pro Lys Met Ile Ser Asn Leu Gln Val Phe
                20                  25                  30
```

Ala Ile Gly Pro Gln Cys Ser Lys Val Glu Val Ala Ser Leu Lys
            35                  40                  45

Asn Gly Lys Glu Ile Cys Leu Asp Pro Glu Ala Pro Phe Leu Lys Lys
 50                  55                  60

Val Ile Gln Lys Ile Leu Asp Gly Gly Asn Lys Glu Asn
 65                  70                  75

<210> SEQ ID NO 268
<211> LENGTH: 77
<212> TYPE: PRT
<213> ORGANISM: Artificial Sequence
<220> FEATURE:
<223> OTHER INFORMATION: CXCL6/GCP-2
<220> FEATURE:
<221> NAME/KEY: L-Protein
<222> LOCATION: (1)..(77)
<223> OTHER INFORMATION: synthetic

<400> SEQUENCE: 268

Gly Pro Val Ser Ala Val Leu Thr Glu Leu Arg Cys Thr Cys Leu Arg
 1               5                  10                  15

Val Thr Leu Arg Val Asn Pro Lys Thr Ile Gly Lys Leu Gln Val Phe
                20                  25                  30

Pro Ala Gly Pro Gln Cys Ser Lys Val Glu Val Ala Ser Leu Lys
            35                  40                  45

Asn Gly Lys Gln Val Cys Leu Asp Pro Glu Ala Pro Phe Leu Lys Lys
 50                  55                  60

Val Ile Gln Lys Ile Leu Asp Ser Gly Asn Lys Lys Asn
 65                  70                  75

<210> SEQ ID NO 269
<211> LENGTH: 94
<212> TYPE: PRT
<213> ORGANISM: Artificial Sequence
<220> FEATURE:
<223> OTHER INFORMATION: CXCL7/NAP-2
<220> FEATURE:
<221> NAME/KEY: L-Protein
<222> LOCATION: (1)..(94)
<223> OTHER INFORMATION: synthetic

<400> SEQUENCE: 269

Ser Ser Thr Lys Gly Gln Thr Lys Arg Asn Leu Ala Lys Gly Lys Glu
 1               5                  10                  15

Glu Ser Leu Asp Ser Asp Leu Tyr Ala Glu Leu Arg Cys Met Cys Ile
                20                  25                  30

Lys Thr Thr Ser Gly Ile His Pro Lys Asn Ile Gln Ser Leu Glu Val
            35                  40                  45

Ile Gly Lys Gly Thr His Cys Asn Gln Val Glu Val Ile Ala Thr Leu
 50                  55                  60

Lys Asp Gly Arg Lys Ile Cys Leu Asp Pro Asp Ala Pro Arg Ile Lys
 65                  70                  75                  80

Lys Ile Val Gln Lys Lys Leu Ala Gly Asp Glu Ser Ala Asp
                85                  90

<210> SEQ ID NO 270
<211> LENGTH: 79
<212> TYPE: PRT
<213> ORGANISM: artificial sequence
<220> FEATURE:
<223> OTHER INFORMATION: CXCL8/IL-8
<220> FEATURE:
<221> NAME/KEY: L-Protein

```
<222> LOCATION: (1)..(79)
<223> OTHER INFORMATION: synthetic

<400> SEQUENCE: 270

Glu Gly Ala Val Leu Pro Arg Ser Ala Lys Glu Leu Arg Cys Gln Cys
1               5                   10                  15

Ile Lys Thr Tyr Ser Lys Pro Phe His Pro Lys Phe Ile Lys Glu Leu
            20                  25                  30

Arg Val Ile Glu Ser Gly Pro His Cys Ala Asn Thr Glu Ile Ile Val
        35                  40                  45

Lys Leu Ser Asp Gly Arg Glu Leu Cys Leu Asp Pro Lys Glu Asn Trp
    50                  55                  60

Val Gln Arg Val Val Glu Lys Phe Leu Lys Arg Ala Glu Asn Ser
65                  70                  75

<210> SEQ ID NO 271
<211> LENGTH: 103
<212> TYPE: PRT
<213> ORGANISM: artificial sequence
<220> FEATURE:
<223> OTHER INFORMATION: CXCL9/MIG
<220> FEATURE:
<221> NAME/KEY: L-Protein
<222> LOCATION: (1)..(103)
<223> OTHER INFORMATION: synthetic

<400> SEQUENCE: 271

Thr Pro Val Val Arg Lys Gly Arg Cys Ser Cys Ile Ser Thr Asn Gln
1               5                   10                  15

Gly Thr Ile His Leu Gln Ser Leu Lys Asp Leu Lys Gln Phe Ala Pro
            20                  25                  30

Ser Pro Ser Cys Glu Lys Ile Glu Ile Ile Ala Thr Leu Lys Asn Gly
        35                  40                  45

Val Gln Thr Cys Leu Asn Pro Asp Ser Ala Asp Val Lys Glu Leu Ile
    50                  55                  60

Lys Lys Trp Glu Lys Gln Val Ser Gln Lys Lys Lys Gln Lys Asn Gly
65                  70                  75                  80

Lys Lys His Gln Lys Lys Val Leu Lys Val Arg Lys Ser Gln Arg
                85                  90                  95

Ser Arg Gln Lys Lys Thr Thr
            100

<210> SEQ ID NO 272
<211> LENGTH: 77
<212> TYPE: PRT
<213> ORGANISM: artificial sequence
<220> FEATURE:
<223> OTHER INFORMATION: CXCL10/IP-10
<220> FEATURE:
<221> NAME/KEY: L-Protein
<222> LOCATION: (1)..(77)
<223> OTHER INFORMATION: synthetic

<400> SEQUENCE: 272

Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Cys Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60
```

Leu Lys Ala Val Ser Lys Glu Arg Ser Lys Arg Ser Pro
65                  70                  75

<210> SEQ ID NO 273
<211> LENGTH: 73
<212> TYPE: PRT
<213> ORGANISM: artificial sequence
<220> FEATURE:
<223> OTHER INFORMATION: CXCL11/I-TAC
<220> FEATURE:
<221> NAME/KEY: L-Protein
<222> LOCATION: (1)..(73)
<223> OTHER INFORMATION: synthetic

<400> SEQUENCE: 273

Phe Pro Met Phe Lys Arg Gly Arg Cys Leu Cys Ile Gly Pro Gly Val
1               5                   10                  15

Lys Ala Val Lys Val Ala Asp Ile Glu Lys Ala Ser Ile Met Tyr Pro
            20                  25                  30

Ser Asn Asn Cys Asp Lys Ile Glu Val Ile Ile Thr Leu Lys Glu Asn
        35                  40                  45

Lys Gly Gln Arg Cys Leu Asn Pro Lys Ser Lys Gln Ala Arg Leu Ile
    50                  55                  60

Ile Lys Lys Val Glu Arg Lys Asn Phe
65                  70

<210> SEQ ID NO 274
<211> LENGTH: 72
<212> TYPE: PRT
<213> ORGANISM: artificial sequence
<220> FEATURE:
<223> OTHER INFORMATION: CXCL12alpha/SDF-1alpha
<220> FEATURE:
<221> NAME/KEY: L-Protein
<222> LOCATION: (1)..(72)
<223> OTHER INFORMATION: synthetic

<400> SEQUENCE: 274

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro
            20                  25                  30

Asn Cys Ala Leu Gln Ile Val Ala Arg Leu Lys Asn Asn Asn Arg Gln
        35                  40                  45

Val Cys Ile Asp Pro Lys Leu Lys Trp Ile Gln Glu Tyr Leu Glu Lys
    50                  55                  60

Ala Leu Asn Lys Arg Phe Lys Met
65                  70

<210> SEQ ID NO 275
<211> LENGTH: 72
<212> TYPE: PRT
<213> ORGANISM: Artificial Sequence
<220> FEATURE:
<223> OTHER INFORMATION: CXCL12beta/SDF-1beta
<220> FEATURE:
<221> NAME/KEY: L-Protein
<222> LOCATION: (1)..(72)
<223> OTHER INFORMATION: synthetic

<400> SEQUENCE: 275

Lys Pro Val Ser Leu Ser Tyr Arg Cys Pro Cys Arg Phe Phe Glu Ser
1               5                   10                  15

His Val Ala Arg Ala Asn Val Lys His Leu Lys Ile Leu Asn Thr Pro

-continued

```
                20                  25                  30
Asn Cys Ala Leu Gln Ile Val Ala Arg Leu Lys Asn Asn Arg Gln
         35                  40                  45

Val Cys Ile Asp Pro Lys Leu Lys Trp Ile Gln Glu Tyr Leu Glu Lys
 50                  55                  60

Ala Leu Asn Lys Arg Phe Lys Met
 65                  70

<210> SEQ ID NO 276
<211> LENGTH: 76
<212> TYPE: PRT
<213> ORGANISM: Artificial Sequence
<220> FEATURE:
<223> OTHER INFORMATION: CX3CL1/Fractalkine
<220> FEATURE:
<221> NAME/KEY: L-Protein
<222> LOCATION: (1)..(76)
<223> OTHER INFORMATION: synthetic

<400> SEQUENCE: 276

Gln His His Gly Val Thr Lys Cys Asn Ile Thr Cys Ser Lys Met Thr
 1               5                  10                  15

Ser Lys Ile Pro Val Ala Leu Leu Ile His Tyr Gln Gln Asn Gln Ala
                 20                  25                  30

Ser Cys Gly Lys Arg Ala Ile Ile Leu Glu Thr Arg Gln His Arg Leu
         35                  40                  45

Phe Cys Ala Asp Pro Lys Glu Gln Trp Val Lys Asp Ala Met Gln His
 50                  55                  60

Leu Asp Arg Gln Ala Ala Ala Leu Thr Arg Asn Gly
 65                  70                  75

<210> SEQ ID NO 277
<211> LENGTH: 93
<212> TYPE: PRT
<213> ORGANISM: Artificial Sequence
<220> FEATURE:
<223> OTHER INFORMATION: XCL1/Lymphotactin
<220> FEATURE:
<221> NAME/KEY: L-Protein
<222> LOCATION: (1)..(93)
<223> OTHER INFORMATION: artificial

<400> SEQUENCE: 277

Val Gly Ser Glu Val Ser Asp Lys Arg Thr Cys Val Ser Leu Thr Thr
 1               5                  10                  15

Gln Arg Leu Pro Val Ser Arg Ile Lys Thr Tyr Thr Ile Thr Glu Gly
                 20                  25                  30

Ser Leu Arg Ala Val Ile Phe Ile Thr Lys Arg Gly Leu Lys Val Cys
         35                  40                  45

Ala Asp Pro Gln Ala Thr Trp Val Arg Asp Val Val Arg Ser Met Asp
 50                  55                  60

Arg Lys Ser Asn Thr Arg Asn Asn Met Ile Gln Thr Lys Pro Thr Gly
 65                  70                  75                  80

Thr Gln Gln Ser Thr Asn Thr Ala Val Thr Leu Thr Gly
                 85                  90

<210> SEQ ID NO 278
<211> LENGTH: 40
<212> TYPE: RNA
<213> ORGANISM: Artificial
<220> FEATURE:
<223> OTHER INFORMATION: synthetic
```

```
<400> SEQUENCE: 278
gcacgucccu caccggugca agugaagccg uggcucugcg                                40

<210> SEQ ID NO 279
<211> LENGTH: 40
<212> TYPE: RNA
<213> ORGANISM: Artificial
<220> FEATURE:
<223> OTHER INFORMATION: synthetic

<400> SEQUENCE: 279
uaaggaaacu cggucugaug cgguagcgcu gugcagagcu                                40

<210> SEQ ID NO 280
<211> LENGTH: 40
<212> TYPE: RNA
<213> ORGANISM: Artificial
<220> FEATURE:
<223> OTHER INFORMATION: synthetic

<400> SEQUENCE: 280
uaaggaaacu cggucugaug cgguagcgcu gugcagagcu                                40

<210> SEQ ID NO 281
<211> LENGTH: 11
<212> TYPE: DNA
<213> ORGANISM: Artificial
<220> FEATURE:
<223> OTHER INFORMATION: synthetic

<400> SEQUENCE: 281
ccaatgtcgc c                                                              11

<210> SEQ ID NO 282
<211> LENGTH: 9
<212> TYPE: DNA
<213> ORGANISM: Artificial
<220> FEATURE:
<223> OTHER INFORMATION: synthetic

<400> SEQUENCE: 282 cgcagagcc                                                                  9

<210> SEQ ID NO 283
<211> LENGTH: 76
<212> TYPE: PRT
<213> ORGANISM: Equus caballus

<400> SEQUENCE: 283

Gln Pro Asp Ala Ile Asn Ser Pro Val Thr Cys Cys Tyr Thr Phe Thr
1               5                   10                  15

Gly Lys Lys Ile Ser Ser Gln Arg Leu Gly Ser Tyr Lys Arg Val Thr
            20                  25                  30

Ser Ser Lys Cys Pro Lys Glu Ala Val Ile Phe Lys Thr Ile Leu Ala
        35                  40                  45

Lys Glu Ile Cys Ala Asp Pro Glu Gln Lys Trp Val Gln Asp Ala Val
    50                  55                  60

Lys Gln Leu Asp Lys Lys Ala Gln Thr Pro Lys Pro
65                  70                  75

<210> SEQ ID NO 284
<211> LENGTH: 76
<212> TYPE: PRT
<213> ORGANISM: Bos Taurus
```

-continued

<400> SEQUENCE: 284

Gln Pro Asp Ala Ile Asn Ser Gln Val Ala Cys Cys Tyr Thr Phe Asn
1               5                   10                  15

Ser Lys Lys Ile Ser Met Gln Arg Leu Met Asn Tyr Arg Arg Val Thr
            20                  25                  30

Ser Ser Lys Cys Pro Lys Glu Ala Val Ile Phe Lys Thr Ile Leu Gly
        35                  40                  45

Lys Glu Leu Cys Ala Asp Pro Lys Gln Lys Trp Val Gln Asp Ser Ile
    50                  55                  60

Asn Tyr Leu Asn Lys Lys Asn Gln Thr Pro Lys Pro
65                  70                  75

<210> SEQ ID NO 285
<211> LENGTH: 125
<212> TYPE: PRT
<213> ORGANISM: Rattus norvegicus

<400> SEQUENCE: 285

Gln Pro Asp Ala Val Asn Ala Pro Leu Thr Cys Cys Tyr Ser Phe Thr
1               5                   10                  15

Gly Lys Met Ile Pro Met Ser Arg Leu Glu Asn Tyr Lys Arg Ile Thr
            20                  25                  30

Ser Ser Arg Cys Pro Lys Glu Ala Val Val Phe Val Thr Lys Leu Lys
        35                  40                  45

Arg Glu Ile Cys Ala Asp Pro Asn Lys Glu Trp Val Gln Lys Tyr Ile
    50                  55                  60

Arg Lys Leu Asp Gln Asn Gln Val Arg Ser Glu Thr Thr Val Phe Tyr
65                  70                  75                  80

Lys Ile Ala Ser Thr Leu Arg Thr Ser Ala Pro Leu Asn Val Asn Leu
                85                  90                  95

Thr His Lys Ser Glu Ala Asn Ala Ser Thr Leu Phe Ser Thr Thr Thr
            100                 105                 110

Ser Ser Thr Ser Val Glu Val Thr Ser Met Thr Glu Asn
        115                 120                 125

<210> SEQ ID NO 286
<211> LENGTH: 50
<212> TYPE: RNA
<213> ORGANISM: Artificial
<220> FEATURE:
<223> OTHER INFORMATION: synthetic

<400> SEQUENCE: 286
accggcgccu aaguaguuuc ccggagcgga guacggguug guuacagcgg          50

<210> SEQ ID NO 287
<211> LENGTH: 33
<212> TYPE: RNA
<213> ORGANISM: Artificial
<220> FEATURE:
<223> OTHER INFORMATION: synthetic

<400> SEQUENCE: 287 csuccccucac cggugcaagu gaagccgygg cuc                           33

<210> SEQ ID NO 288
<211> LENGTH: 33
<212> TYPE: RNA

```
<213> ORGANISM: Artificial
<220> FEATURE:
<223> OTHER INFORMATION: synthetic

<400> SEQUENCE: 288
cgucccucac cggugcaagu gaagccgugg cuc                                    33

<210> SEQ ID NO 289
<211> LENGTH: 23
<212> TYPE: RNA
<213> ORGANISM: Artificial
<220> FEATURE:
<223> OTHER INFORMATION: synthetic
<220> FEATURE:
<221> NAME/KEY: misc_feature
<222> LOCATION: (3)..(3)
<223> OTHER INFORMATION: n is a, c, g, or u

<400> SEQUENCE: 289
agndrdgbkg gurgyargua aag                                               23

<210> SEQ ID NO 290
<211> LENGTH: 22
<212> TYPE: RNA
<213> ORGANISM: Artificial
<220> FEATURE:
<223> OTHER INFORMATION: synthetic

<400> SEQUENCE: 290
aggugggugg uaguaaguaa ag                                                22

<210> SEQ ID NO 291
<211> LENGTH: 24
<212> TYPE: RNA
<213> ORGANISM: Artificial
<220> FEATURE:
<223> OTHER INFORMATION: synthetic

<400> SEQUENCE: 291
caggugggug guagaaugua aaga                                              24

<210> SEQ ID NO 292
<211> LENGTH: 13
<212> TYPE: RNA
<213> ORGANISM: Artificial
<220> FEATURE:
<223> OTHER INFORMATION: synthetic

<400> SEQUENCE: 292
gggggrcgcg ayc                                                          13

<210> SEQ ID NO 293
<211> LENGTH: 10
<212> TYPE: RNA
<213> ORGANISM: Artificial
<220> FEATURE:
<223> OTHER INFORMATION: synthetic

<400> SEQUENCE: 293
ugcaauaaug                                                              10

<210> SEQ ID NO 294
<211> LENGTH: 13
<212> TYPE: RNA
<213> ORGANISM: Artificial
<220> FEATURE:
<223> OTHER INFORMATION: synthetic
```

```
<400> SEQUENCE: 294 gggggggcgcg acc                                                13
```